United States Patent
Gerusz et al.

(10) Patent No.: US 8,846,711 B2
(45) Date of Patent: Sep. 30, 2014

(54) HETEROCYCLIC ACRYLAMIDES AND THEIR USE AS PHARMACEUTICALS

(75) Inventors: Vincent Gerusz, Paris (FR); Sonia Escaich, Paris (FR); Mayalen Oxoby, Paris (FR); Alexis Denis, Paris (FR)

(73) Assignee: Fab Pharma S.A.S., Paris (FR)

( * ) Notice: Subject to any disclaimer, the term of this patent is extended or adjusted under 35 U.S.C. 154(b) by 199 days.

(21) Appl. No.: 13/510,564

(22) PCT Filed: Nov. 17, 2010

(86) PCT No.: PCT/EP2010/067647
§ 371 (c)(1),
(2), (4) Date: Jul. 12, 2012

(87) PCT Pub. No.: WO2011/061214
PCT Pub. Date: May 26, 2011

(65) Prior Publication Data
US 2012/0277207 A1    Nov. 1, 2012

Related U.S. Application Data

(60) Provisional application No. 61/262,309, filed on Nov. 18, 2009.

(51) Int. Cl.
*A61K 31/44* (2006.01)
*C07D 471/02* (2006.01)

(52) U.S. Cl.
USPC .......................................... 514/300; 546/123

(58) Field of Classification Search
USPC .......................................... 546/123; 514/300
See application file for complete search history.

(56) References Cited

U.S. PATENT DOCUMENTS

| | | |
|---|---|---|
| 6,846,819 B1 | 1/2005 | Miller et al. |
| 7,790,716 B2 * | 9/2010 | Miller et al. ............... 514/230.5 |
| 2005/0250810 A1 | 11/2005 | Miller et al. |
| 2006/0183908 A1 | 8/2006 | Berman et al. |
| 2008/0125423 A1 | 5/2008 | Miller et al. |
| 2009/0156578 A1 | 6/2009 | Pauls et al. |
| 2009/0275572 A1 | 11/2009 | Miller et al. |
| 2010/0016272 A1 | 1/2010 | Strobel et al. |
| 2010/0016278 A1 | 1/2010 | Strobel et al. |
| 2010/0093705 A1 | 4/2010 | Sargent et al. |
| 2010/0130470 A1 | 5/2010 | Pauls et al. |

FOREIGN PATENT DOCUMENTS

| | | |
|---|---|---|
| WO | WO 01/27103 | 4/2001 |
| WO | WO 03/088897 | 10/2003 |
| WO | WO 2004/052890 | 6/2004 |
| WO | WO 2007/053131 | 5/2007 |
| WO | WO 2007/067416 | 6/2007 |
| WO | WO 2008/009122 | 1/2008 |
| WO | WO 2008/074413 | 6/2008 |
| WO | WO 2008/080511 | 7/2008 |

OTHER PUBLICATIONS

International Search Report for PCT/EP2010/067647 mailed Jan. 26, 2011.
Written Opinion of the International Searching Authority mailed Jan. 26, 2011.

* cited by examiner

*Primary Examiner* — Niloofar Rahmani
(74) *Attorney, Agent, or Firm* — Nixon & Vanderhye P.C.

(57) ABSTRACT

The invention relates to novel heterocyclic acrylamide compounds (I), to the preparation of the compounds and intermediates used therein, to the use of the compounds as antibacterial medicaments and pharmaceutical compositions containing the compounds.

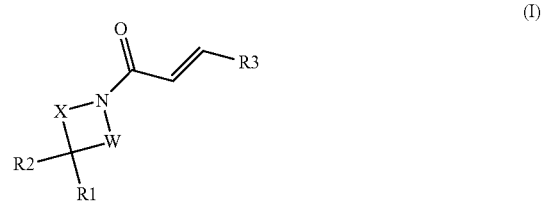

(I)

21 Claims, 2 Drawing Sheets

HETEROCYCLIC ACRYLAMIDES AND THEIR USE AS PHARMACEUTICALS

This application is the U.S. national phase of International Application No. PCT/EP2010/067647 filed 17 Nov. 2010 which designated the U.S. and claims priority to U.S. Provisional Application No. 61/262,309 filed 18 Nov. 2009, the entire contents of each of which are hereby incorporated by reference.

FIELD OF THE INVENTION

The invention relates to novel heterocyclic acrylamide compounds, to the preparation of the compounds and intermediates used therein, to the use of the compounds as antibacterial medicaments and pharmaceutical compositions containing the compounds.

BACKGROUND OF THE INVENTION

The invention particularly relates to new compounds capable of inhibiting bacterial and/or parasite fatty acid biosynthesis and their use as antibacterial and/or antiparasitic agents.

The emergence of antibiotic-resistant pathogens has become a serious worldwide healthcare problem. Indeed, some infections are now caused by multi-drug resistant organisms that are no longer responsive to currently available treatments. There is therefore an immediate need for new antibacterial/antiparasitic agents with a novel mode of action.

The bacterial fatty acid biosynthesis (FASII system) has recently generated a lot of interest for the development of novel antibacterial/antiparasitic agents (Rock et al. *J. Biol. Chem.* 2006, 281, 17541; Wright and Reynolds *Curr. Opin. Microbiol.* 2007, 10, 447). The organization of components in the bacterial fatty acid biosynthesis pathway based on discrete enzymes is fundamentally different from the multifunctional FASI system found in mammals, therefore allowing good prospects of selective inhibition. The overall high degree of conservation in many enzymes of the bacterial FASII system should also allow the development of broader-spectrum antibacterial/antiparasitic agents.

Among all the monofunctional enzymes of the bacterial FASII system, FabI represents the enoyl-ACP reductase responsible for the last step of the fatty acid biosynthetic elongation cycle. Using the cofactor NAD(P)H as a hydride source, FabI reduces the double bond in the trans-2-enoyl-ACP intermediate to the corresponding acyl-ACP product. This enzyme has been shown to constitute an essential target in major pathogens such as *E. coli* (Heath et al. *J. Biol. Chem.* 1995, 270, 26538; Bergler et al. *Eur. J. Biochem.* 1996, 242, 689) and *S. aureus* (Heath et al. *J. Biol. Chem.* 2000, 275, 4654). However, other isoforms have been isolated such as FabK from *S. pneumoniae* (Heath et al. *Nature* 2000, 406, 145) and FabL from *B. subtilis* (Heath et al. *J. Biol. Chem.* 2000, 275, 40128). Although FabK is structurally and mechanistically unrelated to FabI (Marrakchi et al. *Biochem J.* 2003, 370, 1055), the similarity of FabI with FabL (*B. subtilis*), InhA (*M. tuberculosis*) and PfENR (*P. falciparum*) still offers opportunities of interesting activity spectra (Heath et al. *Prog. Lipid Res.* 2001, 40, 467).

Several FabI inhibitors have already been reported in the literature (Tonge et al. *Acc. Chem. Res.* 2008, 41, 11). Some of them such as diazaborines (Baldock et al. *Science* 1996, 274, 2107) and isoniazid in its activated form (Tonge et al. *Proc. Natl. Acad. Sci. U.S.A.* 2003, 100, 13881) act by covalently modifying the cofactor NAD+. However some drawbacks are associated with these products. Diazaborines are only used experimentally because of their inherent toxicity (Baldock et al. *Biochem. Pharmacol.* 1998, 55, 1541) while isoniazid is a prodrug restricted to the treatment of susceptible tuberculosis. The fact that isoniazid requires activation by hydrogen-peroxide inducible enzymes (Schultz et al. *J. Am. Chem. Soc.* 1995, 117, 5009) enhances the possibilities of resistance by lack of activation or increased detoxification (Rosner et al. *Antimicrob. Agents Chemother.* 1993, 37, 2251 and ibid 1994, 38, 1829).

Other inhibitors act by interacting noncovalently with the enzyme-cofactor complex. For instance Triclosan, a widely used consumer goods preservative with broad spectrum antimicrobial activity, has been found to be a reversible, tight-binding inhibitor of *E. coli* FabI (Ward et al. *Biochemistry* 1999, 38, 12514). Intravenous toxicology studies on this compound indicated a $LD_{50}$ on rats of 29 mg/kg clearly ruling out intravenous injection (Lyman et al. *Ind. Med. Surg.* 1969, 38, 42).

Derivatives based on the 2-hydroxydiphenyl ether core of Triclosan have been reported (Tonge et al. *J. Med. Chem.* 2004, 47, 509, ACS Chem. Biol. 2006, 1, 43 and *Bioorg. Med. Chem. Lett.* 2008, 18, 3029; Surolia et al. *Bioorg. Med. Chem.* 2006, 14, 8086 and ibid 2008, 16, 5536; Freundlich et al. *J. Biol. Chem.* 2007, 282, 25436) as well as other inhibitors based on various classes of high throughput screening derived templates (Seefeld et al. *Bioorg. Med. Chem. Lett.* 2001, 11, 2241 and *J. Med. Chem.* 2003, 46, 1627; Heerding et al. *Bioorg. Med. Chem. Lett.* 2001, 11, 2061; Miller et al. *J. Med. Chem.* 2002, 45, 3246; Payne et al. *Antimicrob. Agents Chemother.* 2002, 46, 3118; Sacchettini et al. *J. Biol. Chem.* 2003, 278, 20851; Moir et al. *Antimicrob. Agents Chemother.* 2004, 48, 1541; Montellano et al. *J. Med. Chem.* 2006, 49, 6308; Kwak et al. *Int. J. Antimicro. Ag.* 2007, 30, 446; Lee et al. *Antimicrob. Agents Chemother.* 2007, 51, 2591; Kitagawa et al. *J. Med. Chem.* 2007, 50, 4710, *Bioorg. Med. Chem.* 2007, 15, 1106 and *Bioorg. Med. Chem. Lett.* 2007, 17, 4982; Takahata et al. *J. Antibiot.* 2007, 60, 123; Kozikowski et al. *Bioorg. Med. Chem. Lett.* 2008, 18, 3565), nevertheless none of these inhibitors have succeeded yet as a drug. Interestingly, some classes of these inhibitors display activity on both FabI and FabK: predominantly FabK for the dual compounds based on phenylimidazole derivatives of 4-pyridones (Kitagawa et al. *J. Med. Chem.* 2007, 50, 4710), predominantly FabI for the indole derivatives (Payne et al. *Antimicrob. Agents Chemother.* 2002, 46, 3118; Seefeld et al. *J. Med. Chem.* 2003, 46, 1627). However, the moderate activity on the second enzyme might prove to be a drawback for such compounds as it may lead to an increase of resistance mechanisms due to the added selection pressure (Tonge et al. *Acc. Chem. Res.* 2008, 41, 11).

Despite the attractiveness of FabI as an antibacterial/antiparasitic target, it is still largely unexploited at this time since there are no drugs on the market or within advanced clinical phases.

WO 2007/135562 (Mutabilis SA) describes a series of hydroxyphenyl derivatives that display a selective spectrum of activity on species containing FabI and related targets, in contrast to Triclosan. WO 2008/098374, WO 2008/009122, WO 2007/067416, WO 2007/053131, WO 03/088897 and WO 01/27103 (Affinium Pharmaceuticals Inc) all describe a series of acrylamide derivatives which are claimed to be FabI inhibitors.

One of the purposes of the invention is to provide novel compounds active on FabI and related targets with improved pharmacological and/or physico-chemical properties over existing compounds.

SUMMARY OF THE INVENTION

According to a first aspect of the invention, there is provided a compound of formula (I):

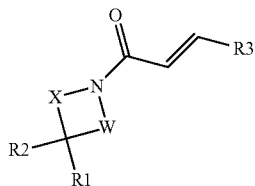

wherein:
W and X independently represent a bond or a —$(CH_2)_{1-4}$ group, such that W and X together contain 1-5 carbon atoms;
R1 represents an H, F, CN, ($C_1$-$C_6$) alkyl, ($C_2$-$C_6$) alkenyl, ($C_2$-$C_6$) alkynyl, $CO_2R_d$, $COR_d$, $CONR_aR_b$, $OCOR_d$, $OR_d$, $NR_aR_b$, ON=$CR_dR_e$, $NR_cCOR_d$, $NR_cCOOR_d$, $OCONR_aR_b$, $NR_cCONR_aR_b$, $NR_c$ $SO_2R_a$, $S(O)_nR_a$, $SO_2NR_aR_b$, —C($R_a$)=N—O—$R_f$, Y—Ar or a Z-Het group, wherein Ar represents phenyl or naphthyl, Het represents a 4-10 membered monocyclic or bicyclic saturated or unsaturated heterocycle containing 1-5 heteroatoms selected from N, O and S and Y and Z independently represent a bond or a linker selected from O, S, CO, ($C_1$-$C_6$) alkylene, —O—($C_1$-$C_6$) alkylene, —CO—($C_1$-$C_6$) alkylene or —ON=$CR_d$—($C_1$-$C_6$) alkylene, wherein said R1 group may be optionally substituted by one or more R4 groups;
R2 represents an H, F, CN, ($C_1$-$C_6$) alkyl, ($C_2$-$C_6$) alkenyl, ($C_2$-$C_6$) alkynyl, $CO_2R_d$, $COR_d$, $CONR_aR_b$, $OCOR_d$, $OR_d$, $NR_aR_b$, ON=$CR_dR_e$, $NR_cCOR_d$, $NR_cCOOR_d$, $OCONR_aR_b$, $NR_cCONR_aR_b$, $NR_c$ $SO_2R_a$, $S(O)_nR_a$ or $SO_2NR_aR_b$ group;
$R_a$, $R_b$ and $R_c$ independently represent H, ($C_1$-$C_6$) alkyl, ($C_2$-$C_6$) alkenyl, ($C_2$-$C_6$) alkynyl, or an $NR_aR_b$ group may optionally form a 3- to 7-membered nitrogen containing saturated heterocycle optionally containing 1 to 3 additional heteroatoms selected from N, O or S wherein said heterocycle may be optionally substituted by one or more ($C_1$-$C_6$) alkyl groups;
$R_d$ and $R_e$ independently represent H, ($C_1$-$C_6$) alkyl, ($C_2$-$C_6$) alkenyl, ($C_2$-$C_6$) alkynyl, halo($C_1$-$C_6$) alkyl, halo ($C_1$-$C_6$) alkyl-O—($C_1$-$C_6$) alkyl- or ($C_1$-$C_6$) alkyl-O—($C_1$-$C_6$) alkyl-;
$R_f$ represents ($C_1$-$C_6$) alkyl, ($C_2$-$C_6$) alkenyl, ($C_2$-$C_6$) alkynyl, halo($C_1$-$C_6$) alkyl or —($C_1$-$C_6$) alkyl-Ar, wherein Ar represents phenyl or naphthyl;
R4 represents halogen, CN, ($C_1$-$C_6$) alkyl, ($C_2$-$C_6$) alkenyl, ($C_2$-$C_6$) alkynyl, $CO_2R_d$, $COR_d$, $CONR_aR_b$, $OCOR_d$, $OR_d$, $NR_aR_b$, ON=$CR_dR_e$, $NR_cCOR_d$, $NR_cCOOR_d$, $OCONR_aR_b$, $NR_cCONR_aR_b$, $NR_c$ $SO_2R_a$, $S(O)_nR_a$, or $SO_2NR_aR_b$;
n represents an integer selected from 0 to 2;
R3 is a pyridyl ring optionally fused to a 5, 6 or 7 membered aromatic, partially aromatic or saturated heterocycle containing 1-3 heteroatoms selected from N, O and S, wherein said $R_3$ group may be optionally substituted by one or more R5 groups;
R5 is selected from the group consisting of F, $CO_2R_d$, $COR_d$, $CONR_aR_b$, $OR_d$, =O, $NR_aR_b$, $NR_cCOR_d$ or ($C_1$-$C_6$) alkyl optionally substituted by F, $CO_2R_d$, CON-$R_aR_b$, $OR_d$, $NR_aR_b$, $NR_aCOR_d$ or Het optionally substituted by one or more ($C_1$-$C_6$) alkyl groups, or two R5 groups together with the atom to which they are attached may together form a Het group optionally substituted by one or more ($C_1$-$C_6$) alkyl groups;
or a pharmaceutically acceptable salt or solvate thereof.

DETAILED DESCRIPTION OF THE INVENTION

Figure 1:
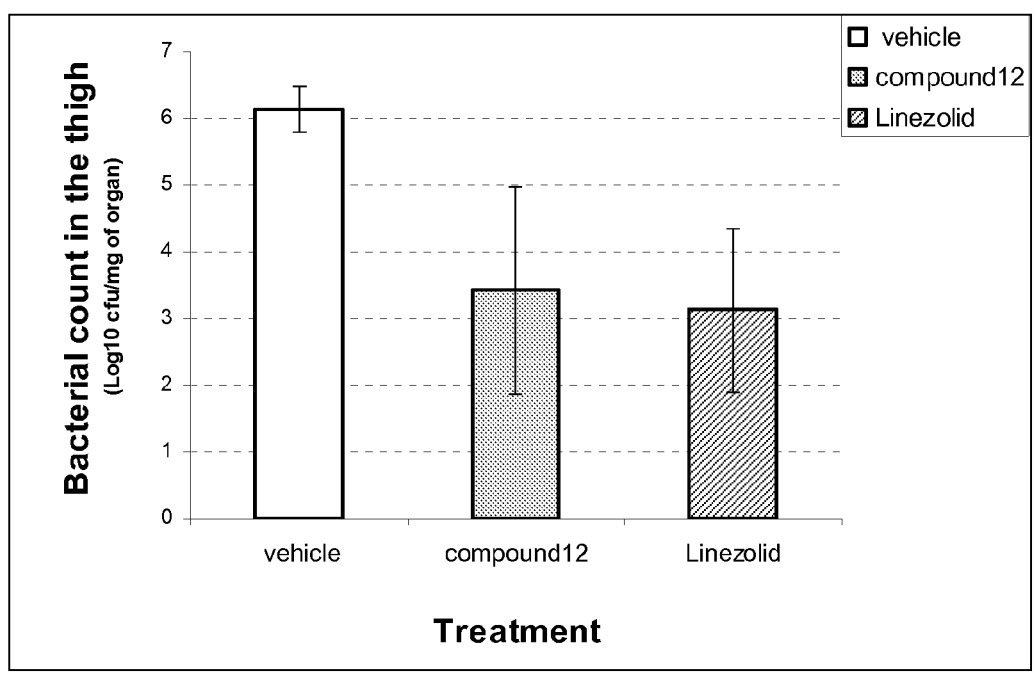
FIG. 1 relates to the in vivo antibacterial activity of Example 12 at 100 mg/kg.

According to one particular aspect of the invention which may be mentioned, there is provided a compound of formula (I):

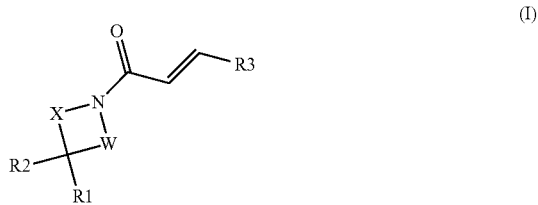

wherein:
W and X independently represent a bond or a —$(CH_2)_{1-4}$ group, such that W and X together contain 1-5 carbon atoms;
R1 represents an H, F, CN, ($C_1$-$C_6$) alkyl, ($C_2$-$C_6$) alkenyl, ($C_2$-$C_6$) alkynyl, $CO_2R_d$, $COR_d$, $CONR_aR_b$, $OCOR_d$, $OR_d$, $NR_aR_b$, ON=$CR_dR_e$, $NR_cCOR_d$, $NR_cCOOR_d$, $OCONR_aR_b$, $NR_cCONR_aR_b$, $NR_c$ $SO_2R_a$, $S(O)_nR_a$, $SO_2NR_aR_b$, Y—Ar or a Z-Het group, wherein Ar represents phenyl or naphthyl, Het represents a 4-10 membered monocyclic or bicyclic saturated or unsaturated heterocycle containing 1-5 heteroatoms selected from N, O and S and Y and Z independently represent a bond or a linker selected from O, CO, ($C_1$-$C_6$) alkylene, —O—($C_1$-$C_6$) alkylene, —CO—($C_1$-$C_6$) alkylene or —ON=$CR_d$—($C_1$-$C_6$) alkylene, wherein said R1 group may be optionally substituted by one or more R4 groups;
R2 represents an H, F, CN, ($C_1$-$C_6$) alkyl, ($C_2$-$C_6$) alkenyl, ($C_2$-$C_6$) alkynyl, $CO_2R_d$, $COR_d$, $CONR_aR_b$, $OCOR_d$, $OR_d$, $NR_aR_b$, ON=$CR_dR_e$, $NR_cCOR_d$, $NR_cCOOR_d$, $OCONR_aR_b$, $NR_cCONR_aR_b$, $NR_c$ $SO_2R_a$, $S(O)_nR_a$ or $SO_2NR_aR_b$ group;
$R_a$, $R_b$ and $R_c$ independently represent H, ($C_1$-$C_6$) alkyl, ($C_2$-$C_6$) alkenyl, ($C_2$-$C_6$) alkynyl, or an $NR_aR_b$ group may optionally form a 3- to 7-membered nitrogen containing saturated heterocycle optionally containing 1 to 3 additional heteroatoms selected from N, O or S wherein said heterocycle may be optionally substituted by one or more ($C_1$-$C_6$) alkyl groups;
$R_d$ and $R_e$ independently represent H, ($C_1$-$C_6$) alkyl, ($C_2$-$C_6$) alkenyl, ($C_2$-$C_6$) alkynyl, halo($C_1$-$C_6$) alkyl, halo ($C_1$-$C_6$) alkyl-O—($C_1$-$C_6$) alkyl- or ($C_1$-$C_6$) alkyl-O—($C_1$-$C_6$) alkyl-;
R4 represents halogen, CN, ($C_1$-$C_6$) alkyl, ($C_2$-$C_6$) alkenyl, ($C_2$-$C_6$) alkynyl, $CO_2R_d$, $COR_d$, $CONR_aR_b$, $OCOR_d$, $OR_d$, $NR_aR_b$, $ON=CR_dR_e$, $NR_cCOR_d$, $NR_cCOOR_d$, $OCONR_aR_b$, $NR_cCONR_aR_b$, $NR_c SO_2R_a$, $S(O)_nR_a$, or $SO_2NR_aR_b$;

n represents an integer selected from 0 to 2;

R3 is a pyridyl ring optionally fused to a 5, 6 or 7 membered aromatic, partially aromatic or saturated heterocycle containing 1-3 heteroatoms selected from N, O and S, wherein said $R_3$ group may be optionally substituted by one or more R5 groups;

R5 is selected from the group consisting of F, $CO_2R_d$, $COR_d$, $CONR_aR_b$, $OR_d$, =O, $NR_aR_b$, $NR_cCOR_d$ or $(C_1-C_6)$ alkyl optionally substituted by F, $CO_2R_d$, $CONR_aR_b$, $OR_d$, $NR_aR_b$, $NR_aCOR_d$, or two R5 groups together with the atom to which they are attached may together form a Het group optionally substituted by one or more $(C_1-C_6)$ alkyl groups;

or a pharmaceutically acceptable salt or solvate thereof.

The compounds of the invention may have good in vitro and/or in vivo activity and display surprisingly improved pharmacological, physical and/or chemical properties over previously described FabI inhibitors as confirmed by data presented herein. For example, compounds of the invention which have been tested display surprisingly less serum binding than previously described acrylamide derivatives. Furthermore, compounds of the invention which have been tested appear to demonstrate parenteral (such as subcutaneous) and oral bioavailability. Certain compounds of the invention also appear to reduce the apparition of resistance mechanisms by being selective of FabI and related targets while avoiding hitting structurally unrelated targets such as FabK. In addition, compounds of the invention which have been tested appear to demonstrate greater solubility than previously described FabI inhibitors.

In the present context, the term "pharmaceutically acceptable salt" is intended to indicate salts which are not harmful to the patient. Such salts include pharmaceutically acceptable acid addition salts, pharmaceutically acceptable metal salts and pharmaceutically acceptable akaline addition salts. Acid addition salts include salts of inorganic acids as well as organic acids.

Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Representative examples of alkaline salts include, for example, sodium, potassium, lithium, calcium, magnesium or ammonium or organic bases such as, for example, methylamine, ethylamine, propylamine, trimethylamine, diethylamine, triethylamine, N,N-dimethylethanolamine, tris(hydroxymethyl)aminomethane, ethanolamine, pyridine, piperidine, piperazine, picoline, dicyclohexylamine, morpholine, benzylamine, procaine, lysine, arginine, histidine, N-methylglucamine.

According to the invention, the compounds of formula (I) can be in racemic forms, as well as in the form of pure enantiomers or non racemic (scalemic) mixture of enantiomers, including when the compounds of formula (I) have more than one stereogenic centre. In case the compounds of formula (I) have unsaturated carbon carbon double bonds, both the cis (Z) and trans (E) isomers and their mixtures belong to the invention.

References herein to "halogen" means a fluorine, chlorine, bromine or iodine atom.

References herein to "$(C_1-C_6)$ alkyl" means any linear, branched hydrocarbon groups having 1 to 6 carbon atoms, or cyclic hydrocarbon groups having 3 to 6 carbon atoms. Representative examples of such alkyl groups include methyl, ethyl, n-propyl, isopropyl, n-butyl, isobutyl and t-butyl, n-pentyl, isopentyl, neopentyl, cyclopropyl, cyclobutyl, cyclopentyl and cyclohexyl.

References herein to "$(C_2-C_6)$ alkenyl" means any linear, branched hydrocarbon groups of 2 to 6 carbon atoms, or cyclic hydrocarbon group having 3 to 6 carbon atoms having at least one double bond. Representative examples of such alkenyl groups include ethenyl, propenyl, butenyl and cyclohexenyl. References to "halo$(C_2-C_6)$ alkenyl" mean a $(C_2-C_6)$ alkenyl group substituted by one or more halogen atoms as herein defined.

References herein to "$(C_2-C_6)$ alkynyl" means any linear, or branched hydrocarbon groups of 2 to 6 carbon atoms, having at least one triple bond. Representative examples of such alkynyl groups include ethynyl, propargyl and butynyl. References to "halo$(C_2-C_6)$ alkynyl" mean a $(C_2-C_6)$ alkynyl group substituted by one or more halogen atoms as herein defined.

Illustrative examples of Het within the definition of R1 and R5 include those selected from the group comprising furyl, tetrahydrofuryl, benzofuryl, tetrahydrobenzofuryl, thienyl, tetrahydrothienyl, benzothienyl, tetrahydrobenzothienyl, pyrrolyl, pyrrolidinyl, indolyl, indolinyl, tetrahydroindolyl, oxazolyl, oxazolinyl, oxazolidinyl, benzoxazolyl, tetrahydrobenzoxazolyl, oxazolopyridinyl, tetrahydrooxazolopyridinyl, oxazolopyrimidinyl, tetrahydrooxazolopyrimidinyl, oxazolopyrazinyl, oxazolopyridazinyl, oxazolotriazinyl, isoxazolyl, benzoisoxazolyl, tetrahydrobenzoisoxazolyl, thiazolyl, thiazolinyl, thiazolidinyl, benzothiazolyl, tetrahydrobenzothiazolyl, thiazolopyridinyl, tetrahydrothiazolopyridinyl, thiazolopyrimidinyl, tetrahydrothiazolopyrimidinyl, thiazolopyrazinyl, thiazolopyridazinyl, thiazolotriazinyl, isothiazolyl, benzoisothiazolyl, tetrahydrobenzoisothiazolyl, imidazolyl, benzimidazolyl, tetrahydrobenzimidazolyl, pyrazolyl, indazolyl, tetrahydroindazolyl, triazolyl, oxadiazolyl, thiadiazolyl, tetrazolyl, pyranyl, dihydropyranyl, tetrahydropyranyl, benzopyranyl, dioxanyl, benzodioxanyl, dioxolanyl, benzodioxolanyl, pyridinyl, pyridonyl, piperidinyl, tetrahydropyridinyl, quinolinyl, isoquinolinyl, tetra- and perhydro-quinolinyl and isoquinolinyl, pyrimidinyl, quinazolinyl, pyrazinyl, pyrazidinyl, piperazinyl, quinoxalinyl, piridazinyl, cinnolinyl, phtalazinyl, triazinyl, purinyl, pyrazolopyridinyl, tetrahydropyrazolopyridinyl, pyrazolopyrimidinyl, pyrazolopyrazinyl, pyrazolotriazinyl, triazolopyridinyl, tetrahydrotriazolopyridinyl, triazolopyrimidinyl, triazolopyrazinyl, triazolotriazinyl, oxetanyl, azetidinyl and morpholinyl.

Illustrative examples of saturated nitrogen containing heterocycles within the definition of $NR_aR_b$ include those selected from the group comprising, pyrrolidinyl, oxazolidinyl, thiazolidinyl, piperidinyl, piperazinyl and morpholinyl.

In one embodiment, W and X both represent $CH_2$, thus forming an azetidinyl ring which is substituted at the 3 position by R1 and R2.

In an alternative embodiment, one of W and X represents $CH_2$ and the other represents $CH_2CH_2$, thus forming a pyrrolidinyl ring which is substituted at the 3 position by R1 and R2.

In an alternative embodiment, one of W and X represents a bond and the other represents $CH_2CH_2CH_2$, thus forming a pyrrolidinyl ring which is substituted at the 2 position by R1 and R2.

In a further alternative embodiment, W and X both represent $CH_2CH_2$, thus forming a piperidinyl ring which is substituted at the 4 position by R1 and R2.

In a further alternative embodiment, one of W and X represents $CH_2$ and the other represents $CH_2CH_2$, thus forming a piperidinyl ring which is substituted at the 3 position by R1 and R2.

In a yet further alternative embodiment, one of W and X represents a bond and the other represents $CH_2CH_2CH_2CH_2$, thus forming a piperidinyl ring which is substituted at the 2 position by R1 and R2.

In a most particular embodiment, W and X both represent $CH_2$, thus forming an azetidinyl ring which is substituted at the 3 position by R1 and R2.

In one embodiment, R1 represents an H, F, $(C_1-C_6)$ alkyl, $(C_2-C_6)$ alkenyl, $OR_d$, $S(O)_nR_a$, $—C(R_a)=N—O—R_f$, Y—Ar or Z-Het group each of which may be optionally substituted by one or more R4 groups.

In a further embodiment, R1 represents an H, F, $(C_1-C_6)$ alkyl, $(C_2-C_6)$ alkenyl, $OR_d$, $S(O)_nR_a$, Y—Ar or Z-Het group each of which may be optionally substituted by one or more R4 groups.

In a yet further embodiment, R1 represents an H, $(C_1-C_6)$ alkyl, $OR_d$, $S(O)_nR_a$, Y—Ar or Z-Het group each of which may be optionally substituted by one or more R4 groups.

In a still yet further embodiment, R1 represents $OR_d$, Z-Het or $—C(R_a)=N—O—R_f$, such as a Z-Het group (i.e. benzofuranyl optionally substituted by a methyl group).

In one embodiment, R1 represents H.

When R1 represents $(C_1-C_6)$ alkyl optionally substituted by one or more R4 groups, in one embodiment R1 represents ethyl or propyl optionally substituted by one or more $OR_d$ groups (such as —OH). In a further embodiment, R1 represents propyl or ethyl substituted by an OH group. In a yet further embodiment, R1 represents propyl or $(CH_2)_2OH$.

When R1 represents $OR_d$, in one embodiment $R_d$ represents $(C_1-C_6)$ alkyl (e.g. butyl, pentyl or $—(CH_2)_2—CH(Me)$), halo$(C_1-C_6)$ alkyl (e.g. $—CH_2—CF_3$ or $—CH_3—CF_3$), $—(C_1-C_6)$ alkyl-O—$(C_1-C_6)$ alkyl (e.g. $—(CH_2)_2—OMe$ or $—(CH_2)_3—OMe$) or $(C_2-C_6)$ alkenyl (e.g. $—CH_2—CH=CH-Me$ or $—CH_2—C(Me)=CH-Me$).

When R1 represents $OR_d$, in a further embodiment $R_d$ represents $(C_1-C_6)$ alkyl, such as pentyl or $(C_2-C_6)$ alkenyl such as $—CH_2—CH=CH-Me$.

When R1 represents $OR_d$, in a yet further embodiment $R_d$ represents $(C_1-C_6)$ alkyl, such as butyl.

When R1 represents $S(O)_nR_a$, in one embodiment n represents 2 and $R_a$ represents $(C_1-C_6)$ alkyl, such as pentyl.

When R1 represents Y—Ar, in one embodiment, R1 represents phenyl, —O-phenyl, —O—$CH_2$-phenyl or —$CH_2$—O-phenyl each of which may be optionally substituted by one or more R4 groups (such as —$CH_2$—O-fluorophenyl).

In one embodiment, Ar represents phenyl.

In one embodiment, Y represents a bond or a linker selected from O or —O—$(C_1-C_6)$ alkylene (such as —O—$CH_2$— or —$CH_2$—O—).

When R1 represents Z-Het, in one embodiment, R1 represents benzoxazolyl, oxadiazolyl, benzofuranyl, —S-thienyl, —O-benzothiophenyl, —O-benzofuranyl, —O-pyridyl, —O—$CH_2$-pyridyl, —O—$CH_2$-thienyl, —O—$(CH_2)_2$-thienyl, —O—$(CH_2)_3$-thienyl, —O—$CH_2$-thiazolyl, —O—$CH_2$-pyrazolyl, —O—$CH_2$-furanyl, —O—$CH_2$-benzothiophenyl, or —ON=C(Me)-$CH_2$-pyrimidinyl each of which may be optionally substituted by one or more R4 groups.

When R1 represents Z-Het, in a further embodiment, R1 represents benzoxazolyl, oxadiazolyl, —O-pyridyl, —O—$CH_2$-pyridyl, —O—$CH_2$-thienyl, —O—$CH_2$-thiazolyl or —ON=C(Me)-$CH_2$-pyrimidinyl each of which may be optionally substituted by one or more R4 groups (such as methyloxadiazolyl).

When R1 represents Z-Het, in a yet further embodiment, R1 represents —O—$CH_2$-thienyl, —O—$(CH_2)_2$-thienyl or -benzofuranyl optionally substituted by an R4 group (such as methyl).

When R1 represents Z-Het, in a still yet further embodiment, R1 represents -benzofuranyl optionally substituted by an R4 group (such as methyl).

When R1 represents $—C(R_a)=N—O—R_f$, in one embodiment, $R_a$ represents $(C_1-C_6)$ alkyl (e.g. methyl) and $R_f$ represents $(C_1-C_6)$ alkyl (e.g. ethyl or propyl), halo$(C_1-C_6)$ alkyl (e.g. $—CH_2—CF_3$) or $—(C_1-C_6)$ alkyl-Ar (e.g. $—CH_2$-phenyl).

When R1 represents $—C(R_a)=N—O—R_f$, in a further embodiment, $R_a$ represents $(C_1-C_6)$ alkyl (e.g. methyl) and $R_f$ represents $(C_1-C_6)$ alkyl (e.g. propyl).

In one embodiment, Het represents benzothiophenyl, benzofuranyl, benzoxazolyl, oxadiazolyl, pyridyl, pyrazolyl, thienyl, thiazolyl, furanyl or pyrimidinyl each of which may be optionally substituted by one or more R4 groups.

In a further embodiment, Het represents benzoxazolyl, oxadiazolyl, pyridyl, thienyl, thiazolyl or pyrimidinyl each of which may be optionally substituted by one or more R4 groups.

In one embodiment, Z represents a bond or a linker selected from O, S or —O—$(C_1-C_6)$ alkylene (such as —O—$CH_2$—, —O—$(CH_2)_2$— or —O—$(CH_2)_3$—) or —ON=$CR_d$—$(C_1-C_6)$ alkylene (such as —ON=C(Me)-$CH_2$—).

In a further embodiment, Z represents a bond or a linker selected from O or —O—$(C_1-C_6)$ alkylene (such as —O—$CH_2$—) or —ON=$CR_d$—$(C_1-C_6)$ alkylene (such as —ON=C(Me)-$CH_2$—).

In one embodiment, R1 represents $OR_d$ (such as —O-pentyl) or Z-Het (such as —O—$CH_2$-thienyl). In a further embodiment, R1 represents Z-Het, such as —O—$CH_2$-thienyl.

In one embodiment, R2 represents an H or $OR_d$ group. In a further embodiment, R2 represents an H or OH group. In a yet further embodiment, R2 represents H.

In one embodiment, R4 represents halogen (such as bromine, chlorine or fluorine), $(C_1-C_6)$ alkyl (such as methyl), $(C_2-C_6)$ alkenyl or $(C_2-C_6)$ alkynyl. In a further embodiment, R4 represents halogen (such as fluorine) or $(C_1-C_6)$ alkyl (such as methyl). In a yet further embodiment, R4 represents fluorine or methyl.

In a further embodiment, R4 represents halogen (such as fluorine), $(C_1-C_6)$ alkyl (such as methyl), $(C_2-C_6)$ alkenyl or $(C_2-C_6)$ alkynyl. In a further embodiment, R4 represents halogen (such as fluorine) or ($C_1$-$C_6$) alkyl (such as methyl). In a yet further embodiment, R4 represents fluorine or methyl.

Examples of ring systems within the definition of R3 include heterocycles of formula (a)-(i):

(a)
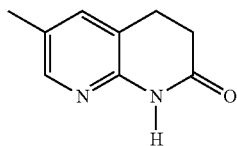

(b)
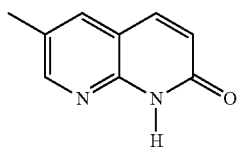

(c)
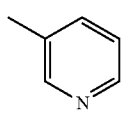

(d)
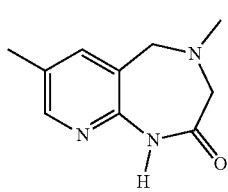

(e)
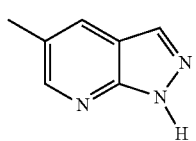

(f)
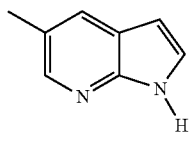

(g)
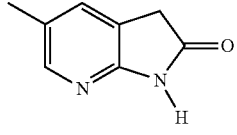

(h)
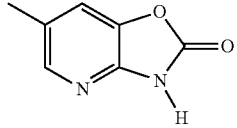

(i)
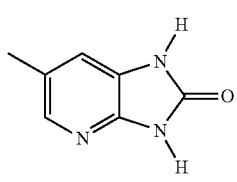

each of which may be optionally substituted, or further substituted as appropriate, by one or more R5 groups.

An example of a compound of formula (I) wherein two R5 groups together with the atom to which they are attached together form a Het group optionally substituted by one or more ($C_1$-$C_6$) alkyl groups include a spiro ring system of formula (j):

(j)
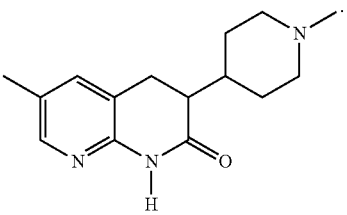

A further examples of a ring system within the definition of R3 includes the heterocycle of formula (k):

(k)
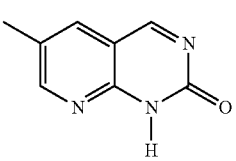

which may be optionally substituted, or further substituted as appropriate, by one or more R5 groups.

In one embodiment, R3 is a pyridyl ring or a pyridyl ring fused to a 5, 6 or 7 membered aromatic, partially aromatic or saturated heterocycle containing 1-5 heteroatoms selected from N, O and S, wherein said R3 group may be optionally substituted by one or more R5 groups.

In a further embodiment, R3 is a pyridyl ring or a pyridyl ring fused to a 5 or 6 membered aromatic, partially aromatic or saturated heterocycle containing 1-5 heteroatoms selected from N, O and S, wherein said R3 group may be optionally substituted by one or more R5 groups.

In a yet further embodiment, R3 is a pyridyl ring or a pyridyl ring fused to a 6 membered aromatic, partially aromatic or saturated heterocycle containing 1-5 heteroatoms selected from N, O and S, wherein said R3 group may be optionally substituted by one or more R5 groups.

In a still yet further embodiment, R3 is a pyridyl ring fused to a 6 membered aromatic, partially aromatic or saturated heterocycle containing 1-5 heteroatoms selected from N, O and S, wherein said R3 group may be optionally substituted by one or more R5 groups.

In one embodiment, R3 represents a heterocycle of formula (k):

(k)
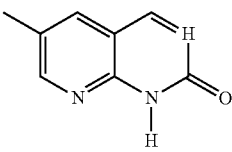

which may be optionally substituted, or further substituted as appropriate, by one or more R5 groups, such as ($C_1$-$C_6$) alkyl optionally substituted by $CO_2R_d$ (e.g. —$CH_2$—$CO_2H$), $NR_aR_b$ (e.g. —$CH_2$—$N(Me)_2$) or Het optionally substituted by one or more ($C_1$-$C_6$) alkyl groups (e.g. —$(CH_2)_2$-piperazinyl-Me).

In one embodiment, R3 represents a heterocycle of formula (a), (b), (c), (d), (f), (i), (j) or (k):

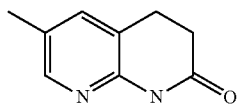
(a)

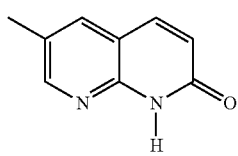
(b)

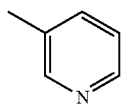
(c)

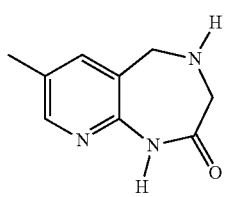
(d)

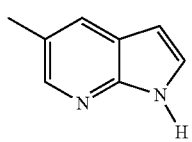
(f)

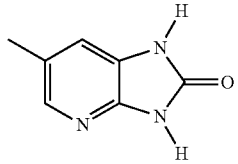
(i)

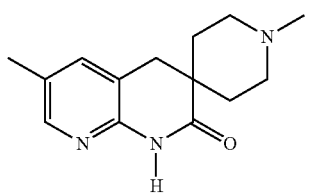
(j)

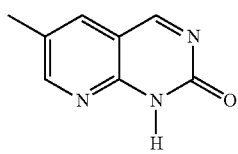
(k)

each of which may be optionally substituted, or further substituted as appropriate, by one or more R5 groups, such as $CO_2R_d$ (e.g. $CO_2Me$), $NR_aR_b$ (e.g. $NH_2$), $CONR_aR_b$ (e.g. $CONH_2$), $NR_cCOR_d$ (e.g. NHCOMe) or ($C_1$-$C_6$) alkyl optionally substituted by F, $CO_2R_d$ (e.g. —$CH_2$—$CO_2H$), $CONR_aR_b$, $OR_d$ (e.g. $CH_2OH$), $NR_aR_b$ (e.g. —$CH_2$—N(Me)$_2$), $NR_aCOR_d$ or Het optionally substituted by one or more ($C_1$-$C_6$) alkyl groups (e.g. —(CH$_2$)$_2$-piperazinyl-Me).

In a further embodiment, R3 represents a heterocycle of formula (a) or (j):

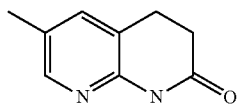
(a)

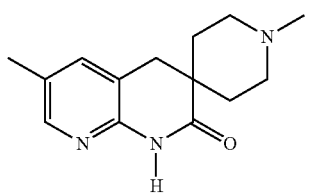
(j)

each of which may be optionally substituted, or further substituted as appropriate, by one or more R5 groups, such as $CO_2R_d$ (e.g. $CO_2Me$), $NR_aR_b$ (e.g. $NH_2$), $CONR_aR_b$ (e.g. $CONH_2$), $NR_cCOR_d$ (e.g. NHCOMe) or ($C_1$-$C_6$) alkyl optionally substituted by F, $CO_2R_d$ (e.g. —$CH_2$—$CO_2H$), $CONR_aR_b$, $OR_d$ (e.g. $CH_2OH$), $NR_aR_b$ (e.g. —$CH_2$—N(Me)$_2$), $NR_aCOR_d$ or Het optionally substituted by one or more ($C_1$-$C_6$) alkyl groups (e.g. —(CH$_2$)$_2$-piperazinyl-Me).

In a further embodiment, R3 represents a heterocycle of formula (a), (b) or (c):

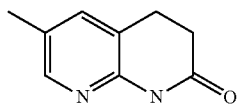
(a)

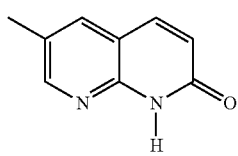
(b)

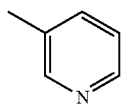
(c)

each of which may be optionally substituted, or further substituted as appropriate, by one or more R5 groups, such as $CO_2R_d$ (e.g. $CO_2Me$), $NR_aR_b$ (e.g. $NH_2$), $CONR_aR_b$ (e.g. $CONH_2$), $NR_cCOR_d$ (e.g. NHCOMe) or ($C_1$-$C_6$) alkyl optionally substituted by F, $CO_2R_d$, $CONR_aR_b$, $OR_d$ (e.g. $CH_2OH$), $NR_aR_b$ or $NR_aCOR_d$.

In a further embodiment, $R_3$ represents a heterocycle of formula (c):

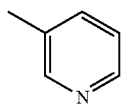
(c)

optionally substituted by one or more R5 groups, such as $NR_aR_b$ (e.g. 2-$NH_2$) or $NR_cCOR_d$ (e.g. 2-NHCOMe).

In a yet further embodiment, $R_3$ represents a heterocycle of formula (a) or (b):

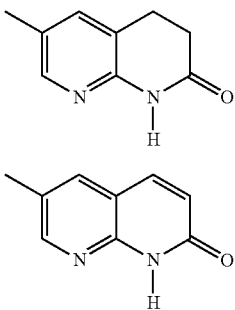

(a)

(b)

optionally further substituted by one or more R5 groups, such as $CO_2R_d$ (e.g. 3-$CO_2Me$), $CONR_aR_b$ (e.g. 3-$CONH_2$) or ($C_1$-$C_6$) alkyl optionally substituted by $OR_d$ (e.g. 3-$CH_2OH$).

In a yet further embodiment, R3 represents a heterocycle of formula (a):

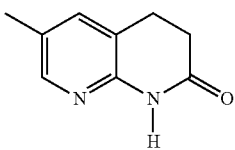

(a)

optionally further substituted by one or more R5 groups, such as $CO_2R_d$ (e.g. 3-$CO_2Me$), $CONR_aR_b$ (e.g. 3-$CONH_2$) or ($C_1$-$C_6$) alkyl optionally substituted by $OR_d$ (e.g. 3-$CH_2OH$).

In a still yet further embodiment, R3 represents a heterocycle of formula (a):

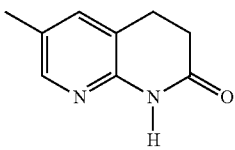

(a)

which has no further R5 substituents.

In one embodiment, n represents 1 or 2. In a further embodiment, n represents 2.

In one embodiment, $R_a$, $R_b$ and $R_c$ independently represent H, ($C_1$-$C_6$) alkyl, or an $NR_aR_b$ group may optionally form a 3- to 7-membered nitrogen containing saturated heterocycle optionally containing 1 to 3 additional heteroatoms selected from N, O or S wherein said heterocycle may be optionally substituted by one or more ($C_1$-$C_6$) alkyl groups.

In one embodiment, $R_d$ and $R_e$ independently represent H, ($C_1$-$C_6$) alkyl, ($C_2$-$C_6$) alkenyl, halo($C_1$-$C_6$) alkyl, halo($C_1$-$C_6$) alkyl-O—($C_1$-$C_6$) alkyl- or ($C_1$-$C_6$) alkyl-O—($C_1$-$C_6$) alkyl-.

In a further embodiment, $R_d$ and $R_e$ independently represent H, ($C_1$-$C_6$) alkyl, halo($C_1$-$C_6$) alkyl-O—($C_1$-$C_6$) alkyl- or ($C_1$-$C_6$) alkyl-O—($C_1$-$C_6$) alkyl-.

In one embodiment, $R_f$ represents ($C_1$-$C_6$) alkyl (e.g. ethyl or propyl), halo($C_1$-$C_6$) alkyl (e.g. —$CH_2$—$CF_3$) or —($C_1$-$C_6$) alkyl-Ar (e.g. —$CH_2$-phenyl).

In one embodiment, the compound of formula (I) is selected from:

6-[(1E)-3-Azetidin-1-yl-3-oxoprop-1-en-1-yl]-3,4-dihydro-1,8-naphthyridin-2(1H)-one (E1);

6-[(1E)-3-Oxo-3-pyrrolidin-1-ylprop-1-en-1-yl]-3,4-dihydro-1,8-naphthyridin-2(1H)-one (E2);

6-[(1E)-3-Oxo-3-piperidin-1-ylprop-1-en-1-yl]-3,4-dihydro-1,8-naphthyridin-2(1H)-one (E3);

6-{(1E)-3-[4-(2-Hydroxyethyl)piperidin-1-yl]-3-oxoprop-1-en-1-yl}-3,4-dihydro-1,8-naphthyridin-2(1H)-one (E4);

6-[(1E)-3-{[4-(4-Fluorophenoxy)methyl]piperidin-1-yl}-3-oxoprop-1-en-1-yl]-3,4-dihydro-1,8-naphthyridin-2(1H)-one (E5);

6-[(1E)-3-Oxo-3-(3-phenoxyazetidin-1-yl)prop-1-en-1-yl]-3,4-dihydro-1,8-naphthyridin-2(1H)-one (E6);

6-[(1E)-3-Oxo-3-(2-phenylpyrrolidin-1-yl)prop-1-en-1-yl]-3,4-dihydro-1,8-naphthyridin-2(1H)-one (E7);

6-[(1E)-3-Oxo-3-(4-propylpiperidin-1-yl)prop-1-en-1-yl]-3,4-dihydro-1,8-naphthyridin-2(1H)-one (E8);

6-[(1E)-3-{[3-(4-Fluorophenoxy)methyl]piperidin-1-yl}-3-oxoprop-1-en-1-yl]-3,4-dihydro-1,8-naphthyridin-2(1H)-one (E9);

6-[(1E)-3-Oxo-3-(3-phenoxypyrrolidin-1-yl)prop-1-en-1-yl]-3,4-dihydro-1,8-naphthyridin-2(1H)-one (E10);

6-{(1E)-3-[3-(5-Methyl-1,2,4-oxadiazol-3-yl)azetidin-1-yl]-3-oxoprop-1-en-1-yl}-3,4-dihydro-1,8-naphthyridin-2(1H)-one (E11);

6-{(1E)-3-Oxo-3-[3-(2-thienylmethoxy)azetidin-1-yl]prop-1-en-1-yl}-3,4-dihydro-1,8-naphthyridin-2(1H)-one (E12);

6-{(1E)-3-[2-(5-Methyl-1,2,4-oxadiazol-3-yl)piperidin-1-yl]-3-oxoprop-1-en-1-yl}-3,4-dihydro-1,8-naphthyridin-2(1H)-one (E13);

6-{(1E)-3-[4-Hydroxy-4-phenylpiperidin-1-yl]-3-oxoprop-1-en-1-yl}-3,4-dihydro-1,8-naphthyridin-2(1H)-one (E14);

6-{(1E)-3-Oxo-3-[3-(pentyloxy)azetidin-1-yl]prop-1-en-1-yl}-3,4-dihydro-1,8-naphthyridin-2(1H)-one (E15);

6-{(1E)-3-Oxo-3-[3-(pyridin-3-yloxy)pyrrolidin-1-yl]prop-1-en-1-yl}-3,4-dihydro-1,8-naphthyridin-2(1H)-one (E16);

6-{(1E)-3-[3-(Benzyloxy)azetidin-1-yl]-3-oxoprop-1-en-1-yl}-3,4-dihydro-1,8-naphthyridin-2(1H)-one (E17);

6-{(1E)-3-[2-(1,3-Benzoxazol-2-yl)piperidin-1-yl]-3-oxoprop-1-en-1-yl}-3,4-dihydro-1,8-naphthyridin-2(1H)-one (E18);

6-[(1E)-3-{3-[(2-Methylprop-2-en-1-yl)oxy]azetidin-1-yl}-3-oxoprop-1-en-1-yl]-3,4-dihydro-1,8-naphthyridin-2(1H)-one (E19);

6-{(1E)-3-Oxo-3-[3-(1,3-thiazol-2-ylmethoxy)azetidin-1-yl]prop-1-en-1-yl}-3,4-dihydro-1,8-naphthyridin-2(1H)-one (E20);

6-{(1E)-3-[3-({[(1E)-1-Methyl-2-pyrimidin-2-ylethylidene]amino}oxy)azetidin-1-yl]-3-oxoprop-1-en-1-yl}-3,4-dihydro-1,8-naphthyridin-2(1H)-one (E21);

6-{(1E)-3-[3-(Pentylsulfonyl)azetidin-1-yl]-3-oxoprop-1-en-1-yl}-3,4-dihydro-1,8-naphthyridin-2(1H)-one (E22);

5-{(1E)-3-Oxo-3-[3-(pyridin-4-ylmethoxy)azetidin-1-yl]prop-1-en-1-yl}pyridin-2-amine (E23);

N-(5-{(1E)-3-Oxo-3-[3-(pyridin-4-ylmethoxy)azetidin-1-yl]prop-1-en-1-yl}pyridin-2-yl)acetamide (E24);

Methyl 6-[(1E)-3-{4-[(4-fluorophenoxy)methyl]piperidin-1-yl}-3-oxoprop-1-en-1-yl]-2-oxo-1,2,3,4-tetrahydro-1,8-naphthyridine-3-carboxylate (E25);

6-[(1E)-3-{4-[(4-Fluorophenoxy)methyl]piperidin-1-yl}-3-oxoprop-1-en-1-yl]-2-oxo-1,2,3,4-tetrahydro-1,8-naphthyridine-3-carboxamide (E26);

6-[(1E)-3-{4-[(4-Fluorophenoxy)methyl]piperidin-1-yl}-3-oxoprop-1-en-1-yl]-2-oxo-1,2-dihydro-1,8-naphthyridine-3-carboxamide (E27); and 3-(Hydroxymethyl)-6-[(1E)-3-{4-[(4-fluorophenoxy)methyl]piperidin-1-yl}-3-oxoprop-1-en-1-yl]-3,4-dihydro-1,8-naphthyridin-2(1H)-one (E28);

or a pharmaceutically acceptable salt or solvate thereof.

In an alternative embodiment, the compound of formula (I) is selected from:

(E)-6-(3-Oxo-3-(3-(2-(thiophen-2-yl)ethoxy)azetidin-1-yl)prop-1-enyl)-3,4-dihydro-1,8-naphthyridin-2(1H)-one (E29);

(E)-6-(3-Oxo-3-(3-(3-(thiophen-2-yl)propoxy)azetidin-1-yl)prop-1-enyl)-3,4-dihydro-1,8-naphthyridin-2(1H)-one (E30);

(E)-6-(3-(3-((3-Methylthiophen-2-yl)methoxy)azetidin-1-yl)-3-oxoprop-1-enyl)-3,4-dihydro-1,8-naphthyridin-2(1H)-one (E31);

6-[3-(3-(4-Methyl-thiophen-2-ylmethoxy)-azetidin-1-yl)-3-oxo-propenyl]-3,4-dihydro-1H-[1,8]naphthyridin-2-one (E32);

(E)-6-(3-(3-((5-Methylthiophen-2-yl)methoxy)azetidin-1-yl)-3-oxoprop-1-enyl)-3,4-dihydro-1,8-naphthyridin-2(1H)-one (E33);

(E)-6-[3-(2-Methoxyethoxy)azetidin-1-yl)-3-oxoprop-1-enyl]-3,4-dihydro-1,8-naphthyridin-2(1H)-one (E34);

(E)-6-[3-(3-Methoxypropoxy)azetidin-1-yl)-3-oxoprop-1-enyl]-3,4-dihydro-1,8-naphthyridin-2(1H)-one (E35);

(E)-6-[3-(3-Butoxyazetidin-1-yl)-3-oxoprop-1-enyl]-3,4-dihydro-1,8-naphthyridin-2(1H)-one (E36);

(E)-6-[3-(3-Isobutoxyazetidin-1-yl)-3-oxoprop-1-enyl]-3,4-dihydro-1,8-naphthyridin-2(1H)-one (E37);

(E)-6-(3-(3-((1-Methyl-1H-pyrazol-3-yl)methoxy)azetidin-1-yl)-3-oxoprop-1-enyl)-3,4-dihydro-1,8-naphthyridin-2(1H)-one (E38);

(E)-6-(3-Oxo-3-(3-(thiazol-5-ylmethoxy)azetidin-1-yl)prop-1-enyl)-3,4-dihydro-1,8-naphthyridin-2(1H)-one (E39);

(E)-6-(3-(3-(Furan-2-ylmethoxy)azetidin-1-yl)-3-oxoprop-1-enyl)-3,4-dihydro-1,8-naphthyridin-2(1H)-one (E40);

(E)-1'-Methyl-6-(3-oxo-3-(3-(thiophen-2-ylmethoxy)azetidin-1-yl)prop-1-enyl)-1H-spiro[[1,8]naphthyridine-3,4'-piperidin]-2(4H)-one (E41);

(E)-7-(3-Oxo-3-(3-(thiophen-2-ylmethoxy)azetidin-1-yl)prop-1-enyl)-4,5-dihydro-1H-pyrido[2,3-e][1,4]diazepin-2(3H)-one (E42);

(E)-Ethyl 2-(2-oxo-6-(3-oxo-3-(3-(thiophen-2-ylmethoxy)azetidin-1-yl)prop-1-enyl)-1,2-dihydropyrido[2,3-d]pyrimidin-3(4H)-yl)acetate (E43);

(E)-3-(2-(4-Methylpiperazin-1-yl)ethyl)-6-(3-oxo-3-(3-(thiophen-2-ylmethoxy)azetidin-1-yl)prop-1-enyl)-3,4-dihydropyrido[2,3-d]pyrimidin-2(1H)-one (E44);

(E)-3-(3-((Dimethylamino)methyl)-1H-pyrrolo[2,3-b]pyridin-5-yl)-1-(3-(thiophen-2-ylmethoxy)azetidin-1-yl)prop-2-en-1-one (E45);

(E)-6-(3-Oxo-3-(3-(thiophen-2-ylmethoxy)azetidin-1-yl)prop-1-enyl)-1H-imidazo[4,5-b]pyridin-2(3H)-one (E46);

(E)-6-(3-Oxo-3-(3-(3,3,3-trifluoropropoxy)azetidin-1-yl)prop-1-enyl)-3,4-dihydro-1,8-naphthyridin-2(1H)-one (E47);

(E)-6-(3-Oxo-3-(3-(4,4,4-trifluorobutoxy)azetidin-1-yl)prop-1-enyl)-3,4-dihydro-1,8-naphthyridin-2(1H)-one (E48);

6-((E)-3-(3-((E)-But-2-enyloxy)azetidin-1-yl)-3-oxoprop-1-enyl)-3,4-dihydro-1,8-naphthyridin-2(1H)-one (E49);

6-((E)-3-(3-((Z)-But-2-enyloxy)azetidin-1-yl)-3-oxoprop-1-enyl)-3,4-dihydro-1,8-naphthyridin-2(1H)-one (E50);

6-((E)-3-(3-((E)-2-Methylbut-2-enyloxy)azetidin-1-yl)-3-oxoprop-1-enyl)-3,4-dihydro-1,8-naphthyridin-2(1H)-one (E51);

(E)-6-(3-(3-(Benzo[b]thiophen-2-ylmethoxy)azetidin-1-yl)-3-oxoprop-1-enyl)-3,4-dihydro-1,8-naphthyridin-2(1H)-one (E52);

(E)-6-(3-(3-((4-Bromothiophen-2-yl)methoxy)azetidin-1-yl)-3-oxoprop-1-enyl)-3,4-dihydro-1,8-naphthyridin-2(1H)-one (E53);

(E)-6-(3-(3-((4-Chlorothiophen-2-yl)methoxy)azetidin-1-yl)-3-oxoprop-1-enyl)-3,4-dihydro-1,8-naphthyridin-2(1H)-one (E54);

6-((E)-3-Oxo-3-(3-((Z)-1-(propoxyimino)ethyl)azetidin-1-yl)prop-1-enyl)-3,4-dihydro-1,8-naphthyridin-2(1H)-one (E55);

6-((E)-3-Oxo-3-(3-((Z)-1-(2,2,2-trifluoroethoxyimino)ethyl)azetidin-1-yl)prop-1-enyl)-3,4-dihydro-1,8-naphthyridin-2(1H)-one (E56);

6-((E)-3-(3-((Z)-1-(Ethoxyimino)ethyl)azetidin-1-yl)-3-oxoprop-1-enyl)-3,4-dihydro-1,8-naphthyridin-2(1H)-one (E57);

(E)-6-(3-(3-(Benzofuran-3-yl)azetidin-1-yl)-3-oxoprop-1-enyl)-3,4-dihydro-1,8-naphthyridin-2(1H)-one (E58);

(E)-6-(3-(3-(Benzofuran-2-yl)azetidin-1-yl)-3-oxoprop-1-enyl)-3,4-dihydro-1,8-naphthyridin-2(1H)-one (E59);

(E)-6-(3-(3-(Benzofuran-7-yloxy)azetidin-1-yl)-3-oxoprop-1-enyl)-3,4-dihydro-1,8-naphthyridin-2(1H)-one (E60);

(E)-6-(3-(3-(Benzo[b]thiophen-3-yloxy)azetidin-1-yl)-3-oxoprop-1-enyl)-3,4-dihydro-1,8-naphthyridin-2(1H)-one (E61);

(E)-6-(3-Oxo-3-(3-(thiophen-2-ylthio)azetidin-1-yl)prop-1-enyl)-3,4-dihydro-1,8-naphthyridin-2(1H)-one (E62);

(E)-6-(3-(3-Butoxyazetidin-1-yl)-3-oxoprop-1-enyl)-1'-methyl-1H-spiro[[1,8]naphthyridine-3,4'-piperidin]-2(4H)-one (E63);

1'-Methyl-6-((E)-3-oxo-3-(3-((E)-1-(benzyloxyimino)ethyl)azetidin-1-yl)prop-1-enyl)-1H-spiro[[1,8]naphthyridine-3,4'-piperidin]-2(4H)-one (E64);

1'-Methyl-6-((E)-3-oxo-3-(3-((E)-1-(propoxyimino)ethyl)azetidin-1-yl)prop-1-enyl)-1H-spiro[[1,8]naphthyridine-3,4'-piperidin]-2(4H)-one (E65);

(E)-1'-Methyl-6-(3-oxo-3-(3-(2-(thiophen-2-yl)ethoxy)azetidin-1-yl)prop-1-en-1-yl)-1H-spiro[[1,8]naphthyridine-3,4'-piperidin]-2(4H)-one (E66);

(E)-6-(3-(3-(3-Methylbenzofuran-2-yl)azetidin-1-yl)-3-oxoprop-1-enyl)-3,4-dihydro-1,8-naphthyridin-2(1H)-one (E67);

(E)-1'-Methyl-6-(3-(3-(3-methylbenzofuran-2-yl)azetidin-1-yl)-3-oxoprop-1-enyl)-1H-spiro[[1,8]naphthyridine-3,4'-piperidin]-2(4H)-one (E68);

(E)-6-(3-(3-(Benzofuran-2-yl)azetidin-1-yl)-3-oxoprop-1-en-1-yl)-1'-methyl-1H-spiro[[1,8]naphthyridine-3,4'-piperidin]-2(4H)-one (E69);

6-((E)-3-Oxo-3-(3-((E)-1-(propoxyimino)ethyl)azetidin-1-yl)prop-1-enyl)-3,4-dihydro-1,8-naphthyridin-2(1H)-one (E70); and 6-((E)-3-Oxo-3-(3-((Z)-1-(propoxyimino)ethyl)azetidin-1-yl)prop-1-enyl)-3,4-dihydro-1,8-naphthyridin-2(1H)-one (E71);

or a pharmaceutically acceptable salt or solvate thereof.

In a further embodiment, the compound of formula (I) is selected from 6-{(1E)-3-Oxo-3-[3-(2-thienylmethoxy)azetidin-1-yl]prop-1-en-1-yl}-3,4-dihydro-1,8-naphthyridin-2(1H)-one (E12) or 6-{(1E)-3-Oxo-3-[3-(pentyloxy)azetidin-1-yl]prop-1-en-1-yl}-3,4-dihydro-1,8-naphthyridin-2(1H)-one (E15) or a pharmaceutically acceptable salt or solvate thereof.

In a further embodiment, the compound of formula (I) is selected from
- 6-{(1E)-3-Oxo-3-[3-(2-thienylmethoxy)azetidin-1-yl]prop-1-en-1-yl}-3,4-dihydro-1,8-naphthyridin-2(1H)-one (E12);
- (E)-6-(3-Oxo-3-(3-(2-(thiophen-2-yl)ethoxy)azetidin-1-yl)prop-1-enyl)-3,4-dihydro-1,8-naphthyridin-2(1H)-one (E29);
- (E)-6-(3-(3-(Benzofuran-2-yl)azetidin-1-yl)-3-oxoprop-1-enyl)-3,4-dihydro-1,8-naphthyridin-2(1H)-one (E59);
- (E)-6-(3-(3-Butoxyazetidin-1-yl)-3-oxoprop-1-enyl)-1'-methyl-1H-spiro[[1,8]naphthyridine-3,4'-piperidin]-2(4H)-one (E63);
- (E)-1'-Methyl-6-(3-oxo-3-(3-(2-(thiophen-2-yl)ethoxy)azetidin-1-yl)prop-1-en-1-yl)-1H-spiro[[1,8]naphthyridine-3,4'-piperidin]-2(4H)-one (E66);
- (E)-6-(3-(3-(3-Methylbenzofuran-2-yl)azetidin-1-yl)-3-oxoprop-1-enyl)-3,4-dihydro-1,8-naphthyridin-2(1H)-one (E67);
- (E)-1'-Methyl-6-(3-(3-(3-methylbenzofuran-2-yl)azetidin-1-yl)-3-oxoprop-1-enyl)-1H-spiro[[1,8]naphthyridine-3,4'-piperidin]-2(4H)-one (E68);
- (E)-6-(3-(3-(Benzofuran-2-yl)azetidin-1-yl)-3-oxoprop-1-en-1-yl)-1'-methyl-1H-spiro[[1,8]naphthyridine-3,4'-piperidin]-2(4H)-one (E69);
- 6-((E)-3-Oxo-3-(3-((E)-1-(propoxyimino)ethyl)azetidin-1-yl)prop-1-enyl)-3,4-dihydro-1,8-naphthyridin-2(1H)-one (E70); and
- 6-((E)-3-Oxo-3-(3-((Z)-1-(propoxyimino)ethyl)azetidin-1-yl)prop-1-enyl)-3,4-dihydro-1,8-naphthyridin-2(1H)-one (E71);

or a pharmaceutically acceptable salt or solvate thereof.

In a further embodiment, the compound of formula (I) is selected from 6-{(1E)-3-Oxo-3-[3-(2-thienylmethoxy)azetidin-1-yl]prop-1-en-1-yl}-3,4-dihydro-1,8-naphthyridin-2(1H)-one (E12) or a pharmaceutically acceptable salt or solvate thereof.

In a yet further embodiment, the compound of formula (I) is selected from
- (E)-6-(3-(3-(Benzofuran-2-yl)azetidin-1-yl)-3-oxoprop-1-enyl)-3,4-dihydro-1,8-naphthyridin-2(1H)-one (E59); and
- (E)-6-(3-(3-(3-Methylbenzofuran-2-yl)azetidin-1-yl)-3-oxoprop-1-enyl)-3,4-dihydro-1,8-naphthyridin-2(1H)-one (E67);

or a pharmaceutically acceptable salt or solvate thereof.

The compounds of formula (I) and their salts may be prepared by processes known to the skilled chemist to be applicable for preparing chemically related compounds. Such processes use known starting materials or intermediates which may be obtained by standard procedures of organic chemistry. The following processes provide a variety of non-limiting routes for the production of the compounds of formula (I) and their intermediates used therein. These processes constitute further aspects of the invention.

According to a further aspect of the invention, there is provided a process for preparing a compound of formula (I) as defined above which comprises:
(a) reacting a compound of formula (II):

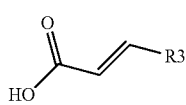

(II)

wherein R3 is as defined above for compounds of formula (I), with a compound of formula (III):

(III)

wherein W, X, R1 and R2 are as defined above for compounds of formula (I); or
(b) reacting a compound of formula (IV):

(IV)

wherein R3 is as defined above for compounds of formula (I) and $L^1$ represents a suitable leaving group, such as a halogen atom, e.g. fluorine, chlorine, bromine or an alkoxy group, with a compound of formula (III):

(III)

wherein W, X, R1 and R2 are as defined above for compounds of formula (I); or
(c) reacting a compound of formula (V):

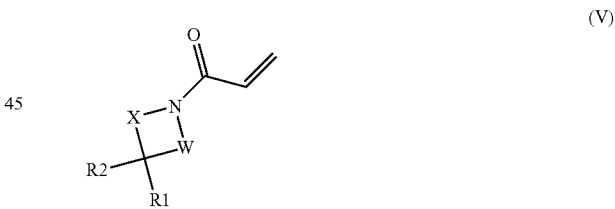

(V)

wherein W, X, R1 and R2 are as defined above for compounds of formula (I), with a compound of formula $L^2$-R3, wherein $L^2$ represents a suitable leaving group, such as a halogen atom, e.g. fluorine, chlorine, bromine or an alkoxy group; optionally thereafter followed by:
(d) deprotecting a protected derivative of compound (I); and optionally thereafter followed by:
(e) interconversion of a compound of formula (I) to a further compound of formula (I).

Process (a) typically comprises the use of EDC, a base such as TEA or DIPEA or DMAP, the optional use of HOBT, and a solvent such as DMF.

Process (b) typically comprises the use of a base such as TEA or DIPEA or DMAP, and a solvent such as DCM, THF, ACN or DMF.

Process (c) typically comprises the use of suitable coupling conditions known to the one skilled in the art such as the Heck coupling (*Chem. Rev.* 2000, 100, 3009), a non-limiting example comprises the use of a palladium catalyst, a phosphine ligand, a suitable base and solvent.

Process (d) typically comprises any suitable deprotection reaction, the conditions of which will depend upon the nature of the protecting group. In most instances such a deprotection reaction will typically comprise the use of a suitable acid.

Process (e) typically comprises interconversion procedures known by one skilled in the art. For example, compounds of formula (I) in which R1 or R2 represents hydrogen may be converted by methods known by one skilled in the art into compounds of formula (I) in which R1 or R2 represents $CO_2R_a$, $COR_a$, $CONR_aR_b$, $CH_2OR_c$, $CH_2NR_aR_b$, $SO_2NR_aR_b$, wherein $R_a$, $R_b$ and $R_c$ are as defined above for compounds of formula (I).

If appropriate, the reactions previously described in processes (a), (b), (c), (d) or (e) are followed or preceded by one or more reactions known to the skilled of the art and are performed in an appropriate order to achieve the requisite substitutions on W, X, R1, R2 and R3 defined above to afford other compounds of formula (I). Non-limiting examples of such reactions whose conditions can be found in the literature include:

protection of reactive functions,
deprotection of reactive functions,
halogenation,
dehalogenation,
dealkylation,
alkylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of esters groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

The compounds of formula (II), (III), (IV), (V) and $L^2$-R3 are either known or may be prepared in accordance with known procedures such as those described herein.

As illustrated by the examples given below, the hereinbefore disclosed compounds of formula (I) have valuable biological properties. They are particularly useful as antibacterial agents having a selective spectrum of activity in vitro and in vivo against bacterial strains relying on FabI and related targets. Such strains encompass *Staphylococcus aureus* including multiresistant strains (such as methicillin-susceptible *Staphylococcus aureus* (MSSA), methicillin-resistant *Staphylococcus aureus* (MRSA), vancomycin-intermediate *Staphylococcus aureus* (VISA) and vancomycin-resistant *Staphylococcus aureus* (VRSA) strains), *Acinetobacter baumannii, Bacillus anthracis, Chlamydophila pneumoniae, Escherichia coli, Haemophilus influenzae, Helicobacter pylori, Klebsiella pneumoniae, Neisseria meningitidis* and also bacteria such as *Mycobacterium tuberculosis* carrying homologous FabI enzymes such as InhA or other organisms such as *Plasmodium falciparum*. In one embodiment, the compound of the invention is used in the treatment of *Staphylococcus aureus* microbial infections including multiresistant strains such as methicillin-susceptible *Staphylococcus aureus* (MSSA), methicillin-resistant *Staphylococcus aureus* (MRSA), vancomycin-intermediate *Staphylococcus aureus* (VISA) and vancomycin-resistant *Staphylococcus aureus* (VRSA) strains.

The compounds of formula (I) are therefore particularly suitable as active principles of a medicament.

According to a further aspect of the invention, there is provided a compound of formula (I) as hereinbefore defined for use in therapy.

According to a further aspect of the invention, there is provided a pharmaceutical composition comprising a compound of formula (I) as hereinbefore defined, in association with a pharmaceutically acceptable excipient or carrier.

Said pharmaceutical compositions are advantageously formulated to be administered under oral, topical, parental including injectable routes, such as intravenous administration, with individual doses appropriate for the patient to be treated.

The compositions according to the invention can be solid, liquid or in the form of a gel/cream and be present in the pharmaceutical forms commonly used in human medicine, such as for example, plain or sugar-coated tablets, gelatin capsules, granules, suppositories, injectable preparations, ointments, creams, gels; they are prepared according to the customary methods. The active ingredient/s can be incorporated using excipients which are customarily used in these pharmaceutical compositions, such as talc, gum arabic, lactose, starch, magnesium stearate, aqueous or non-aqueous vehicles, fatty substances of animal or vegetable origin, paraffin derivatives, glycols, various wetting agents, dispersants or emulsifiers, preservatives. These compositions can also be present in the form of a powder intended to be dissolved extemporaneously in an appropriate vehicle, for example, non-pyrogenic sterile water.

The dose administered varies according to the condition treated, the patient in question, the administration route and the product envisaged. It can, for example, be comprised between 0.01 g and 10 g per day, by oral route or by intramuscular or intravenous route in humans.

Said compositions are particularly useful to treat human or animal infections by microbial pathogens such as *Staphylococcus aureus* including multiresistant strains, *Acinetobacter baumannii, Bacillus anthracis, Chlamydophila pneumoniae, Escherichia coli, Haemophilus influenzae, Helicobacter pylori, Klebsiella pneumoniae, Neisseria meningitidis, S. intermedius, P. multocida, B. bronchiseptica, M. haemolytica* and *A. pleuropneumoniae*. and also bacteria such as *Mycobacterium tuberculosis* or other organisms such as *Plasmodium falciparum*.

Said compositions can also be useful in multitherapy, in combination with other medicaments, for example with antibiotics. It will be appreciated that such multitherapy may typically comprise either a composition comprising the compound of formula (I) additionally comprising one or more other medicaments, such as antibiotics or co-administration (i.e. sequential or simultaneous administration).

The invention therefore also relates to a method of treatment of microbial infections which comprises administering to a patient in need thereof an efficient amount of a compound of formula (I) as hereinbefore defined.

The invention also relates to a compound of formula (I) as hereinbefore defined for use in the treatment of microbial infections.

The invention also relates to the use of a compound of formula (I) as hereinbefore defined in the manufacture of a medicament for the treatment of microbial infections.

The invention also relates to a pharmaceutical composition comprising a compound of formula (I) as hereinbefore defined for use in the treatment of microbial infections.

EXAMPLES

Proton nuclear magnetic resonance ($^1$H NMR) spectra were recorded on a 400 MHz Brüker instrument, and chemical shifts are reported in parts per million downfield from the internal standard tetramethylsilane (TMS). Abbreviations for NMR data are as follows: s=singlet, d=doublet, t=triplet, q=quadruplet, m=multiplet, dd=doublet of doublets, dt=doublet of triplets, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray ionization (ESI) techniques on an Agilent 1100 Series LCMS. Analtech Silica Gel GF and E. Merck Silica Gel 60 F-254 thin layer plates were used for thin layer chromatography. Flash chromatography was carried out on Flashsmart Pack cartridge irregular silica 40-60 μm or spherical silica 20-40 μm. Preparative thin layer chromatography was carried out on Analtech Silica Gel GF 1000 μm 20×20 cm.

The meaning of certain abbreviations is given herein. ESI refers to electrospray ionization, HPLC refers to high pressure liquid chromatography, LCMS refers to liquid chromatography coupled with a mass spectrometer, M in the context of mass spectrometry refers to the molecular peak, MS refers to mass spectrometer, NMR refers to nuclear magnetic resonance, pH refers to potential of hydrogen, TEA refers to triethylamine, DIPEA refers to N,N-diisopropylethylamine, HOBt refers to 1-hydroxybenzotriazole, DCM refers to dichloromethane, EtOAc refers to ethyl acetate, DMF refers to N,N-dimethylformamide, EDAC refers N-(3-dimethylaminopropyl)-N'-ethylcarbodiimide hydrochloride, DMAP or 4-DMAP refers to 4-(dimethylamino)pyridine, TLC refers to thin layer chromatography.

The starting materials are commercially available unless indicated otherwise.

Intermediate 1

(E)-3-(7-Oxo-5,6,7,8-tetrahydro-1,8-naphthyridin-3-yl)-acrylic acid hydrochloride (D1)

Step 1: 2-Amino-3-(hydroxymethyl)pyridine

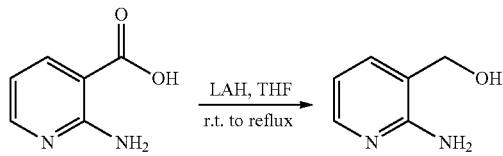 [SMILES: Nc1ncccc1C(=O)O ; Nc1ncccc1CO]

Lithium aluminum hydride (12.4 g, 326.7 mmol) was portionwisely added to a suspension of 2-amino-3-carboxypyridine (30.0 g, 217.2 mmol) in THF (350 mL) at 0° C. Once the addition was completed, the reaction mixture was stirred at room temperature for 15 minutes and then at reflux overnight. The mixture was then cooled to 0° C. and hydrolyzed by the successive addition of water (18 mL), a solution of sodium hydroxyde (18 mL) and water (30 mL) again. The resulting white suspension was filtered on Clarcel® and the cake was washed with THF (200 mL) and a mixture of CHCl$_3$/MeOH (250 mL, 9:1). After concentration to dryness of the filtrate, the title product was obtained as a yellow solid (24.2 g, 90%).

$^1$H NMR (DMSO-d$_6$, 400 MHz): δ (ppm): 7.84 (d, J=4 Hz, 1H), 7.37 (d, J=7.2 Hz, 1H), 6.55-6.52 (m, 1H), 5.64 (br s, NH$_2$), 4.34 (s, 2H).

Step 2: 2-Amino-5-bromo-3-(hydroxymethyl)pyridine

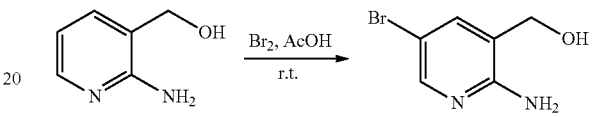

Bromine (8.4 mL, 189.4 mmol) was added dropwise over 1 hour to a solution of 2-amino-3-(hydroxymethyl)pyridine (19.6 g, 157.8 mmol; which may be prepared as described in D1, Step 1) in acetic acid (350 mL) at room temperature. The reaction mixture was then stirred overnight. After concentration to dryness, the residue was partitioned between a saturated solution of potassium carbonate (300 mL) and ethyl acetate (200 mL). The aqueous layer was separated and extracted with ethyl acetate (2×200 mL). The combined organic phases were washed with a saturated solution of sodium chloride (200 mL), dried over sodium sulfate, filtered and concentrated to dryness. After trituration of the residue in pentane, the title product was obtained as a yellow solid (27.0 g, 84%).

$^1$H NMR (DMSO-d$_6$, 400 MHz): δ (ppm): 7.90 (d, J=2.8 Hz, 1H), 7.53 (d, J=2 Hz, 1H), 5.93 (br s, NH$_2$), 5.29 (br s, OH), 4.31 (s, 2H).

Step 3: 2-Amino-5-bromo-3-(bromomethyl)pyridine hydrobromide

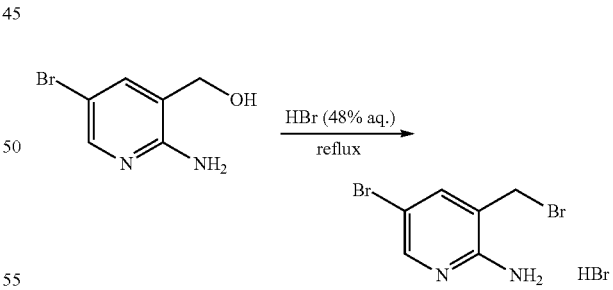

A solution of 2-amino-5-bromo-3-(hydroxymethyl)pyridine (27.0 g, 133.0 mmol; which may be prepared as described in D1, Step 2) in hydrobromic acid (48% in H$_2$O, 72 mL) was stirred at reflux overnight. The reaction mixture was then concentrated to dryness (toluene was used to azeotrope the residual H$_2$O). The title product was obtained as pale brown solid (47.0 g, 100%) which was used in the next step without further purification.

$^1$H NMR (DMSO-d$_6$, 400 MHz): δ (ppm): 8.1 (d, J=2 Hz, 1H), 7.97 (d, J=2 Hz, 1H), 4.41 (s, 2H).

Step 4: 6-Bromo-2-oxo-1,2,3,4-tetrahydro-1H-1,8-naphthyridine-3-methylcarboxylate

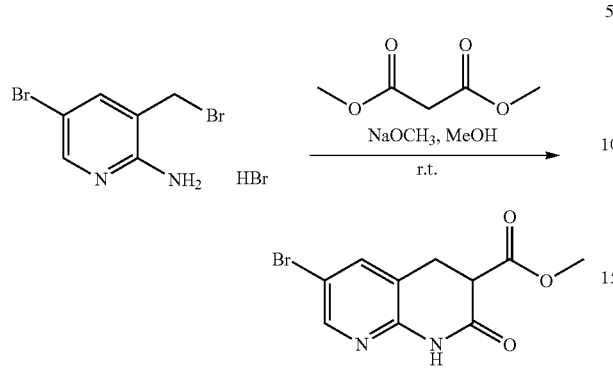

Dimethylmalonate (32 mL, 276.7 mmol) was added to a solution of sodium methoxide (25% in methanol, 63 mL, 76.1 mmol) in methanol (150 mL) at room temperature. After 45 minutes stirring, 2-amino-5-bromo-3-(bromomethyl)pyridine hydrobromide (24 g, 69.2 mmol; which may be prepared as described in D1, Step 3) was added to the mixture which was stirred at room temperature overnight. A large quantity of water was finally added to the mixture. The formed precipitate was filtered, washed with petroleum ether and dried under high vacuum to afford the title product as a brown solid (16.6 g, 84%).

LCMS (ESI-APCI) m/z 285.0-287.0 (M+H)$^+$

Step 5: 6-Bromo-3,4-dihydro-1H-1,8-naphthyridin-2-one

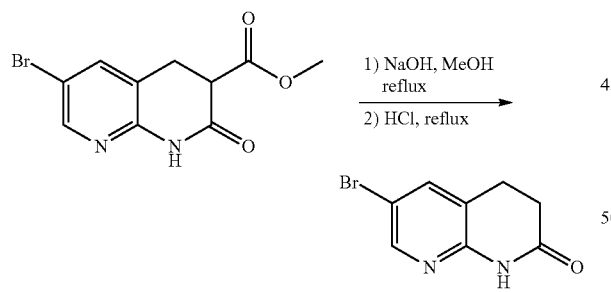

A solution of sodium hydroxide (1N, 248 mL) was added to a suspension of 6-bromo-2-oxo-1,2,3,4-tetrahydro-1H-1,8-naphthyridine-3-methylcarboxylate (16.6 g, 58.24 mmol; which may be prepared as described in D1, Step 4) in methanol (620 mL) at room temperature. The reaction mixture was then refluxed for 4 hours and cooled down to room temperature. A solution of hydrochloric acid (1N, 248 mL) was then added and the mixture was refluxed overnight. The methanol was removed and the residue filtered. The resulting precipitate was washed with water and dried under high vacuum to afford the title product as a white solid (7.7 g, 58%).

LCMS (ESI-APCI) m/z 227.0-229.0 (M+H)$^+$

Step 6: tert-Butyl (E)-3-(7-Oxo-5,6,7,8-tetrahydro-1,8-naphthyridin-3-yl)-acrylate t-butyl acrylate

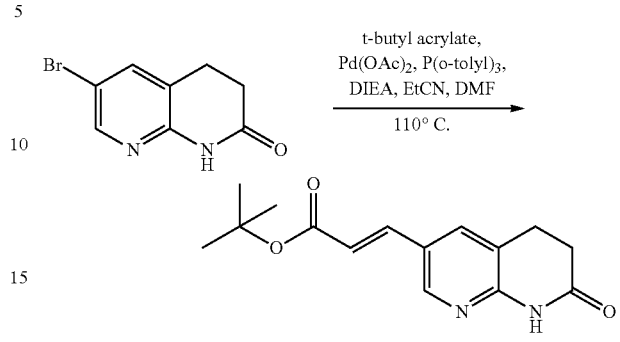

tert-Butyl acrylate (31.2 mL, 210 mmol), diisopropylethylamine (19.4 mL, 110 mmol) and P(o-tolyl)$_3$ (3.2 g, 10.5 mmol) were successively added to a suspension of 6-bromo-3,4-dihydro-1H-1,8-naphthyridin-2-one (11.9 g, 52.5 mmol; which may be prepared as described in D1, Step 5) in propionitrile (83 mL) and dimethylformamide (46 mL). The resulting mixture was then purged with argon prior to the addition of palladium acetate (1.2 g, 5.2 mmol). The mixture was purged with argon again and refluxed overnight. The reaction mixture was then filtered on Celite®. The filtrate was concentrated to dryness and the residue was solubilized in ethyl acetate (200 mL). The resulting solution was washed with a saturated solution of sodium chloride (3×100 mL), dried over sodium sulfate, filtered and concentrated to dryness. The residue was purified by chromatography on silica gel, using dichloromethane/methanol (98:2) as eluent. After trituration with Et$_2$O/petroleum ether (1/1), the title product was obtained as a yellow solid (4.35 g, 40%).

LCMS (ESI-APCI) m/z 275.0 (M+H)$^+$

Step 7: (E)-3-(7-Oxo-5,6,7,8-tetrahydro-1,8-naphthyridin-3-yl)-acrylic acid hydrochloride

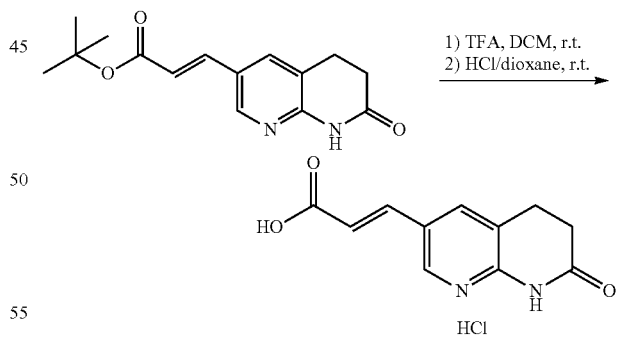

Trifluoroacetic acid (31 mL) was added to a suspension of tert-butyl (E)-3-(7-Oxo-5,6,7,8-tetrahydro-1,8-naphthyridin-3-yl)-acrylate (1.1 g, 3.76 mmol; which may be prepared as described in D1, Step 6) in dichloromethane (31 mL). The reaction mixture was stirred at room temperature for 1 hour and concentrated to dryness. The resulting residue was solubilized in a solution of hydrochloric acid in dioxane (4N, 60 mL). After 10 minutes stirring at room temperature, the precipitate was filtered and washed with diethyl ether to afford the title product as a pale yellow solid (4.5 g, quantitative).

LCMS (ESI-APCI) m/z 219 (M+H)+

¹H NMR (DMSO-d₆, 400 MHz): δ (ppm): 10.68 (br s, OH), 8.35 (s, 1H), 8.02 (s, 1H), 7.54 (d, J=16.0 Hz, 1H), 6.50 (d, J=16.0 Hz, 1H), 2.90 (t, J=7.6 Hz, 2H), 2.50 (t, J=7.6 Hz, 2H). The triplet CH₂ at 2.5 ppm is hidden by DMSO.

Intermediate 2

(E)-Ethyl 3-(1'-methyl-2-oxo-2,4-dihydro-1H-spiro[[1,8]naphthyridine-3,4'-piperidine]-6-yl)acrylate (D2)

Step 1: 2-Amino-3-(hydroxymethyl)pyridine

A solution of 2.4M lithium aluminum hydride in THF (181 mL g, 434 mmol) was added portionwise to a suspension of 2-amino-3-carboxypyridine (30.0 g, 217 mmol) in THF (350 mL) at 0° C. Once the addition was completed, the reaction mixture was stirred at room temperature for 15 minutes and then at reflux overnight. The mixture was then cooled to 0° C. and hydrolyzed by the successive addition of water (18 mL), a 1M solution of sodium hydroxide (18 mL) and water (50 mL). The resulting white suspension was stirred for one hour, filtered over Celite® and the cake was washed with THF (400 mL). After concentration to dryness of the filtrate, the title product was obtained as a light brown oil (25.1 g, 87%, py 93.1%).

LCMS m/z 125.0 (M+H)+

Step 2: 2-Amino-5-bromo-3-(hydroxymethyl)pyridine

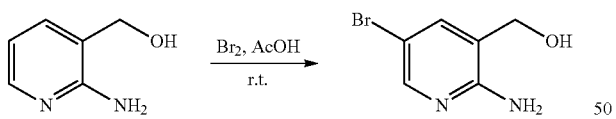

Bromine (10.4 mL, 202 mmol) was added dropwise over 1 hour to a solution of 2-amino-3-(hydroxymethyl)pyridine (25.1 g, 202 mmol) in acetic acid (500 mL) at room temperature. After complete addition the reaction mixture was stirred for an extra hour. After concentration to dryness, the residue was partitioned between 1M Na2CO3 (750 mL) and ethyl acetate (500 mL). The aqueous layer was separated and extracted one more time with ethyl acetate (500 mL). The combined organic phases were washed with a saturated solution of sodium chloride (500 mL), dried over sodium sulfate, filtered and concentrated to dryness. After trituration of the residue in DCM/heptane and extra washing with DCM the title product was obtained as a light yellow solid (30.0 g, 70%, py 97.3%).

LCMS m/z 203.0 (M+H)+

Step 3: 2-Amino-5-bromo-3-(bromomethyl)pyridine hydrobromide

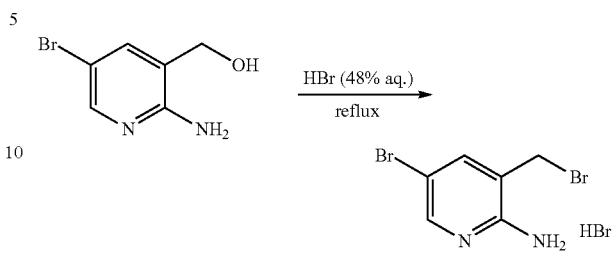

A solution of 2-amino-5-bromo-3-(hydroxymethyl)pyridine (34.6 g, 170.0 mmol) in hydrobromic acid (48% in H₂O, 93 mL) was stirred at reflux overnight. The reaction mixture was cooled to room temperature, the precipitated product filtered and washed with H₂O (100 mL) and dried. The title product was obtained as a light yellow solid (36.1 g, 56%, py 96.5%).

¹H NMR (DMSO-d₆, 400 MHz): δ (ppm): 8.27 (dd, J=2 Hz and 6 Hz, 2H), 4.75 (s, 2H).

Step 4: N-Boc ethylisonipecotate

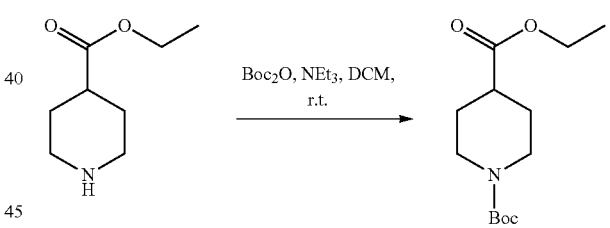

Boc₂O (15.58 g, 71.4 mmol) and triethylamine (10.85 mL, 78 mmol) were successively added to a solution of ethyl isonipecotate (10.2 g, 64.9 mmol) in dichloromethane (50 mL) at room temperature. The reaction mixture was stirred overnight. The reaction mixture was diluted by addition of a saturated solution of ammonium chloride (50 mL). The aqueous layer was separated and extracted with dichloromethane (2×50 mL). The combined organic phases were dried over sodium sulphate, filtered and concentrated to dryness. The title product was obtained as a colorless oil (16.1 g, 96%, py >95%).

¹H NMR (CDCl₃, 400 MHz): δ (ppm): 4.14 (q, J=7 Hz, 2H), 4.02 (br, 2H), 2.83 (m, 2H), 2.44 (m, 1H), 1.87 (m, 2H), 1.62 (m, 2H), 1.45 (s, 9H), 1.25 (t, J=7 Hz, 3H).

Step 5: tert-Butyl 6-bromo-2-oxo-2,4-dihydro-1H-spiro[[1,8]naphthyridine-3,4'-piperidine]-1'-carboxylate

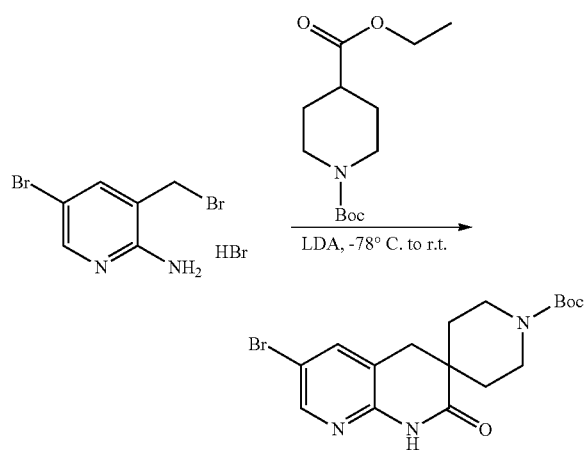

A solution of 1.8 M LDA in THF (1.6 mL, 2.88 mmol) was added dropwise over 15 minutes to a cold (−78° C.) solution of 5-bromo-3-(bromomethyl)pyridine-2-amine hydrobromide (1.0 g, 2.88 mmol) in dry THF (10 mL) under argon. The reaction mixture was stirred for an additional 15 minutes. In a separate flask, a solution of 1.8 M LDA in THF (4.81 mL, 8.65 mmol) was added dropwise over 30 minutes to a cold solution of N-Boc ethylisonipecotate (2.23 g, 8.65 mmol) in dry THF (20 ml). The reaction mixture was stirred for an additional 30 minutes. The lithium salt of N-Boc ethylisonipecotate was then added via cannula dropwise over 30 minutes to the lithium salt of 5-bromo-3-(bromomethyl)pyridine-2-amine. The mixture was stirred at −78° C. for 2 hours and allowed to warm to room temperature. The reaction mixture was quenched with a saturated solution of ammonium chloride (30 mL) and ethyl acetate (30 mL) was added. The layers were separated and the organic phase was washed with water (2×30 mL) and brine (50 mL), dried over sodium sulphate, filtered and concentrated to dryness. The residue was triturated with EtOAc. The title product was obtained as a white solid (257 mg, 19%, py 85.7%).

LCMS m/z 394 (M−H)⁻

Step 6: (E)-tert-Butyl 6-(3-tert-butoxy-3-oxoprop-1-enyl)-2-oxo-2,4-dihydro-1H-spiro[[1,8]naphthyridine-3,4'-piperidine]-1'-carboxylate

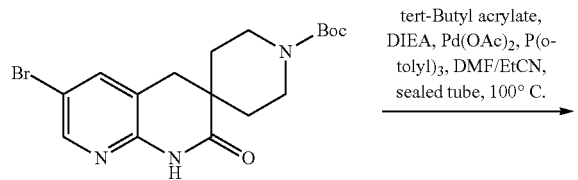

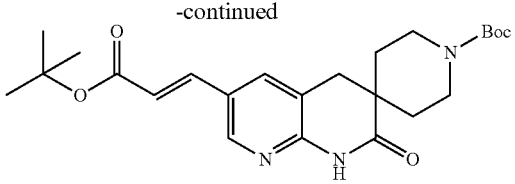

Tert-Butyl acrylate (3.9 mL, 26.8 mmol), diisopropylethylamine (2.46 mL, 14.1 mmol) and P(o-tolyl)₃ (409 mg, 1.34 mmol) were successively added to a suspension of tert-butyl 6-bromo-2-oxo-2,4-dihydro-1H-spiro[[1,8]naphthyridine-3,4'-piperidine]-1'-carboxylate (2.66 g, 6.7 mmol) in propionitrile (107 mL) and dimethylformamide (40 mL) in a sealed tube. The resulting mixture was then purged with argon prior to the addition of palladium acetate (151 mg, 0.673 mmol). The mixture was purged with argon again and refluxed overnight. The reaction mixture was then filtered on Celite® and the cake was washed with DCM (50 mL). The filtrate was concentrated to dryness and the residue was triturated with dichloromethane. The title product was obtained as a light grey solid (1.83 g, 61%, py 79.9%).

LCMS m/z 442 (M−H)⁻

Step 7: (E)-3-(2-Oxo-2,4-dihydro-1H-spiro[[1,8]naphthyridine-3,4'-piperidine]-6-yl)acrylic acid hydrochloride

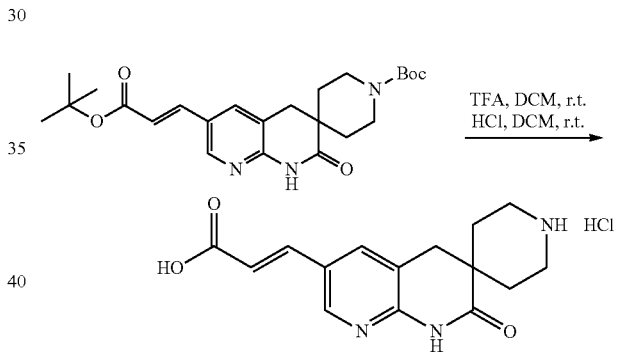

Trifluoroacetic acid (5.5 mL) was added to a suspension of (E)-3-(2-oxo-2,4-dihydro-1H-spiro[[1,8]naphthyridine-3,4'-piperidine]-6-yl)acrylic acid hydrochloride (540 mg, 1.21 mmol) in dichloromethane (5.5 mL). The reaction mixture was stirred at room temperature for 1 hour and concentrated to dryness. The resulting residue was suspended in a solution of hydrochloric acid, 4N in dioxane (11 ml). After 10 minutes stirring at room temperature, the precipitate was filtered and triturated with diethyl ether. The title product was obtained as a white solid (455 mg, 109%, py 98.9%).

LCMS m/z 288 (M+H−HCl)⁺

Step 8: (E)-3-(1'-Methyl-2-oxo-2,4-dihydro-1H-spiro[[1,8]naphthyridine-3,4'-piperidine]-6-yl)acrylic acid

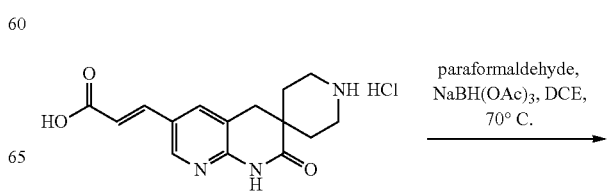

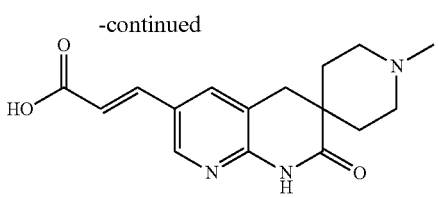

Sodium triacetoxyborohydride (671 mg, 3.17 mmol) and paraformaldehyde (95 mg, 3.17 mmol) were successively added to a suspension of (E)-3-(2-oxo-2,4-dihydro-1H-spiro[[1,8]naphthyridine-3,4'-piperidine]-6-yl)acrylic acid (455 mg, 1.58 mmol) in 1,2-dichloroethane (40 mL) at room temperature. The reaction mixture was then heated to 70° C. and stirred for 2 hours. The reaction mixture was cooled to room temperature, the precipitated product filtered and washed with H$_2$O (50 mL) and MeOH (3×50 mL) and dried. The title product was obtained as a white solid (319 mg, 66%, py 74.1%).

LCMS m/z 302 (M+H)$^+$

Example 1

6-[(1E)-3-Azetidin-1-yl-3-oxoprop-1-en-1-yl]-3,4-dihydro-1,8-naphthyridin-2(1H)-one (E1)

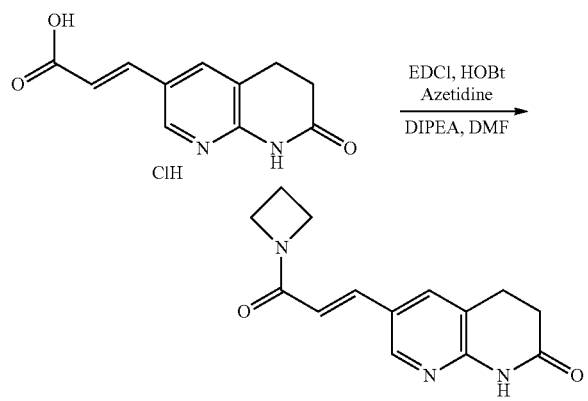

A 16 mL vial flask was successively charged with (2E)-3-(7-oxo-5,6,7,8-tetrahydro-1,8-naphthyridin-3-yl)acrylic acid hydrochloride (50 mg, 0.20 mmol), prepared (as in *J. Med. Chem.* 2003, 46, 9, 1627-1635) from 6-bromo-3,4-dihydro-1,8-naphthyridin-2(1H)-one described in U.S. Pat. No. 4,866,074 (Rorer Pharmaceutical Corp.), DMF (4.8 mL), HOBt (32 mg, 0.23 mmol), DIPEA (78 µL, 0.47 mmol), azetidine (16 µL, 0.23 mmol) and EDAC (45 mg, 0.23 mmol). The reaction mixture was stirred at room temperature overnight and concentrated to dryness. The residue was purified twice on preparative TLC (eluent: dichloromethane/MeOH, 95/5) to give the title compound (31 mg, 62%) as a white solid.

LCMS (ESI+) m/z 258 (M+H)$^+$: 100%.

$^1$H NMR (DMSO-d$_6$, 300 MHz): δ (ppm): 10.65 (br s, 1H), 8.40-8.31 (m, 1H), 8.06-7.98 (m, 1H), 7.37 (d, J=15.9 Hz, 1H), 6.68 (d, J=15.9 Hz, 1H), 4.27 (t, J=7.5 Hz, 2H), 3.93 (t, J=7.5 Hz, 2H), 2.90 (t, J=7.2 Hz, 2H), 2.23 (qt, J=7.5 Hz, 2H). The other CH$_2$ of the naphthyridinone moiety is hidden by DMSO signal.

Example 2

6-[(1E)-3-Oxo-3-pyrrolidin-1-ylprop-1-en-1-yl]-3,4-dihydro-1,8-naphthyridin-2(1H)-one (E2)

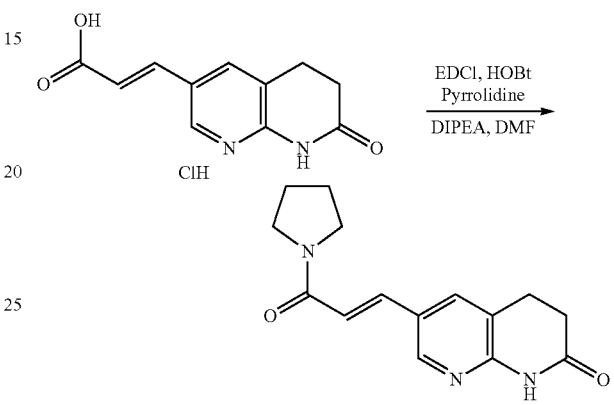

A 16 mL vial flask was successively charged with (2E)-3-(7-oxo-5,6,7,8-tetrahydro-1,8-naphthyridin-3-yl)acrylic acid hydrochloride (50 mg, 0.20 mmol), DMF (4.8 mL), HOBt (32 mg, 0.23 mmol), DIPEA (78 µL, 0.47 mmol), pyrrolidine (20 µL, 0.23 mmol) and EDAC (45 mg, 0.23 mmol). The reaction mixture was stirred at room temperature overnight and concentrated to dryness. The residue was diluted in dichloromethane and washed with water. The organic layer was concentrated to dryness and the residue was purified on preparative TLC (eluent: dichloromethane/MeOH, 95/5) to give the title compound (33 mg, 62%) as a white solid.

LCMS (ESI+) m/z 272 (M+H)$^+$: 100%.

$^1$H NMR (DMSO-d$_6$, 300 MHz): δ (ppm): 10.64 (br s, 1H), 8.38-8.31 (m, 1H), 8.07-8.01 (m, 1H), 7.42 (d, J=15.3 Hz, 1H), 6.96 (d, J=15.3 Hz, 1H), 3.63 (t, J=6.8 Hz, 2H), 3.39 (t, J=6.8 Hz, 2H), 2.91 (t, J=7.2 Hz, 2H), 1.91 (qt, J=6.8 Hz, 2H), 1.81 (qt, J=6.8 Hz, 2H). The other CH$_2$ of the naphthyridinone moiety is hidden by DMSO signal.

Example 3

6-[(1E)-3-Oxo-3-piperidin-1-ylprop-1-en-1-yl]-3,4-dihydro-1,8-naphthyridin-2(1H)-one (E3)

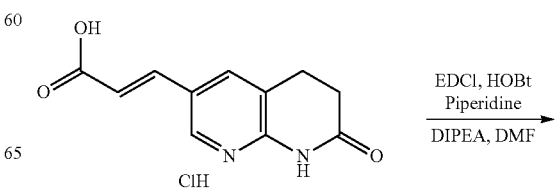

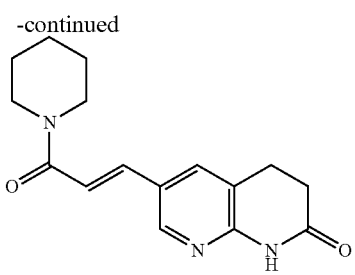

A 16 mL vial flask was successively charged with (2E)-3-(7-oxo-5,6,7,8-tetrahydro-1,8-naphthyridin-3-yl)acrylic acid hydrochloride (50 mg, 0.20 mmol), DMF (4.8 mL), HOBt (32 mg, 0.23 mmol), DIPEA (78 μL, 0.47 mmol), piperidine (23 μL, 0.23 mmol) and EDAC (45 mg, 0.23 mmol). The reaction mixture was stirred at room temperature overnight and concentrated to dryness. The residue was diluted in dichloromethane and washed with water. The organic layer was concentrated to dryness and the residue was purified on preparative TLC (eluent: dichloromethane/MeOH, 95/5) to give the title compound (39 mg, 69%) as a white solid.

LCMS (ESI+) m/z 286 (M+H)$^+$: 100%.

$^1$H NMR (DMSO-d$_6$, 300 MHz): δ (ppm): 10.64 (br s, 1H), 8.39-8.31 (m, 1H), 8.12-8.07 (m, 1H), 7.42 (d, J=15.3 Hz, 1H), 7.24 (d, J=15.3 Hz, 1H), 3.72-3.58 (m, 2H), 3.58-3.46 (m, 2H), 2.91 (t, J=6.9 Hz, 2H), 1.70-1.57 (m, 2H), 1.57-1.42 (m, 4H). The other CH$_2$ of the naphthyridinone moiety is hidden by DMSO signal.

Example 4

6-{(1E)-3-[4-(2-Hydroxyethyl)piperidin-1-yl]-3-oxoprop-1-en-1-yl}-3,4-dihydro-1,8-naphthyridin-2(1H)-one (E4)

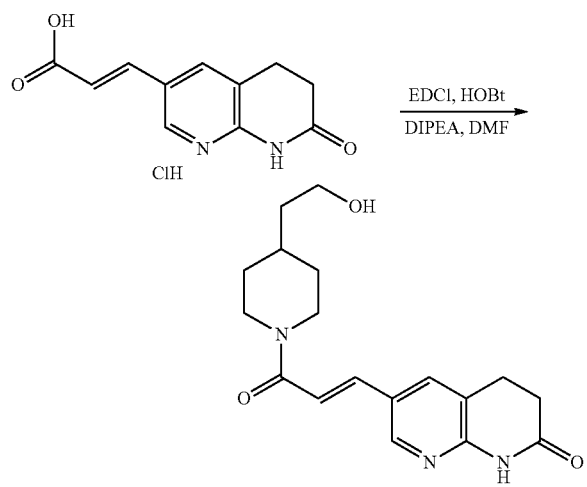

A 16 mL vial flask was successively charged with (2E)-3-(7-oxo-5,6,7,8-tetrahydro-1,8-naphthyridin-3-yl)acrylic acid hydrochloride (50 mg, 0.20 mmol), DMF (4.8 mL), HOBt (32 mg, 0.23 mmol), DIPEA (78 μL, 0.47 mmol), 4-piperidineethanol (30 mg, 0.23 mmol) and EDAC (45 mg, 0.23 mmol). The reaction mixture was stirred at room temperature overnight and concentrated to dryness. The residue was purified on column chromatography (eluent: dichloromethane/MeOH, 95/5) to give a white solid. This solid was triturated in MeOH, filtered, washed with MeOH and diethyl ether and dried to give the title compound (35 mg, 55%) as a white solid.

LCMS (ESI+) m/z 330 (M+H)$^+$: 100%. Two peaks due to its protonation during the analysis.

$^1$H NMR (DMSO-d$_6$, 300 MHz): δ (ppm): 10.64 (br s, 1H), 8.35-8.32 (m, 1H), 8.11-8.07 (m, 1H), 7.42 (d, J=15.3 Hz, 1H), 7.24 (d, J=15.3 Hz, 1H), 4.52-4.42 (m, 1H), 4.38 (t, J=5.1 Hz, 1H), 4.32-4.22 (m, 1H), 3.52-3.42 (m, 2H), 3.11-2.96 (m, 1H), 2.91 (t, J=7.5 Hz, 2H), 2.69-2.57 (m, 1H), 1.81-1.57 (m, 3H), 1.37 (q, J=6.6 Hz, 2H), 1.12-0.93 (m, 2H). The other CH$_2$ is hidden by DMSO signal.

Example 5

6-[(1E)-3-{[4-(4-Fluorophenoxy)methyl]piperidin-1-yl}-3-oxoprop-1-en-1-yl]-3,4-dihydro-1,8-naphthyridin-2(1H)-one (E5)

Step 1: tert-Butyl 4-[(4-fluorophenoxy)methyl]piperidine-1-carboxylate

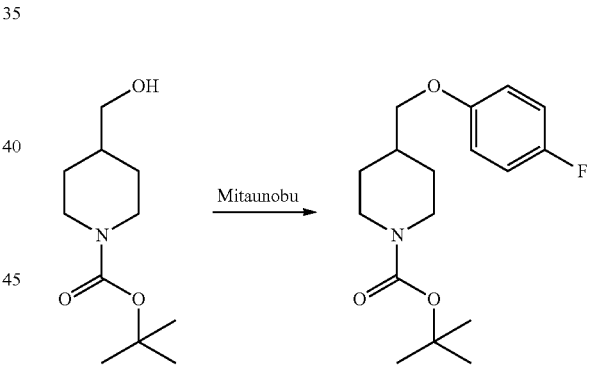

4-Fluorophenol (0.52 g, 4.64 mmol) and triphenylphosphine (1.22 g, 4.64 mmol) were added to a solution of N-boc-piperidine-4-methanol (500 mg, 2.32 mmol) in anhydrous THF (12 mL) under nitrogen. The reaction mixture was cooled to 0° C. and DEAD (670 μL, 3.69 mmol) was added dropwise. The solution was allowed to warm to room temperature and stirred overnight. The reaction mixture was concentrated under reduced pressure then diluted with dichloromethane and filtered. The filtrate was washed three times with NaOH 0.2N, dried over Na$_2$SO$_4$ and concentrated. The residue was purified on column chromatography (eluent: pentane/EtOAc 95/5) to give the title compound (538 mg, 75%) as a yellow oil.

$^1$H NMR (DMSO-d$_6$, 300 MHz): δ (ppm): 7.17-7.02 (m, 2H), 6.98-6.88 (m, 2H), 4.02-3.88 (m, 2H), 3.79 (d, J=6.3 Hz, 2H), 2.83-2.60 (m, 2H), 1.96-1.79 (m, 1H), 1.79-1.64 (m, 2H), 1.39 (s, 9H), 1.23-1.04 (m, 2H).

Step 2: 4-[(4-Fluorophenoxy)methyl]piperidine hydrochloride

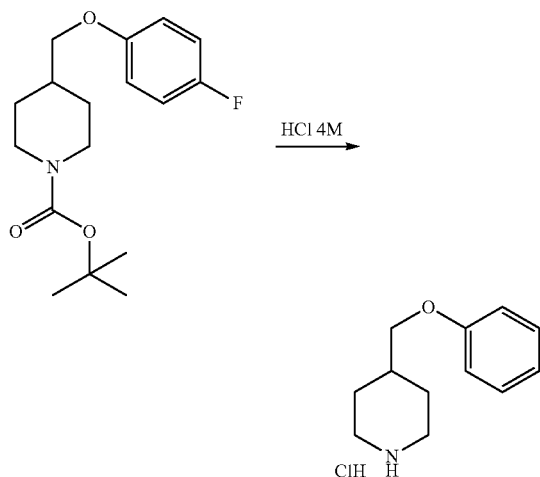

To a cooled solution of tert-butyl 4-[(4-fluorophenoxy)methyl]piperidine-1-carboxylate (538 mg, 1.74 mmol; which may be prepared as described in Step 1) in dichloromethane (11.5 mL) was added dropwise HCl 4N in dioxane (8.5 mL). The solution was warmed to room temperature and stirred for 1 h. The solvent was evaporated under reduced pressure to give the title compound (416 mg, 97%) as a white solid.

$^1$H NMR (DMSO-d$_6$, 300 MHz): δ(ppm): 9.12-8.88 (m, 1H), 8.80-8.56 (m, 1H), 7.17-7.02 (m, 2H), 7.01-6.86 (m, 2H), 3.82 (d, J=6.6 Hz, 2H), 3.32-3.21 (m, 2H), 2.97-2.78 (m, 2H), 2.10-1.95 (m, 1H), 1.94-1.81 (m, 2H), 1.58-1.37 (m, 2H).

Step 3: 6-[(1E)-3-{[4-(4-Fluorophenoxy)methyl]piperidin-1-yl}-3-oxoprop-1-en-1-yl]-3,4-dihydro-1,8-naphthyridin-2(1H)-one

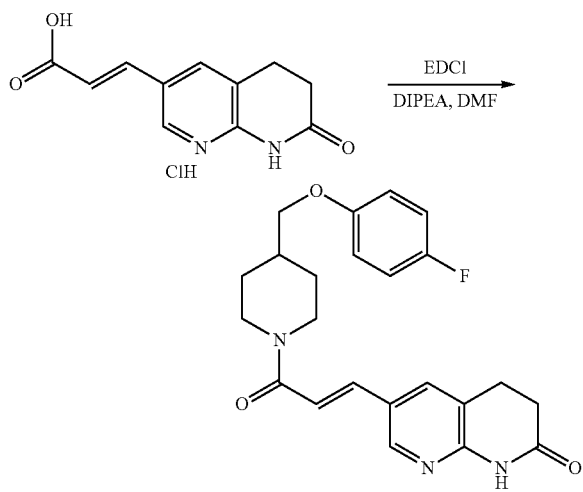

A 16 mL vial flask was successively charged with (2E)-3-(7-oxo-5,6,7,8-tetrahydro-1,8-naphthyridin-3-yl)acrylic acid hydrochloride (30 mg, 0.12 mmol), DMF (3 mL), 4-[(4-fluorophenoxy)methyl]piperidine hydrochloride (34 mg, 0.14 mmol; which may be prepared as described in Step 2), DIPEA (48 μL, 0.28 mmol) and EDAC (27 mg, 0.14 mmol). The reaction mixture was stirred at room temperature overnight and concentrated to dryness. The residue was purified on preparative TLC (eluent: dichloromethane/NH$_3$ 7N in MeOH, 2.5%) to give a pale yellow solid. This solid was triturated in acetone, filtered, washed with acetone and diethyl ether then dried to give the title compound (22 mg, 45%) as a white solid.

LCMS (ESI+) m/z 410 (M+H)$^+$: 100%.

$^1$H NMR (DMSO-d$_6$, 300 MHz): δ (ppm): 10.64 (br s, 1H), 8.40-8.25 (m, 1H), 8.16-8.04 (m, 1H), 7.44 (d, J=15.3 Hz, 1H), 7.26 (d, J=15.3 Hz, 1H), 7.18-7.05 (m, 2H), 7.02-6.85 (m, 2H), 4.60-4.25 (m, 2H), 3.90-3.73 (m, 2H), 3.16-3.01 (m, 1H), 2.98-2.80 (m, 2H), 2.77-2.60 (m, 1H), 2.13-1.93 (m, 1H), 1.91-1.70 (m, 2H), 1.34-1.05 (m, 2H). The CH$_2$ missing is hidden by DMSO signal.

Example 6

6-[(1E)-3-Oxo-3-(3-phenoxyazetidin-1-yl)prop-1-en-1-yl]-3,4-dihydro-1,8-naphthyridin-2(1H)-one (E6)

Step 1: 1-(Diphenylmethyl)azetidin-3-yl methanesulfonate

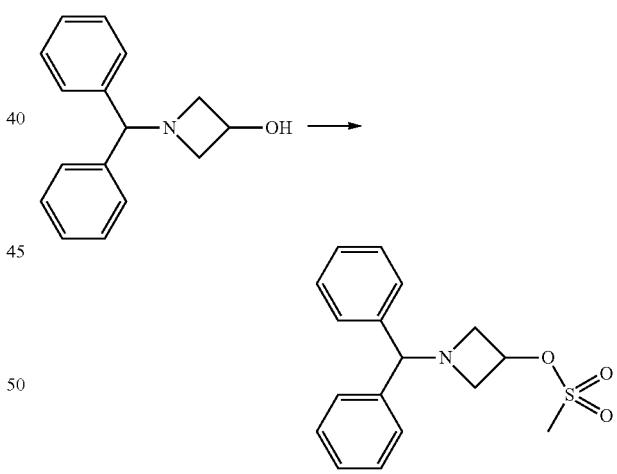

A 100 mL flask was charged with 1-diphenylmethylazetidin-3-ol (1.5 g, 6.27 mmol) and pyridine (15 mL). The solution was cooled to −20° C. and methane sulfonyl chloride (0.73 mL, 9.4 mmol) was added dropwise. The reaction mixture was stirred at −20° C. for 1 h and then left 3 days at 4° C. The solution was poured on ice and the resulting precipitate was filtered, washed 3 times with H$_2$O and 3 times with pentane. The solid was dried under reduced pressure to give the title compound (1.92 g, 96%) as a white solid.

$^1$H NMR (DMSO-d$_6$, 300 MHz): δ (ppm): 7.44-7.03 (m, 10H), 5.16-4.96 (m, 1H), 4.59-4.42 (m, 1H), 3.61-3.21 (m, 4H), 3.18 (s, 3H).

Step 2: 1-(Diphenylmethyl)-3-phenoxyazetidine alkylation

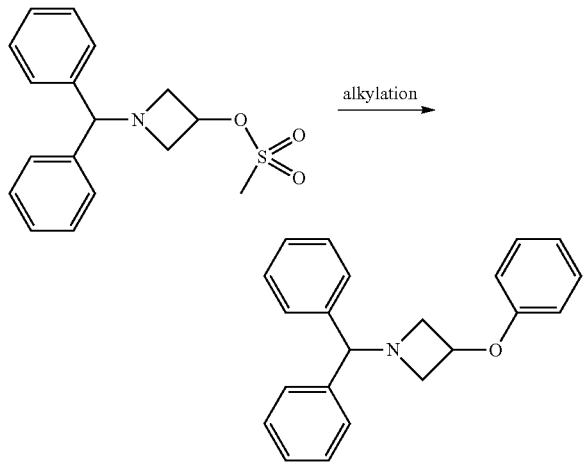

To a cooled solution of phenol (149 mg, 1.58 mmol) in DMF (3.9 mL), NaH (60% in oil, 95 mg, 2.37 mmol) was added portionwise and the suspension was stirred at 0° C. for 15 min. 1-(Diphenylmethyl)azetidin-3-yl methanesulfonate (500 mg, 1.58 mmol; which may be prepared as described in Step 1) was then added and the reaction mixture stirred at 80° C. overnight and concentrated under reduced pressure. The residue was purified on column chromatography (eluent: pentane/EtOAc 98/2 to 95/5) to give the title compound (332 mg, 67%) as a light yellow solid.

$^1$H NMR (DMSO-d$_6$, 300 MHz): δ (ppm): 7.49-7.34 (m, 3H), 7.32-7.07 (m, 9H), 6.96-6.87 (m, 1H), 6.85-6.72 (m, 2H), 4.88-4.75 (m, 1H), 4.51 (br s, 1H), 3.66-3.58 (m, 2H), 3.00-2.92 (m, 2H).

Step 3: 3-Phenoxyazetidine hydrochloride

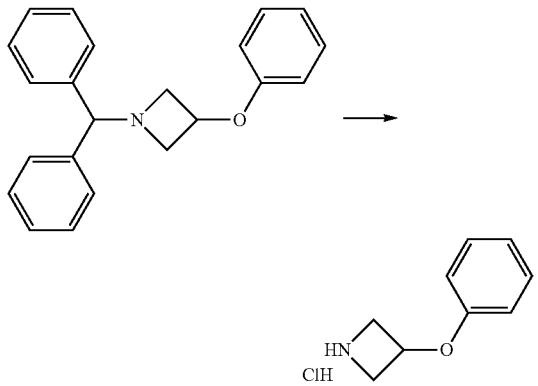

A 50 mL flask was charged with 1-(diphenylmethyl)-3-phenoxyazetidine (328 mg, 1.04 mmol; which may be prepared as described in Step 2) and 1,2-dichloroethane (4.6 mL). 1-Chloroethyl chloroformate (164 μL, 1.35 mmol) was added and the reaction mixture was stirred at 70° C. for 1.5 h. After cooling to room temperature, MeOH (4.6 mL) was added and the reaction mixture was stirred at 70° C. for 1.5 h. The reaction mixture was concentrated to dryness. The crude product was triturated in pentane to give the title compound (204 mg, quantitative) as pale yellow crystals. This product was used in the next step without further purification.

$^1$H NMR (DMSO-d$_6$, 300 MHz): δ (ppm): 9.70-9.38 (m, 2H), 7.29-7.18 (m, 2H), 7.08-6.93 (m, 1H), 6.90-6.78 (m, 2H), 5.13-4.98 (m, 1H), 4.51-4.29 (m, 2H), 4.04-3.80 (m, 2H).

Step 4: 6-[(1E)-3-Oxo-3-(3-phenoxyazetidin-1-yl)prop-1-en-1-yl]-3,4-dihydro-1,8-naphthyridin-2(1H)-one

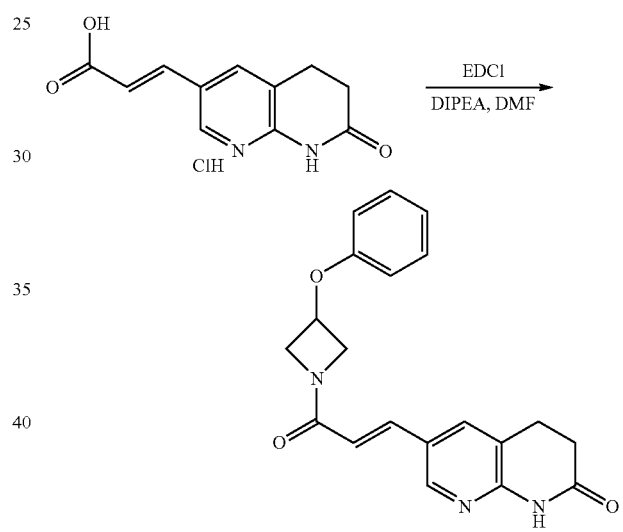

A 16 mL vial flask was successively charged with (2E)-3-(7-oxo-5,6,7,8-tetrahydro-1,8-naphthyridin-3-yl)acrylic acid hydrochloride (30 mg, 0.12 mmol), DMF (3 mL), 3-phenoxyazetidine hydrochloride (26 mg, 0.14 mmol; which may be prepared as described in Step 3), DIPEA (48 μL, 0.28 mmol) and EDAC (27 mg, 0.14 mmol). The reaction mixture was stirred at room temperature overnight and concentrated to dryness. The residue was purified on preparative TLC (eluent: dichloromethane/NH$_3$ 7N in MeOH, 2.5%) to give a pale yellow solid. This solid was triturated in acetone, filtered, washed with acetone and diethyl ether then dried to give the title compound (15 mg, 36%) as a white solid.

LCMS (ESI+) m/z 350 (M+H)$^+$: 100%.

$^1$H NMR (DMSO-d$_6$, 300 MHz): δ (ppm): 10.66 (br s, 1H), 8.37-8.29 (m, 1H), 8.05-7.98 (m, 1H), 7.42 (d, J=15.8 Hz, 1H), 7.37-7.25 (m, 2H), 7.04-6.94 (m, 1H), 6.91-6.82 (m, 2H), 6.76 (d, J=15.8 Hz, 1H), 5.14-5.03 (m, 1H), 4.79-4.67 (m, 1H), 4.47-4.37 (m, 1H), 4.26-4.15 (m, 1H), 3.95-3.84 (m, 1H), 2.95-2.80 (m, 2H). The CH$_2$ missing is hidden by the DMSO signal.

Example 7

6-[(1E)-3-Oxo-3-(2-phenylpyrrolidin-1-yl)prop-1-en-1-yl]-3,4-dihydro-1,8-naphthyridin-2(1H)-one (E7)

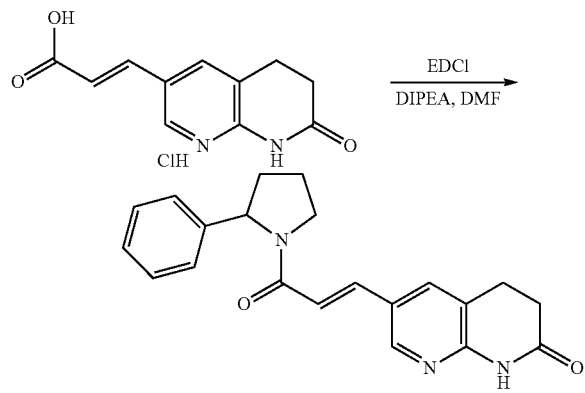

A 16 mL vial flask was successively charged with (2E)-3-(7-oxo-5,6,7,8-tetrahydro-1,8-naphthyridin-3-yl)acrylic acid hydrochloride (30 mg, 0.12 mmol), DMF (3 mL), 2-phenylpyrrolidine (21 mg, 0.14 mmol), DIPEA (48 μL, 0.28 mmol) and EDAC (27 mg, 0.14 mmol). The reaction mixture was stirred at room temperature and concentrated to dryness. LC/MS showed the presence of the target compound and no starting material after 24 h. The residue was purified on preparative TLC (eluent: dichloromethane/NH₃ 7N in MeOH, 2.5%) to give a pale yellow solid. This solid as triturated in acetone, filtered, washed with acetone and dried to give the title compound (7 mg, 17%) as a white solid.

LCMS (ESI+) m/z 348 (M+H)⁺: 100%.

¹H NMR (DMSO-d₆, 300 MHz): δ (ppm): 10.73-10.49 (m, 1H), 8.41-8.35 (m, 0.5H), 8.19-8.05 (m, 1H), 7.66-7.56 (m, 0.5H), 7.48-7.00 (m, 6.5H), 6.58 (d, J=15.3 Hz, 0.5H), 5.46-5.09 (m, 1H), 4.05-3.55 (m, 2H), 2.99-2.77 (m, 2H), 2.01-1.61 (m, 4H). The other CH₂ is hidden by DMSO signal.

Example 8

6-[(1E)-3-Oxo-3-(4-propylpiperidin-1-yl)prop-1-en-1-yl]-3,4-dihydro-1,8-naphthyridin-2(1H)-one (E8)

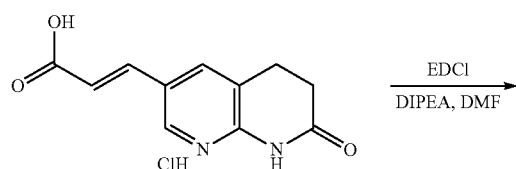

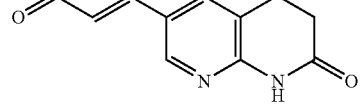

A 16 mL vial flask was successively charged with (2E)-3-(7-oxo-5,6,7,8-tetrahydro-1,8-naphthyridin-3-yl)acrylic acid hydrochloride (30 mg, 0.12 mmol), DMF (3 mL), 4-N-propylpiperidine (18 mg, 0.14 mmol), DIPEA (48 μL, 0.28 mmol) and EDAC (27 mg, 0.14 mmol). The reaction mixture was stirred at room temperature overnight and concentrated to dryness. LC/MS showed the presence of the target compound and no starting material after 24 h. The residue was purified on preparative TLC (eluent: dichloromethane/NH₃ 7N in MeOH, 2.5%) to give a white solid. This solid was triturated in acetone, filtered, washed with acetone and diethyl ether to give the title compound (15 mg, 38%) as a white solid.

LCMS (ESI+) m/z 328 (M+H)⁺: 100%.

¹H NMR (DMSO-d₆, 300 MHz): δ (ppm): 10.64 (br s, 1H), 8.40-8.27 (m, 1H), 8.14-8.02 (m, 1H), 7.42 (d, J=15.3 Hz, 1H), 7.23 (d, J=15.3 Hz, 1H), 4.55-4.15 (m, 2H), 3.10-2.97 (m, 1H), 2.96-2.81 (m, 2H), 1.80-1.62 (m, 2H), 1.60-1.40 (m, 1H), 1.39-1.11 (m, 4H), 1.07-0.91 (m, 1H), 0.87 (t, J=7.2 Hz, 3H). The 2 CH₂ missing are hidden by the DMSO signal.

Example 9

6-[(1E)-3-{[3-(4-Fluorophenoxy)methyl]piperidin-1-yl}-3-oxoprop-1-en-1-yl]-3,4-dihydro-1,8-naphthyridin-2(1H)-one (E9)

Step 1: tert-Butyl 3-[(4-fluorophenoxy)methyl]piperidine-1-carboxylate

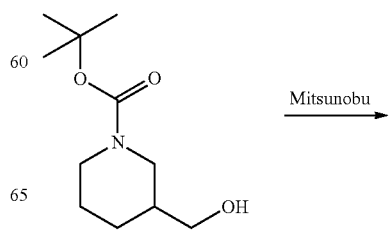

Step 3: 6-[(1E)-3-{[3-(4-Fluorophenoxy)methyl]piperidin-1-yl}-3-oxoprop-1-en-1-yl]-3,4-dihydro-1,8-naphthyridin-2(1H)-one

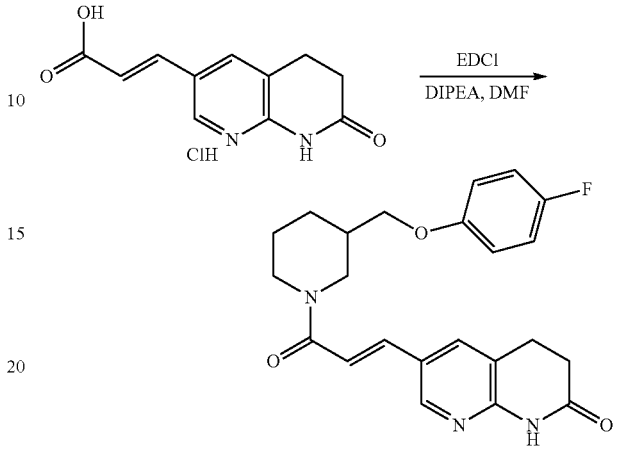

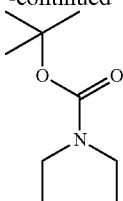

4-Fluorophenol (520 mg, 4.64 mmol) and triphenylphosphine (1.22 g, 4.64 mmol) were added to a solution of N-boc-piperidine-3-methanol (500 mg, 2.32 mmol) in anhydrous THF (12 mL) under nitrogen. The reaction mixture was cooled to 0° C. and DEAD (673 μL, 3.71 mmol) was added dropwise. The solution was allowed to warm to room temperature and stirred overnight. The reaction mixture was concentrated under reduced pressure then diluted with dichloromethane and filtered. The filtrate was washed three times with NaOH 0.2N, dried over $Na_2SO_4$ and concentrated. The residue was purified on column chromatography (eluent: pentane/EtOAc 95/5) to give the title compound (300 mg, 42%) as a yellow oil.

$^1$H NMR (DMSO-$d_6$, 300 MHz): δ (ppm): 7.18-7.03 (m, 2H), 7.01-6.87 (m, 2H), 4.09-3.55 (m, 4H), 3.02-2.76 (m, 1H), 1.95-1.52 (m, 3H), 1.49-1.19 (m, 12H).

A 16 mL vial flask was successively charged with (2E)-3-(7-oxo-5,6,7,8-tetrahydro-1,8-naphthyridin-3-yl)acrylic acid hydrochloride (30 mg, 0.12 mmol), DMF (3 mL), 3-[(4-fluorophenoxy)methyl]piperidine hydrochloride (35 mg, 0.14 mmol; which may be prepared as described in Step 2), DIPEA (48 μL, 0.28 mmol) and EDAC (27 mg, 0.14 mmol). The reaction mixture was stirred at room temperature overnight and concentrated to dryness. The residue was purified on preparative TLC (eluent: dichloromethane/$NH_3$ 7N in MeOH, 2.5%) to give a pale yellow solid. This solid was triturated in methanol, filtered, washed with methanol and diethyl ether then dried to give the title compound (23 mg, 47%) as a white solid.

LCMS (ESI+) m/z 410 (M+H)$^+$: 100%.

$^1$H NMR (DMSO-$d_6$, 300 MHz): δ (ppm): 10.64 (br s, 1H), 8.38-8.22 (m, 1H), 8.15-7.87 (m, 1H), 7.53-6.84 (m, 6H), 4.60-3.95 (m, 2H), 3.95-3.73 (m, 2H), 3.20-2.98 (m, 1H), 2.98-2.78 (m, 2H), 2.77-2.58 (m, 1H), 2.00-1.58 (m, 3H), 1.56-1.26 (m, 2H). The $CH_2$ missing is hidden by the DMSO signal.

Step 2: 3-[(4-Fluorophenoxy)methyl]piperidine hydrochloride

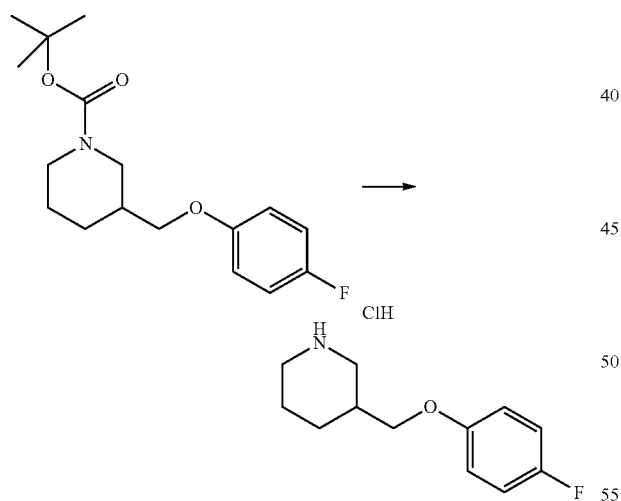

To a cooled solution of tert-butyl 3-[(4-fluorophenoxy)methyl]piperidine-1-carboxylate (300 mg, 1.03 mmol; which may be prepared as described in Step 1) in dichloromethane (6.8 mL) was added dropwise HCl 4N in dioxane (5.0 mL). The solution was warmed to room temperature and stirred for 1 h. The solvent was evaporated under reduced pressure to give the title compound (267 mg, quantitative) as a white solid.

The product was used in the next step without further analysis.

Example 10

6-[(1E)-3-Oxo-3-(3-phenoxypyrrolidin-1-yl)prop-1-en-1-yl]-3,4-dihydro-1,8-naphthyridin-2(1H)-one (E10)

Step 1: tert-Butyl 3-hydroxypyrrolidine-1-carboxylate

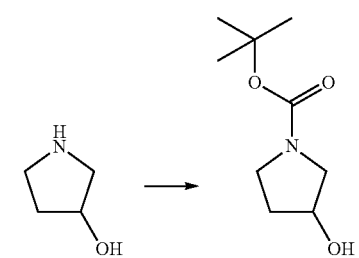

To a solution of 3-pyrrolidinol (1.82 g, 20.87 mmol) and triethylamine (6.4 mL, 45.92 mmol) in dichloromethane (104 mL) was added di-tert-butyldicarbonate (5.01 g, 22.96 mmol) in portions at 5° C. After stirring at room temperature for 16 h the reaction mixture was washed with HCl 0.1N, saturated NaHCO$_3$ solution and brine then dried over Na$_2$SO$_4$. The combined organic layers were concentrated under reduced pressure to give the title compound (3.78 g, 97%) as a dark orange oil.

$^1$H NMR (DMSO-d$_6$, 300 MHz): δ (ppm): 4.95-4.84 (m, 1H), 4.30-4.13 (m, 1H), 3.35-3.01 (m, 4H), 1.92-1.64 (m, 2H), 1.39 (s, 9H).

Step 2: tert-Butyl 3-phenoxypyrrolidine-1-carboxylate

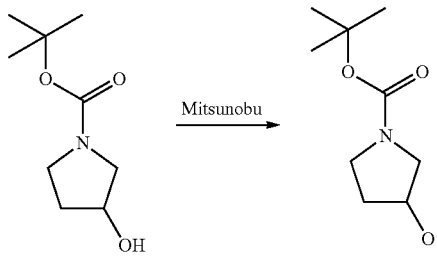

Phenol (503 mg, 5.34 mmol) and triphenylphosphine (1.40 g, 5.34 mmol) were added to a solution of tert-butyl 3-hydroxypyrrolidine-1-carboxylate (500 mg, 2.67 mmol; which may be prepared as described in Step 1) in anhydrous THF (13 mL) under nitrogen. The reaction mixture was cooled to 0° C. and DEAD (775 µL, 4.27 mmol) was added dropwise. The solution was allowed to warm to room temperature and stirred overnight. The reaction mixture was concentrated under reduced pressure then diluted with dichloromethane and filtered. The filtrate was washed three times with NaOH 0.2N and brine, dried over Na$_2$SO$_4$ then concentrated. The residue was purified on column chromatography (eluent: pentane EtOAc 9/1) to give the title compound (175 mg, 25%) as a yellow oil.

$^1$H NMR (DMSO-d$_6$, 300 MHz): δ (ppm): 7.37-7.21 (m, 2H), 7.03-6.85 (m, 3H), 5.08-4.92 (m, 1H), 3.60-3.32 (m, 4H), 2.19-1.93 (m, 2H), 1.47-1.27 (m, 9H).

Step 3: 3-Phenoxypyrrolidine hydrochloride

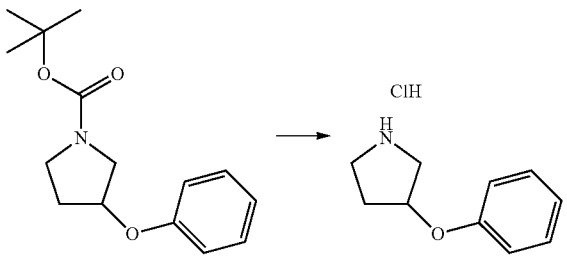 [SMILES: CC(C)(C)OC(=O)N1CCC(Oc2ccccc2)C1 ; c1ccc(OC2CCNC2)cc1 ; Cl]

To a cooled solution of tert-butyl 3-phenoxypyrrolidine-1-carboxylate (172 mg, 0.65 mmol; which may be prepared as described in Step 2) in dichloromethane (4.3 mL) was added dropwise HCl 4N in dioxane (3.2 mL). The solution was warmed to room temperature and stirred for 1 h. The solvent was evaporated under reduced pressure to give the title compound (135 mg, quantitative) as an orange oil.

$^1$H NMR (DMSO-d$_6$, 300 MHz): δ (ppm): 9.77-9.58 (m, 1H), 9.57-9.38 (m, 1H), 7.37-7.26 (m, 2H), 7.03-6.90 (m, 3H), 5.18-5.09 (m, 1H), 3.59-3.07 (m, 4H), 2.27-2.03 (m, 2H).

Step 4: 6-[(1E)-3-Oxo-3-(3-phenoxypyrrolidin-1-yl)prop-1-en-1-yl]-3,4-dihydro-1,8-naphthyridin-2(1H)-one

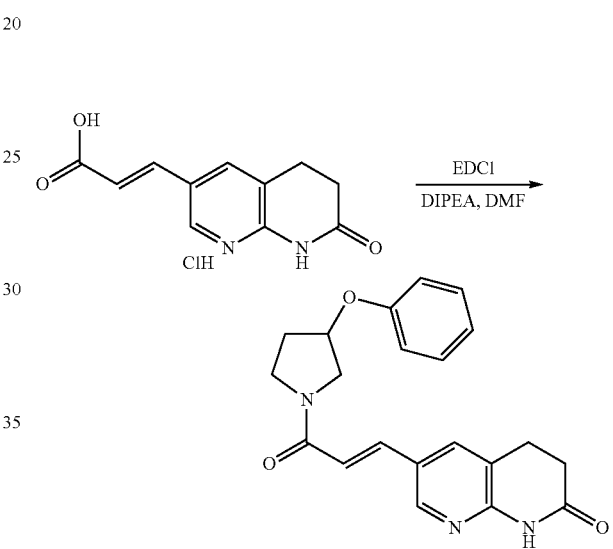

A 16 mL vial flask was successively charged with (2E)-3-(7-oxo-5,6,7,8-tetrahydro-1,8-naphthyridin-3-yl)acrylic acid hydrochloride (30 mg, 0.12 mmol), DMF (3 mL), 3-phenoxypyrrolidine hydrochloride (28 mg, 0.14 mmol; which may be prepared as described in Step 3), DIPEA (48 µL, 0.28 mmol) and EDAC (27 mg, 0.14 mmol). The reaction mixture was stirred at room temperature overnight and concentrated to dryness. The residue was purified on preparative TLC (eluent: dichloromethane/NH$_3$ 7N in MeOH, 2.5%) to give a pale yellow solid. This solid was triturated in methanol, filtered, washed with methanol, acetone and diethyl ether then dried to give the title compound (30 mg, 68%) as a white solid.

LCMS (ESI+) m/z 364 (M+H)$^+$: 100%.

$^1$H NMR (DMSO-$_{d6}$, 300 MHz): δ (ppm): 10.74-10.61 (m, 1H), 8.42-8.29 (m, 1H), 8.14-8.00 (m, 1H), 7.46 (d, J=15.6 Hz, 1H), 7.37-7.21 (m, 2H), 7.11-6.81 (m, 4H), 5.22-5.02 (m, 1H), 4.03-3.47 (m, 4H), 3.00-2.78 (m, 2H), 2.37-1.99 (m, 2H). The CH$_2$ missing is hidden by the DMSO signal.

Example 11

6-{(1E)-3-[3-(5-Methyl-1,2,4-oxadiazol-3-yl)azetidin-1-yl]-3-oxoprop-1-en-1-yl}-3,4-dihydro-1,8-naphthyridin-2(1H)-one (E11)

Step 1: Azetidine-3-carbonitrile hydrochloride

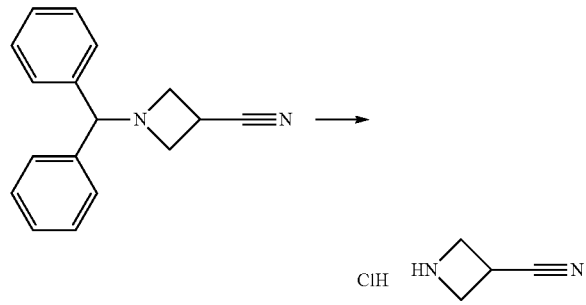

A 50 mL flask was charged with 1-benzhydrylazetane-3-carbonitrile (500 mg, 2.01 mmol) and 1,2-dichloroethane (8.9 mL). 1-chloroethyl chloroformate (285 μL, 2.61 mmol) was added and the reaction mixture was stirred at 70° C. for 1.5 h. After cooling to room temperature, methanol (8.9 mL) was added and the reaction mixture was stirred at 70° C. for 1.5 h. The reaction mixture was concentrated to dryness. The crude mixture was triturated in pentane to give a dark solid (250 mg, quantitative) which was used without further purification.

Step 2: tert-Butyl 3-cyanoazetidine-1-carboxylate

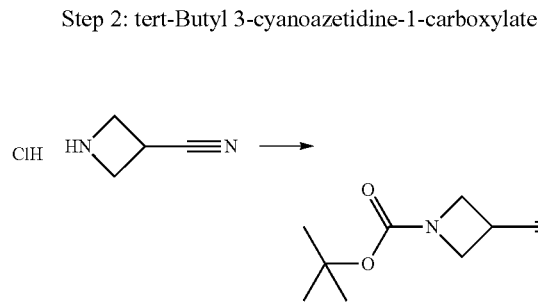

To a solution of azetidine-3-carbonitrile hydrochloride (250 mg, 2.01 mmol theoretical; which may be prepared as described in Step 1) and triethylamine (1.12 mL, 8.04 mmol) in dichloromethane (10.2 mL) was added di-tert-butyldicarbonate (482 mg, 2.21 mmol) portionwise at 5° C. After stirring at room temperature for 16 h, the reaction mixture was washed with HCl 0.5N and brine then dried over $Na_2SO_4$. The solvent was removed under reduced pressure and the crude mixture purified on column chromatography (eluent: Pentane/EtOAc 95/5 to 4/1) to give the compound (190 mg, 52%) as a clear oil.

$^1$H NMR ($CDCl_3$, 300 MHz): δ (ppm): 4.29-4.05 (m, 4H), 3.48-3.29 (m, 1H), 1.44 (s, 9H).

Step 3: tert-Butyl 3-[(Z)-amino(hydroxyimino)methyl]azetidine-1-carboxylate

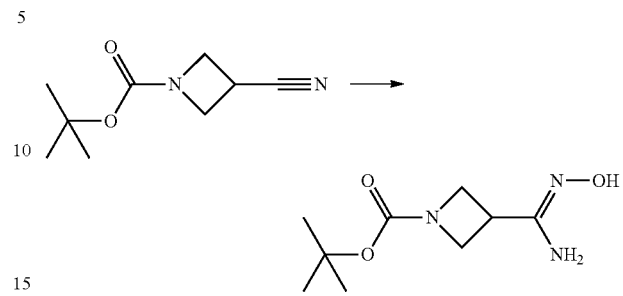

In a 16 mL vial, tert-butyl 3-cyanoazetidine-1-carboxylate (190 mg, 1.04 mmol; which may be prepared as described in Step 2) was dissolved in ethanol (2.9 mL), then hydroxylamine hydrochloride (101 mg, 1.46 mmol) and triethylamine (247 μL, 1.77 mmol) were added. The reaction mixture was stirred at reflux for 3 h, cooled and concentrated. The residue was taken up in EtOAc and water, the aqueous layer extracted with EtOAc, dried over $Na_2SO_4$ and concentrated to give the product as a white solid (170 mg, 76%).

$^1$H NMR (DMSO-$d_6$, 300 MHz) δ (ppm): 9.10 (s, 1H), 5.54-5.43 (br s, 2H), 4.00-3.78 (m, 4H), 3.23-3.08 (m, 1H), 1.37 (s, 9H).

Step 4: tert-Butyl 3-(5-methyl-1,2,4-oxadiazol-3-yl)azetidine-1-carboxylate In a 16 mL vial, tert-butyl 3-[(Z)-amino(hydroxyimino)methyl]azetidine-1-carboxylate (170 mg, 0.74 mmol; which may be prepared as described in Step 3) was dissolved in acetonitrile (7.4 mL) and cooled to 0° C. under nitrogen. DIPEA (387 μL, 2.22 mmol) and acetyl chloride (105 μL, 1.48 mmol) were added dropwise and the reaction mixture was allowed to warm to room temperature then heated to 80° C. overnight, cooled and concentrated. The residue was taken up in EtOAc and water, the aqueous layer extracted with EtOAc, dried over $Na_2SO_4$ and concentrated. The residue was taken up in o-xylene (8.4 mL) and heated to 150° C. for 2 h and concentrated. The crude mixture was purified on column chromatography (eluent: Pentane/EtOAc 7/3) to give the title compound (97 mg, 55%) as an oil.

$^1$H NMR (DMSO-$d_6$, 300 MHz): δ (ppm): 4.30-4.13 (m, 2H), 4.03-3.84 (m, 3H), 2.59 (s, 3H), 1.39 (s, 9H).

Step 5: 3-Azetidin-3-yl-5-methyl-1,2,4-oxadiazole hydrochloride

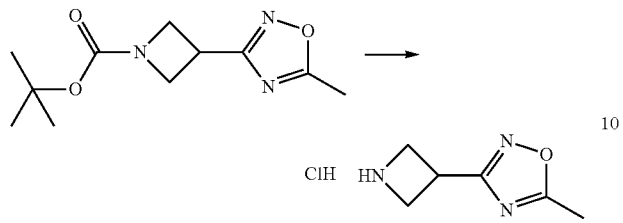

To a cooled solution of tert-butyl 3-(5-methyl-1,2,4-oxadiazol-3-yl)azetidine-1-carboxylate (97 mg, 0.41 mmol; which may be prepared as described in Step 4) in dichloromethane was added dropwise HCl 4N in dioxane (2.0 mL). The solution was warmed to room temperature and stirred for 1 h. The solvent was evaporated under reduced pressure to give the title compound (101 mg, quantitative) as a white solid. The product was used in the next step without further analysis.

Step 6: 6-{(1E)-3-[3-(5-Methyl-1,2,4-oxadiazol-3-yl)azetidin-1-yl]-3-oxoprop-1-en-1-yl}-3,4-dihydro-1,8-naphthyridin-2(1H)-one

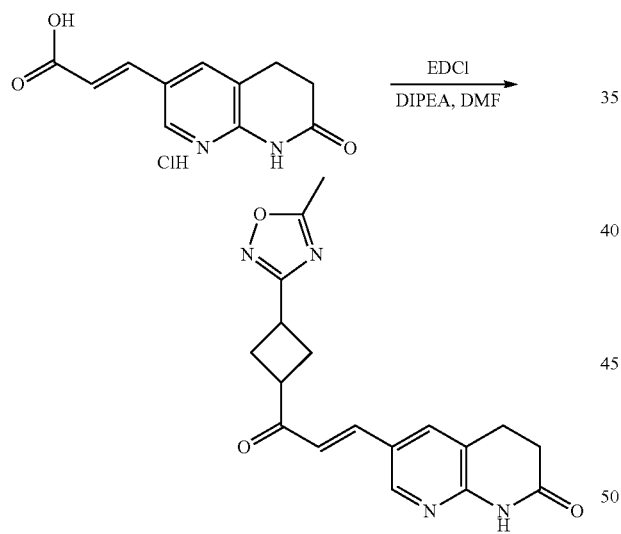

A 16 mL vial flask was successively charged with (2E)-3-(7-oxo-5,6,7,8-tetrahydro-1,8-naphthyridin-3-yl)acrylic acid hydrochloride (30 mg, 0.12 mmol), DMF (3 mL), 3-azetidin-3-yl-5-methyl-1,2,4-oxadiazole hydrochloride (25 mg, 0.14 mmol; which may be prepared as described in Step 5), DIPEA (48 μL, 0.28 mmol) and EDAC (27 mg, 0.14 mmol). The reaction mixture was stirred at room temperature overnight and concentrated to dryness. The residue was purified on preparative TLC (eluent: dichloromethane/NH$_3$ 7N in MeOH, 2.5%) to give a white solid. This solid was triturated in acetone and diethyl ether, filtered, washed with acetone and diethyl ether then dried to give the title compound (23 mg, 56%) as a white solid.

LCMS (ESI+) m/z 340 (M+H)$^+$: 100%.

$^1$H NMR (DMSO-d$_6$, 300 MHz): δ (ppm): 10.67 (br s, 1H), 8.41-8.30 (m, 1H), 8.07-7.98 (m, 1H), 7.43 (d, J=15.8 Hz, 1H), 6.75 (d, J=15.8 Hz, 1H), 4.75-4.62 (m, 1H), 4.48-4.25 (m, 2H), 4.16-3.95 (m, 2H), 2.96-2.81 (m, 2H), 2.60 (s, 3H). The CH$_2$ missing is hidden by the DMSO signal.

Example 12

6-{(1E)-3-Oxo-3-[3-(2-thienylmethoxy)azetidin-1-yl]prop-1-en-1-yl}-3,4-dihydro-1,8-naphthyridin-2(1H)-one (E12)

Step 1: 2-(Chloromethyl)thiophene

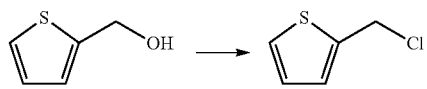 [SMILES: OCc1cccs1 ; ClCc1cccs1]

In a 15 mL flask, thiophene-2-methanol (332 μL, 3.50 mmol) was dissolved in tetrahydrofuran (2 mL) and cooled at 0° C. under nitrogen. Thionyl chloride (305 μL, 4.20 mmol) was added dropwise and the reaction mixture was allowed to warm to room temperature and heated at 50° C. for 2 h. The crude mixture was concentrated under reduced pressure to give a dark oil (480 mg, quantitative). The product was used in the next step without further purification.

$^1$H NMR (CDCl$_3$, 300 MHz): δ (ppm): 7.36-7.30 (m, 1H), 7.11-7.04 (m, 1H), 6.99-6.93 (m, 1H), 4.82 (s, 2H).

Step 2: 1-(Diphenylmethyl)-3-(2-thienylmethoxy)azetidine

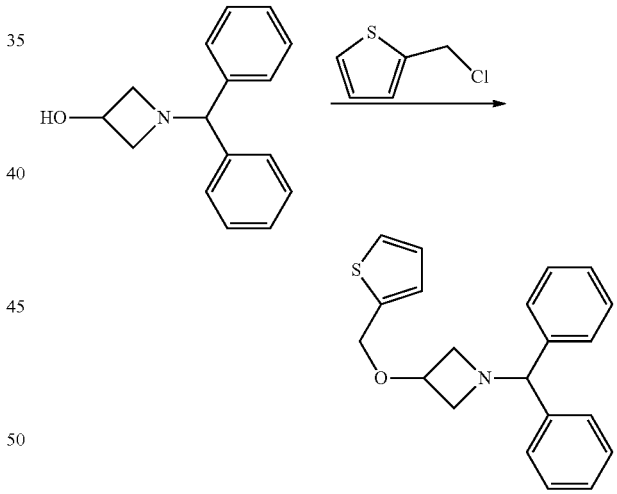

To a solution of 1-diphenylmethylazetidin-3-ol (359 mg, 1.5 mmol) in DMF (1 mL) at 0° C. under nitrogen was added NaH (60% in oil, 66 mg, 1.65 mmol). The suspension was stirred for 0.5 h at 0° C. then treated with 2-(chloromethyl)thiophene (464 mg, 3.5 mmol; which may be prepared as described in Step 1) dissolved in DMF (2 mL).

The mixture was allowed to warm to room temperature then heated at 80° C. overnight. The reaction mixture was cooled, acetic acid (2 drops) was added and the mixture concentrated under reduced pressure. The crude material was purified on column chromatography (eluent: Pentane/EtOAc, 9/1 to 7/3) to give the product (204 mg, 41%) as an orange oil.

$^1$H NMR (DMSO-d$_6$, 300 MHz): δ (ppm): 7.50-7.46 (m, 1H), 7.43-7.36 (m, 4H), 7.29-7.21 (m, 4H), 7.20-7.12 (m, 2H), 7.06-7.02 (m, 1H), 6.99-6.94 (m, 1H), 4.62-4.48 (m, 2H), 4.39 (br s, 1H), 4.23-4.12 (m, 1H), 3.36-3.27 (m, 2H), 2.80-2.70 (m, 2H).

Step 3: 3-(2-Thienylmethoxy)azetidine hydrochloride

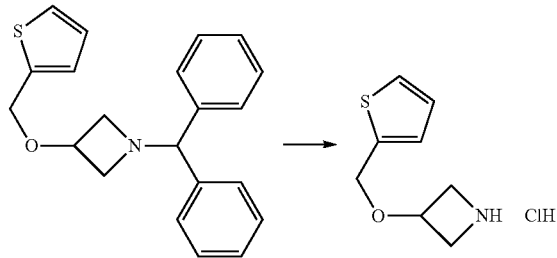 [SMILES: c1ccc(C(c2ccccc2)N2CC(OCc3cccs3)C2)cc1 ; c1csc(COC2CNC2)c1 ; Cl]

A 50 mL flask was charged with 1-(diphenylmethyl)-3-(2-thienylmethoxy)azetidine (204 mg, 0.61 mmol; which may be prepared as described in Step 2) and 1,2-dichloroethane (2.7 mL). 1-Chloroethyl chloroformate (86 μL, 0.79 mmol) was added and the reaction mixture was stirred at 70° C. for 1.5 h. After cooling to room temperature, methanol (2.7 mL) was added and the reaction mixture was stirred at 70° C. for 1.5 h. The reaction mixture was concentrated to dryness. The crude mixture was triturated in pentane to give a dark wax (140 mg, quantitative) which was used without further purification.

$^1$H NMR (DMSO-d$_6$, 300 MHz): δ (ppm): 9.21-8.85 (m, 2H), 7.62-7.52 (m, 1H), 7.16-7.08 (m, 1H), 7.04-6.97 (m, 1H), 4.67 (s, 2H), 4.51-4.39 (m, 1H), 4.13-3.96 (m, 2H), 3.84-3.68 (m, 2H).

Step 4: 6-{(1E)-3-Oxo-3-[3-(2-thienylmethoxy)azetidin-1-yl]prop-1-en-1-yl}-3,4-dihydro-1,8-naphthyridin-2(1H)-one

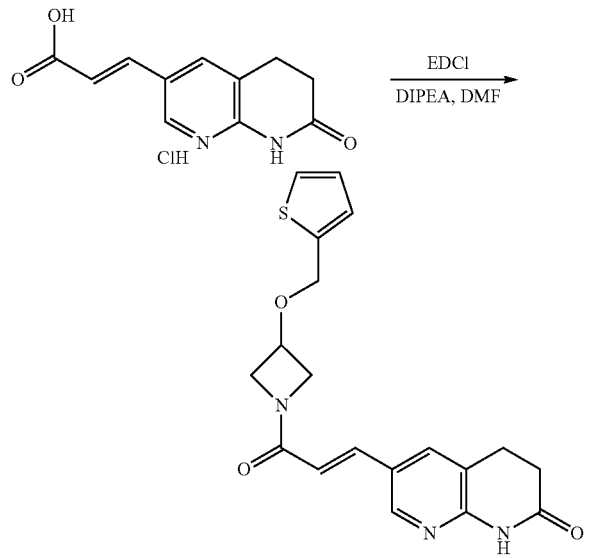

A 16 mL vial flask was successively charged with (2E)-3-(7-oxo-5,6,7,8-tetrahydro-1,8-naphthyridin-3-yl)acrylic acid hydrochloride (30 mg, 0.12 mmol), DMF (3 mL), 3-(2-thienylmethoxy)azetidine hydrochloride (29 mg, 0.14 mmol; which may be prepared as described in Step 3), DIPEA (48 μL, 0.28 mmol) and EDAC (27 mg, 0.14 mmol). The reaction mixture was stirred at room temperature overnight and concentrated to dryness. The residue was purified on preparative TLC (eluent: dichloromethane/NH$_3$ 7N in MeOH, 2.5%) to give a brown solid. This solid was triturated in acetone and diethyl ether, filtered, washed with diethyl ether then dried to give the title compound (8 mg, 18%) as a pale brown solid.

LCMS (ESI+) m/z 370 (M+H)$^+$: 100%.

$^1$H NMR (DMSO-d$_6$, 300 MHz): δ (ppm): 10.66 (br s, 1H), 8.39-8.30 (m, 1H), 8.04-7.98 (m, 1H), 7.58-7.51 (m, 1H), 7.39 (d, J=15.6 Hz, 1H), 7.15-7.07 (m, 1H), 7.04-6.98 (m, 1H), 6.70 (d, J=15.6 Hz, 1H), 4.67 (s, 2H), 4.51-4.39 (m, 2H), 4.18-4.05 (m, 2H), 3.77-3.68 (m, 1H), 2.95-2.85 (m, 2H). The CH$_2$ missing is hidden by the DMSO signal.

Example 13

6-{(1E)-3-[2-(5-Methyl-1,2,4-oxadiazol-3-yl)piperidin-1-yl]-3-oxoprop-1-en-1-yl}-3,4-dihydro-1,8-naphthyridin-2(1H)-one (E13)

Step 1: tert-Butyl 2-[(Z)-amino(hydroxyimino)methyl]piperidine-1-carboxylate

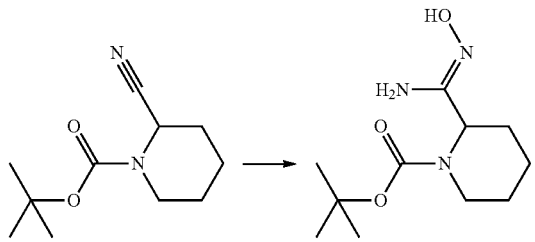 [SMILES: CC(C)(C)OC(=O)N1CCCCC1C#N ; CC(C)(C)OC(=O)N1CCCCC1/C(N)=N/O]

In a 16 mL vial, N-boc-2-cyanopiperidine (500 mg, 2.38 mmol) was dissolved in ethanol (6.7 mL), then hydroxylamine hydrochloride (231 mg, 3.33 mmol) and triethylamine (0.56 mL, 4.05 mmol) were added. The reaction mixture was stirred at reflux for 5 h, cooled and concentrated. The residue was taken up in EtOAc and water. The two layers were separated and the aqueous phase extracted with EtOAc. The combined organics were dried on Na$_2$SO$_4$ and concentrated to give the product as a white solid (550 mg, 95%).

$^1$H NMR (DMSO-d$_6$, 300 MHz): δ (ppm): 9.16 (s, 1H), 5.19 (br s, 2H), 4.71-4.57 (m, 1H), 3.87-3.70 (m, 1H), 3.07-2.89 (m, 1H), 2.11-1.89 (m, 1H), 1.62-1.36 (m, 5H), 1.38 (s, 9H).

Step 2: tert-Butyl 2-(5-methyl-1,2,4-oxadiazol-3-yl)piperidine-1-carboxylate

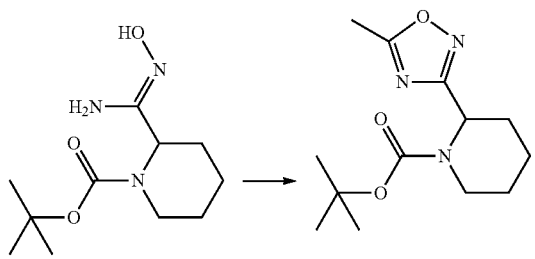 [SMILES: CC(C)(C)OC(=O)N1CCCCC1/C(N)=N/O ; Cc1nc(C2CCCCN2C(=O)OC(C)(C)C)no1]

In a 16 mL vial, tert-butyl 2-[(Z)-amino(hydroxyimino) methyl]piperidine-1-carboxylate (150 mg, 0.62 mmol; which may be prepared as described in Step 1) was dissolved in acetonitrile (6.2 mL) and cooled at 0° C. under nitrogen. DIPEA (324 μL, 1.86 mmol) and acetyl chloride (88 μL, 1.24 mmol) were added dropwise and the reaction mixture was allowed to warm to room temperature then heated to 100° C. for 4 h, cooled and concentrated. The residue was taken up in EtOAc and water. The two layers were separated and the aqueous phase extracted with EtOAc. The combined organics were dried on $Na_2SO_4$ and concentrated. The residue was taken up in o-xylene (7 mL) and heated to 150° C. for 3 h then concentrated. The crude mixture was purified on column chromatography (eluent: Pentane/EtOAc 7/3) to give the product (55 mg, 33%) as a yellow oil.

$^1$H NMR (DMSO-$d_6$, 300 MHz): δ (ppm): 5.38-5.26 (m, 1H), 3.95-3.81 (m, 1H), 2.99-2.76 (m, 1H), 2.57 (s, 3H), 2.17-2.05 (m, 1H), 1.87-1.68 (m, 1H), 1.66-1.52 (m, 2H), 1.45-1.20 (m, 11H).

Step 3: 2-(5-Methyl-1,2,4-oxadiazol-3-yl)piperidine hydrochloride

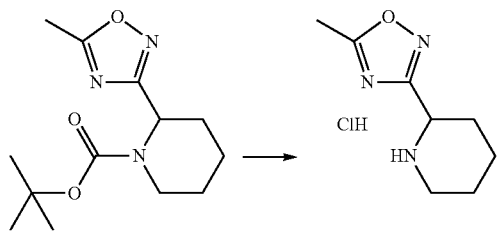 [SMILES: Cc1nc(C2CCCCN2C(=O)OC(C)(C)C)no1 ; Cc1nc(C2CCCCN2)no1 ; Cl]

To a cooled solution of tert-butyl 2-(5-methyl-1,2,4-oxadiazol-3-yl)piperidine-1-carboxylate (55 mg, 0.21 mmol; which may be prepared as described in Step 2) in dichloromethane (1.7 mL) was added dropwise HCl 4N in dioxane (1.3 mL). The solution was warmed to room temperature and stirred for 2 h. The solvent was evaporated under reduced pressure to give the title compound (47 mg, quantitative) as a white powder.

$^1$H NMR (DMSO-$d_6$, 300 MHz): δ (ppm): 9.58-9.09 (m, 2H), 4.73-4.52 (m, 1H), 3.17-2.94 (m, 2H), 2.68 (s, 3H), 2.20-2.04 (m, 1H), 1.88-1.51 (m, 5H).

Step 4: 6-{(1E)-3-[2-(5-Methyl-1,2,4-oxadiazol-3-yl)piperidin-1-yl]-3-oxoprop-1-en-1-yl}-3,4-dihydro-1,8-naphthyridin-2(1H)-one

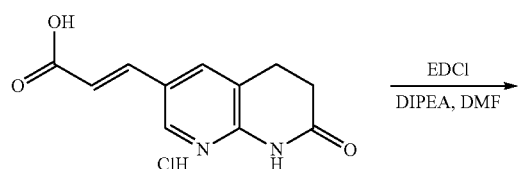

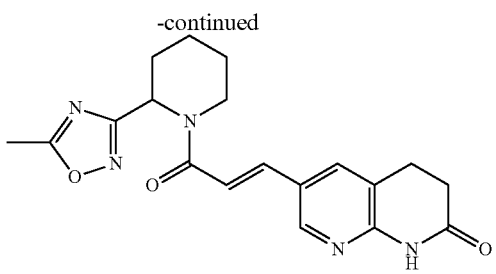

A 16 mL vial flask was successively charged with (2E)-3-(7-oxo-5,6,7,8-tetrahydro-1,8-naphthyridin-3-yl)acrylic acid hydrochloride (30 mg, 0.12 mmol), DMF (3 mL), 2-(5-methyl-1,2,4-oxadiazol-3-yl)piperidine hydrochloride (29 mg, 0.14 mmol; which may be prepared as described in Step 3), DIPEA (48 μL, 0.28 mmol) and EDAC (27 mg, 0.14 mmol). The reaction mixture was stirred at room temperature overnight and concentrated to dryness. The residue was purified on preparative TLC (eluent: dichloromethane/$NH_3$ 7N in MeOH, 2.5%) to give an oil. This oil was taken up in acetone, diethyl ether and concentrated. The resulting wax was finally dissolved in dichloromethane, concentrated and dried to give the title compound (15 mg, 34%) as a yellow solid.

LCMS (ESI+) m/z 368 (M+H)$^+$: 100%.

$^1$H NMR (DMSO-$d_6$, 300 MHz): δ (ppm): 10.65 (br s, 1H), 8.44-8.29 (m, 1H), 8.17-8.02 (m, 1H), 7.49 (d, J=15.3 Hz, 1H), 7.31 (d, J=15.3 Hz, 1H), 5.97-5.77 (m, 1H), 4.57-4.23 (m, 1H), 3.26-3.04 (m, 1H), 2.98-2.78 (m, 2H), 2.58 (s, 3H), 2.37-2.12 (m, 1H), 1.97-1.09 (m, 5H). The $CH_2$ missing is hidden by the DMSO signal.

Example 14

6-{(1E)-3-[4-Hydroxy-4-phenylpiperidin-1-yl]-3-oxoprop-1-en-1-yl}-3,4-dihydro-1,8-naphthyridin-2(1H)-one (E14)

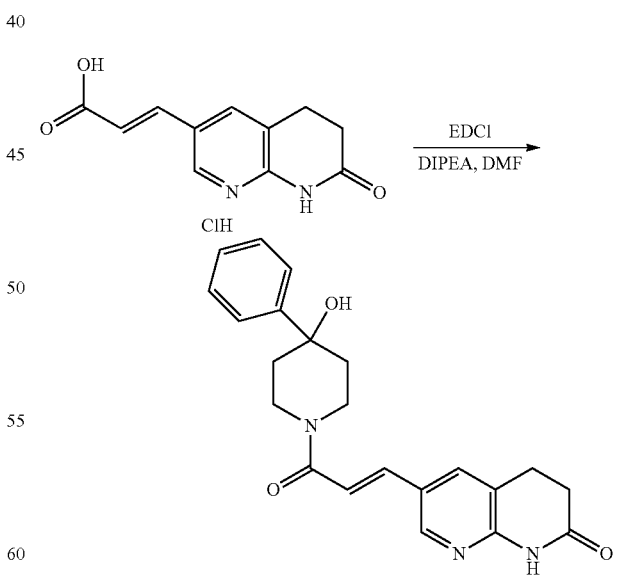

A 16 mL vial flask was successively charged with (2E)-3-(7-oxo-5,6,7,8-tetrahydro-1,8-naphthyridin-3-yl)acrylic acid hydrochloride (30 mg, 0.12 mmol), DMF (3 mL), 4-hydroxy-4-phenylpiperidine (25 mg, 0.14 mmol), DIPEA (48 μL, 0.28 mmol) and EDAC (27 mg, 0.14 mmol). The reaction mixture was stirred at room temperature overnight and concentrated to dryness. The residue was purified on preparative TLC (eluent: dichloromethane/MeOH, 95/5) to give a white solid. This solid was triturated in acetone and diethyl ether, filtered, washed with diethyl ether and then dried to give the title compound (18.5 mg, 41%) as a white solid.

LCMS (ESI+) m/z 378 (M+H)+: 100%.

$^1$H NMR (DMSO-$d_6$, 300 MHz): δ (ppm): 10.64 (br s, 1H), 8.39-8.30 (m, 1H), 8.14-8.06 (m, 1H), 7.57-7.45 (m, 3H), 7.40-7.16 (m, 4H), 5.17 (s, 1H), 4.52-4.11 (m, 2H), 3.57-3.39 (m, 1H), 3.16-2.99 (m, 1H), 2.97-2.82 (m, 2H), 1.98-1.56 (m, 4H). The CH$_2$ missing is hidden by the DMSO signal.

Example 15

6-{(1E)-3-Oxo-3-[3-(pentyloxy)azetidin-1-yl]prop-1-en-1-yl}-3,4-dihydro-1,8-naphthyridin-2(1H)-one (E15)

Step 1: 1-(Diphenylmethyl)-3-(pentyloxy)azetidine

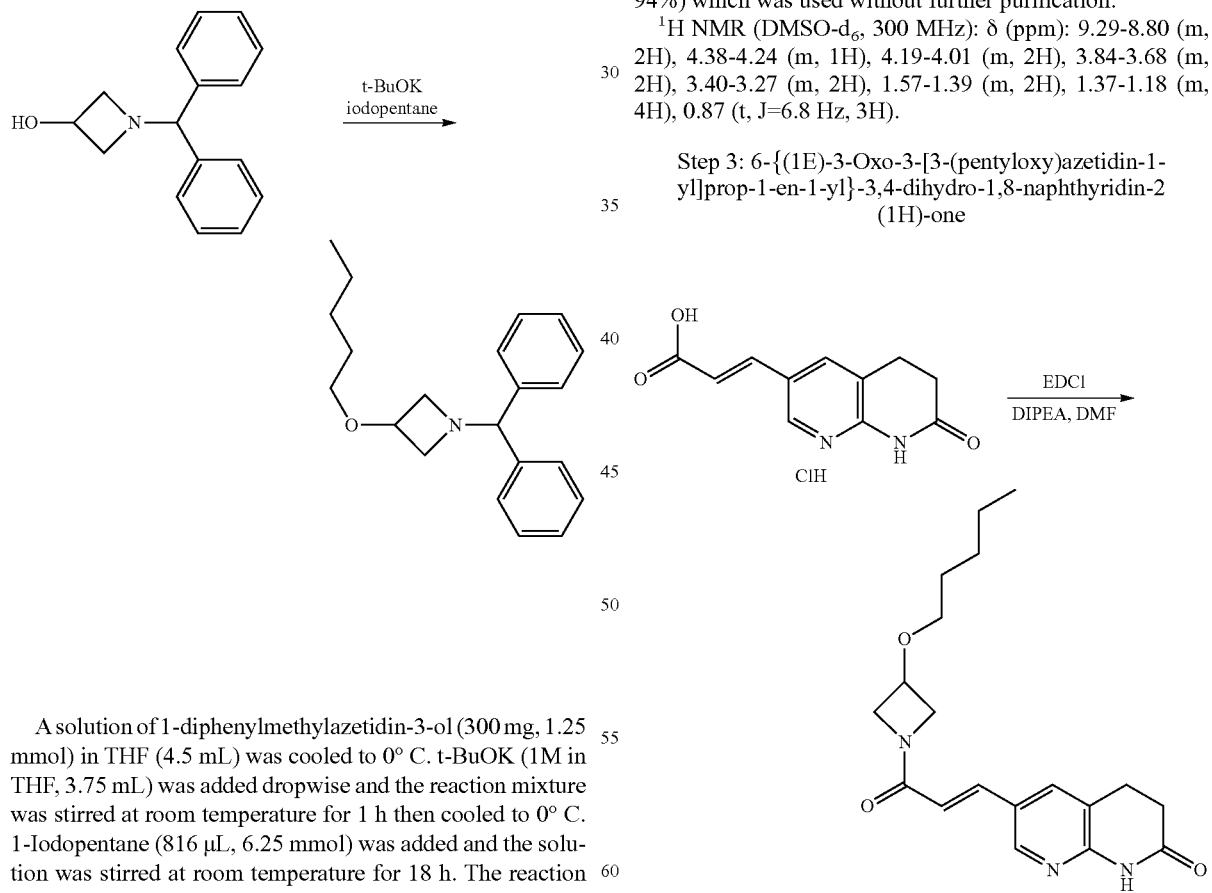

A solution of 1-diphenylmethylazetidin-3-ol (300 mg, 1.25 mmol) in THF (4.5 mL) was cooled to 0° C. t-BuOK (1M in THF, 3.75 mL) was added dropwise and the reaction mixture was stirred at room temperature for 1 h then cooled to 0° C. 1-Iodopentane (816 μL, 6.25 mmol) was added and the solution was stirred at room temperature for 18 h. The reaction mixture was diluted with H$_2$O and extracted twice with EtOAc. The organic layers were combined, dried over Na$_2$SO$_4$ and concentrated to dryness. The residue was purified on column chromatography (eluent: pentane/EtOAc, 95/5) to give the title compound (267 mg, 69%) as a clear oil.

LCMS (ESI+) m/z 310 (M+H)+: 100%.

Step 2: 1-(Diphenylmethyl)-3-(pentyloxy)azetidine

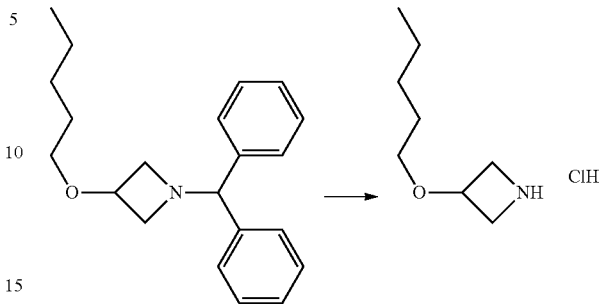

A 25 mL flask was charged with 1-(diphenylmethyl)-3-(pentyloxy)azetidine (267 mg, 0.86 mmol; which may be prepared as described in Step 1) and 1,2-dichloroethane (3.8 mL). 1-Chloroethyl chloroformate (123 μL, 1.13 mmol) was added and the reaction mixture was stirred at 70° C. for 1.5 h. After cooling to room temperature, methanol (3.8 mL) was added and the reaction mixture was stirred at 70° C. for 1.5 h. The reaction mixture was concentrated to dryness. The crude mixture was triturated in pentane to give a clear oil (145 mg, 94%) which was used without further purification.

$^1$H NMR (DMSO-$d_6$, 300 MHz): δ (ppm): 9.29-8.80 (m, 2H), 4.38-4.24 (m, 1H), 4.19-4.01 (m, 2H), 3.84-3.68 (m, 2H), 3.40-3.27 (m, 2H), 1.57-1.39 (m, 2H), 1.37-1.18 (m, 4H), 0.87 (t, J=6.8 Hz, 3H).

Step 3: 6-{(1E)-3-Oxo-3-[3-(pentyloxy)azetidin-1-yl]prop-1-en-1-yl}-3,4-dihydro-1,8-naphthyridin-2(1H)-one

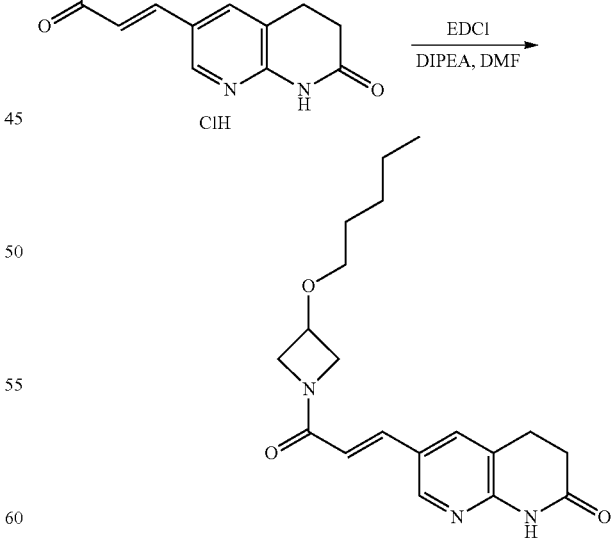

A 16 mL vial flask was successively charged with (2E)-3-(7-oxo-5,6,7,8-tetrahydro-1,8-naphthyridin-3-yl)acrylic acid hydrochloride (40 mg, 0.16 mmol), DMF (3.8 mL), 1-(diphenylmethyl)-3-(pentyloxy)azetidine (34 mg, 0.19 mmol; which may be prepared as described in Step 2), DIPEA (63 µL, 0.38 mmol) and EDAC (36 mg, 0.19 mmol). The reaction mixture was stirred at room temperature for 48 h and concentrated to dryness. The residue was purified on preparative TLC (eluent: dichloromethane/MeOH, 9/1) to give a beige solid. This solid was triturated in acetone to give the title compound (5 mg, 9%) as a white solid.

LCMS (ESI+) m/z 344 (M+H)$^+$: 85%.

$^1$H NMR (DMSO-d$_6$, 300 MHz): δ (ppm): 10.67 (br s, 1H), 8.37-8.28 (m, 1H), 8.03-7.93 (m, 1H), 7.40 (d, J=15.6 Hz, 1H), 6.70 (d, J=15.6 Hz, 1H), 4.52-4.39 (m, 1H), 4.36-4.25 (m, 1H), 4.18-3.98 (m, 2H), 3.76-3.62 (m, 1H), 2.96-2.82 (m, 2H), 1.58-1.44 (m, 2H), 1.36-1.18 (m, 4H), 0.92-0.77 (m, 3H). The two CH$_2$ missing are hidden by the DMSO signal and the water peak.

Example 16

6-{(1E)-3-Oxo-3-[3-(pyridin-3-yloxy)pyrrolidin-1-yl]prop-1-en-1-yl}-3,4-dihydro-1,8-naphthyridin-2(1H)-one (E16)

Step 1: tert-Butyl 3-(pyridin-3-yloxy)pyrrolidine-1-carboxylate

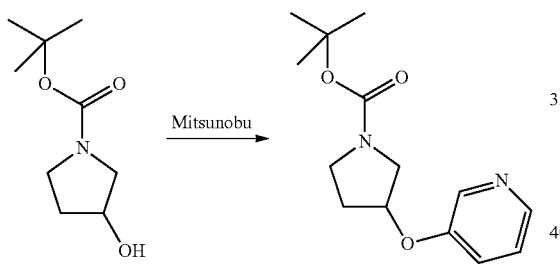

To a solution of tert-butyl 3-hydroxypyrrolidine-1-carboxylate (500 mg, 2.67 mmol) in anhydrous THF (13 mL) under nitrogen were added 3-hydroxypyridine (508 mg, 5.34 mmol) and triphenylphosphine (1.40 g, 5.34 mmol). The reaction mixture was cooled to 0° C. and DEAD (775 µL, 4.27 mmol) was added dropwise. The solution was allowed to warm to room temperature and stirred overnight. The reaction mixture was concentrated under reduced pressure then diluted with dichloromethane and filtered. The filtrate was washed three times with NaOH 0.2N, dried over Na$_2$SO$_4$ then concentrated. The residue was purified on column chromatography (eluent: pentane/acetone 9/1 to 7/3) to give the title compound (606 mg, 86%) as a wax.

$^1$H NMR (DMSO-d$_6$, 300 MHz): δ (ppm): 8.35-8.23 (m, 1H), 8.22-8.12 (m, 1H), 7.48-7.25 (m, 2H), 5.16-4.99 (m, 1H), 3.64-3.31 (m, 4H), 2.27-1.95 (m, 2H), 1.49-1.28 (m, 9H). The desired product is contaminated with some hydrogenated DEAD residue.

Step 2: 3-(Pyrrolidin-3-yloxy)pyridine hydrochloride

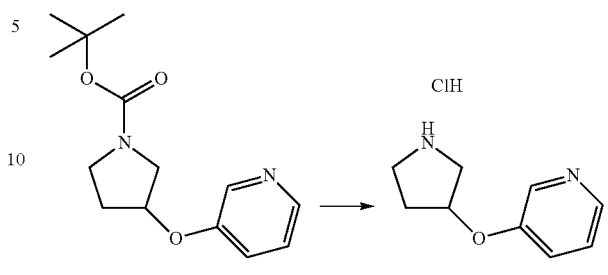

To a cooled solution of tert-butyl 3-(pyridin-3-yloxy)pyrrolidine-1-carboxylate (600 mg, 2.27 mmol; which may be prepared as described in Step 1) in dichloromethane (15 mL) was added dropwise HCl 4N in dioxane (11.1 mL). The solution was warmed to room temperature and stirred for 1 h. The solvent was evaporated under reduced pressure to give the title compound (263 mg, 58%) as a yellow wax.

LCMS (ESI+) m/z 165 (M+H(—HCl))$^+$: 100%.

Step 3: 6-{(1E)-3-Oxo-3-[3-(pyridin-3-yloxy)pyrrolidin-1-yl]prop-1-en-1-yl}-3,4-dihydro-1,8-naphthyridin-2(1H)-one

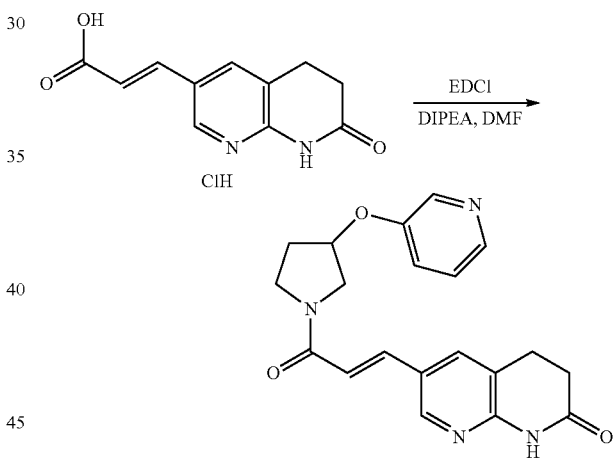

A 16 mL vial was successively charged with (2E)-3-(7-oxo-5,6,7,8-tetrahydro-1,8-naphthyridin-3-yl)acrylic acid hydrochloride (40 mg, 0.16 mmol), DMF (3.8 mL), 3-(pyrrolidin-3-yloxy)pyridine hydrochloride (64 mg, 0.32 mmol; which may be prepared as described in Step 2), DIPEA (63 µL, 0.38 mmol) and HATU (72 mg, 0.19 mmol). The reaction mixture was stirred at room temperature overnight and concentrated to dryness. The residue was purified on chromatography column (eluent: dichloromethane/MeOH, 95/5) to give a beige solid. This solid was triturated in acetone and diethyl ether, filtered, washed with acetone and diethyl ether then dried to give the title compound (7.3 mg, 13%) as a beige solid.

LCMS (ESI+) m/z 365 (M+H)$^+$: 100%.

$^1$H NMR (DMSO-d$_6$, 300 MHz): δ (ppm): 10.71-10.62 (m, 1H), 8.40-8.28 (m, 2H), 8.24-8.17 (m, 1H), 8.02 (s, 1H), 7.51-7.41 (m, 2H), 7.40-7.32 (m, 1H), 7.08-6.91 (m, 1H), 5.29-5.11 (m, 1H), 4.03-3.61 (m, 3.5H), 3.55-3.41 (m, 0.5H), 2.98-2.84 (m, 2H), 2.33-2.03 (m, 2H). The CH$_2$ missing is hidden by the DMSO signal.

Example 17

6-{(1E)-3-[3-(Benzyloxy)azetidin-1-yl]-3-oxoprop-1-en-1-yl}-3,4-dihydro-1,8-naphthyridin-2(1H)-one (E17)

Step 1: 3-(Benzyloxy)-1-(diphenylmethyl)azetidine

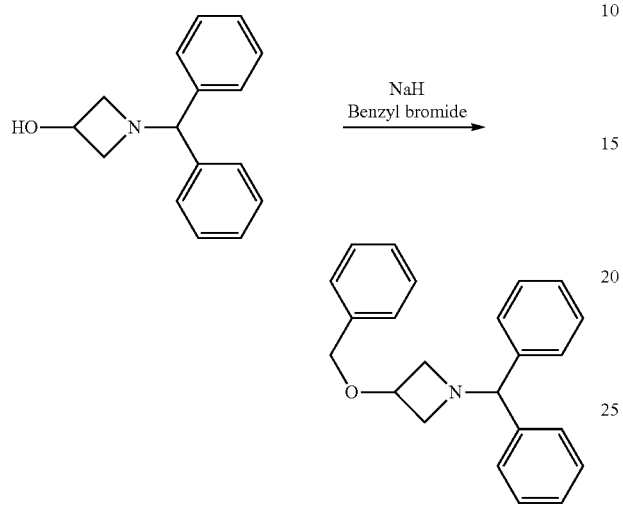

To a solution of 1-diphenylmethylazetidin-3-ol (300 mg, 1.3 mmol) in DMF (2.6 mL) at 0° C. under nitrogen was added NaH (60% in oil, 56 mg, 1.4 mmol). The suspension was stirred for 0.5 h at 0° C. then treated with benzyl bromide (236 μL, 2.0 mmol). The mixture was allowed to warm to room temperature then heated to 80° C. overnight. The reaction mixture was cooled, acetic acid (20 drops) was added and the mixture concentrated under reduced pressure. The crude material was purified on column chromatography (eluent: Pentane/EtOAc, 95/5 to 70/30) to give the product (104 mg, 24%) as an orange oil.

$^1$H NMR (DMSO-$d_6$, 300 MHz): δ (ppm): 7.47-7.12 (m, 15H), 4.40 (s, 1H), 4.37 (s, 2H), 4.22-4.11 (m, 1H), 3.38-3.28 (m, 2H), 2.82-2.74 (m, 2H).

Step 2: 3-(Benzyloxy)azetidine hydrochloride

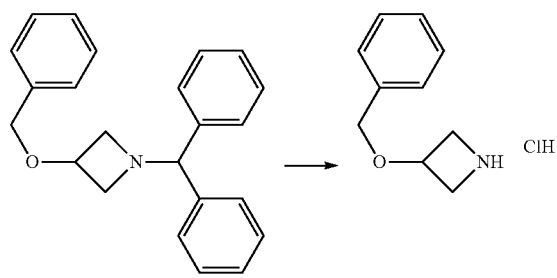 [SMILES: c1ccc(COC2CN(C(c3ccccc3)c3ccccc3)C2)cc1 ; c1ccc(COC2CNC2)cc1 ; Cl]

A 16 mL vial was charged with 3-(benzyloxy)-1-(diphenylmethyl)azetidine (103 mg, 0.31 mmol; which may be prepared as described in Step 1) and 1,2-dichloroethane (1.4 mL). 1-Chloroethyl chloroformate (45 μL, 0.41 mmol) was added and the reaction mixture was stirred at 70° C. for 1.5 h. After cooling to room temperature, methanol (1.4 mL) was added and the reaction mixture was stirred at 70° C. for 1.5 h. The reaction mixture was cooled and concentrated to dryness. The residue was purified on column chromatography (eluent: Pentane/NH$_3$ 7N in MeOH, 98/2) to give the title compound (57 mg, 92%).

LCMS (ESI+) m/z 164 (M+H$^+$ (—HCl)): 100%.

$^1$H NMR (DMSO-$d_6$, 300 MHz): δ (ppm): 7.40-7.23 (m, 5H), 4.36 (s, 2H), 4.34-4.21 (m, 1H), 3.57-3.24 (m, 4H).

Step 3: 6-{(1E)-3-[3-(Benzyloxy)azetidin-1-yl]-3-oxoprop-1-en-1-yl}-3,4-dihydro-1,8-naphthyridin-2(1H)-one

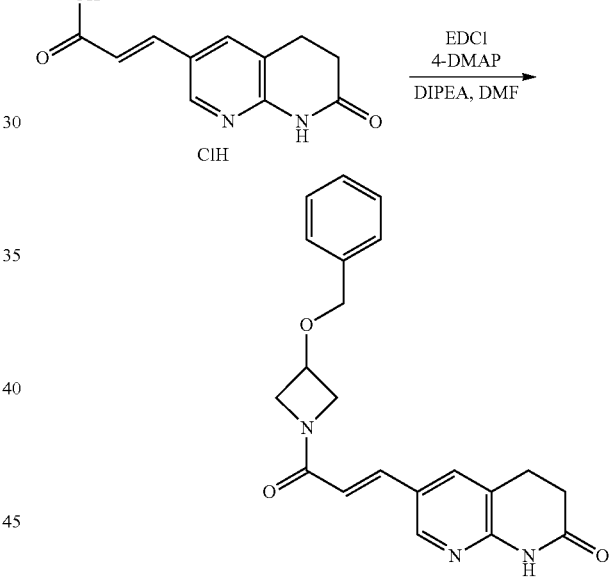

A 16 mL vial flask was successively charged with (2E)-3-(7-oxo-5,6,7,8-tetrahydro-1,8-naphthyridin-3-yl)acrylic acid hydrochloride (60 mg, 0.24 mmol), DMF (5.8 mL), 3-(benzyloxy)azetidine hydrochloride (58 mg, 0.29 mmol; which may be prepared as described in Step 2), DIPEA (96 μL, 0.58 mmol), DMAP (2.4 mg, 0.02 mmol) and EDAC (56 mg, 0.29 mmol). The reaction mixture was stirred at room temperature overnight and concentrated to dryness. The residue was purified by precipitation in MeOH/H$_2$O and then triturated in acetone/diethyl ether to give the title compound as a beige solid (33 mg, 38%).

LC-MS (ESI+) m/z 364 (M+H)$^+$: 100%.

$^1$H NMR (DMSO-$d_6$, 300 MHz): δ (ppm): 10.66 (br s, 1H), 8.40-8.30 (m, 1H), 8.06-7.97 (m, 1H), 7.46-7.26 (m, 6H), 6.71 (d, J=15.6 Hz, 1H), 4.53-4.35 (m, 4H), 4.19-4.04 (m, 2H), 3.82-3.70 (m, 1H), 2.98-2.84 (m, 2H). The CH$_2$ missing is hidden by the DMSO signal.

Example 18

6-{(1E)-3-[2-(1,3-Benzoxazol-2-yl)piperidin-1-yl]-3-oxoprop-1-en-1-yl}-3,4-dihydro-1,8-naphthyridin-2(1H)-one (E18)

Step 1: tert-Butyl (2R)-2-{[(2-bromophenyl)amino]carbonyl}pyrrolidine-1-carboxylate

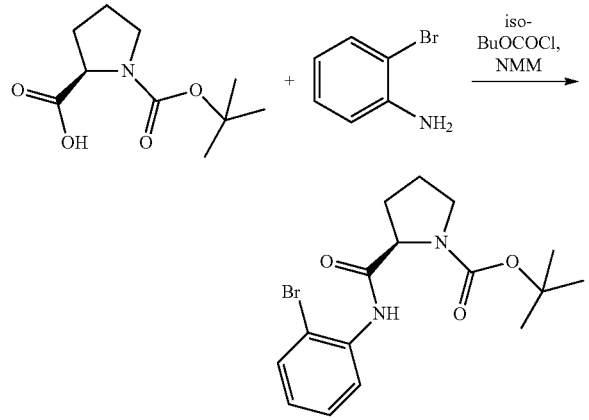

In a 500 mL flask, N-Boc-D-Proline (300 mg, 1.39 mmol) was dissolved in dichloromethane (35 mL) and cooled to 0° C. under nitrogen. N-Methylmorpholine (153 μL, 1.39 mmol) was added followed by dropwise addition of iso-butyl chloroformate (180 μL, 1.39 mmol) and the reaction mixture stirred at 0° C. for 1 h. 2-Bromoaniline (1.31 mL, 1.39 mmol) was dissolved in dichloromethane (5 mL) then added quickly to the activated acid at 0° C. The mixture was stirred overnight from 0° C. to room temperature. The reaction mixture was diluted with dichloromethane, washed with water, dried over Na$_2$SO$_4$ and concentrated under reduced pressure. The crude mixture was purified on column chromatography (eluent: Pentane/EtOAc, 50/50 to 0/100 then EtOAc/MeOH 80/20) to give the product (394 mg, 77%) as a yellow oil. This product was used in the next step without further purification.

LCMS (ESI+) m/z 369 (M+)$^+$: 7%.

Step 2: tert-Butyl (2R)-2-(1,3-benzoxazol-2-yl)pyrrolidine-1-carboxylate

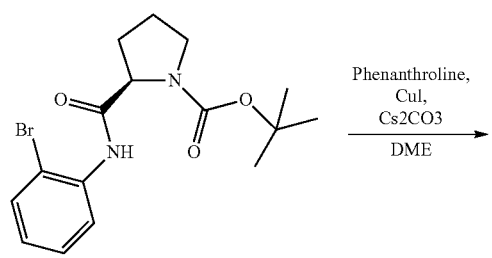

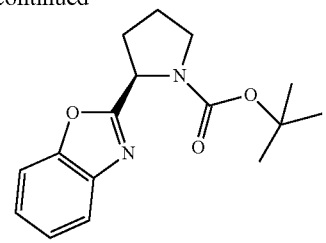

In a 25 mL flask, tert-butyl (2R)-2-{[(2-bromophenyl)amino]carbonyl}pyrrolidine-1-carboxylate (194 mg, 0.53 mmol; which may be prepared as described in Step 1) was dissolved in DME (4 mL) under nitrogen at room temperature. CuI (6 mg, 0.03 mmol), Cs$_2$CO$_3$ (261 mg, 0.80 mmol) and 1,10-phenanthroline (26 mg, 0.14 mmol) were added then the reaction mixture was heated at 85° C. for 24 h. The mixture was cooled to room temperature and concentrated to dryness. The residue was dissolved in dichloromethane and filtered on Celite to eliminate the cupper residue. The filtrate was concentrated and the residue purified on preparative TLC (Pentane/EtOAc, 85/15 to 50/50) to give the title compound (88 mg, 58%) as a solid.

LCMS (ESI+) m/z 289 (M+H)$^+$: 9%.

$^1$H NMR (DMSO-d$_6$, 300 MHz): δ (ppm): 7.78-7.62 (m, 2H), 7.43-7.31 (m, 2H), 5.08-4.94 (m, 1H), 4.60-4.34 (m, 2H), 2.42-1.80 (m, 4H), 1.37 (s, 3H), 1.06 (s, 6H).

Step 3: 2-[(2R)-Pyrrolidin-2-yl]-1,3-benzoxazole trifluoroacetate

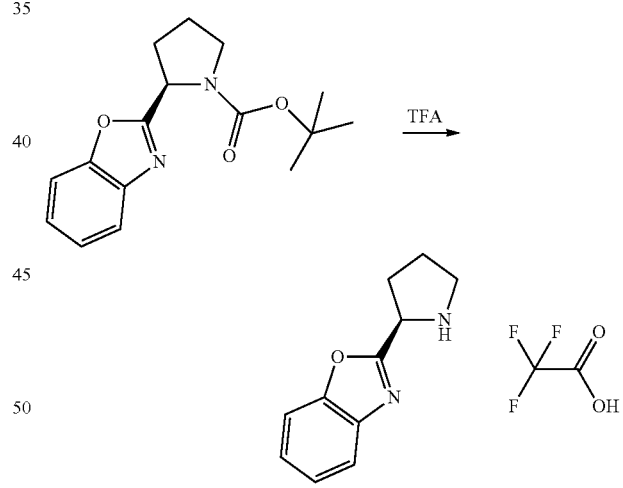

In a 16 mL flask, trifluoroacetic acid (4 mL) was added to a mixture of tert-butyl (2R)-2-(1,3-benzoxazol-2-yl)pyrrolidine-1-carboxylate (88 mg, 0.31 mmol; which may be prepared as described in Step 2) dissolved in dichloromethane (4 mL) at 0° C. under nitrogen. The reaction was allowed to warm to room temperature and stirred for 3 h. The reaction mixture was concentrated to dryness and the residue used in the next step without further purification.

LCMS (ESI+) m/z 189 (M+H)$^+$: 100%.

$^1$H NMR (DMSO-d$_6$, 300 MHz): δ (ppm): 10.20-9.80 (m, 1H), 9.70-9.30 (m, 1H), 7.88-7.77 (m, 2H), 7.54-7.41 (m, 2H), 5.17-5.05 (m, 1H), 3.45-3.33 (m, 2H), 2.43-2.24 (m, 2H), 2.16-2.02 (m, 2H).

Step 4: 6-{(1E)-3-[2-(1,3-Benzoxazol-2-yl)piperidin-1-yl]-3-oxoprop-1-en-1-yl}-3,4-dihydro-1,8-naphthyridin-2(1H)-one

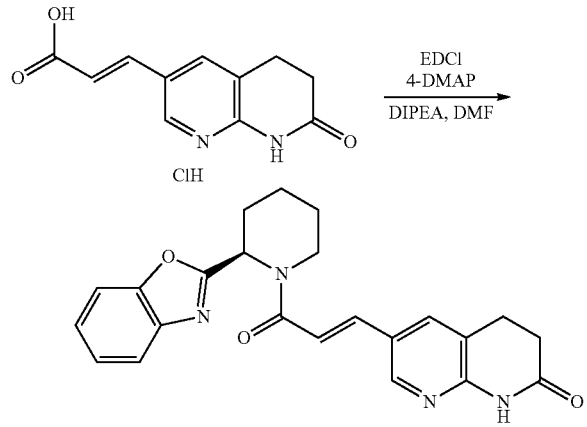

A 16 mL vial flask was successively charged with (2E)-3-(7-oxo-5,6,7,8-tetrahydro-1,8-naphthyridin-3-yl)acrylic acid hydrochloride (60 mg, 0.24 mmol), DMF (5.8 mL), 2-[(2R)-pyrrolidin-2-yl]-1,3-benzoxazole trifluoroacetate (0.31 mmol theory; which may be prepared as described in Step 3), DIPEA (96 µL, 0.58 mmol), DMAP (2.4 mg, 0.02 mmol) and EDAC (56 mg, 0.29 mmol). The reaction mixture was stirred at room temperature overnight and concentrated to dryness. The residue was purified on preparative TLC (eluent: dichloromethane/MeOH, 95/5) and column chromatography (eluent: dichloromethane/MeOH, 98/2) to give the title compound (12 mg, 13%) as a white solid.

LC-MS (ESI+) m/z 389 (M+H)+: 100%.

$^1$H NMR (DMSO-d$_6$, 300 MHz): δ (ppm): 10.71-10.51 (m, 1H), 8.45-8.18 (m, 1H), 8.12-7.78 (m, 1H), 7.75-7.54 (m, 2H), 7.47-7.26 (m, 3H), 7.12-6.92 (m, 1H), 5.83-5.71 (m, 0.2H), 5.31-5.16 (m, 0.8H), 4.04-3.56 (m, 2H), 3.04-2.74 (m, 4H), 2.16-1.94 (m, 2H). The CH$_2$ missing is hidden by the DMSO signal.

Example 19

6-[(1E)-3-{3-[(2-Methylprop-2-en-1-yl)oxy]azetidin-1-yl}-3-oxoprop-1-en-1-yl]-3,4-dihydro-1,8-naphthyridin-2(1H)-one (E19)

Step 1: 1-(Diphenylmethyl)-3-[(2-methylprop-2-en-1-yl)oxy]azetidine

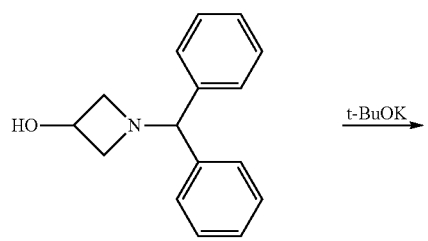

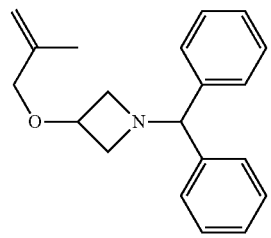

A solution of 1-diphenylmethylazetidin-3-ol (239 mg, 1.0 mmol) in THF (3.6 mL) was cooled to 0° C. t-BuOK (1M in THF, 3.6 mL) was added dropwise and the reaction mixture was stirred at room temperature for 1 h then cooled to 0° C. 3-Bromo-2-methyl-1-propene (504 µL, 5.0 mmol) was added and the solution was stirred from 0° C. to room temperature overnight. The reaction mixture was diluted with H$_2$O and extracted twice with EtOAc. The organic layers were combined, dried over Na$_2$SO$_4$ and concentrated to dryness to give the title compound (276 mg, 94%) as a yellow oil.

$^1$H NMR (CDCl$_3$, 300 MHz): δ (ppm): 7.50-7.07 (m, 10H), 4.89 (d, J=17.4 Hz, 2H), 4.36 (br s, 1H), 4.21-4.10 (m, 1H), 3.77 (br s, 2H), 3.55-3.46 (m, 2H), 2.95-2.85 (m, 2H), 1.72 (s, 3H).

Step 2: 3-[(2-Methylprop-2-en-1-yl)oxy]azetidine hydrochloride

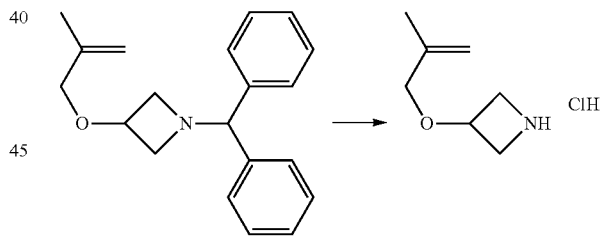

A 16 mL flask was charged with 1-(diphenylmethyl)-3-[(2-methylprop-2-en-1-yl)oxy]azetidine (276 mg, 0.94 mmol; which may be prepared as described in Step 1) and 1,2-dichloroethane (4.1 mL). 1-Chloroethyl chloroformate (135 µL, 1.24 mmol) was added and the reaction mixture was stirred at 70° C. for 1.5 h. After cooling to room temperature, methanol (4.1 mL) was added and the reaction mixture was stirred at 70° C. for 1.5 h. The reaction mixture was concentrated to dryness and the residue was triturated in pentane to give the final product (192 mg, quantitative) as a brown oil.

$^1$H NMR (DMSO-d$_6$, 300 MHz): δ (ppm): 9.37-8.88 (m, 2H), 4.92 (d, J=20.2 Hz, 2H), 4.40-4.28 (m, 1H), 4.15-4.03 (m, 2H), 3.88-3.72 (m, 4H), 1.67 (s, 3H).

Step 3: 6-[(1E)-3-{3-[(2-Methylprop-2-en-1-yl)oxy]azetidin-1-yl}-3-oxoprop-1-en-1-yl]-3,4-dihydro-1,8-naphthyridin-2(1H)-one

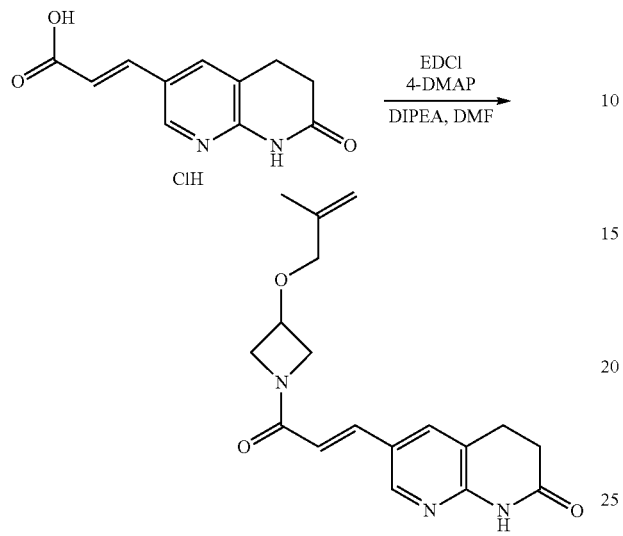

A 16 mL vial flask was successively charged with (2E)-3-(7-oxo-5,6,7,8-tetrahydro-1,8-naphthyridin-3-yl)acrylic acid hydrochloride (60 mg, 0.24 mmol), DMF (5.8 mL), 3-[(2-methylprop-2-en-1-yl)oxy]azetidine hydrochloride (78 mg, 0.48 mmol; which may be prepared as described in Step 2), DIPEA (119 µL, 0.72 mmol), DMAP (2.4 mg, 0.02 mmol) and EDAC (56 mg, 0.29 mmol). The reaction mixture was stirred at room temperature overnight and concentrated to dryness. The residue was precipitated in methanol/water and then filtered. The resulting solid was dissolved in chloroform and washed with water to give a beige solid. This solid was triturated in diethyl ether to give the title compound (13 mg, 16%) as a white solid.

LCMS (ESI+) m/z 328 (M+H)+: 100%.

$^1$H NMR (DMSO-d$_6$, 300 MHz): δ (ppm): 10.67 (br s, 1H), 8.41-8.29 (m, 1H), 8.06-7.96 (m, 1H), 7.39 (d, J=15.9 Hz, 1H), 6.71 (d, J=15.9 Hz, 1H), 5.03-4.94 (m, 1H), 4.92-4.82 (m, 1H), 4.53-4.42 (m, 1H), 4.41-4.27 (m, 1H), 4.21-4.03 (m, 2H), 3.88-3.69 (m, 3H), 2.95-2.84 (m, 2H), 1.69 (m, 3H). The CH$_2$ missing is hidden by the DMSO signal.

Example 20

6-{(1E)-3-Oxo-3-[3-(1,3-thiazol-2-ylmethoxy)azetidin-1-yl]prop-1-en-1-yl}-3,4-dihydro-1,8-naphthyridin-2(1H)-one (E20)

Step 1: 2-(Chloromethyl)-1,3-thiazol-3-ium chloride

In a 50 mL flask, thiazole-2-methanol (500 mg, 4.3 mmol) was dissolved in THF (2.6 mL) and cooled to 0° C. under nitrogen. Thionyl chloride (377 µL, 5.2 mmol) was added dropwise and the reaction mixture was allowed to warm to room temperature then heated at 50° C. for 2 h. The crude mixture was concentrated under reduced pressure to give an orange solid (684 mg, 94%).

$^1$H NMR (DMSO-d$_6$, 300 MHz): δ (ppm): 7.88-7.76 (m, 2H), 5.16-5.01 (m, 2H).

Step 2: tert-Butyl 3-(1,3-thiazol-2-ylmethoxy)azetidine-1-carboxylate

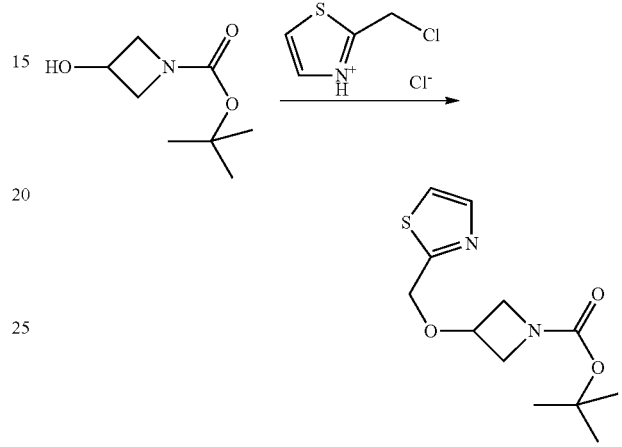

To a solution of N-Boc-azetidin-3-ol (260 mg, 1.5 mmol) in DMF (3.5 mL) at 0° C. under nitrogen was added NaH (60% in oil, 126 mg, 3.15 mmol). The suspension was stirred for 0.5 h at 0° C. then treated with 2-(chloromethyl)-1,3-thiazol-3-ium chloride (510 mg, 3.0 mmol; which may be prepared as described in Step 1) dissolved in DMF (1 mL) and DIPEA (1.05 mL). The mixture was allowed to warm to room temperature then heated to 80° C. overnight. The reaction mixture was cooled, water (20 drops) was added and the mixture concentrated under reduced pressure. The crude material was purified on column chromatography (eluent: Pentane/EtOAc, 90/10 to 50/50) to give the product (193 mg, 48%) as a brown oil.

LCMS (ESI+) m/z 271 (M+H)+: 100%.

Step 3: 2-[(Azetidin-3-yloxy)methyl]-1,3-thiazole hydrochloride

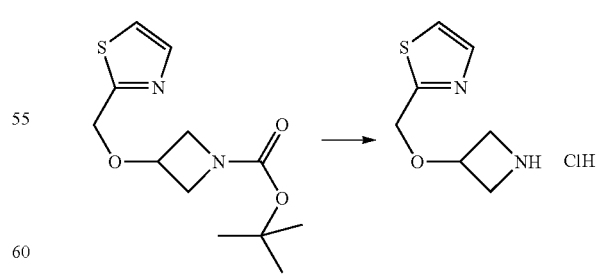

To a solution of tert-butyl 3-(1,3-thiazol-2-ylmethoxy)azetidine-1-carboxylate (193 mg, 0.71 mmol; which may be prepared as described in Step 2) dissolved in diethyl ether (2.6 mL) at room temperature was added HCl 2N in diethyl ether (7.1 mL). The reaction mixture was stirred for 1.5 h then concentrated to dryness. The resulting solid was triturated with diethyl ether, collected and dried to give the title compound (138 mg, quantitative) as a brown oil.

¹H NMR (CDCl₃, 300 MHz): δ (ppm): 9.40-8.90 (m, 2H), 7.89-7.71 (m, 2H), 4.83 (s, 2H), 4.64-4.59 (m, 1H), 4.18-4.03 (m, 2H), 3.91-3.79 (m, 2H).

Step 4: 6-{(1E)-3-Oxo-3-[3-(1,3-thiazol-2-yl-methoxy)azetidin-1-yl]prop-1-en-1-yl}-3,4-dihydro-1,8-naphthyridin-2(1H)-one

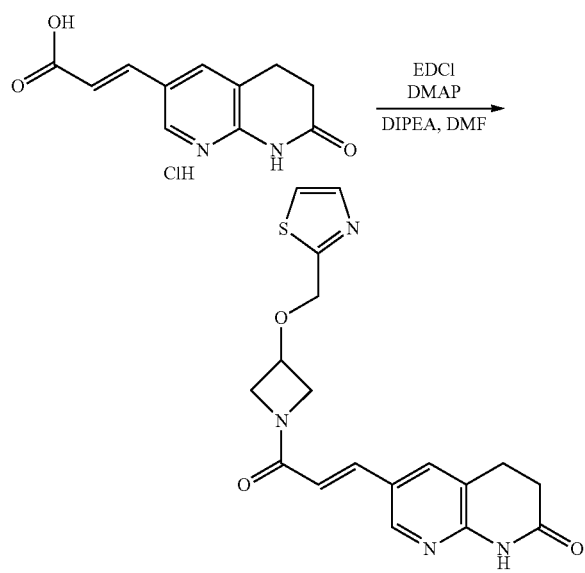

A 16 mL vial flask was successively charged with (2E)-3-(7-oxo-5,6,7,8-tetrahydro-1,8-naphthyridin-3-yl)acrylic acid hydrochloride (60 mg, 0.24 mmol), DMF (5.8 mL), 2-[(azetidin-3-yloxy)methyl]-1,3-thiazole hydrochloride (99 mg, 0.48 mmol; which may be prepared as described in Step 3), DIPEA (119 µL, 0.72 mmol), DMAP (2.4 mg, 0.02 mmol) and EDAC (56 mg, 0.29 mmol). The reaction mixture was stirred at room temperature overnight and concentrated to dryness. The residue was precipitated in methanol/water and then filtered. The resulting solid was purified on column chromatography (eluent: 96/4 dichloromethane/MeOH) then triturated in pentane and MeOH to give the title compound (21 mg, 24%) as a white solid.

LCMS (ESI+) m/z 371 (M+H)⁺: 100%.

¹H NMR (DMSO-d₆, 300 MHz): δ (ppm): 10.66 (br s, 1H), 8.40-8.29 (m, 1H), 8.03-7.99 (m, 1H), 7.84-7.74 (m, 2H), 7.40 (d, J=15.6 Hz, 1H), 6.72 (d, J=15.5 Hz, 0.9H), 6.48 (d, J=16.0 Hz, 0.1H), 4.82 (s, 2H), 4.61-4.45 (m, 2H), 4.20-4.11 (m, 2H), 3.85-3.74 (m, 1H), 2.95-2.84 (m, 2H). The CH₂ missing is hidden by the DMSO signal.

Example 21

6-{(1E)-3-[3-({[(1E)-1-Methyl-2-pyrimidin-2-ylethylidene]amino}oxy)azetidin-1-yl]-3-oxoprop-1-en-1-yl}-3,4-dihydro-1,8-naphthyridin-2(1H)-one (E21)

Step 1: 1-Pyrimidin-2-ylacetone

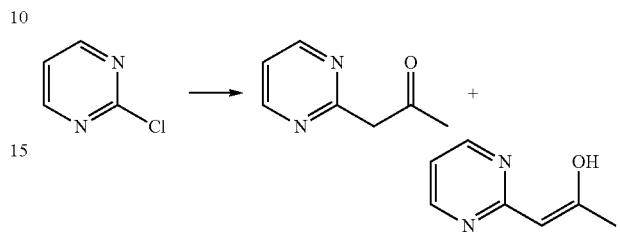

In a 100 mL flask, acetone (1.44 mL, 19.6 mmol) was added to KH (30% in oil, 2.89 g, 21.6 mmol) in THF (15 mL) at 0° C. under nitrogen. The reaction mixture was stirred for 0.25 h then additional THF (15 mL) was added. AIBN (74 mg, 0.45 mmol) followed by 2-chloropyrimidine (500 mg, 4.36 mmol) were added cautiously and the reaction mixture kept at 0° C. for 1 h. HCl 3N was added until the pH=6. The two layers were separated and the aqueous phase extracted with dichloromethane. The combined extracts were dried over Na₂SO₄ then concentrated. The residue was purified on column chromatography (eluent: EtOAc/pentane 20/80 to 80/20) to give the title compound (247 mg, 42%) as a yellow oil (keto/enol form 2:1).

LCMS (ESI+) m/z 137 (M+H)⁺: 100%.

¹H NMR (CDCl₃, 300 MHz): δ (ppm): 13.71-13.67 (m, 0.3H), 8.71 (d, J=5.0 Hz, 2H), 8.60-8.48 (m, 0.8H), 7.21 (t, J=5.0 Hz, 1H), 6.97-6.87 (m, 0.4H), 5.57 (br s, 0.4H), 4.13 (s, 2H), 2.29 (s, 3H), 2.09 (s, 1.2H).

Step 2: 2-{[1-(Diphenylmethyl)azetidin-3-yl]oxy}-1H-isoindole-1,3(2H)-dione

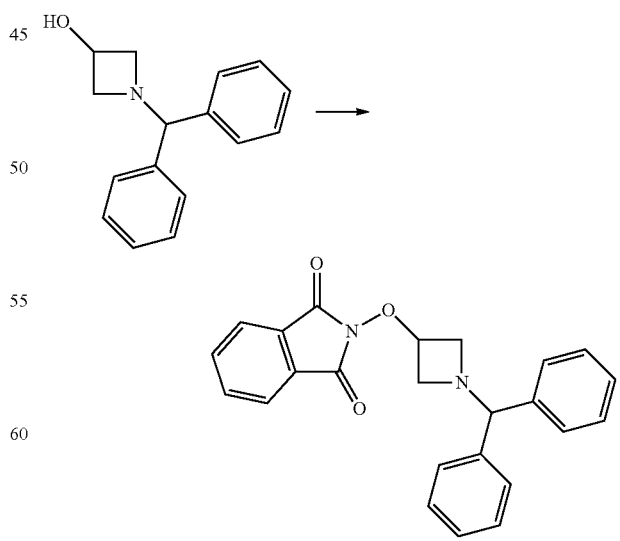

To a solution of N-benzhydrylazetidin-3-ol (1.0 g, 4.18 mmol) in anhydrous THF (66 mL) under nitrogen were added N-hydroxyphthalimide (750 mg, 4.60 mmol) and triphenylphosphine (2.19 g, 8.36 mmol). The reaction mixture was cooled to 0° C. and DEAD (1.52 mL, 8.36 mmol) was added dropwise. The solution was allowed to warm to room temperature and stirred overnight. The reaction mixture was concentrated under reduced. The residue was purified on column chromatography (eluent: pentane/EtOAc 7/3 to 4/6) to give the title compound (600 mg, 37%) as a wax.

LCMS (ESI+) m/z 385 (M+H)$^+$: 100%.

$^1$H NMR (CDCl$_3$, 300 MHz): δ (ppm): 7.88-7.79 (m, 2H), 7.78-7.68 (m, 2H), 7.50-7.35 (m, 4H), 7.30-7.25 (m, 4H), 7.20-7.00 (m, 2H), 4.97-4.86 (m, 1H), 4.49 (s, 1H), 3.62-3.50 (m, 2H), 3.40-3.26 (m, 2H).

Step 3: 3-(Aminooxy)-1-(diphenylmethyl)azetidine

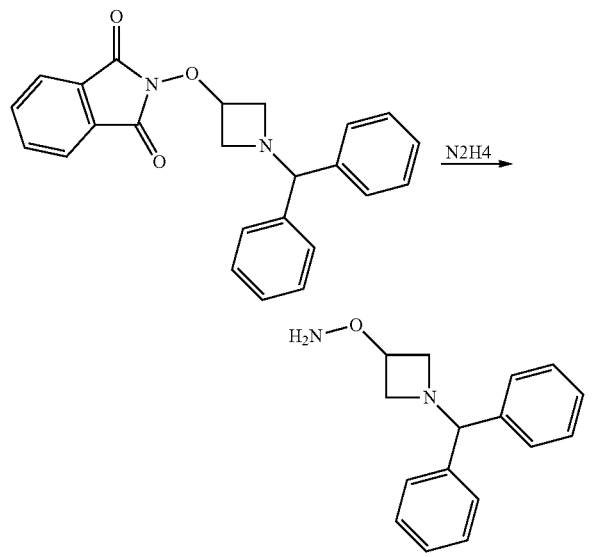

To a solution of 2-{[1-(diphenylmethyl)azetidin-3-yl]oxy}-1H-isoindole-1,3(2H)-dione (600 mg, 1.56 mmol; which may be prepared as described in Step 2) in ethanol (13.3 mL) was added hydrazine hydrate (100 μL, 2.06 mmol). The resulting mixture was heated to reflux for 2 h then concentrated under reduced pressure. The residue was taken up in dichloromethane/methanol mixture then filtered. The filtrate was concentrated and the residue purified on column chromatography (eluent: Dichloromethane/NH$_3$ 7N in MeOH, 2% to 5%) to give the title compound (307 mg, 77%) as a clear oil.

LCMS (ESI+) m/z 255 (M+H)$^+$: 100%.

Step 4: (2E)-1-Pyrimidin-2-ylacetone O-(1-diphenylmethylazetidin-3-yl)oxime

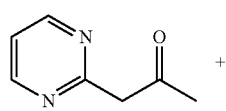 +

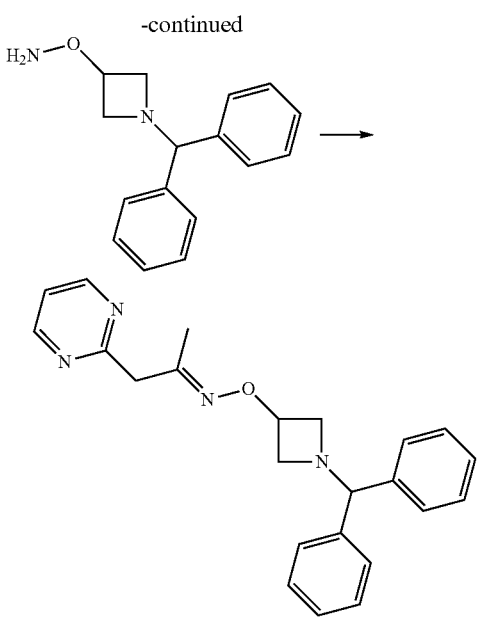

A solution of 1-pyrimidin-2-ylacetone (27 mg, 0.2 mmol; which may be prepared as described in Step 1) and 3-(aminooxy)-1-(diphenylmethyl)azetidine (51 mg, 0.2 mmol; which may be prepared as described in Step 3) in ethanol (2 mL) under nitrogen was stirred at 80° C. overnight. The crude mixture was concentrated to dryness to give the title compound (75 mg, quantitative) as a brown oil.

LC-MS (ESI+) m/z 373 (M+H)$^+$: 100%.

$^1$H NMR (CDCl$_3$, 300 MHz): δ (ppm): 8.69 (dd, J=5.1, 1.5 Hz, 2H), 7.51-7.31 (m, 6H), 7.26-7.11 (m, 5H), 4.98-4.73 (m, 1H), 4.54-4.30 (m, 1H), 4.07 (s, 1H), 3.84 (s, 1H), 3.67-3.40 (m, 2H), 3.18-2.91 (m, 2H), 1.91 (s, 3H).

Step 5: (2E)-1-Pyrimidin-2-ylacetone O-azetidin-3-yloxime hydrochloride

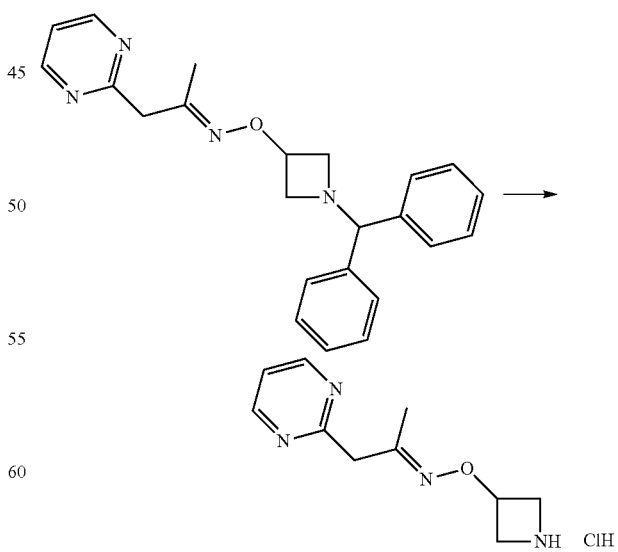

A 25 mL flask was charged with (2E)-1-pyrimidin-2-ylacetone O-(1-diphenylmethylazetidin-3-yl)oxime (372 mg, 1.0 mmol; which may be prepared as described in Step 4) and 1,2-dichloroethane (8.8 mL). 1-Chloroethylchloroformate (576 µL, 5.28 mmol) was added and the reaction mixture was heated to 70° C. for 3 h. After cooling to room temperature, methanol (8.8 mL) was added and the reaction mixture was heated to 70° C. for 3 h. The reaction mixture was concentrated to dryness and the crude mixture triturated in pentane and diethyl ether to give the title compound (240 mg, 99%) as a dark solid.

LCMS (ESI+) m/z 207 (M+H(—HCl))+: 17%.

Step 6: 6-{(1E)-3-[3-({[(±)-1-Methyl-2-pyrimidin-2-ylethylidene]amino}oxy)azetidin-1-yl]-3-oxoprop-1-en-1-yl}-3,4-dihydro-1,8-naphthyridin-2(1H)-one

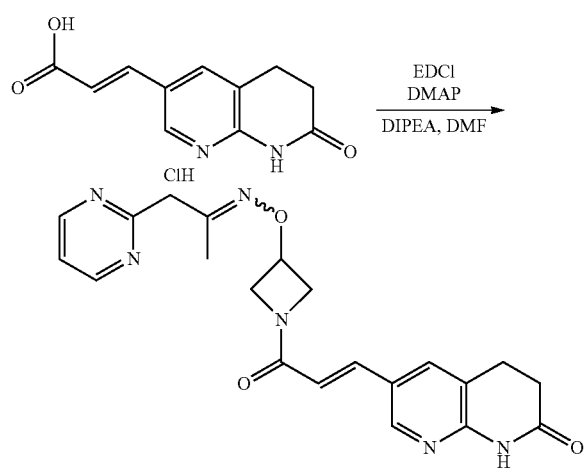

A 16 mL vial was successively charged with (2E)-3-(7-oxo-5,6,7,8-tetrahydro-1,8-naphthyridin-3-yl)acrylic acid hydrochloride (60 mg, 0.24 mmol), DMF (6 mL), (2E)-1-pyrimidin-2-ylacetone O-azetidin-3-yloxime hydrochloride (117 mg, 0.48 mmol; which may be prepared as described in Step 5), DIPEA (160 µL, 0.96 mmol) and DMAP (3 mg, 0.024 mmol). The reaction mixture was cooled to 0° C. and EDAC (56 mg, 0.29 mmol) was added. The reaction mixture was allowed to warm to room temperature, stirred overnight then concentrated to dryness. The crude mixture was purified on column chromatography (eluent: dichloromethane/MeOH, 2% to 6%) then triturated in diethyl ether and dichloromethane to give the product (8 mg, 8%) and as a beige solid.

LCMS (ESI+) m/z 407 (M+H)+: 100%.

$^1$H NMR (DMSO-d$_6$, 300 MHz): δ (ppm): 10.66 (br s, 1H), 8.82-8.71 (2×d, J=4.8 Hz, 1H), 8.40-8.31 (m, 1H), 8.08-7.98 (m, 1H), 7.52-7.17 (m, 3H), 6.81-6.65 (2×d, J=15.9 Hz, 1H), 5.18-4.99 (m, 1H), 4.60-4.40 (m, 1H), 4.32-4.13 (m, 2H), 4.12-4.06 (m, 1H), 4.04-3.77 (m, 2H), 2.98-2.86 (m, 2H), 1.90-1.85 (2×s, 3H). The CH$_2$ missing is hidden by the DMSO signal.

Example 22

6-{(1E)-3-[3-(Pentylsulfonyl)azetidin-1-yl]-3-oxo-prop-1-en-1-yl}-3,4-dihydro-1,8-naphthyridin-2(1H)-one (E22)

Step 1: 1-(Diphenylmethyl)azetidin-3-yl methanesulfonate

To a solution of dibenzylazetidin-3-ol (500 mg, 2.09 mmol) in THF (21 mL) at 0° C. under nitrogen was added methanesulfonyl chloride (194 µL, 2.51 mmol) and triethylamine (612 µL, 4.39 mmol). The reaction mixture was stirred for 1 h then concentrated to dryness. The residue was dissolved in dichloromethane, washed with water and brine. The organic layer was dried over Na$_2$SO$_4$, filtered and concentrated to dryness to give the title product (0.61 g, 92%) as a yellow oil.

LCMS (ESI+) m/z 318 (M+H)+: 20%.

$^1$H NMR (DMSO-d$_6$, 300 MHz): δ (ppm): 7.45-7.14 (m, 10H), 5.16-5.05 (m, 1H), 4.40 (s, 1H), 3.67-3.58 (m, 2H), 3.25-3.14 (m, 2H), 2.99 (s, 3H).

Step 2: 1-(Diphenylmethyl)-3-(pentylthio)azetidine

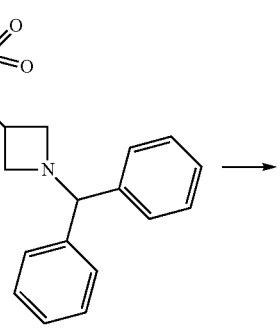

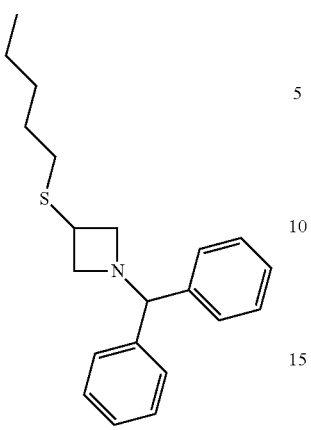

To a solution of pentanethiol (248 μL, 2.0 mmol) in DMSO (2.5 mL) at 0° C. under nitrogen was added NaH (60% in oil, 80 mg, 2.0 mmol). The suspension was stirred for 0.5 h at 0° C. then treated with 1-(diphenylmethyl)azetidin-3-yl methanesulfonate (317 mg, 1.0 mmol; which may be prepared as described in Step 1) and the mixture allowed to warm to room temperature overnight. Saturated NaHCO$_3$ (5 mL) was added and the mixture was extracted with diethyl ether. The organic layer was separated from the aqueous and the organic washed with brine, dried over Na$_2$SO$_4$ and concentrated to give the product (312 mg, 96%) as a yellow oil.

$^1$H NMR (CDCl$_3$, 300 MHz): δ (ppm): 7.83-7.69 (m, 10H), 4.39 (br s, 1H), 3.63-3.49 (m, 3H), 3.01-2.90 (m, 2H), 2.61 (br s, 2H), 2.53-2.43 (m, 2H), 1.56-1.45 (m, 2H), 1.35-1.27 (m, 4H), 0.93-0.82 (m, 3H).

Step 3:
1-(Diphenylmethyl)-3-(pentylsulfonyl)azetidine

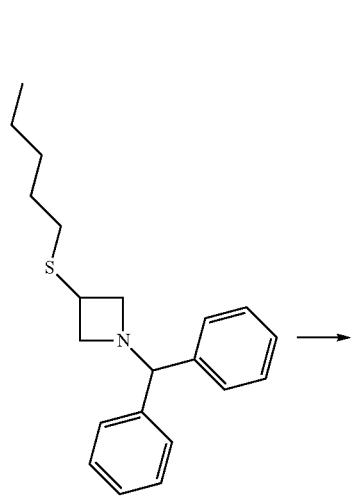

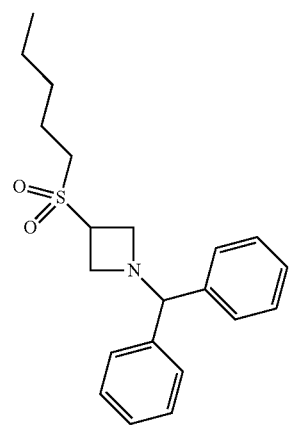

To a solution of 1-(diphenylmethyl)-3-(pentylthio)azetidine (228 mg, 0.70 mmol; which may be prepared as described in Step 2) in methanol (6.3 mL) and water (6.3 mL) was added H$_2$SO$_4$ 1N (0.7 mL). The reaction mixture was stirred for 10 minutes, then oxone (1.08 g, 1.75 mmol) was added and the mixture stirred at room temperature for 12 h. A solution of saturated NaHCO$_3$ (5 mL) was added and the mixture extracted with ethyl acetate. The two layers were separated and the organic washed with brine, dried over Na$_2$SO$_4$, filtered and concentrated. The crude was then purified on column chromatography (pentane/EtOAc, 100/0 then 90/10) to give the title product (75 mg, 30%) as a pale yellow oil. The less pure fraction (N-oxide) can be recycled in hydrogenolysis conditions.

LC-MS (ESI+) m/z 358 (M+H)$^+$: 100%.

$^1$H NMR (CDCl$_3$, 300 MHz): δ (ppm): 7.45-7.15 (m, 10H), 4.51 (s, 1H), 3.97-3.84 (m, 1H), 3.58-3.42 (m, 4H), 2.92-2.83 (m, 2H), 1.84-1.70 (m, 2H), 1.43-1.27 (m, 4H), 0.93-0.85 (m, 3H).

Step 4: 3-(Pentylsulfonyl)azetidine hydrochloride

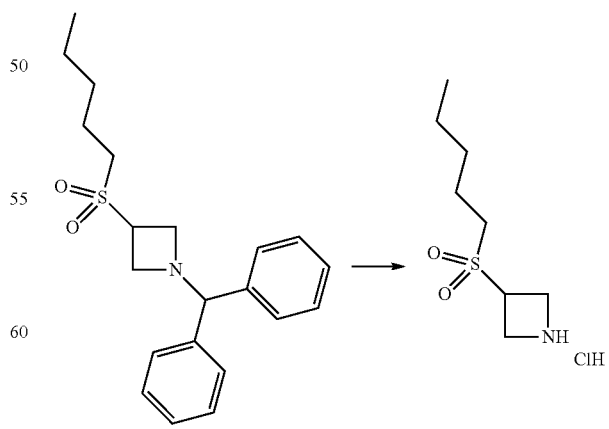

A 16 mL flask was charged with 1-(diphenylmethyl)-3-(pentylsulfonyl)azetidine (136 mg, 0.38 mmol; which may be prepared as described in Step 3) and 1,2-dichloroethane (1.7 mL). 1-Chloroethyl chloroformate (53 μL, 0.49 mmol) was added and the reaction mixture was stirred at 70° C. for 1.5 h. After cooling to room temperature, methanol (1.7 mL) was added and the reaction mixture stirred at 70° C. for 1.5 h. The reaction mixture was concentrated dryness. LCMS analysis showed a mixture of the final product and the starting material. The residue was dissolved again in 1,2-dichloroethane and 1-chloroethyl chloroformate (4 eq., 164 μL) was added. The reaction mixture was stirred at 70° C. for 5 h and overnight after addition of methanol. No starting material was detected by TLC monitoring, so the reaction mixture was concentrated to dryness and the resulting solid triturated in pentane to give the title product (39 mg, 45%) as a dark orange oil.

LCMS (ESI+) m/z 192 (M+H(—HCl))$^+$: 100%.

Step 5: 6-{(1E)-3-[3-(Pentylsulfonyl)azetidin-1-yl]-3-oxoprop-1-en-1-yl}-3,4-dihydro-1,8-naphthyridin-2(1H)-one

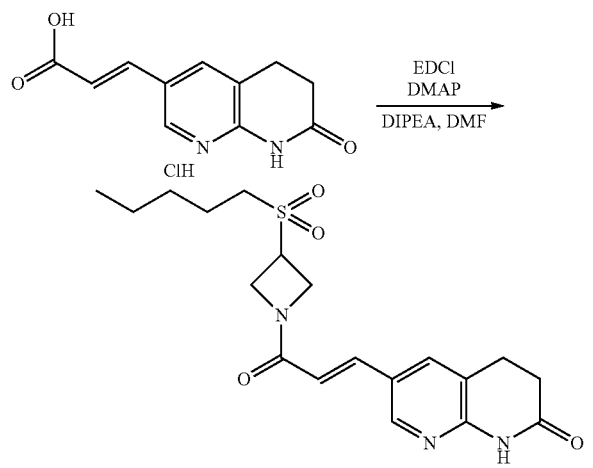

A 16 mL vial flask was successively charged with (2E)-3-(7-oxo-5,6,7,8-tetrahydro-1,8-naphthyridin-3-yl)acrylic acid hydrochloride (40 mg, 0.16 mmol), DMF (3.9 mL), 3-(pentylsulfonyl)azetidine hydrochloride (39 mg, 0.17 mmol; which may be prepared as described in Step 4), DIPEA (106 μL, 0.64 mmol), DMAP (2 mg, 0.02 mmol) and EDAC (36 mg, 0.19 mmol). The reaction mixture was stirred at room temperature overnight and concentrated to dryness. The residue was purified on preparative TLC (eluent: 90/10 DCM/MeOH) then triturated in pentane with a drop of acetone to give the title compound (12 mg, 19%) as a white solid.

LCMS (ESI+) m/z 392 (M+H)$^+$: 100%.

$^1$H NMR (DMSO-d$_6$, 300 MHz): δ (ppm): 10.68 (br s, 1H), 8.41-8.25 (m, 1H), 8.06-7.76 (m, 1H), 7.50-7.36 (m, 1H), 6.84-5.94 (m, 1H), 4.63-4.03 (m, 4H), 3.23-3.11 (m, 2H), 2.97-2.85 (m, 2H), 1.72-1.45 (m, 2H), 1.43-1.22 (m, 4H), 0.92-0.80 (m, 3H). The CH$_2$ missing is hidden by the DMSO signal.

Example 23

5-{(1E)-3-Oxo-3-[3-(pyridin-4-ylmethoxy)azetidin-1-yl]prop-1-en-1-yl}pyridin-2-amine (E23)

Step 1: tert-Butyl (2E)-3-(6-aminopyridin-3-yl)acrylate

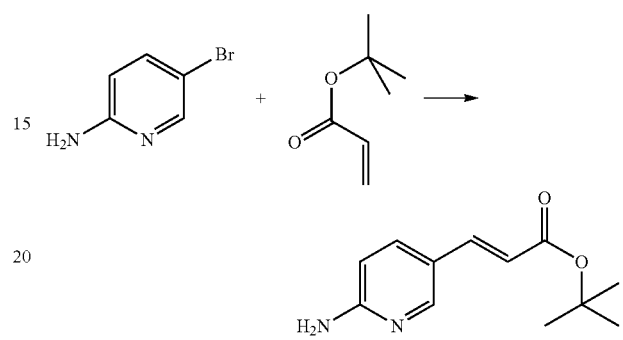

To a solution of 2-amino-5-bromopyridine (300 mg, 1.73 mmol) in DMF (1.5 mL) and proprionitrile (3.5 mL) under Argon were added DIPEA (613 μL, 3.71 mmol), tert-butyl acrylate (1.02 mL, 7.06 mmol), tri(o-tolyl)phosphine (106 mg, 0.35 mmol) and palladium acetate (39 mg, 0.17 mmol). The mixture was stirred at 100° C. for 20 h, then allowed to come back to room temperature, filtered through Celite pad and rinsed with EtOAc. The residue obtained after concentration was purified by flash chromatography (eluent: 95/5 DCM/MeOH) to give the title compound as an orange solid (380 mg, quantitative).

LCMS (ESI+) m/z 221 (M+H)$^+$: 100%.

Step 2: (2E)-3-(6-Aminopyridin-3-yl)acrylic acid hydrochloride

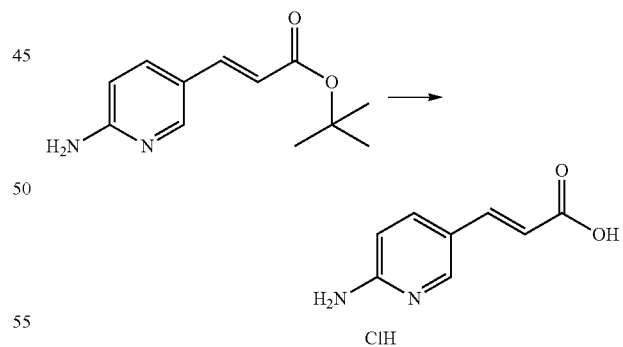

To a solution of tert-butyl (2E)-3-(6-aminopyridin-3-yl)acrylate (380 mg, 1.73 mmol; which may be prepared as described in Step 1) in DCM (3.45 mL) under Argon was added trifluoroacetic acid (3.45 mL). The mixture was stirred at room temperature for 1 h, then HCl 4N in dioxane (6.9 mL) was added. A beige solid started precipitating at the half of the addition. After concentration, the solid was triturated in Et$_2$O, filtered, rinsed with Et$_2$O and dried under vacuum to give the title compound as a beige solid (265 mg, 76%).

LCMS (ESI+) m/z 165 (M−(HCl)+H)$^+$: 100%.

Step 3: tert-Butyl 3-(pyridin-4-ylmethoxy)azetidine-1-carboxylate

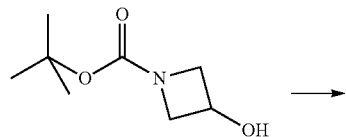

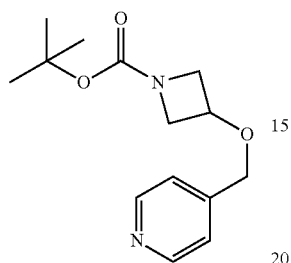

A solution of N-Boc-azetidin-3-ol (500 mg, 2.89 mmol) in THF (10 mL) was cooled to 0° C. t-BuOK (1M in THF, 11.6 mL) was added dropwise and the reaction mixture was stirred at room temperature for 0.25 h then cooled to 0° C. A solution of 4-bromomethylpyridine hydrobromide (2.19 g, 8.67 mmol) in dichloromethane (5 mL) stirred with DIPEA (4 mL, 24 mmol) for 0.5 h was then added. The reaction mixture was stirred at room temperature for 24 h. The reaction mixture was diluted with H$_2$O and extracted twice with EtOAc. The organics were separated from the aqueous layer and combined, dried over Na$_2$SO$_4$ and concentrated to dryness. The crude mixture was purified by column chromatography (eluent: Pentane/EtOAc, 1/1 to 7/3) to give the title product (313 mg, 41%) as a yellow oil.

LCMS (ESI+) m/z 265 (M)+: 28%.

$^1$H NMR (DMSO-d$_6$, 300 MHz): δ (ppm): 8.54 (d, J=5.9 Hz, 2H), 7.34 (d, J=5.9 Hz, 2H), 4.49 (s, 2H), 4.39-4.25 (m, 1H), 4.06-3.90 (m, 2H), 3.80-3.65 (m, 2H), 1.37 (s, 9H).

Step 4: 4-[(Azetidin-3-yloxy)methyl]pyridine dihydrochloride

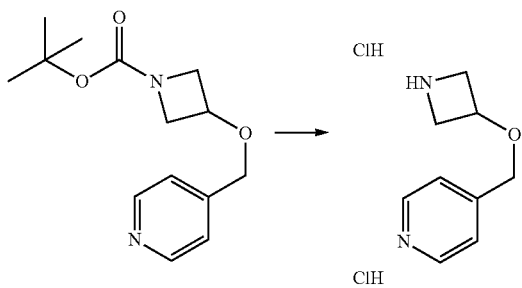 [SMILES: CC(C)(C)OC(=O)N1CC(OCc2ccncc2)C1 ; Cl ; c1cc(COC2CNC2)ccn1 ; Cl]

To a solution of tert-butyl 3-(pyridin-4-ylmethoxy)azetidine-1-carboxylate (313 mg, 1.18 mmol; which may be prepared as described in Step 3) in diethyl ether (4 mL) at 0° C. was added HCl 2N in diethyl ether (12 mL). The reaction mixture was stirred for 1 h then mixture was filtered. The resulting solid was rinsed with diethyl ether and collected to give the title compound as a white solid (155 mg, 65%).

$^1$H NMR (DMSO-d$_6$, 300 MHz): δ (ppm): 9.76-9.17 (m, 2H), 8.92-8.84 (m, 2H), 8.01-7.88 (m, 2H), 4.81 (s, 2H), 4.60-4.46 (m, 1H), 4.23-4.09 (m, 2H), 3.98-3.84 (m, 2H).

Step 5: 5-{(1E)-3-Oxo-3-[3-(pyridin-4-ylmethoxy)azetidin-1-yl]prop-1-en-1-yl}pyridin-2-amine

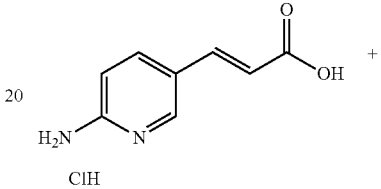

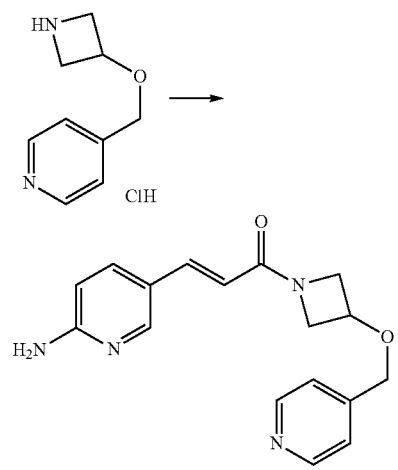

To a solution of (2E)-3-(6-aminopyridin-3-yl)acrylic acid hydrochloride (42 mg, 0.21 mmol; which may be prepared as described in Step 2) in DMF (5 mL) were added 4-[(azetidin-3-yloxy)methyl]pyridine dihydrochloride (50 mg, 0.25 mmol; which may be prepared as described in Step 4), DIPEA (171 μL, 1.04 mmol), DMAP (2.5 mg, 0.02 mmol) and EDAC (48 mg, 0.25 mmol). The reaction mixture was stirred at room temperature overnight and concentrated to dryness. The residue was partitioned between a NaHCO$_3$ 5% solution and DCM. The aqueous phase was extracted twice with DCM, dried over sodium sulfate, filtered and concentrated under vacuum to give an orange solid. The crude was purified on preparative TLC (eluent: 90/10 DCM/MeOH+1% NH$_4$OH) to give the title compound (21 mg, 33%) as a pale yellow solid.

LCMS (ESI+) m/z 156 (M/2+H)$^{2+}$: 100%; m/z 311 (M+H)$^+$: 25%.

$^1$H NMR (DMSO-d$_6$, 400 MHz): δ (ppm): 8.55 (dd, J=1.5, 4.4 Hz, 2H), 8.12 (d, J=2.2 Hz, 1H), 7.75 (dd, J=2.4, 8.8 Hz, 1H), 7.36 (dd, J=1.5, 4.4 Hz, 2H), 7.29 (d, J=15.7 Hz, 1H), 6.47-6.41 (m, 4H), 4.54 (s, 2H), 4.48-4.43 (m, 2H), 4.16-4.09 (m, 2H), 3.83-3.76 (m, 1H)

Example 24

N-(5-{(1E)-3-Oxo-3-[3-(pyridin-4-ylmethoxy)azetidin-1-yl]prop-1-en-1-yl}pyridin-2-yl)acetamide (E24)

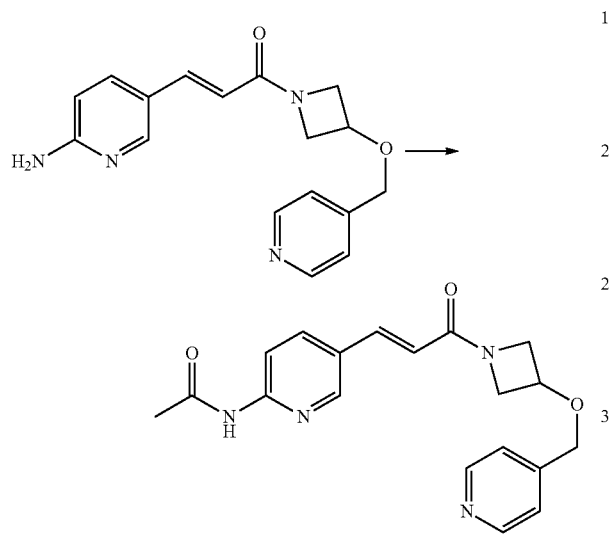

To a solution of 5-{(1E)-3-oxo-3-[3-(pyridin-4-ylmethoxy)azetidin-1-yl]prop-1-en-1-yl}pyridin-2-amine (16 mg, 0.05 mmol) and acetic anhydride (6 µL, 0.06 mmol) in THF (2.4 mL) was added NaHCO$_3$ (5.5 mg, 0.065 mmol). The reaction mixture was warmed at 60° C. and stirred for 40 h. LCMS showed that some starting material was remaining. Another portion of acetic anhydride (6 µL) and NaHCO$_3$ (5.5 mg) were added and the mixture was stirred at 60° C. for 24 h. These additions were repeated twice over 48 h. The mixture was then concentrated, partitioned between water and ethyl acetate. The aqueous layer was extracted twice with ethyl acetate. The combined organic layers were washed with brine, dried over sodium sulfate, filtered and concentrated under vacuum to give an oil. The crude was purified on preparative TLC (eluent: 90/10 DCM/MeOH) to give the title compound (2.3 mg, 12%) as a pale yellow solid.

LCMS (ESI+) m/z 177 (M/2+H)$^{2+}$: 100%; m/z 353 (M+H)$^+$: 22%.

$^1$H NMR (DMSO-d$_6$, 400 MHz): δ (ppm): 10.66 (s, 1H), 8.58-8.54 (m, 3H), 8.14-8.07 (m, 2H), 7.42 (d, J=15.7 Hz, 1H), 7.37 (d, J=5.9 Hz, 2H), 6.76 (d, J=15.7 Hz, 1H), 4.54 (s, 2H), 4.53-4.45 (m, 2H), 4.21-4.13 (m, 2H), 3.86-3.80 (m, 1H), 2.10 (s, 3H)

Example 25

Methyl 6-[(1E)-3-{4-[(4-fluorophenoxy)methyl]piperidin-1-yl}-3-oxoprop-1-en-1-yl]-2-oxo-1,2,3,4-tetrahydro-1,8-naphthyridine-3-carboxylate (E25)

Step 1: tert-Butyl 4-[(4-fluorophenoxy)methyl]piperidine-1-carboxylate

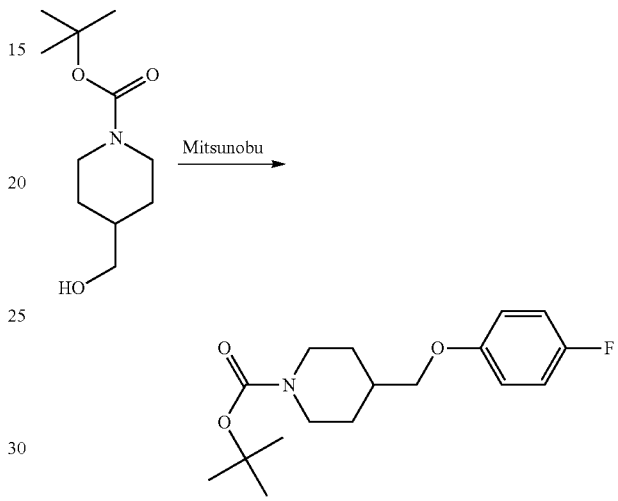

4-Fluorophenol (520 mg, 4.64 mmol) and triphenylphosphine (1.22 g, 4.64 mmol) were added to a solution of N-boc-piperidine-4-methanol (500 mg, 2.32 mmol) in anhydrous THF (12 mL) under nitrogen. The reaction mixture was cooled to 0° C. and DEAD (670 µL, 3.69 mmol) was added dropwise. The solution was allowed to warm to room temperature and stirred overnight. The reaction mixture was concentrated under reduced pressure then diluted with dichloromethane and filtered. The filtrate was washed three times with NaOH 0.2N, dried over Na$_2$SO$_4$ and concentrated. The residue was purified on column chromatography (eluent: pentane/EtOAc 95/5) to give the title compound (538 mg, 75%) as a yellow oil.

$^1$H NMR (DMSO-d$_6$, 300 MHz): δ (ppm): 7.17-7.02 (m, 2H), 6.98-6.88 (m, 2H), 4.02-3.88 (m, 2H), 3.79 (d, J=6.3 Hz, 2H), 2.83-2.60 (m, 2H), 1.96-1.79 (m, 1H), 1.79-1.64 (m, 2H), 1.39 (s, 9H), 1.23-1.04 (m, 2H).

Step 2: 4-[(4-Fluorophenoxy)methyl]piperidine hydrochloride

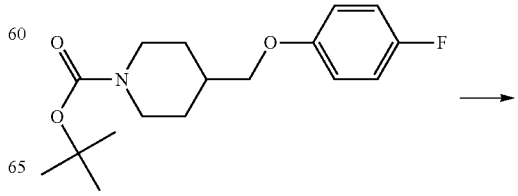

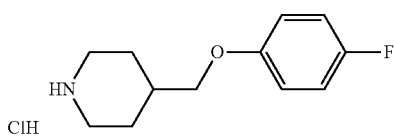

To a cooled solution of tert-butyl 4-[(4-fluorophenoxy)methyl]piperidine-1-carboxylate (538 mg, 1.74 mmol; which may be prepared as described in Step 1) in dichloromethane (11.5 mL) was added dropwise HCl 4N in dioxane (8.5 mL). The solution was warmed to room temperature and stirred for 1 h. The solvent was evaporated under reduced pressure to give the title compound (416 mg, 97%) as a white solid.

$^1$H NMR (DMSO-d$_6$, 300 MHz): δ (ppm): 9.12-8.88 (m, 1H), 8.80-8.56 (m, 1H), 7.17-7.02 (m, 2H), 7.01-6.86 (m, 2H), 3.82 (d, J=6.6 Hz, 2H), 3.32-3.21 (m, 2H), 2.97-2.78 (m, 2H), 2.10-1.95 (m, 1H), 1.94-1.81 (m, 2H), 1.58-1.37 (m, 2H).

Step 3: Methyl 6-[(1E)-3-tert-butoxy-3-oxoprop-1-en-1-yl]-2-oxo-1,2,3,4-tetrahydro-1,8-naphthyridine-3-carboxylate

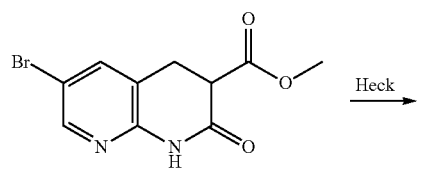

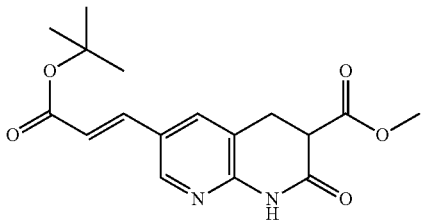

To a suspension of methyl 6-bromo-2-oxo-1,2,3,4-tetrahydro-1,8-naphthyridine-3-carboxylate (300 mg, 1.06 mmol), prepared as in *J. Med. Chem.* 2003, 46, 9, 1627-1635, in DMF (1 mL) and proprionitrile (3.5 mL) under Argon were added DIPEA (175 µL, 2.271 mmol), tert-butyl acrylate (615 mL, 4.24 mmol), tri(o-tolyl)phosphine (64 mg, 0.21 mmol) and palladium acetate (48 mg, 0.21 mmol). The mixture was stirred at 100° C. overnight. LCMS analysis showed that some unreacted starting material was remaining, so 24 mg of palladium acetate and 64 mg of tri(o-tolyl)phosphine were added. After 5 h at 100° C., the reaction was allowed to come back to room temperature, filtered through Celite pad and rinsed with methanol. The residue obtained after concentration was purified by flash chromatography (eluent: gradient DCM/EtOAc) to give the title compound as an orange solid (115 mg, 32%) contaminated with traces of tri(o-tolyl)phosphine oxide.

LCMS (ESI+) m/z 333 (M+H)$^+$: 100%.

Step 4: (2E)-3-[6-(Methoxycarbonyl)-7-oxo-5,6,7,8-tetrahydro-1,8-naphthyridin-3-yl]acrylic acid

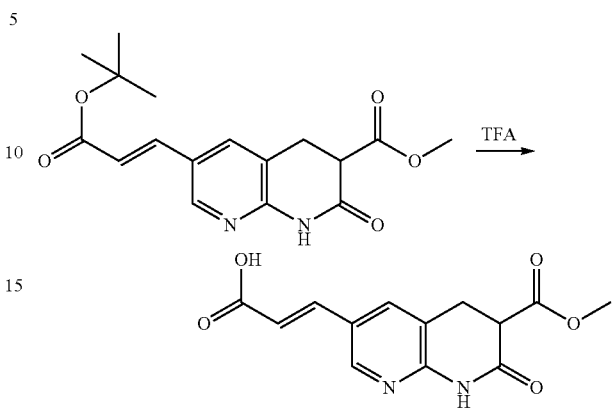

To a solution of methyl 6-[(1E)-3-tert-butoxy-3-oxoprop-1-en-1-yl]-2-oxo-1,2,3,4-tetrahydro-1,8-naphthyridine-3-carboxylate (115 mg, 0.346 mmol; which may be prepared as described in Step 3) in DCM (693 µL) at 0° C. under Argon was added TFA (693 µL). The reaction was allowed to come back to room temperature under stirring for 2 h and then concentrated under vacuo to give the title compound (103 mg, quantitative) as a brown solid. The product was used without further purification.

LCMS (ESI+) m/z 277 (M+H)$^+$: 100%.

Step 5: Methyl 6-[(1E)-3-{4-[(4-fluorophenoxy)methyl]piperidin-1-yl}-3-oxoprop-1-en-1-yl]-2-oxo-1,2,3,4-tetrahydro-1,8-naphthyridine-3-carboxylate

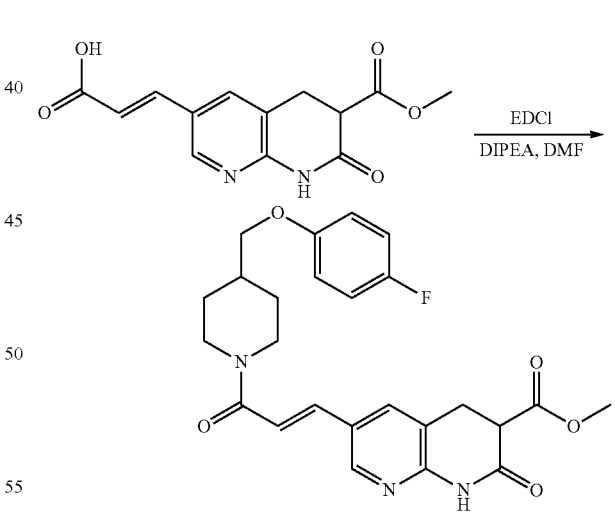

To a solution of (2E)-3-[6-(methoxycarbonyl)-7-oxo-5,6,7,8-tetrahydro-1,8-naphthyridin-3-yl]acrylic acid (96 mg, 0.35 mmol; which may be prepared as described in Step 4) in DMF (8 mL) were added 4-[(4-fluorophenoxy)methyl]piperidine hydrochloride (102 mg, 0.42 mmol; which may be prepared as described in Step 2), DIPEA (144 µL, 0.83 mmol), 4-DMAP (17 mg, 0.14 mmol) and EDAC (80 mg, 0.42 mmol). The reaction mixture was stirred at room temperature overnight and concentrated to dryness. The residue was purified by flash chromatography on silica gel (eluent:

dichloromethane/MeOH from 100/0 to 80/20) to give a first solid which is purified again on preparative TLC (eluent: dichloromethane/MeOH 95/5) to give the title compound (15 mg, 8%) as a white solid.

LCMS (ESI+) m/z 468 (M+H)$^+$: 100%.

$^1$H NMR (CDCl$_3$, 400 MHz): δ (ppm): 10.23 (s, 1H), 8.44 (s, 1H), 7.69 (s, 1H), 7.60 (d, J=16.0 Hz, 1H), 6.99-6.89 (m, 3H), 6.83-6.80 (m, 2H), 4.85-4.71 (m, 1H), 4.21-4.10 (m, 1H), 3.84-3.74 (m, 5H), 3.71 (t, J=6.9 Hz, 1H), 3.45-3.38 (m, 1H), 3.20-3.14 (m, 2H), 2.80-2.68 (m, 1H), 2.15-2.03 (m, 1H), 2.03-1.88 (m, 2H), 1.40-1.34 (m, 2H).

Examples 26 and 27

6-[(1E)-3-{4-[(4-Fluorophenoxy)methyl]piperidin-1-yl}-3-oxoprop-1-en-1-yl]-2-oxo-1,2,3,4-tetrahydro-1,8-naphthyridine-3-carboxamide (E26); and 6-[(1E)-3-{4-[(4-Fluorophenoxy)methyl]piperidin-1-yl}-3-oxoprop-1-en-1-yl]-2-oxo-1,2-dihydro-1,8-naphthyridine-3-carboxamide (E27)

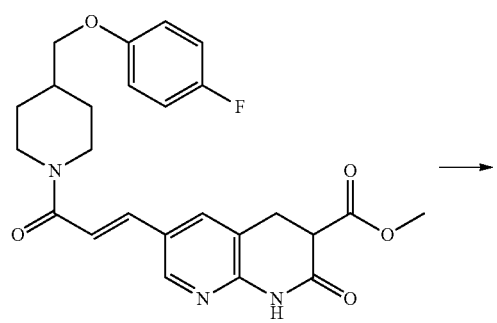

Example 26

Example 27

A solution of methyl 6-[(1E)-3-{4-[(4-fluorophenoxy)methyl]piperidin-1-yl}-3-oxoprop-1-en-1-yl]-2-oxo-1,2,3,4-tetrahydro-1,8-naphthyridine-3-carboxylate (13 mg, 0.028 mmol) in ammonium hydroxide (33% in water, 0.5 mL) and in ammonia (2M in ethanol, 0.5 mL) was stirred at 90° C. for 1 h 30. The mixture was concentrated to dryness and the residue was purified on preparative TLC (eluent: dichloromethane/MeOH 90/10) to give 6-[(1E)-3-{4-[(4-fluorophenoxy)methyl]piperidin-1-yl}-3-oxoprop-1-en-1-yl]-2-oxo-1,2,3,4-tetrahydro-1,8-naphthyridine-3-carboxamide (1.6 mg, 12%) as a white solid.

LCMS (ESI+) m/z 453 (M+H)$^+$: 100%.

$^1$H NMR (CDCl$_3$, 400 MHz): δ (ppm): 8.52 (s, 1H), 8.29 (s, 1H), 7.77 (s, 1H), 7.60 (d, J=16.0 Hz, 1H), 7.17 (br s, 1H), 7.02-6.94 (m, 2H), 6.90 (d, J=15.0 Hz, 1H), 6.85-6.80 (m, 2H), 5.50 (br s, 1H), 4.84-4.72 (m, 1H), 4.22-4.12 (m, 1H), 3.84-3.74 (m, 2H), 3.56 (t, J=7.4 Hz, 1H), 3.50-3.38 (m, 1H), 3.31-3.14 (m, 2H), 2.80-2.70 (m, 1H), 2.16-1.88 (m, 3H), 1.44-1.32 (m, 2H).

The second isolated fraction gave the oxidized derivative (6-[(1E)-3-{4-[(4-fluorophenoxy)methyl]piperidin-1-yl}-3-oxoprop-1-en-1-yl]-2-oxo-1,2-dihydro-1,8-naphthyridine-3-carboxamide) as a white solid (2.3 mg, 18%).

LCMS (ESI+) m/z 451 (M+H)$^+$: 100%.

$^1$H NMR (DMSO-d$_6$, 400 MHz): δ (ppm): 12.92 (s, 1H), 9.00 (d, J=2.0 Hz, 1H), 8.90 (d, J=3.9 Hz, 1H), 8.79-8.77 (m, 2H), 7.84 (d, J=4.3 Hz, 1H), 7.55 (d, J=15.0 Hz, 1H), 7.44 (d, J=15.0 Hz, 1H), 7.13-7.08 (m, 2H), 6.97-6.93 (m, 2H), 4.58-4.50 (m, 1H), 4.40-4.32 (m, 1H), 3.84 (d, J=6.4 Hz, 2H), 3.22-3.12 (m, 1H), 2.77-2.68 (m, 1H), 2.12-1.96 (m, 1H), 1.92-1.80 (m, 2H), 1.30-1.12 (m, 2H).

Example 28

3-(Hydroxymethyl)-6-[(1E)-3-{4-[(4-fluorophenoxy)methyl]piperidin-1-yl}-3-oxoprop-1-en-1-yl]-3,4-dihydro-1,8-naphthyridin-2(1H)-one (E28)

Step 1:
1-Acryloyl-4-[(4-fluorophenoxy)methyl]piperidine

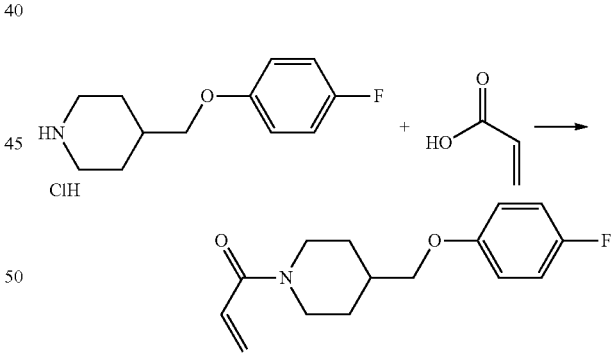

To a solution of acrylic acid (34 μL, 0.49 mmol) in dichloromethane (2.4 mL) cooled at 0° C. was added 4-methylmorpholine (134 μL, 1.22 mol) and isobutyl chloroformate (74 μL, 0.57 mmol). The solution was stirred 15 minutes at 0° C. and then 4-[(4-fluorophenoxy)methyl]piperidine hydrochloride (100 mg, 0.41 mmol) was added. The mixture was stirred at room temperature overnight, diluted with water (7 mL) and extracted twice with DCM (2×5 mL). The combined organic phases were washed with water, dried over sodium sulphate and concentrated in vacuo. The residue obtained was purified by preparative TLC (eluent: dichloromethane/MeOH 95/5) to give the title compound (30 mg, 28%) as a yellow oil.

LCMS (ESI+) m/z 264 (M+H)$^+$: 100%.

Step 2: 6-Bromo-3-(hydroxymethyl)-3,4-dihydro-1,8-naphthyridin-2(1H)-one

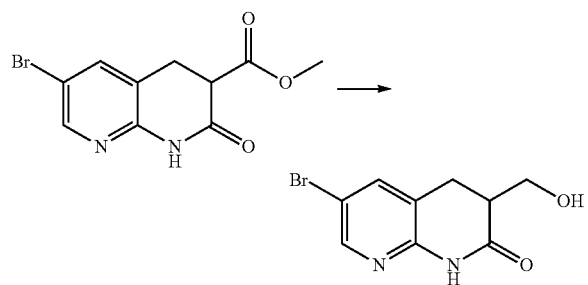

To a suspension of methyl 6-bromo-2-oxo-1,2,3,4-tetrahydro-1,8-naphthyridine-3-carboxylate (285 mg, 1 mmol) in THF (10 mL) under Argon at room temperature was added sodium borohydride (151 mg, 4 mmol). The reaction mixture was stirred at 60° C. for 4 h, then diluted in EtOAc and washed four times with a NH$_4$Cl solution (pH=6.5). The white organic phase was filtered to give the title compound contaminated by impurities as a white solid (59 mg). The filtrate was dried over sodium sulphate, filtered and concentrated in vacuo to give a yellow solid (143 mg). The crude was purified by preparative TLC (eluent: dichloromethane/MeOH 93/7) to give the title compound (10 mg, 4%) as a white solid.

LCMS (ESI+) m/z 257/259 (M+H)$^+$: 100%.

Step 3: 3-(Hydroxymethyl)-6-[(1E)-3-{4-[(4-fluorophenoxy)methyl]piperidin-1-yl}-3-oxoprop-1-en-1-yl]-3,4-dihydro-1,8-naphthyridin-2(1H)-one

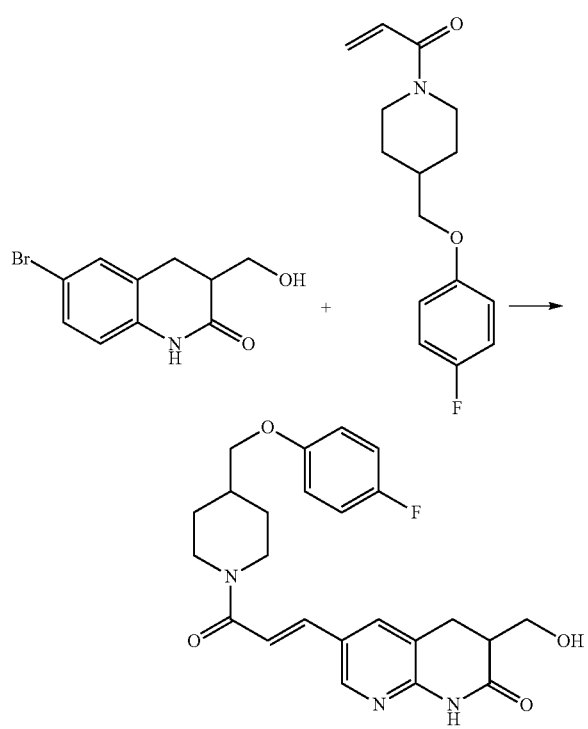

To a suspension of 6-bromo-3-(hydroxymethyl)-3,4-dihydro-1,8-naphthyridin-2(1H)-one (10 mg, 0.039 mmol; which may be prepared as described in Step 2) in DMF (200 µL) and proprionitrile (200 µL) under Argon were added DIPEA (8 µL, 0.047 mmol), 1-acryloyl-4-[(4-fluorophenoxy)methyl]piperidine (14 mg, 0.053 mmol; which may be prepared as described in Step 1), tri(o-tolyl)phosphine (2 mg, 0.008 mmol) and palladium acetate (1 mg, 0.004 mmol). The mixture was stirred at 100° C. for 2 days, then was allowed to come back to room temperature, filtered through Celite pad. The residue obtained after concentration of the filtrate was purified by preparative TLC (eluent: DCM/MeOH 9/1) to give the title compound as a white solid (1 mg, 6%).

LCMS (ESI+) m/z 440 (M+H)$^+$: 100%.

$^1$H NMR (CDCl$_3$, 400 MHz): δ (ppm): 8.31 (s, 1H), 8.20 (br s, 1H), 7.70-7.58 (m, 2H), 6.99-6.80 (m, 5H), 4.84-4.72 (m, 1H), 4.22-4.10 (m, 1H), 4.03-3.87 (m, 2H), 3.85-3.72 (m, 2H), 3.25-3.13 (m, 1H), 3.03-2.61 (m, 5H), 2.15-1.87 (m, 3H), 1.44-1.31 (m, 2H).

Example 29

(E)-6-(3-Oxo-3-(3-(2-(thiophen-2-yl)ethoxy)azetidin-1-yl)prop-1-enyl)-3,4-dihydro-1,8-naphthyridin-2(1H)-one (E29)

Step 1: 1-Benzhydrylazetidin-3-yl methanesulfonate

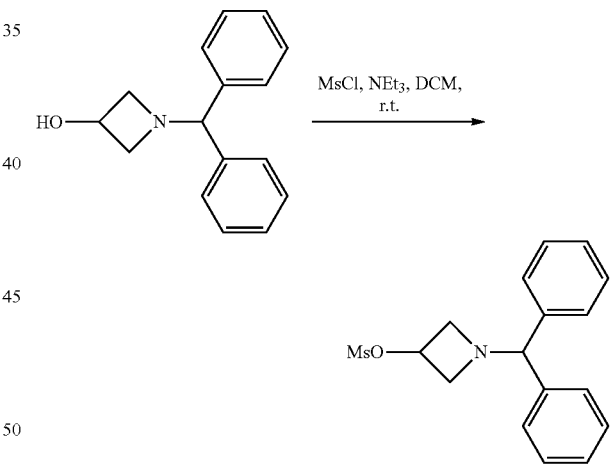

Triethylamine (870 ml, 62.67 mmol) and mesyl chloride (390 µL, 50.13 mmol) were successively added to a solution of 1-benzhydrylazetan-3-ol (1.0 g, 41.78 mmol) in dichloromethane (10 mL) at room temperature. The reaction mixture was stirred for 1 hour and then diluted by addition of water (20 mL). The aqueous phase was separated and extracted with dichloromethane (2×40 mL). The combined organic phases were washed with a saturated solution of sodium chloride (40 mL), dried over sodium sulfate, filtered and concentrated to dryness. The title compound was obtained as a yellow solid (1.5 g, 100%).

$^1$H NMR (CDCl$_3$, 400 MHz): δ (ppm): 7.41-7.19 (m, 10H), 5.12 (q, J=6 Hz, 1H), 4.41 (s, 1H), 3.68-3.66 (m, 2H), 3.23-2.21 (m, 2H), 2.99 (s, 3H).

Step 2: 1-Benzhydryl-3-(2-(thiophen-2-yl)ethoxy)azetidine

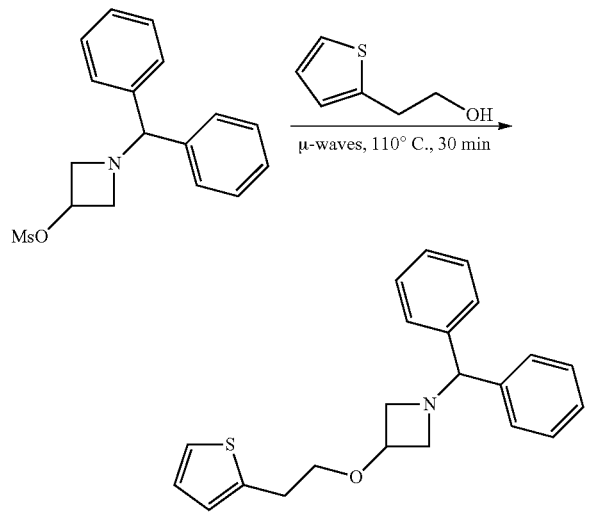

A solution of 1-benzhydrylazetidin-3-yl methanesulfonate (324 mg, 1.0 mmol) in thiophene ethanol (2.3 mL, 20.4 mmol) was stirred under microwave irradiations (100 W) at 110° C. for 30 minutes. The reaction mixture was then partitioned between dichloromethane (20 mL) and a solution of sodium hydroxyde (1N, 10 mL). The aqueous layer was separated and extracted with dichloromethane (2×10 mL). The combined organic phases were dried over sodium sulfate, filtered and concentrated to dryness. The residue was purified by chromatography on silica gel, using petroleum ether/ethyl acetate (85:15) as eluent. The title product was obtained as a yellow solid (210 mg, 59%).

LCMS (ESI-APCI) m/z 350.2 (M+H)$^+$

Step 3: 3-(2-(Thiophen-2-yl)ethoxy)azetidine hydrochloride

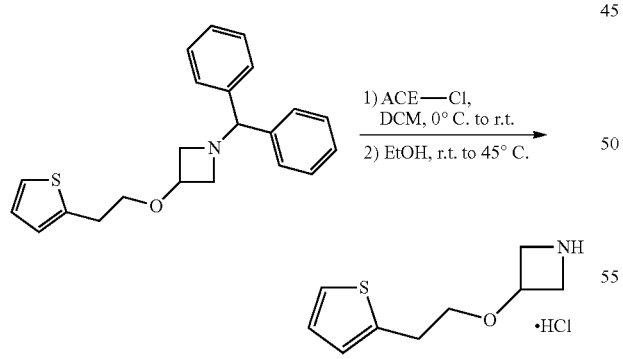

1-Chloroethylchloroformate (361 µL, 3.33 mmol) was added to a solution of 1-benzhydryl-3-(2-(thiophen-2-yl)ethoxy)azetidine (1.11 g, 3.17 mmol) in dichloromethane (15 mL) at room temperature. The reaction mixture was stirred overnight at room temperature, then 1 hour at 70° C. After cooling down to room temperature, ethanol (15 mL) was added and the reaction mixture was stirred at 70° C. for 1 hour. After concentration to dryness, the crude mixture was triturated in pentane (2×15 mL) to give a yellow oil (698 mg, quantitative) which was used in the next step without further purification.

LCMS (ESI-APCI) m/z 184.2 (M+H)$^+$

Step 4: (E)-6-(3-Oxo-3-(3-(2-(thiophen-2-yl)ethoxy)azetidin-1-yl)prop-1-enyl)-3,4-dihydro-1,8-naphthyridin-2(1H)-one

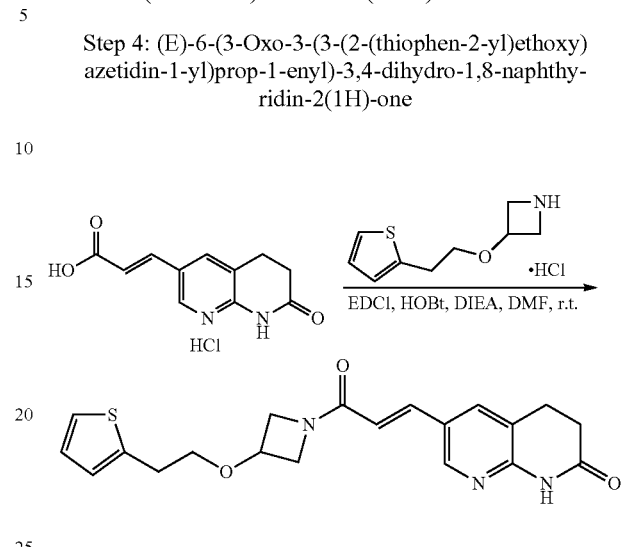

3-(2-(Thiophen-2-yl)ethoxy)azetidine hydrochloride (128 mg, 0.6 mmol), EDCI (113 mg, 0.6 mmol), HOBt (80 mg, 0.6 mmol) and diisopropylethylamine (170 µL, 1.0 mmol) were successively added to a solution of (E)-3-(7-oxo-5,6,7,8-tetrahydro-1,8-naphthyridin-3-yl)-acrylic acid hydrochloride (100 mg, 0.4 mmol) in dimethylformamide (10 mL) at room temperature. The reaction mixture was stirred overnight and then partitioned between ethyl acetate (40 mL) and water (20 mL). The aqueous layer was separated and extracted with ethyl acetate (2×20 mL). The combined organic phases were washed with a saturated solution of sodium chloride (3×30 mL), dried over sodium sulfate and concentrated to dryness. The residue was purified by chromatography on silica gel, using dichloromethane/methanol (99:1 to 95:5) as eluent. The residue was triturated with acetone to give a white solid (40 mg, 27%).

LCMS (ESI-APCI) 384.1 m/z (M+H)$^+$ $^1$H NMR (DMSO-d$_6$, 400 MHz): δ (ppm): 10.68 (s, NH), 8.34 (s, 1H), 8.01 (s, 1H), 7.4 (d, J=15.6 Hz, 1H), 7.36-7.33 (m, 1H), 6.97-6.82 (m, 2H), 6.72 (d, J=15.6 Hz, 1H), 4.50-4.38 (m, 2H), 4.14-4.03 (m, 2H), 3.77-3.70 (m, 1H), 3.63-3.59 (m, 2H), 3.07 (t, J=6.2 Hz, 2H), 2.91 (t, J=7.6 Hz, 2H), 2.5 (t, J=7.6 Hz, 2H). The CH$_2$ at 2.5 ppm is partially hidden by DMSO.

Example 30

(E)-6-(3-Oxo-3-(3-(3-(thiophen-2-yl)propoxy)azetidin-1-yl)prop-1-enyl)-3,4-dihydro-1,8-naphthyridin-2(1H)-one (E30)

Step 1: 3-(2-Thienyl)propanol

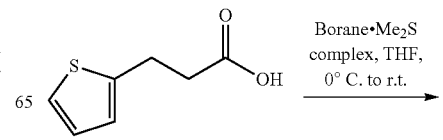

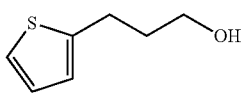

Borane methylsulfide complex (6.4 mL, 12.8 mmol) was added to a solution of 3-(2-thienyl)propanoic acid (1.0 g, 6.4 mmol) in THF (18 mL) at 0° C. The reaction mixture was stirred at 0° C. for 2 hours and at room temperature for 3 additional hours. After cooling down to 0° C., the reaction was quenched by addition of a saturated solution of potassium carbonate (5 mL). The aqueous layer was separated and extracted with ethyl acetate (2×15 mL) and diethyl ether (2×15 mL). The combined organic phases were dried over sodium sulfate, filtered and concentrated to dryness. The title compound was obtained as a colorless oil (1.0 g, 100%).

$^1$H NMR (CDCl$_3$, 400 MHz): δ (ppm): 7.18-7.17 (m, 1H), 6.99-6.96 (m, 1H), 6.87-6.86 (m, 1H), 3.79-3.74 (m, 2H), 3.0 (t, J=7.6 Hz, 2H), 2.4-1.97 (m, 2H).

Step 2: 2-(3-Chloropropyl)thiophene

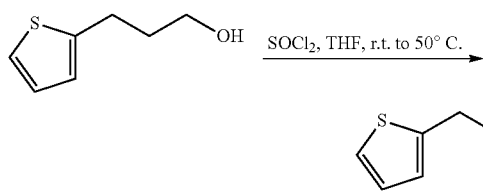

Thionyl chloride (420 μL, 5.7 mmol) was added to a solution of 3-(2-thienyl)propanol (682.0 mg, 4.8 mmol) in THF (3 mL) at room temperature. The reaction mixture was stirred at 50° C. for 2 hours and then concentrated to dryness to afford the title compound as a brown oil. The product was used in the next step without further purification.

$^1$H NMR (DMSO-d$_6$, 400 MHz): δ (ppm): 7.34-7.32 (m, 1H), 6.96-6.94 (m, 1H), 6.89-6.88 (m, 1H), 3.69-3.63 (m, 2H), 2.84 (t, J=7.6 Hz, 2H), 2.08-2.01 (m, 2H).

Step 3:
1-Benzhydryl-3-(3-(thiophen-2-yl)propoxy)azetidine

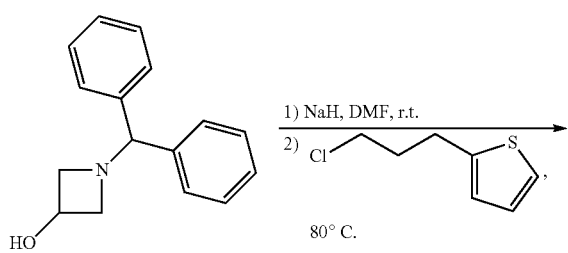

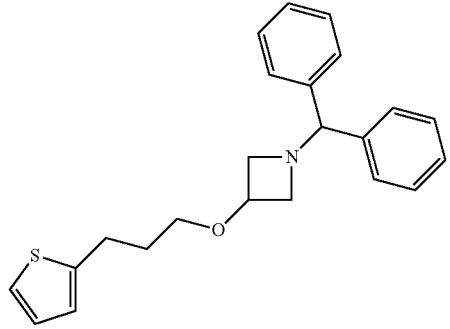

Sodium hydride (60% in oil, 200.0 mg, 5 mmol) was added to a solution of 1-benzhydryl-3-azetidin-3-ol (500.0 mg, 2.1 mmol) in dimethylformamide (3 mL) at room temperature. The mixture was stirred for 30 minutes prior to the addition of 2-(3-chloropropyl)thiophene (772.0 mg, 4.8 mmol) in solution in dimethylformamide (2 mL). The reaction mixture was stirred at 80° C. overnight then concentrated to dryness. The residue was partitioned between ethyl acetate (30 mL) and water (30 mL). The aqueous layer was separated and extracted with ethyl acetate (2×15 mL). The combined organic phases were washed with a saturated solution of sodium chloride (3×30 mL), dried over sodium sulfate, filtered and concentrated to dryness. The residue was purified by chromatography on silica gel, using petroleum ether/ethyl acetate (99:1 to 90:10) as eluent. The title product was obtained as a yellow oil (320 mg, 42%).

LCMS (ESI-APCI) m/z 364.2 (M+H)$^+$

Step 4:
3-(4-Methyl-thiophen-2-ylmethoxy)-azetidine hydrochloride

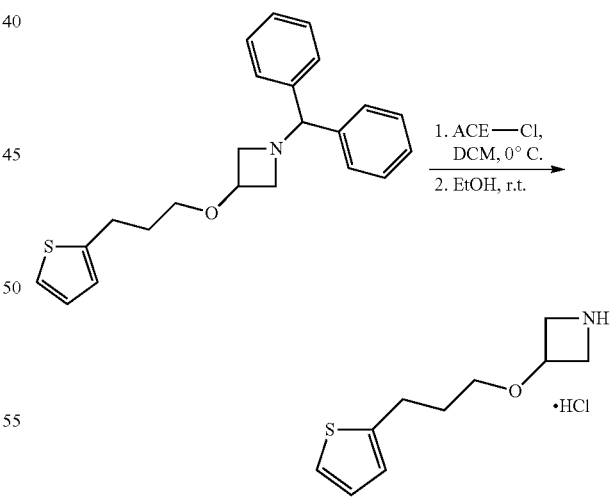

1-Chloroethyl chloroformate (65.5 μL, 21.5 mmol) was added to a solution of 1-benzhydryl-3-(3-(thiophen-2-yl)propoxy)azetidine (220 mg, 0.61 mmol) in dichloromethane (7 mL) at 0° C. The reaction mixture was stirred 2 hours at 0° C. and then allowed to warm up to room temperature. Ethanol (9 mL) was added and the reaction mixture was stirred for 2 additional hours at room temperature. After concentration to dryness, the crude mixture was triturated in pentane (2×15 mL) to give a brown solid (140 mg, quantitative) which was used in the next step without further purification.

LCMS (ESI-APCI) m/z 198.2 (M+H)+

Step 5: (E)-6-(3-Oxo-3-(3-(3-(thiophen-2-yl)propoxy)azetidin-1-yl)prop-1-enyl)-3,4-dihydro-1,8-naphthyridin-2(1H)-one

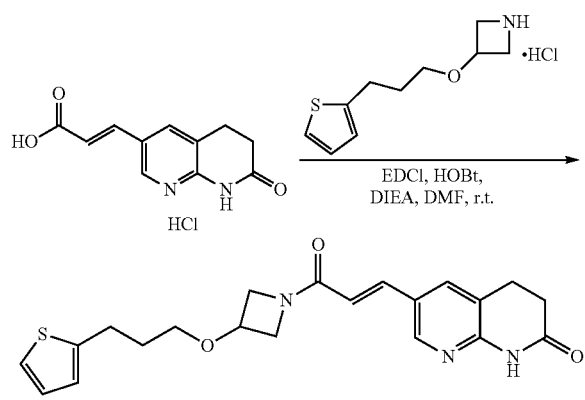

3-(4-Methyl-thiophen-2-ylmethoxy)-azetidine hydrochloride (128.0 mg, 0.6 mmol), EDCI (113. mg, 0.6 mmol), HOBt (80.0 mg, 0.6 mmol) and diisopropylethylamine (170 µL, 1.0 mmol) were successively added to a solution of (E)-3-(7-oxo-5,6,7,8-tetrahydro-1,8-naphthyridin-3-yl)-acrylic acid hydrochloride (100.0 mg, 0.4 mmol) in dimethylformamide (10 mL) at room temperature. The reaction mixture was stirred overnight and then partitioned between ethyl acetate (30 mL) and water (30 mL). The aqueous layer was separated and extracted with ethyl acetate (2×20 mL). The combined organic phases were washed with a saturated solution of sodium chloride (3×30 mL), dried over sodium sulfate, filtered and concentrated to dryness. The residue was purified by chromatography on silica gel using dichloromethane/methanol (99:1 to 95:5) as eluent. The residue was triturated in acetone to give the title compound as a white solid (40.0 mg, 27%).

LCMS (ESI-APCI) 398.1 m/z (M+H)+

$^1$NMR (DMSO-$d_6$, 400 MHz): δ (ppm): 10.69 (br s, NH), 8.34 (s, 1H), 8.02 (s, 1H), 7.40 (d, J=15.6 Hz, 1H), 7.34-7.31 (m, 1H), 6.96-6.94 (m, 1H), 6.88-6.87 (m, 1H), 6.72 (d, J=15.6 Hz, 1H), 4.49-4.47 (m, 1H), 4.45 (m, 1H), 4.34-4.06 (m, 2H), 3.76-3.72 (m, 1H), 3.42 (t, J=7.6 Hz, 2H), 2.92-2.85 (m, 4H), 2.55 (t, J=7.6 Hz, 2H), 1.9-1.83 (m, 2H). The CH$_2$ at 2.5 ppm is partially hidden by DMSO.

Example 31

(E)-6-(3-(3-((3-Methylthiophen-2-yl)methoxy)azetidin-1-yl)-3-oxoprop-1-enyl)-3,4-dihydro-1,8-naphthyridin-2(1H)-one (E31)

Step 1: (3-Methylthiophen-2-yl)methanol

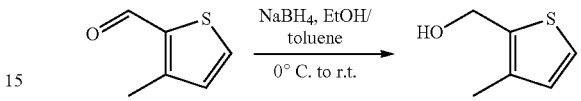

Sodium borohydride (718 mg, 19.02 mmol) was added portionwise, at 0° C., to a solution of 3-methylthiophene-2-carbaldehyde (2.0 g, 15.85 mmol) in a mixture of ethanol and toluene (1:1, 12 mL). The reaction mixture was stirred 2 hours at room temperature and then partitioned between ethyl acetate (15 mL) and water (15 mL). The aqueous layer was separated and extracted with ethyl acetate (3×45 mL). The combined organic phases were washed with a saturated solution of sodium chloride (1×10 mL), dried over sodium sulfate, filtered and concentrated under vacuum to give the title product as a pink oil (2.24 g, 99%).

$^1$NMR (CDCl$_3$, 400 MHz): δ (ppm): 7.16 (d, J=5.2 Hz, 1H), 6.84 (d, J=5.2 Hz, 1H), 4.76 (s, 2H), 2.23 (s, 3H).

Step 2: 2-(Chloromethyl)-3-methylthiophene

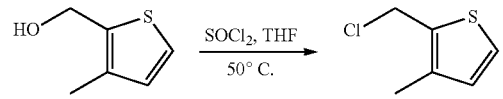

Thionyl chloride (430 µL, 5.8 mmol) was added at 0° C. to a solution of (3-methylthiophen-2-yl)methanol (624 mg, 4.8 mmol) in tetrahydrofuran (3 mL). The reaction mixture was stirred 2 hours at 50° C. then concentrated to dryness. The title compound was used in the next step without further purification.

Step 3: 1-Benzhydryl-3-((3-methylthiophen-2-yl)methoxy)azetidine

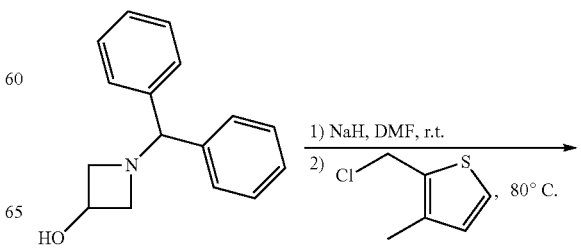

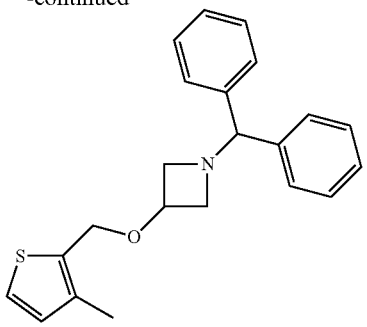

Sodium hydride (60% in oil, 106 mg, 2.3 mmol) was added to a solution of 1-benzhydryl-3-azetidin-3-ol (580 mg, 2.0 mmol) in dimethylformamide (3 mL) at room temperature. The reaction mixture was stirred at room temperature for 30 minutes prior to the addition of 2-(chloromethyl)-3-methylthiophene (714 mg, 4.8 mmol) in solution in dimethylformamide (2 mL). The reaction mixture was stirred at 80° C. overnight and cooled to room temperature. The mixture was then partitioned between ethyl acetate (30 mL) and water (30 mL). The aqueous layer was separated and extracted with ethyl acetate (3×20 mL). The combined organic phases were washed with a saturated solution of sodium chloride (3×30 mL), dried over sodium sulfate, filtered and concentrated to dryness. The residue was purified by chromatography on silica gel, using petroleum ether/ethyl acetate (95:5 to 9:1) as eluent. The title product was obtained as a yellow oil (267 mg, 36%).

LCMS (ESI-APCI) m/z 350.2 (M+H)+

Step 4: 3-((3-Methylthiophen-2-yl)methoxy)azetidine hydrochloride

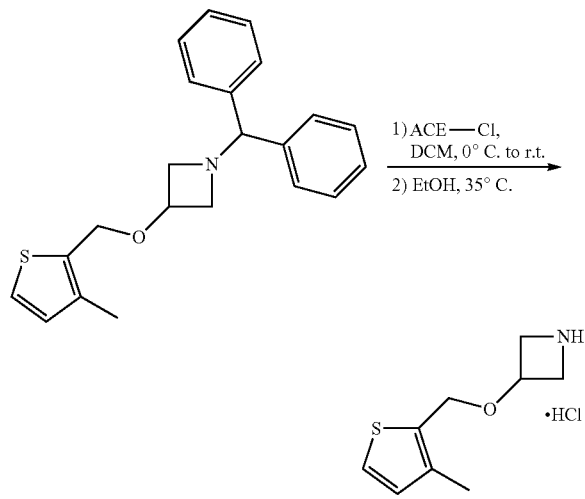

1-Chloroethyl chloroformate (90 μL, 0.84 mmol) was added to a solution of 1-benzhydryl-3-((3-methylthiophen-2-yl)methoxy)azetidine (290 mg, 0.83 mmol) in dichloromethane (9 mL) at 0° C. The reaction mixture was stirred 3 hours, then 30 minutes at room temperature. Ethanol (9 mL) was added and the reaction mixture was stirred at 35° C. for an additional 3 hours. After concentration to dryness, the crude was triturated in pentane to give a yellow solid (200 mg, quantitative) which was used in the next step without further purification.

¹H NMR (CDCl₃, 400 MHz): δ (ppm): 9.79 (s, 1H), 9.50 (s, 1H), 7.19 (d, J=5.6 Hz, 1H), 6.82 (d, J=5.6 Hz, 1H), 4.57 (s, 2H), 4.50-4.46 (m, 1H), 4.06-4.01 (m, 2H), 3.94-3.89 (m, 2H), 2.23 (s, 3H).

Step 5: (E)-6-(3-(3-((3-Methylthiophen-2-yl)methoxy)azetidin-1-yl)-3-oxoprop-1-enyl)-3,4-dihydro-1,8-naphthyridin-2(1H)-one

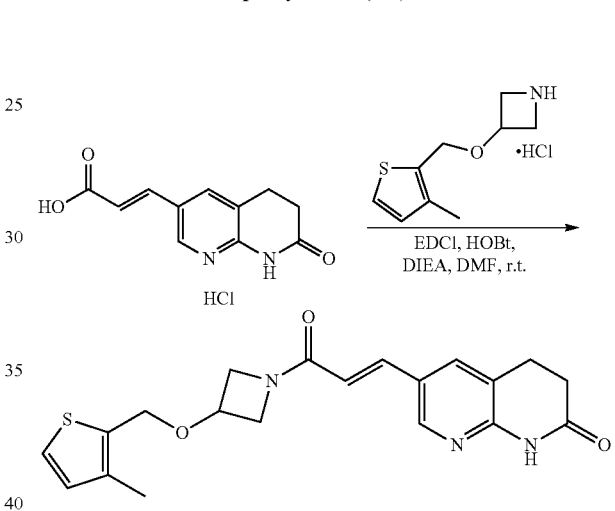

3-((3-methylthiophen-2-yl)methoxy)azetidine hydrochloride (129.0 mg, 0.6 mmol), EDCI (112.0 mg, 0.6 mmol), HOBt (82.0 mg, 0.6 mmol) and diisopropylethylamine (170 μL, 1.0 mmol) were successively added to a solution of (E)-3-(7-Oxo-5,6,7,8-tetrahydro-1,8-naphthyridin-3-yl)-acrylic acid hydrochloride (100.0 mg, 0.4 mmol) in dimethylformamide (10 mL) at room temperature. The reaction mixture was stirred overnight and then partitioned between ethyl acetate (30 mL) and water (30 mL). The aqueous layer was separated and extracted with ethyl acetate (2×20 mL). The combined organic phases were washed with a saturated solution of sodium chloride (3×30 mL), dried over sodium sulfate, filtered and concentrated to dryness. The residue was purified by chromatography on silica gel, using dichloromethane/methanol (100:0 to 95:5) as eluent. The residue was triturated in acetone to give a white solid (66.0 mg, 44%).

LCMS (ESI-APCI) m/z 384.2 (M+H)+

¹H NMR (CDCl₃, 400 MHz): δ (ppm): 8.67 (br s, NH), 8.32 (s, 1H), 7.63 (s, 1H), 7.57 (d, J=15.6 Hz, 1H), 7.21 (d, J=4.8 Hz, 1H), 6.85 (d, J=4.8 Hz, 1H), 6.39 (d, J=15.6 Hz, 1H), 4.62-4.61 (m, 2H), 4.46-4.40 (m, 2H), 4.28-4.23 (m, 1H), 4.16-4.14 (m, 1H), 4.01-3.98 (m, 1H), 2.99 (t, J=8 Hz, 2H), 2.69 (t, J=8 Hz, 2H), 2.25 (s, 3H).

Example 32

6-[3-(3-(4-Methyl-thiophen-2-ylmethoxy)-azetidin-1-yl)-3-oxo-propenyl]-3,4-dihydro-1H-[1,8]naphthyridin-2-one (E32)

Step 1: (4-Methyl-thiophen-2-yl)methanol

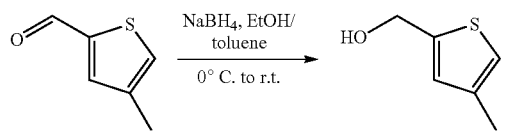

Sodium borohydride (719.0 mg, 19 mmol) was added to a solution of 4-methyl-thiophene-2-carbaldehyde (2.0 g, 15.8 mmol) in a mixture of ethanol and toluene (1:1, 12 mL) at 0° C. The reaction mixture was stirred for 2 hours at room temperature and then directly partitioned between water (10 mL) and ethyl acetate (15 mL). The aqueous layer was separated and extracted with ethyl acetate (2×20 mL). The combined organic phases were washed with a saturated solution of sodium chloride, dried over sodium sulfate, filtered and concentrated to dryness. The title product was obtained as a yellow oil (2.1 g, 95%).

$^1$H NMR (CDCl$_3$, 400 MHz): δ (ppm): 6.85 (s, 1H), 6.83 (s, 1H), 4.76 (d, J=5.6 Hz, 2H), 2.34 (s, 3H), 1.81 (t, J=6 Hz, OH).

Step 2: 2-Chloromethyl-4-methyl-thiophene

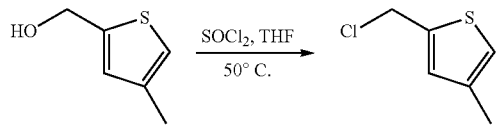

Thionyl chloride (1.3 mL, 17.7 mmol) was added to a solution of (4-methyl-thiophen-2-yl)methanol (1.9 g, 14.8 mmol) in tetrahydrofuran (7 mL) at 0° C. The reaction mixture was stirred at 50° C. for 2 hours then concentrated to dryness. The title product was obtained as a brown oil (2.17 g, quantitative) which was used in the next step without further purification.

Step 3: 1-Benzhydryl-3-(4-methyl-thiophen-2-ylmethoxy)-azetidine

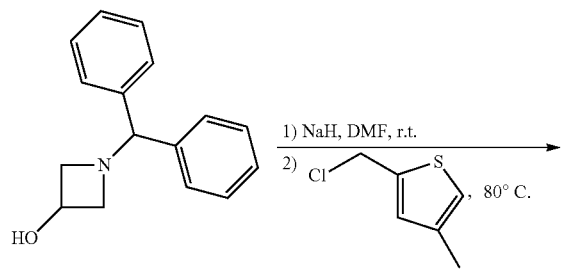

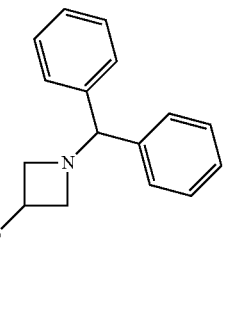

Sodium hydride (60% in oil, 88.0 mg, 2.3 mmol) was added to a solution of 1-benzhydryl-3-azetidin-3-ol (500 mg, 2.0 mmol) in dimethylformamide (3 mL) at room temperature. The reaction mixture was stirred for 30 minutes prior to the addition of 2-chloromethyl-4-methyl-thiophene (714 mg, 4.8 mmol) in solution in dimethylformamide (2 mL). The reaction mixture was stirred at 80° C. overnight and cooled to room temperature. The mixture was then partitioned between ethyl acetate (30 ml) and water (30 mL). The aqueous layer was separated and extracted with ethyl acetate (2×30 mL). The combined organic phases were washed with a saturated solution of sodium chloride (3×30 mL), dried over sodium sulfate, filtered and concentrated to dryness. The residue was purified by chromatography on silica gel, using petroleum ether/ethyl acetate (95:5 to 90:10) as eluent. The title product was obtained as a yellow solid (400 mg, 55%).

LCMS (ESI-APCI) m/z 350.2 (M+H)$^+$

Step 4: 3-(4-Methyl-thiophen-2-ylmethoxy)-azetidine hydrochloride

1-Chloroethyl chloroformate (50.0 μL, 0.4 mmol) was added to a solution of 1-benzhydryl-3-(4-methylthiophen-2-ylmethoxy)-azetidine (150.0 mg, 0.4 mmol) in dichloromethane (4.5 mL) at 0° C. The reaction mixture was stirred 3 hours, then 30 minutes at room temperature. Ethanol (6 mL) was added and the reaction mixture was stirred at 35° C. for an additional 4 hours. After concentration to dryness, the crude was triturated in pentane (2×10 mL) to give a yellow solid (94.0 mg, quantitative) which was used in the next step without further purification.

$^1$H NMR (DMSO-d$_6$, 400 MHz): δ (ppm): 8.99 (br s, NH$_2$), 7.12 (s, 1H), 6.92 (s, 1H), 4.61 (s, 2H), 4.45-4.42 (m, 1H), 4.11-4.05 (m, 2H), 3.78-3.75 (m, 2H), 2.19 (s, 3H).

Step 5: 6-[3-(3-(4-Methyl-thiophen-2-ylmethoxy)-azetidin-1-yl)-3-oxo-propenyl]-3,4-dihydro-1H-[1,8]naphthyridin-2-one

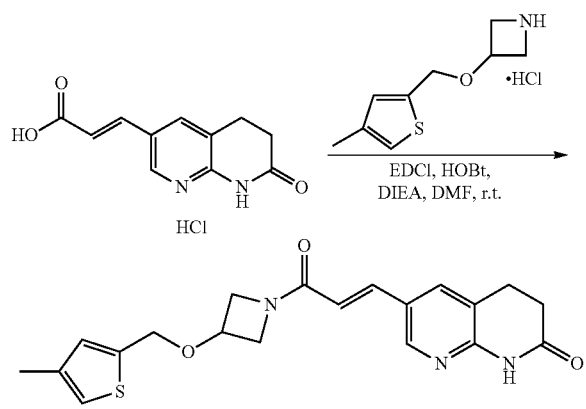

3-(4-methyl-thiophen-2-ylmethoxy)-azetidine hydrochloride (128.0 mg, 0.6 mmol), EDCI (113.0 mg, 0.6 mmol), HOBt (80.0 mg, 0.6 mmol) and diisopropylethylamine (170 μL, 1.0 mmol) were successively added to a solution of (E)-3-(7-Oxo-5,6,7,8-tetrahydro-1,8-naphthyridin-3-yl)-acrylic acid hydrochloride (100.0 mg, 0.4 mmol) in dimethylformamide (10 mL) at room temperature. The reaction mixture was stirred at room temperature overnight and then partitioned between ethyl acetate (20 mL) and water (20 mL). The aqueous layer was separated and extracted with ethyl acetate (2×20 ml). The combined organic phases were washed with a saturated solution of sodium chloride (3×20 mL), dried over sodium sulfate, filtered and concentrated to dryness. The residue was purified by chromatography on silica gel, using dichloromethane/methanol (99:1 to 95:5) as eluent. The residue was triturated with acetone to give a white solid (40 mg, 27%).

LCMS (ESI-APCI) 384.2 m/z (M+H)$^+$ $^1$H NMR (CDCl$_3$, 400 MHz): δ (ppm): 8.39 (br s, NH), 8.30 (s, 1H), 7.64 (s, 1H), 7.57 (d, J=15.6 Hz, 1H), 6.90 (s, 1H), 6.84 (s, 1H), 6.39 (d, J=15.6 Hz, 1H), 4.62 (s, 2H), 4.47-4.39 (m, 2H), 4.28-4.24 (m, 1H), 4.18-4.15 (m, 1H), 4.02-3.99 (m, 1H), 3.00 (t, J=7.2 Hz, 2H), 2.70 (t, J=7.6 Hz, 2H), 2.24 (s, 3H).

Example 33

(E)-6-(3-(3-((5-Methylthiophen-2-yl)methoxy)azetidin-1-yl)-3-oxoprop-1-enyl)-3,4-dihydro-1,8-naphthyridin-2(1H)-one (E33)

Step 1: (5-Methyl-thiophen-2-yl)-methanol

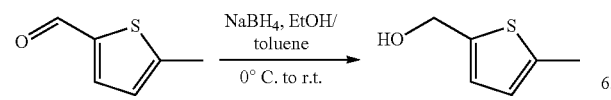

Sodium borohydride (720 mg, 19.02 mmol) was added to a solution of 5-methyl-thiophene-2-carbaldehyde (2.0 g, 15.85 mmol) in a mixture of ethanol and toluene (1:1, 12 mL) at 0° C. The reaction mixture was stirred 2 hours at room temperature and then partitioned between water (15 mL) and ethyl acetate (15 mL). The aqueous layer was separated and extracted with ethyl acetate (2×30 mL). The combined organic phases were washed with a saturated solution of sodium chloride (20 mL), dried over sodium sulfate, filtered and concentrated to dryness. The title product was obtained as a yellow oil (2.01 g, 99%).

$^1$H NMR (CDCl$_3$, 400 MHz): δ (ppm): 6.79 (d, J=2.8 Hz, 1H), 6.61 (d, J=2.8 Hz, 1H), 4.73 (s, 2H), 2.47 (s, 3H).

Step 2: 2-(Chloromethyl)-5-methylthiophene

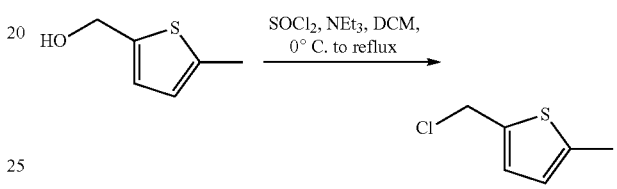

Triethylamine (2.2 mL, 16.0 mmol) and a solution of thionyl chloride (1.3 mL, 17.7 mmol) in dichloromethane (20 mL) were successively added to a solution of (5-methyl-thiophen-2-yl)-methanol (1.9 g, 14.6 mmol) in dichloromethane (20 mL) at 0° C. The reaction mixture was stirred 2 hours at reflux then cooled to room temperature. The mixture was then partitioned between water (15 mL) and ethyl acetate (20 mL). The organic phase was separated, dried over sodium sulfate, filtered and concentrated to dryness. The residue was purified by chromatography on silica gel, using petroleum ether/ethyl acetate (10:0 to 9:1) as eluent. The title product was obtained as a brown oil (1.5 g, 71%).

$^1$H NMR (CDCl$_3$, 400 MHz): δ (ppm): 6.87 (d, J=3.2 Hz, 1H), 6.59 (d, J=3.2 Hz, 1H), 4.75 (s, 2H), 2.47 (s, 3H).

Step 3: 1-Benzhydryl-((5-methylthiophen-2-yl)methoxy)-azetidine

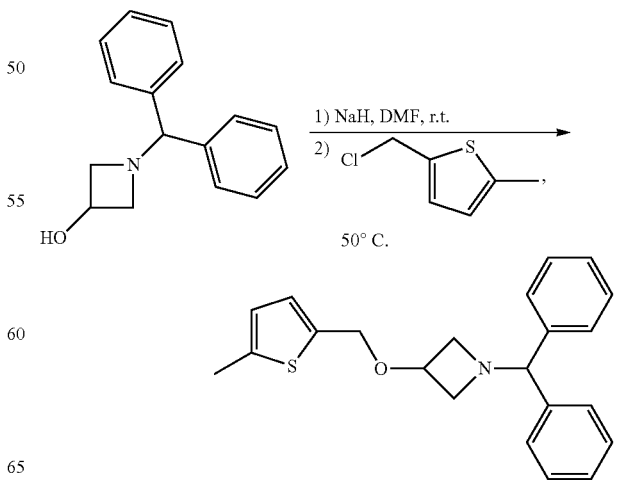

Sodium hydride (60% in oil, 204.0 mg, 5.1 mmol) was added to a solution of 1-benzhydryl-3-azetidin-3-ol (816.0 mg, 3.4 mmol) in dimethylformamide (10 mL) at room temperature. The reaction mixture was stirred for 30 minutes prior to the addition of 2-(chloromethyl)-5-methylthiophene (1.5 g, 10.2 mmol) in solution in dimethylformamide (5 mL). The reaction mixture was stirred at 50° C. for 60 hours and cooled to room temperature. The reaction mixture was then partioned between ethyl acetate (20 mL) and water (20 mL). The aqueous layer was separated and extracted with ethyl acetate (2×20 mL). The combined organic phases were washed with a saturated solution of sodium chloride (3×30 mL). The organic phase was dried over sodium sulfate, filtered and concentrated to dryness. The residue was purified by chromatography on silica gel, using petroleum ether/ethyl acetate (90:10) as eluent. The title product was obtained as a yellow solid (580.0 mg, 49%).

LCMS (ESI-APCI) m/z 350.2 (M+H)+

Step 4:
3-((5-Methylthiophen-2-yl)methoxy)-azetidine hydrochloride

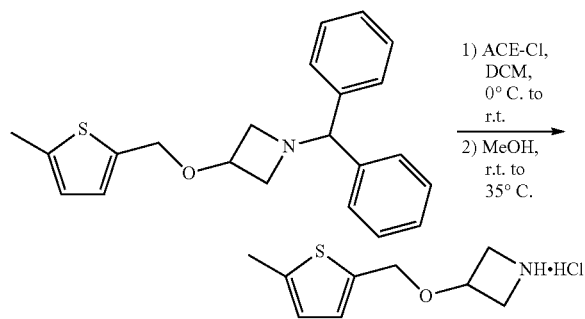

1-Chloroethyl chloroformate (198 µL, 1.8 mmol) was added to a solution of 1-benzhydryl-((5-methylthiophen-2-yl)methoxy)-azetidine (580.0 mg, 1.6 mmol) in dichloromethane (10 mL) at 0° C. The reaction mixture was stirred for 1 h 30 at the same temperature and 30 minutes at room temperature. Methanol (10 mL) was then added and the reaction mixture was stirred for an additional 3 hours at 35° C. After concentration to dryness, the crude was triturated in petroleum ether (10 mL) and diethyl ether (10 mL) to give a yellow oil (190 mg, 52%) which was used in the next step without further purification.

1H NMR (DMSO-d6, 400 MHz): δ (ppm): 8.87 (br s, NH2), 6.89 (d, J=2.8 Hz, 1H), 6.69 (d, J=2.8 Hz, 1H), 4.57 (s, 2H), 4.44-4.40 (m, 1H), 4.07-4.04 (m, 2H), 3.78-3.75 (m, 2H), 2.43 (s, 3H).

Step 5: (E)-6-(3-(3-((5-Methylthiophen-2-yl)methoxy)azetidin-1-yl)-3-oxoprop-1-enyl)-3,4-dihydro-1,8-naphthyridin-2(1H)-one

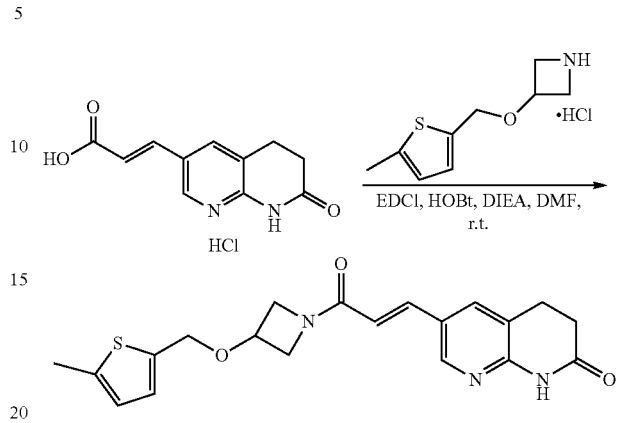

3-((5-Methylthiophen-2-yl)methoxy)-azetidine hydrochloride (190.0 mg, 0.9 mmol), EDCI (190.0 mg, 1.0 mmol), HOBt (137 mg, 1.0 mmol) and diisopropylethylamine (287 µL, 1.6 mmol) were successively added to a solution of (E)-3-(7-Oxo-5,6,7,8-tetrahydro-1,8-naphthyridin-3-yl)-acrylic acid hydrochloride (168.0 mg, 0.7 mmol) in dimethylformamide (15 mL) at room temperature. The reaction mixture was stirred overnight and then partioned between ethyl acetate (30 mL) and water (30 mL). The aqueous layer was separated and extracted with ethyl acetate (2×30 ml). The combined organic phases were washed with a saturated solution of sodium chloride (3×30 mL), dried over sodium sulfate, filtered and concentrated to dryness. The residue was purified by chromatography on silica gel, using dichloromethane/methanol (98:2 to 95:5) as eluent. The residue was triturated in diethyl ether to give a yellow solid (74.0 mg, 30%).

LCMS (ESI-APCI) 384.1 m/z (M+H)+

1H NMR (DMSO-d6, 400 MHz): δ (ppm): 10.68 (br s, NH), 8.33 (s, 1H), 8.01 (s, 1H), 7.39 (d, J=15.6 Hz, 1H), 6.89 (d, J=3.2 Hz, 1H), 6.7 (d, J=15.6 Hz, 1H), 6.69 (d, J=3.2 Hz, 1H), 4.57 (s, 2H), 4.46-4.41 (m, 2H), 4.12-4.06 (m, 2H), 3.73-3.69 (m, 1H), 2.89 (t, J=8 Hz, 2H), 2.50 (t, J=8 Hz, 2H), 2.43 (s, 3H). The CH2 at 2.5 ppm is partially hidden by DMSO.

Example 34

(E)-6-[3-(2-Methoxyethoxy)azetidin-1-yl)-3-oxoprop-1-enyl]-3,4-dihydro-1,8-naphthyridin-2(1H)-one (E34)

Step 1:
1-Benzhydryl-3-(2-methoxyethoxy)-azetidine

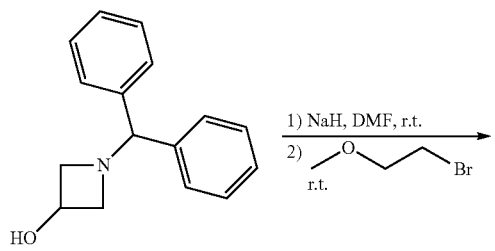

97

-continued

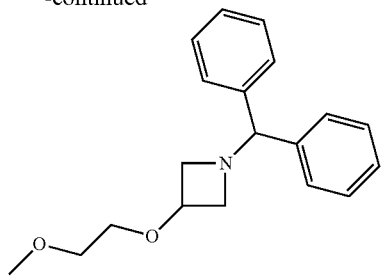

Sodium hydride (60% in oil, 55.0 mg, 1.4 mmol) was added to a solution of 1-benzhydryl-3-azetidin-3-ol (300 mg, 1.2 mmol) in dimethylformamide (2.6 mL) at room temperature. The reaction mixture was stirred for 30 minutes prior to the addition of 1-bromo-2-methoxyethane (1.5 mL, 1.9 mmol). The reaction mixture was stirred overnight and then directly partitioned between dichloromethane (20 mL) and water (20 mL). The aqueous phase was separated and extracted with dichloromethane (2×30 mL). The combined organic layer were washed with a saturated solution of sodium chloride (3×30 mL), dried over sodium sulfate, filtered and concentrated to dryness. The residue was purified by chromatography on silica gel, using pentane/ethyl acetate (98:2 to 80:20) as eluent. The title product was obtained as an orange oil (230 mg, 62%).

LCMS (ESI-APCI) m/z 298.0 (M+H)$^+$.

Step 2: 3-(2-Methoxyethoxy)-azetidine hydrochloride

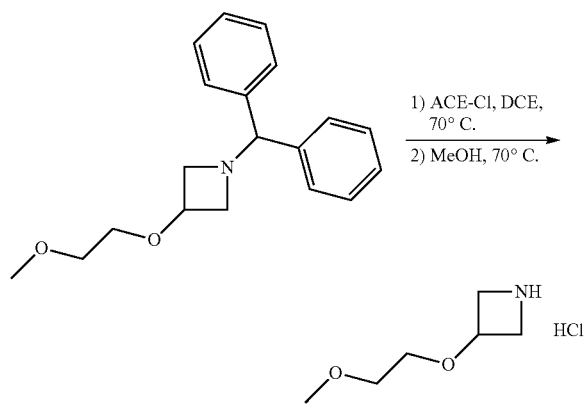

1-Chloroethyl chloroformate (102 µL, 0.9 mmol) was added to a solution of 1-benzhydryl-3-(2-methoxyethoxy)-azetidine (215 mg, 0.7 mmol) in 1,2-dichloroethane (3 mL) at room temperature. The reaction mixture was then heated up to 70° C. and stirred for 2.5 hours. After cooling down to room temperature, methanol (3 mL) was added and the reaction mixture was stirred overnight at 70° C. The mixture was then concentrated to dryness and the residue was triturated in pentane (2×15 mL) to give a yellow oil (109 mg, 90%) which was used in the next step without further purification.

$^1$H NMR (CDCl$_3$, 400 MHz): δ (ppm): 9.69 and 9.45 (br s, NH$_2$), 4.43-4.41 (m, 1H), 4.13-4.10 (m, 2H), 3.97-3.94 (m, 2H), 3.52-3.50 (m, 2H), 3.42-3.40 (m, 2H), 3.28 (s, 3H).

98

Step 3: (E)-6-[3-(2-Methoxyethoxy)azetidin-1-yl)-3-oxoprop-1-enyl]-3,4-dihydro-1,8-naphthyridin-2(1H)-one

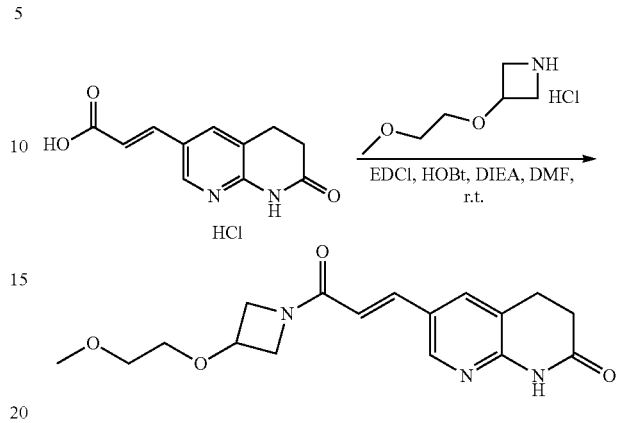

3-(2-Methoxyethoxy)-azetidine hydrochloride (98 mg, 0.6 mmol), EDCI (117 mg, 0.6 mmol), HOBt (82 mg, 0.6 mmol) and diisopropylethylamine (170 µL, 1.0 mmol) were successively added to a solution of (E)-3-(7-Oxo-5,6,7,8-tetrahydro-1,8-naphthyridin-3-yl)-acrylic acid hydrochloride (100.0 mg, 0.4 mmol) in dimethylformamide (10 mL) at room temperature. The reaction mixture was stirred overnight and then partitioned between ethyl acetate (30 mL) and water (30 mL). The aqueous layer was separated and successively extracted with ethyl acetate (2×30 mL) and dichloromethane (2×20 mL). The combined organic phases were washed with a saturated solution of sodium chloride (3×20 mL), dried over sodium sulfate, filtered and concentrated to dryness. The residue was purified by chromatography on silica gel, using dichloromethane/methanol (98:2 to 95:5) as eluent. After precipitation in a mixture of dichloromethane and diethyl ether, the title product was obtained as a yellow solid (70 mg, 54%).

LCMS (ESI-APCI) m/z 332.0 (M+H)$^+$ $^1$H NMR (DMSO-d$_6$, 400 MHz): δ (ppm): 10.65 (br s, NH), 8.35 (s, 1H), 8.01 (s, 1H), 7.40 (d, J=15.6 Hz, 1H), 6.72 (d, J=15.6 Hz, 1H), 4.49-4.45 (m, 1H), 4.38-4.35 (m, 1H), 4.15-4.06 (m, 2H), 3.75-3.72 (m, 1H), 3.72-3.46 (m, 4H), 3.27 (s, 3H), 2.92 (t, J=7.2 Hz, 2H), 2.54 (t, J=7.2 Hz, 2H).

The triplet CH$_2$ at 2.54 ppm is partially hidden by DMSO.

Example 35

(E)-6-[3-(3-Methoxypropoxy)azetidin-1-yl)-3-oxo-prop-1-enyl]-3,4-dihydro-1,8-naphthyridin-2(1H)-one (E35)

Step 1: 1-Benzhydryl-3-(3-methoxypropoxy)-azetidine

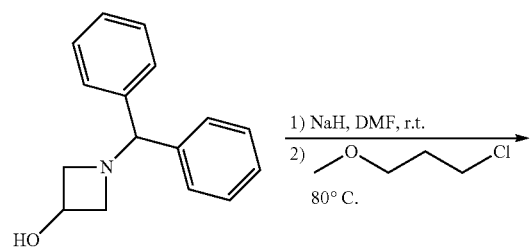

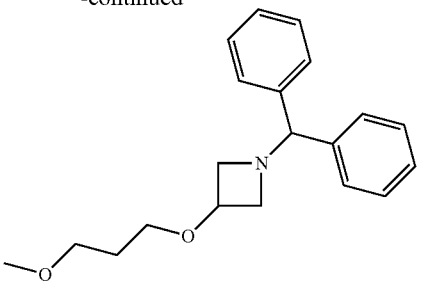

Sodium hydride (60% in oil, 92 mg, 2.3 mmol) was added to a solution of 1-benzhydryl-3-azetidin-3-ol (500 mg, 2.1 mmol) in dimethylformamide (2 mL) at room temperature. The reaction mixture was stirred for 30 minutes prior to the addition of 1-chloro-3-methoxypropane (520 µL, 4.8 mmol) in solution in dimethylformamide (3 mL). The mixture was then stirred at 80° C. overnight. Since the conversion was still incomplete, sodium hydride (60% in oil, 42 mg, 1.1 mmol) and 1-chloro-3-methoxypropane (111 µL, 1.1 mmol) were added a second time. The reaction mixture was then stirred at 80° C. for one extra night. The mixture was then directly partitioned between ethyl acetate (30 mL) and water (30 mL). The aqueous layer was separated and extracted with ethyl acetate (2×30 mL). The combined organic phases were washed with a saturated solution of sodium chloride (3×30 mL), dried over sodium sulfate, filtered and concentrated to dryness. The residue was purified by chromatography on silica gel, using petroleum ether/ethyl acetate (8:2) as eluent. The title product was obtained as a white solid (460 mg, 71%).

LCMS (ESI-APCI) m/z 312.0 (M+H)+

Step 2: 3-(3-Methoxypropoxy)-azetidine hydrochloride

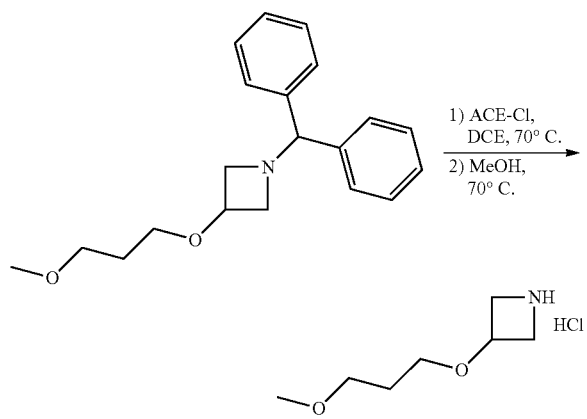

1-Chloroethyl chloroformate (210 µL, 1.9 mmol) was added to a solution of 1-benzhydryl-3-(3-methoxypropoxy)-azetidine (460 mg, 1.5 mmol) in 1,2-dichloroethane (7 mL) at room temperature. The reaction mixture was then heated up to 70° C. and stirred for 1.5 hours. After cooling down to room temperature, methanol (7 mL) was added and the mixture was again warmup up to 70° C. and stirred for an additional 2 hours. After concentration to dryness, the crude was triturated in pentane (2×10 mL) to afford a yellow oil (247 mg, 92%) which was used in the next step without further purification.

$^1$H NMR (DMSO-$d_6$, 400 MHz): δ (ppm): 9.00 (br s, NH$_2$), 4.33-4.30 (m, 1H), 4.13-4.10 (m, 2H), 3.79-3.75 (m, 2H), 3.42-3.35 (m, 4H), 3.22 (s, 3H), 1.74-1.72 (m, 2H).

Step 3: (E)-6-[3-(3-methoxypropoxy)azetidin-1-yl)-3-oxoprop-1-enyl]-3,4-dihydro-1,8-naphthyridin-2 (1H)-one

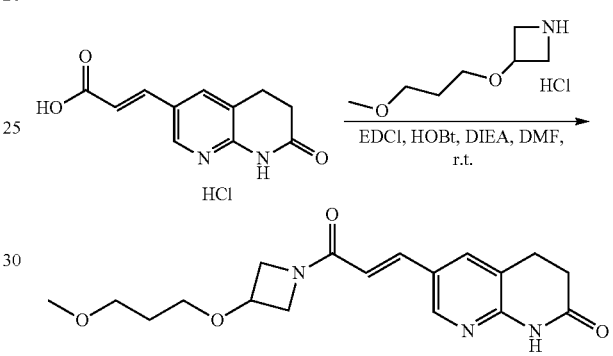

3-(3-Methoxypropoxy)-azetidine hydrochloride (107 mg, 0.6 mmol), EDCI (117 mg, 0.6 mmol), HOBt (82 mg, 0.6 mmol) and diisopropylethylamine (170 µL, 1.0 mmol) were successively added to a solution of (E)-3-(7-Oxo-5,6,7,8-tetrahydro-1,8-naphthyridin-3-yl)-acrylic acid hydrochloride (100 mg, 0.4 mmol) in dimethylformamide (10 mL) at room temperature. The reaction mixture was stirred over the week-end then partitioned between ethyl acetate (30 mL) and water (30 mL). The aqueous layer was separated and successively extracted with ethyl acetate (2×30 mL) and dichloromethane (2×30 mL). The combined organic phases were washed with a saturated solution of sodium chloride (3×20 mL), dried over sodium sulfate, filtered and concentrated to dryness. The residue was purified by chromatography on silica gel, using dichloromethane/methanol (98:2 to 95:5) as eluent. The title product was obtained as a yellow solid (98 mg, 72%).

LCMS (ESI-APCI) m/z 346.2 (M+H)+

$^1$H NMR (DMSO-$d_6$, 400 MHz): δ (ppm): 10.64 (br s, NH), 8.34 (s, 1H), 8.00 (s, 1H), 7.39 (d, J=14.8 Hz, 1H), 6.71 (d, J=16 Hz, 1H), 4.48-4.44 (m, 1H), 4.35-4.30 (m, 1H), 4.14-4.05 (m, 2H), 3.71 (d, J=10.8 Hz, 1H), 3.43-3.39 (m, 4H), 3.22 (s, 3H), 2.90 (t, J=7.6 Hz, 2H), 2.55-2.50 (t, J=7.6 Hz, 2H), 1.77-1.74 (m, 2H). The multiplet CH$_2$ at 2.5 ppm is partially hidden by DMSO.

Example 36

(E)-6-[3-(3-Butoxyazetidin-1-yl)-3-oxoprop-1-enyl]-3,4-dihydro-1,8-naphthyridin-2(1H)-one (E36)

Step 1: 1-Benzhydryl-3-butoxyazetidine

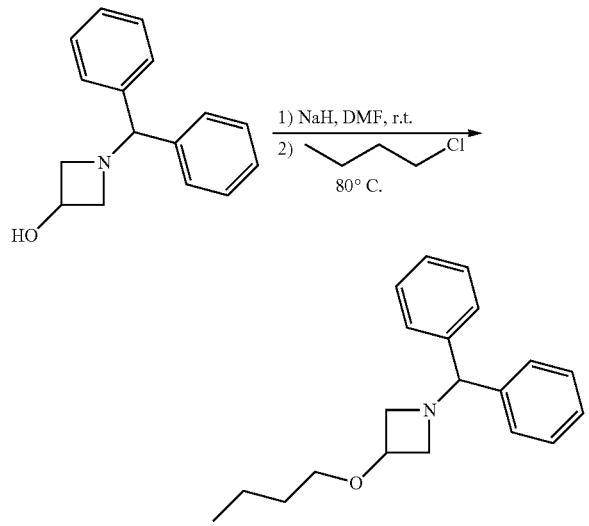

Sodium hydride (60% in oil, 92 mg, 2.3 mmol) was added to a solution of 1-benzhydryl-3-azetidin-3-ol (500 mg, 2.1 mmol) in dimethylformamide (3 mL) at room temperature. The resulting mixture was stirred for 30 minutes prior to the addition of 1-chlorobutane (500 µL, 4.8 mmol) in solution in dimethylformamide (3 mL). The reaction mixture was then stirred at 80° C. overnight and cooled to room temperature prior to the addition of ethyl acetate (20 mL) and water (20 mL). The aqueous layer was separated and extracted with ethyl acetate (2×30 mL). The combined organic phases were washed twice with a saturated solution of sodium chloride (2×100 mL). The organic phase was dried over sodium sulfate, filtered and concentrated to dryness. The residue was purified by chromatography on silica gel, using petroleum ether/ethyl acetate (95:5) as eluent. The title product was obtained as a white solid (370 mg, 60%).

LCMS (ESI-APCI) m/z 296.0 (M+H)$^+$

Step 2: 3-Butoxyazetidine hydrochloride

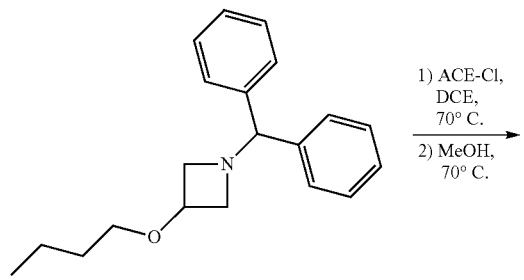

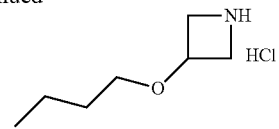

1-Chloroethyl chloroformate (180 µL, 1.6 mmol) was added to a solution of 1-benzhydryl-3-butoxyazetidine (370 mg, 1.2 mmol) in 1,2-dichloroethane (6 mL) at room temperature. The reaction mixture was then heated up to 70° C. and stirred for 1.5 hours. After cooling down to room temperature, methanol (7 mL) was added. The reaction mixture was again heated up to 70° C. and stirred for an additional 1.5 hours. After concentration to dryness, the crude mixture was triturated in pentane (2×5 mL) to give a yellow oil (179 mg, 86%) which was used in the next step without further purification.

$^1$H NMR (CDCl$_3$, 400 MHz): δ (ppm): 9.82 and 9.61 (br s, NH$_2$), 4.43-4.41 (m, 1H), 4.19-4.15 (m, 2H), 4.01-3.98 (m, 2H), 3.37 (t, J=6.8 Hz, 2H), 1.55-1.50 (m, 2H), 1.39-1.33 (m, 2H), 0.94-0.90 (m, 3H).

Step 3: (E)-6-[3-(3-Butoxyazetidin-1-yl)-3-oxoprop-1-enyl]-3,4-dihydro-1,8-naphthyridin-2(1H)-one

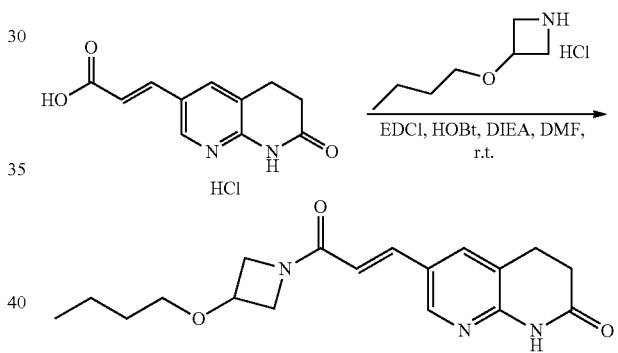

3-Butoxyazetidine hydrochloride (100 mg, 0.6 mmol), EDCI (113 mg, 0.6 mmol), HOBt (80 mg, 0.6 mmol) and diisopropylethylamine (170 µL, 1.0 mmol) were successively added to a solution of (E)-3-(7-oxo-5,6,7,8-tetrahydro-1,8-naphthyridin-3-yl)-acrylic acid hydrochloride (100 mg, 0.4 mmol) in dimethylformamide (10 mL) at room temperature. The reaction mixture was stirred overnight and then partioned between ethyl acetate (30 mL) and water (30 mL). The aqueous layer was separated and extracted successively with ethyl acetate (2×20 mL) and dichloromethane (2×20 mL). The combined organic phases were washed with a saturated solution of sodium chloride (3×20 mL), dried over sodium sulfate, filtered and concentrated to dryness. The residue was purified by chromatography on silica gel, using dichloromethane/methanol (99:1 to 97:3) as eluent. The title product was obtained as a grey solid (30 mg, 23%).

LCMS (ESI-APCI) m/z 330.2 (M+H)$^+$ $^1$H NMR (DMSO-d$_6$, 400 MHz): δ (ppm): 10.64 (br s, NH), 8.33 (s, 1H), 8.00 (s, 1H), 7.38 (d, J=16 Hz, 1H), 6.70 (d, J=15.6 Hz, 1H), 4.48-4.44 (m, 1H), 4.34-4.30 (m, 1H), 4.15-4.05 (m, 2H), 3.73-3.68 (m, 1H), 3.38-3.35 (m, 2H), 2.91 (t, J=8 Hz, 2H), 2.55-2.50 (t, J=8 Hz, 2H), 1.52-1.47 (m, 2H), 1.37-1.31 (m, 2H), 0.89 (t, J=7.2 Hz, 3H). The CH$_2$ at 2.5 ppm is partially hidden by DMSO.

Example 37

(E)-6-[3-(3-Isobutoxyazetidin-1-yl)-3-oxoprop-1-enyl]-3,4-dihydro-1,8-naphthyridin-2(1H)-one (E37)

Step 1: 1-Benzhydryl-3-isobutoxyazetidine

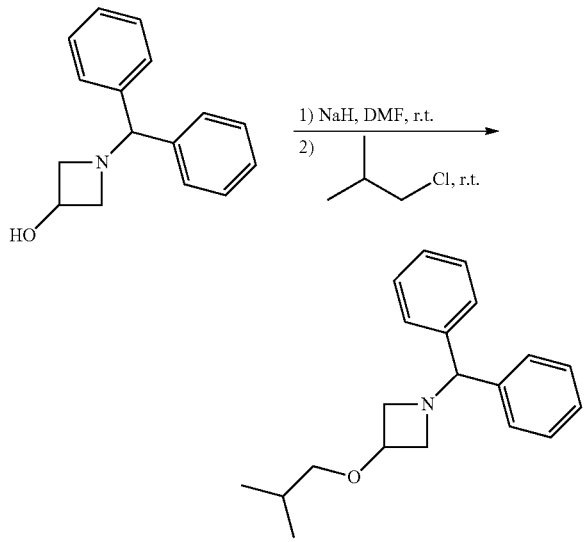

Sodium hydride (60% in oil, 146 mg, 3.6 mmol) was added to a solution of 1-benzhydryl-3-azetidin-3-ol (400 mg, 1.7 mmol) in dimethylformamide (2 mL) at room temperature. The reaction mixture was stirred for 30 minutes prior to the addition of 1-chloro-2-methylpropane (820 μL, 7.8 mmol). The reaction mixture was stirred at 80° C. overnight and cooled to room temperature. The mixture was then immediately partitioned between ethyl acetate (30 mL) and water (30 mL). The aqueous phase was separated and extracted with ethyl acetate (2×20 mL). The combined organic phases were washed with a saturated solution of sodium chloride (3×20 mL), dried over sodium sulfate, filtered and concentrated to dryness. The residue was purified by chromatography on silica gel, using petroleum ether/ethyl acetate (99:1 to 9:1) as eluent. The title product was obtained as a white solid (200 mg, 40%).

LCMS (ESI-APCI) m/z 296.0 (M+H)$^+$

Step 2: 3-Isobutoxyazetidine hydrochloride

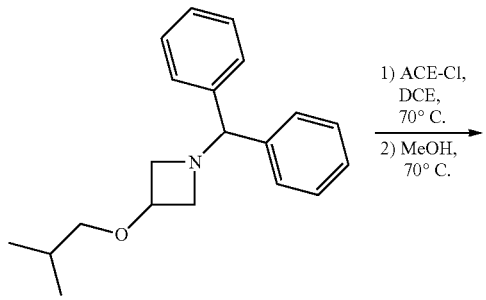

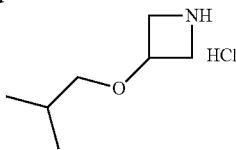

1-Chloroethyl chloroformate (83 μL, 0.77 mmol) was added to a solution of 1-benzhydryl-3-isobutoxyazetidine (175 mg, 0.60 mmol) in 1,2-dichloroethane (3 mL) at room temperature. The reaction mixture was then heated up to 70° C. and stirred for 1.5 hours. After cooling down to room temperature, methanol (3 mL) was added and the reaction mixture was heated again to 70° C. and stirred for an additional 1.5 hours. After concentration to dryness, the crude mixture was triturated in pentane (2×5 mL) to give a yellow oil (98 mg, quantitative) which was used in the next step without further purification.

$^1$H NMR (CDC$_3$, 400 MHz): δ (ppm): 9.78 and 9.61 (br s, NH$_2$), 4.42 (m, 1H), 4.19-4.15 (m, 2H), 4.03-3.98 (m, 2H), 3.11 (d, J=6.4 Hz, 2H), 1.83-1.79 (m, 1H), 0.88 (d, J=2 Hz, 6H).

Step 3: (E)-6-[3-(3-Isobutoxyazetidin-1-yl)-3-oxo-prop-1-enyl]-3,4-dihydro-1,8-naphthyridin-2(1H)-one

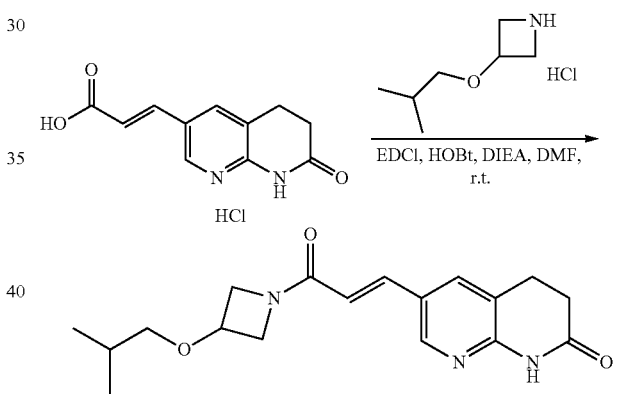

3-Isobutoxyazetidine hydrochloride (98 mg, 0.6 mmol), EDCI (113 mg, 0.6 mmol), HOBt (80 mg, 0.6 mmol) and diisopropylethylamine (170 μL, 1.0 mmol) were successively added to a solution of 3-(chloromethyl)-1-methyl-1H-pyrazole (100 mg, 0.4 mmol) in dimethylormamide (10 mL) at room temperature. The reaction mixture was stirred over a week-end and then diluted by addition ethyl acetate (20 mL) and water (2×20 mL). The aqueous layer was separated and extracted with ethyl acetate (2×20 mL). The combined organic phases were washed with a saturated solution of sodium chloride (3×20 mL), dried over sodium sulfate, filtered and concentrated to dryness. The residue was purified by chromatography on silica gel, using dichloromethane/methanol (98:2 to 92:8) as eluent. The title product was obtained as a white solid (40 mg, 31%).

LCMS (ESI-APCI) m/z 330.2 (M+H)$^+$ $^1$H NMR (CDCl$_3$, 400 MHz): δ (ppm): 8.65 (br s, NH), 8.33 (s, 1H), 7.64 (s, 1H), 7.58 (d, J=15.6 Hz, 1H), 6.43 (d, J=15.6 Hz, 1H), 4.46-4.43 (m, 1H), 4.34-4.26 (m, 2H), 4.17-4.15 (m, 1H), 4.01-3.98 (m, 1H), 3.16-3.15 (m, 2H), 3.00 (t, J=7.2 Hz, 2H), 2.70 (t, J=7.2 Hz, 2H), 1.89-1.83 (m, 1H), 0.93 (d, J=6.8 Hz, 6H).

Example 38

(E)-6-(3-(3-((1-Methyl-1H-pyrazol-3-yl)methoxy)azetidin-1-yl)-3-oxoprop-1-enyl)-3,4-dihydro-1,8-naphthyridin-2(1H)-one (E38)

Step 1: 3-(Chloromethyl)-1-methyl-1H-pyrazole

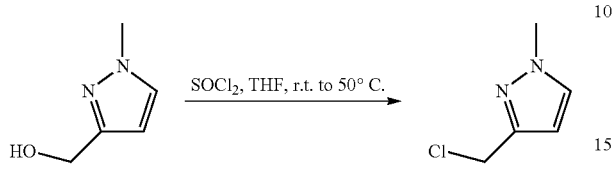

Thionyl chloride (274 μL, 3.75 mmol) was added to a solution of (1-methyl-1H-pyrazol-3-yl)methanol (350 mg, 3.13 mmol) in THF (2 mL) at room temperature. The reaction mixture was then heated up to 50° C. and stirred for 2 hours. After cooling down to room temperature, the mixture was concentrated to dryness. The title compound was used in the next step without further purification.

Step 2: 3-((1-Benzhydrylazetidin-3-yloxy)methyl-1H-pyrazole

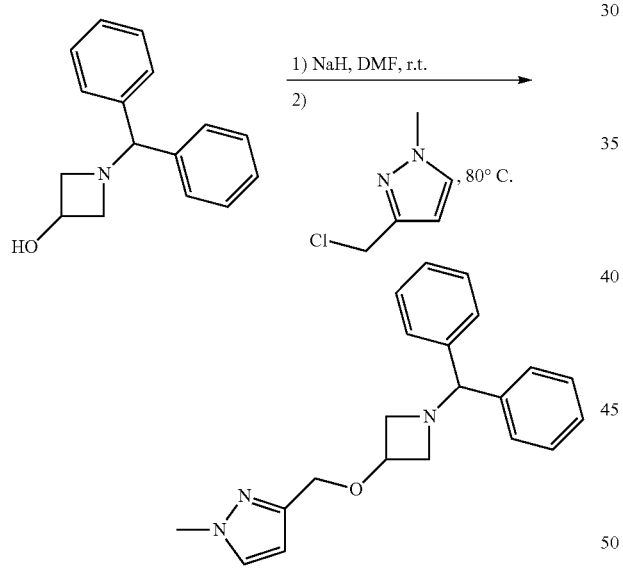

Sodium hydride (60% in oil, 200 mg, 2.30 mmol) was added to a solution of 1-benzhydryl-3-azetidin-3-ol (500 mg, 2.09 mmol) in dimethylformamide (3 mL) at room temperature. The reaction mixture was stirred for 30 minutes prior to the addition of 3-(chloromethyl)-1-methyl-1H-pyrazole (523 mg, 3.13 mmol). The reaction mixture was then heated up to 80° C. and stirred overnight. Since the LCMS monitoring indicated the presence of remained starting material, a second portion of sodium hydride (60% in oil, 200 mg, 2.30 mmol) was added. After an additional 8 hours at 80° C., the reaction mixture was partioned between ethyl acetate (30 mL) and water (30 mL). The aqueous phase was separated and extracted with ethyl acetate (2×20 mL). The combined organic phases were washed with brine (3×30 mL), dried over sodium sulfate, filtered and concentrated to dryness. The residue was purified by chromatography on silica gel, using petroleum ether/dichloromethane/ethyl acetate (5:0:5 to 0:5:5) as eluent. The title product was obtained as a yellow oil (301 mg, 67%).

LCMS (ESI-APCI) m/z 334.2 (M+H)$^+$

Step 3: 3-((Azetidin-3-yloxy)methyl)-1-methyl-1H-pyrazole hydrochloride

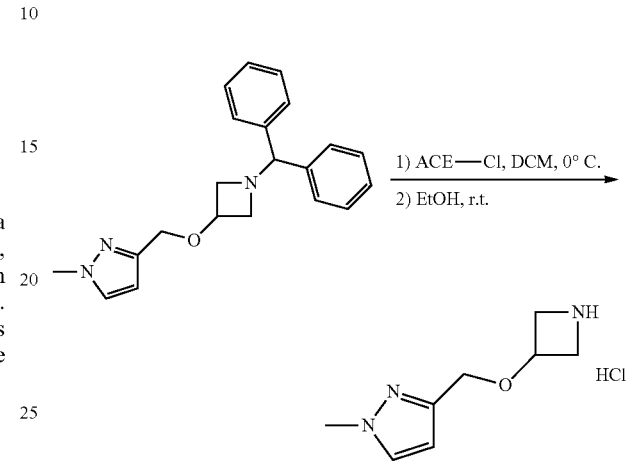

1-Chloroethyl chloroformate (70.8 μL, 0.65 mmol) was added to a solution of 3-((1-benzhydrylazetidin-3-yloxy)-methyl-1H-pyrazole (218 mg, 0.65 mmol) in dichloromethane (7 mL) at 0° C. The reaction mixture was stirred for 2 hours. Ethanol (9 mL) was added and the reaction mixture was stirred for an additional 1 hour at room temperature. After concentration to dryness, the crude mixture was triturated in pentane (4×10 mL) to give a yellow oil (133 mg, quantitative) which was used in the next step without further purification.

$^1$H NMR (CDCl$_3$, 400 MHz): δ (ppm): 9.97 and 9.66 (s, NH$_2$), 7.34 (s, 1H), 6.27 (s, 1H), 4.52 (s, 2H), 4.14-4.10 (m, 2H), 3.97-3.91 (m, 5H), 3.78-1.76 (m, 1H).

Step 4: (E)-6-(3-(3-((1-Methyl-1H-pyrazol-3-yl)methoxy)azetidin-1-yl)-3-oxoprop-1-enyl)-3,4-dihydro-1,8-naphthyridin-2(1H)-one

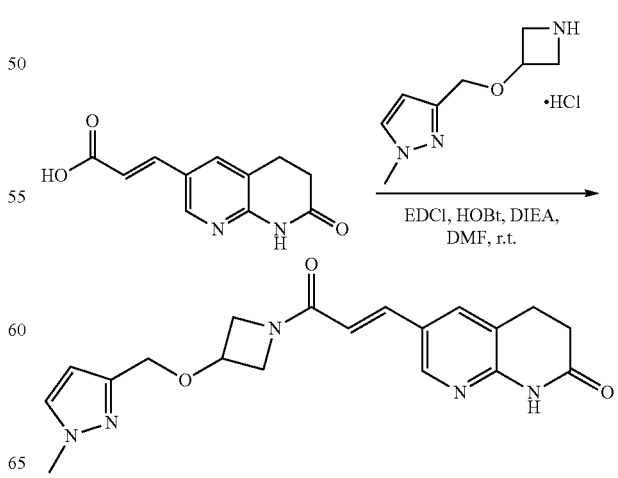

3-((Azetidin-3-yloxy)methyl)-1-methyl-1H-pyrazole hydrochloride (120 mg, 0.59 mmol), EDCI (113 mg, 0.59 mmol), HOBt (80.0 mg, 0.59 mmol) and diisopropylethylamine (3.0 mL, 2.01 mmol) were successively added to a solution of (E)-3-(7-oxo-5,6,7,8-tetrahydro-1,8-naphthyridin-3-yl)-acrylic acid hydrochloride (100 mg, 0.42 mmol) in dimethylformamide (10 mL) at room temperature. The reaction mixture was stirred overnight and then diluted by addition of ethyl acetate (30 mL) and water (20 mL). The aqueous layer was separated and extracted with ethyl acetate (2×30 mL). The combined organic phases were washed with a saturated solution of sodium chloride (4×100 mL), dried over sodium sulfate, filtered and concentrated to dryness. The residue was purified by chromatography on silica gel using dichloromethane/methanol (98:2 to 95:5) as eluent. The trituration of the residue in methanol allowed the isolation of the title product as a white solid (39 mg, 27%).

LCMS (ESI-APCI) m/z 368.2 (M+H)$^+$ $^1$H NMR (DMSO-d$_6$, 400 MHz): δ (ppm): 10.68 (s, NH), 8.33 (s, 1H), 8.01 (s, 1H), 7.64 (d, J=2.2 Hz, 1H), 7.38 (d, J=15.6 Hz, 1H), 6.70 (d, J=15.6 Hz, 1H), 6.24 (d, J=2.2 Hz, 1H), 4.45-438 (m, 2H), 4.38 (s, 2H), 4.11-4.04 (m, 2H), 3.8 (s, 3H), 3.7-3.6 (m, 1H), 2.90 (t, J=7.6 Hz, 2H), 2.51 (t, J=7.6 Hz, 2H). The CH$_2$ at 2.5 ppm is partially hidden by DMSO.

Example 39

(E)-6-(3-Oxo-3-(3-(thiazol-5-ylmethoxy)azetidin-1-yl)prop-1-enyl)-3,4-dihydro-1,8-naphthyridin-2(1H)-one (E39)

Step 1: 5-(Chloromethyl)thiazole hydrochloride

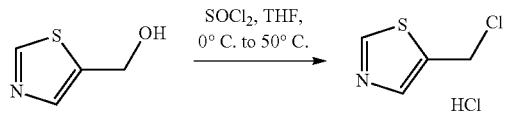 [SMILES: OCc1cncs1 ; ClCc1cncs1 ; Cl]

Thionyl chloride (608 mL, 8.34 mmol) was added to a solution of thiazol-5-methanol (800 mg, 6.95 mmol) in THF (4.3 mL) at 0° C. The reaction mixture was stirred at room temperature for 30 minutes and then at 50° C. for 2 hours. After cooling down to room temperature, the mixture was concentrated to dryness. The title compound was used in the next step without further purification.

$^1$H NMR (DMSO-d$_6$, 400 MHz): δ (ppm): 9.14 (s, 1H), 7.97 (s, 1H), 5.12 (s, 2H).

Step 2: tert-Butyl 3-(thiazol-5-ylmethoxy)-azetidine-1-carboxylate

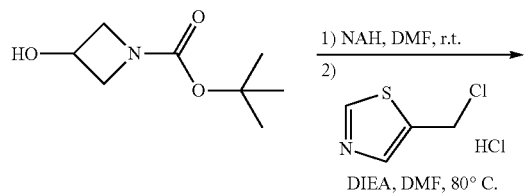

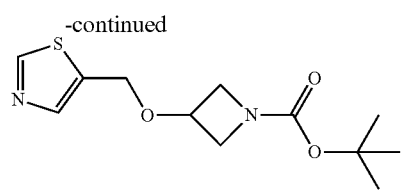

Sodium hydride (60% in oil, 292 mg, 7.30 mmol) was added to a solution of tert-butyl 3-hydroxyazetidine-1-carboxylate (602 mg, 3.47 mmol) in dimethylformamide (8 mL) at room temperature. The reaction mixture was stirred for 30 minutes prior to the addition of a solution of 5-(chloromethyl)thiazole hydrochloride (1.18 g, 6.85 mmol) and diisopropylethylamine (2.42 mL, 13.89 mmol) in dimethylformamide (3 mL) at 0° C. The reaction mixture was then heated up to 80° C. and stirred overnight. Since the LCMS monitoring still indicated the presence of starting material, an additional portion of sodium hydride (60% in oil, 139 mg, 3.47 mmol) was added. The reaction mixture was then stirred again at 80° C. After 17 hours stirring at 80° C., the reaction mixture was partitioned between ethyl acetate (20 mL) and water (20 mL). The aqueous phase was separated and extracted with ethyl acetate (2×40 mL). The combined organic phases were washed with a solution of sodium hydroxide (5×50 mL) and with brine (3×100 mL), dried over sodium sulfate, filtered and concentrated to dryness. The residue was purified by chromatography on silica gel, using petroleum ether/dichloromethane/ethyl acetate (7/0/3 to 2/0/8, then 0:5:5 to 0/2/8) as eluent. A second purification was performed on silica gel, using petroelum dichloromethane/acetone (9/1 to 8/2) as eluent. The title product was obtained as a yellow oil (150 mg, 16%).

$^1$H NMR (CDCl$_3$, 400 MHz): δ (ppm): 8.74 (s, 1H), 7.72 (s, 1H), 4.62 (s, 2H), 4.26-4.23 (m, 1H), 4.01-3.97 (m, 2H), 3.79-3.75 (m, 2H), 1.50 (s, 9H).

Step 3: 5-((Azetidin-3-yloxy)methyl)thiazole hydrochloride

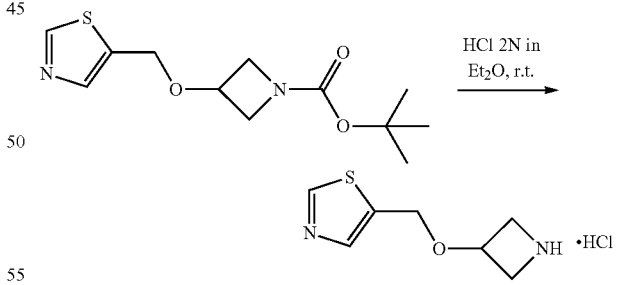

A solution of HCl in diethylether (2N, 5.5 mL) was added to a solution of tert-butyl 3-(thiazol-5-ylmethoxy)-azetidine-1-carboxylate (150 mg, 0.55 mmol) in diethylether (2 mL) at room temperature. The reaction mixture was stirred 30 minutes then concentrated to dryness. After trituration in diethyl ether (10 mL), the title compound was obtained as a yellow solid (113 mg, quantitative).

$^1$H NMR (DMSO-d$_6$, 400 MHz): δ (ppm): 9.16 (s, 1H), 7.92 (s, 1H), 4.76 (s, 2H), 4.48-4.44 (m, 1H), 4.15-4.05 (m, 2H), 3.82-3.77 (m, 2H).

Step 4: (E)-6-(3-Oxo-3-(3-(thiazol-5-ylmethoxy)azetidin-1-yl)prop-1-enyl)-3,4-dihydro-1,8-naphthyridin-2(1H)-one

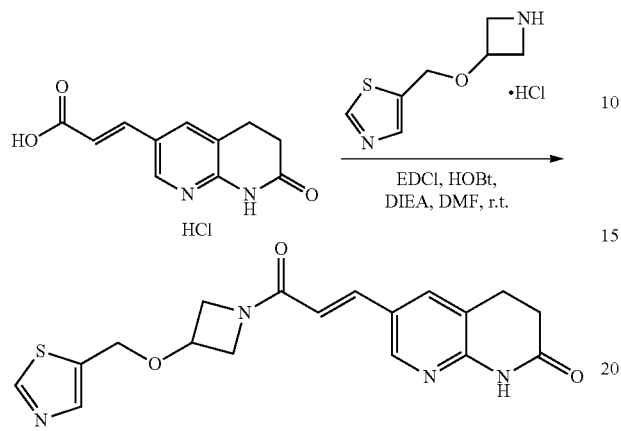

5-((Azetidin-3-yloxy)methyl)thiazole hydrochloride (113 mg, 0.54 mmol), EDCI (121 mg, 0.63 mmol), HOBt (87.7 mg, 0.63 mmol) and diisopropylethylamine (183 µL, 1.05 mmol) were successively added to a solution of (E)-3-(7-oxo-5,6,7,8-tetrahydro-1,8-naphthyridin-3-yl)-acrylic acid hydrochloride (107 mg, 0.42 mmol) in dimethylformamide (10 mL) at room temperature. The reaction mixture was stirred overnight then partitioned between ethyl acetate (30 mL) and water (20 mL). The aqueous layer was separated and extracted with ethyl acetate (2×20 mL). The combined organic phases were washed with a saturated solution of sodium chloride (3×30 mL), dried over sodium sulfate, filtered and concentrated to dryness. The residue was purified by chromatography on silica gel using dichloromethane/methanol (10:0 to 98:2) as eluent then on $C_{18}$ using dichloromethane/methanol (98:2) as eluent. In order to reach the required purity, the residue was finally recrystallized in methanol to afford the title product as a white solid (2.8 mg, 2%).

LCMS (ESI-APCI) m/z 371.1 (M+H)$^+$ $^1$H NMR (CDCl$_3$, 400 MHz): δ (ppm): 8.89 (br s, NH), 8.84 (s, 1H), 8.33 (s, 1H), 7.82 (s, 1H), 7.63 (s, 1H), 7.58 (d, J=15.6 Hz, 1H), 6.39 (d, J=15.6 Hz, 1H), 4.77-4.74 (m, 2H), 4.75-4.41 (m, 2H), 4.31-4.27 (m, 1H), 4.17-4.15 (m, 1H), 4.05-4.01 (m, 1H), 2.99 (t, J=7.6 Hz, 2H), 2.7 (t, J=7.6 Hz, 2H).

Example 40

(E)-6-(3-(3-(Furan-2-ylmethoxy)azetidin-1-yl)-3-oxoprop-1-enyl)-3,4-dihydro-1,8-naphthyridin-2(1H)-one (E40)

Step 1: 2-(Chloromethyl)furan

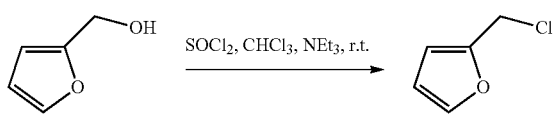

Triethylamine (10.3 mL, 74 mmol) and a solution of thionyl chloride (2.9 mL, 40.7 mmol) in chloroforme (19 mL) were successively added to a solution of furfuryl alcohol (3.7 g, 37 mmol) in chloroforme (38 mL) at 0° C. The reaction mixture was then allowed to reach room temperature and stirred for 2 hours. Water (50 mL) was then added and the organic phase was separated and washed with water (2×50 mL), dried over sodium sulphate, filtered and concentrated to dryness. The resulting residue was distilled under reduced pressure (T=50° C., P=10 mbars) to give a colorless oil (2.0 g, 45%) which was directly used in the next step.

$^1$H NMR (CDCl$_3$, 400 MHz): 7.43 (s, 1H), 6.39-6.35 (m, 2H), 4.60 (s, 2H).

Step 2: 1-Benzhydryl-3-(furan-2-ylmethoxy)-azetidine

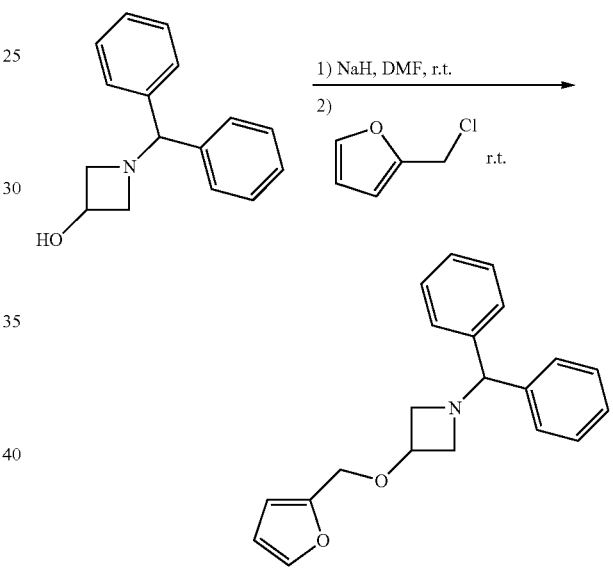

Sodium hydride (60% in oil, 877 mg, 22 mmol) was added to a solution of 1-benzhydryl-3-azetidin-3-ol (2.62 g, 11 mmol) in dimethylformamide (15 mL) at room temperature. The reaction mixture was stirred for 30 minutes prior to the addition of 2-(chloromethyl)furan (2.94 g, 25.2 mmol) in solution in dimethylformamide (10 mL). The reaction mixture was then stirred at room temperature overnight. The reaction mixture was diluted by addition of ethyl acetate (50 mL) and water (50 mL). The aqueous layer was separated and extracted with ethyl acetate (2×50 mL). The combined organic phases were washed with a saturated solution of sodium chloride (3×30 mL), dried over sodium sulphate, filtered and concentrated to dryness. The residue was purified by chromatography on silica gel, using petroleum ether/ethyl acetate (9:1) as eluent. The title product was obtained as a yellow oil (3.2 g, 91%).

LCMS (ESI-APCI) m/z 320.2 (M+H)$^+$

Step 3: 3-(Furan-2-ylmethoxy)-azetidine hydrochloride

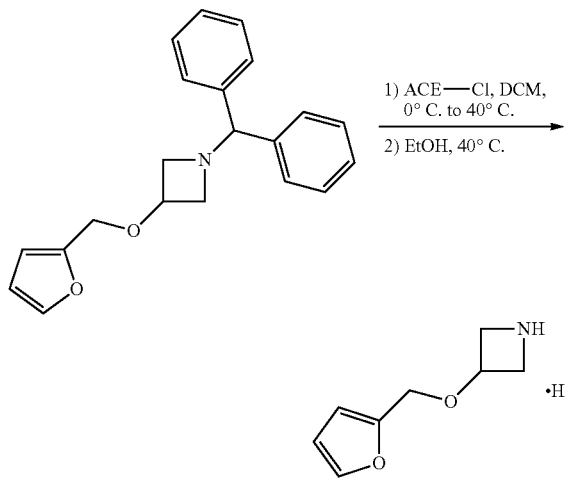

1-Chloroethyl chloroformate (534 μL, 4.93 mmol) was added to a solution of 1-benzhydryl-3-(furan-2-ylmethoxy)-azetidine (1.5 g, 4.7 mmol) in dichloromethane (36 mL) at 0° C. The reaction mixture was then heated up to 40° C. and stirred for 2 hours. Ethanol (50 mL) was added and the reaction mixture was stirred for an additional 1 h 30 at 40° C. After concentration to dryness, the crude mixture was triturated in petroleum ether (2×20 mL) to give a yellow oil (558 mg, 74%) which was used in the next step without further purification.

$^1$H NMR (DMSO-d$_6$, 400 MHz): δ (ppm): 9.22 (br s, NH$_2$), 7.68 (m, 1H), 6.5-6.45 (m, 2H), 4.47 (s, 2H), 4.39-4.45 (m, 1H), 4.06-4.01 (m, 2H), 3.48-3.42 (m, 2H).

Step 4: (E)-6-(3-(3-(Furan-2-ylmethoxy)azetidin-1-yl)-3-oxoprop-1-enyl)-3,4-dihydro-1,8-naphthyridin-2(1H)-one

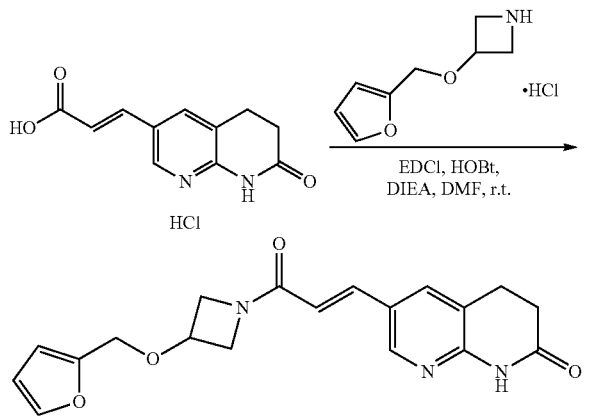

3-(Furan-2-ylmethoxy)-azetidine hydrochloride (558 mg, 2.94 mmol), EDCI (563 mg, 2.94 mmol), HOBt (410 mg, 2.94 mmol) and diisopropylethylamine (853 μL, 4.9 mmol) were successively added to a solution of (E)-3-(7-oxo-5,6,7,8-tetrahydro-1,8-naphthyridin-3-yl)-acrylic acid hydrochloride (500 mg, 1.96 mmol) in dimethylformamide (50 mL) at room temperature. The reaction mixture was stirred for 2 days and then diluted by addition of ethyl acetate (50 mL) and water (50 mL). The aqueous layer was separated and successively extracted with ethyl acetate (2×50 mL) and dichloromethane (2×50 mL). The combined organic phases were washed with a saturated solution of sodium chloride (3×60 mL), dried over sodium sulfate, filtered and concentrated to dryness. The residue was purified by chromatography on silica gel, using dichloromethane/methanol (10:0 to 95:5) as eluent. After trituration of the isolated solid in diethylether, the title product was obtained as a white solid (236 mg, 34%).

LCMS (ESI-APCI) m/z 354.2 (M+H)$^+$ $^1$H NMR (DMSO-d$_6$, 400 MHz): δ (ppm): 10.69 (s, NH), 8.34 (s, 1H), 8.01 (s, 1H), 7.68 (s, 1H), 7.39 (d, J=15.6 Hz, 1H), 6.69 (d, J=15.6 Hz, 1H), 6.49-6.45 (m, 2H), 4.45 (s, 2H), 4.44-4.39 (m, 2H), 4.1-4.02 (m, 2H), 3.66-3.63 (m, 1H), 2.91 (t, J=7.6 Hz, 2H), 2.51 (t, J=7.6 Hz, 2H). The CH$_2$ at 2.5 ppm is partially hidden by DMSO.

Example 41

(E)-1'-Methyl-6-(3-oxo-3-(3-(thiophen-2-ylmethoxy)azetidin-1-yl)prop-1-enyl)-1H-spiro[[1,8]naphthyridine-3,4'-piperidin]-2(4H)-one (E41)

Step 1: N-Boc ethylisopinecotate

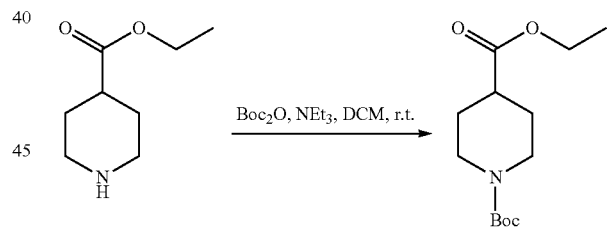

Boc$_2$O (15.8 g, 71.4 mmol) and triethylamine (10 mL, 77.8 mmol) were successively added to a solution of ethylisopinecotate (10.2 g, 64.9 mmol) in dichloromethane (50 mL) at room temperature. The reaction mixture was stirred overnight. The reaction mixture was diluted by addition of a saturated solution of ammonium chloride (50 mL). The aqueous layer was separated and extracted with dichloromethane (2×50 mL). The combined organic phases were dried over sodium sulphate, filtered and concentrated to dryness. The title product was obtained as a yellow oil (16.7 g, 100%).

$^1$H NMR (CDCl$_3$, 400 MHz): δ (ppm): 4.18 (q, J=6.8 Hz, 2H), 4.08-4.04 (m, 2H), 2.88 (m, 2H), 2.49-2.45 (m, 1H), 1.93-1.88 (m, 2H), 1.71-1.63 (m, 2H), 1.50 (s, 9H), 1.30 (t, J=6.8 Hz, 3H).

Step 2: 1-tert-Butyl 4-ethyl 4-((2-amino-5-bromopyridin-3-yl)methyl)piperidine-1,4-dicarboxylate

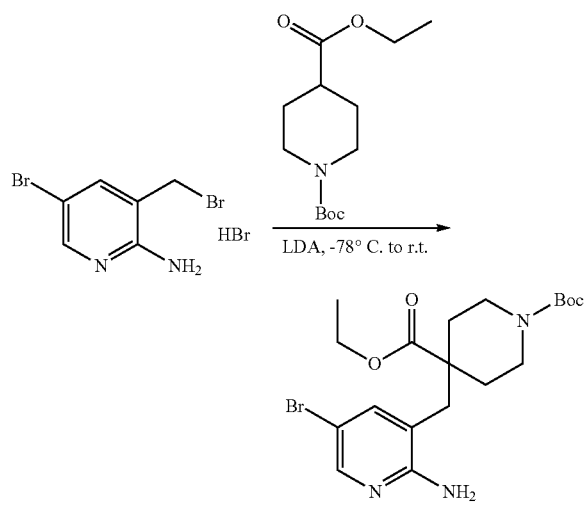

Freshly prepared LDA (14 mL, 1M in THF, 14 mmol) was added dropwise over 15 minutes to a cold (−78° C.) solution of 5-bromo-3-(bromomethyl)pyridine-2-amine hydrobromide (4.8 g, 14 mmol) in THF (56 mL) under argon. The reaction mixture was stirred for an additional 15 minutes. In a separate flask, freshly prepared LDA (42 mL, 1M in THF, 42 mmol) was added dropwise over 30 minutes to a cold solution of N-Boc ethylisopinecotate (10.9 g, 42 mmol) was in THF (100 ml). The reaction mixture was stirred for an additional 30 minutes. The lithium salt of N-Boc ethylisopinecotate was then cannulated dropwise over 30 minutes to the lithium salt of 5-bromo-3-(bromomethyl)pyridine-2-amine. The mixture was stirred at −78° C. for 2 hours and allowed to warm to room temperature. The reaction mixture was quenched with a saturated solution of ammonium chloride (150 mL) and ethyl acetate (150 mL) was added. The organic phase was washed with water (2×50 mL) and brine (100 mL), dried over sodium sulphate, filtered and concentrated to dryness. The residue was purified by chromatography on silica gel, using dichloromethane/AcOEt (95:5 to 9:1) as eluent. The title product was obtained as a yellow oil (1.25 g, 20%).

LCMS (ESI-APCI) m/z 442.1-444.1 (M+H)$^+$

Step 3: tert-Butyl 6-bromo-2-oxo-2,4-dihydro-1H-spiro[[1,8]naphthyridine-3,4'-piperidine]-1'-carboxylate

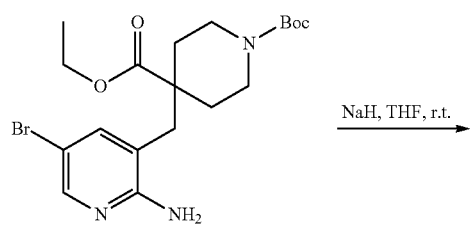

Sodium hydride (201 mg, 5.3 mmol) was added to a solution of 1-tert-butyl 4-ethyl 4-((2-amino-5-bromopyridin-3-yl)methyl)piperidine-1,4-dicarboxylate (1.71 g, 3.87 mmol) suspended in THF (17 mL) at room temperature. The reaction mixture was stirred for 1 hour and then diluted by addition of water (50 mL). The resulting precipitate was filtered and washed with pentane. The title compound was obtained as a beige solid (1.2 g, 78%).

$^1$H NMR (CDCl$_3$, 400 MHz): δ (ppm): 8.23 (s, 1H), 8.03 (br s, 1H), 7.61 (s, 1H), 3.7-3.45 (m, 4H), 2.84 (s, 2H), 2.00-1.88 (m, 2H), 1.45 (s, 9H), 1.45-1.40 (m, 2H).

Step 4: (E)-tert-Butyl 6-(3-ethoxy-3-oxoprop-1-enyl)-2-oxo-2,4-dihydro-1H-spiro[[1,8]naphthyridine-3,4'-piperidine]-1'-carboxylate

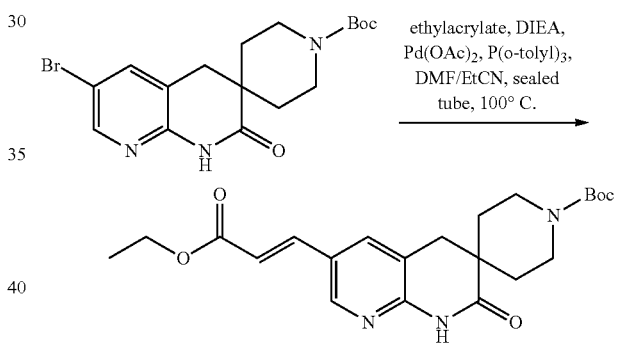

Ethyl acrylate (2.3 mL, 21.2 mmol), diisopropylethylamine (3.7 mL, 21.2 mmol) and P(o-tolyl)$_3$ (323 mg, 1.06 mmol) were successively added to a suspension of tert-butyl 6-bromo-2-oxo-2,4-dihydro-1H-spiro[[1,8]naphthyridine-3,4'-piperidine]-1'-carboxylate (2.10 g, 5.3 mmol) in propionitrile (20 mL) and dimethylformamide (5 mL) in a sealed tube. The resulting mixture was then purged with argon prior to the addition of palladium acetate (120 mg, 0.53 mmol). The mixture was purged with argon again and refluxed overnight. The reaction mixture was then filtered on Celite®. The filtrate was concentrated to dryness and the residue was solubilized in dichloromethane (100 mL). The resulting solution was washed with a saturated solution of ammonium chloride (100 mL), dried over sodium sulfate, filtered and concentrated to dryness. The residue was precipitated in dichloromethane/diethylether/pentane, the title product was obtained as an off-white solid (1.52 g, 70%).

$^1$H NMR (CDCl$_3$, 400 MHz): δ (ppm): 8.39 (br s, 1H), 8.31 (s, 1H), 7.66 (s, 1H), 7.61 (d, J=16 Hz, 1H), 6.40 (d, J=16 Hz, 1H), 4.27 (q, J=7.2 Hz, 2H), 3.65-3.40 (m, 4H), 2.89 (s, 2H), 2.05-1.95 (m, 2H), 1.46 (s, 9H), 1.46-1.43 (m, 2H), 1.34 (t, J=7.2 Hz, 3H).

Step 5: (E)-Ethyl 3-(2-oxo-2,4-dihydro-1H-spiro[[1,8]naphthyridine-3,4'-piperidine]-6-yl)acrylate

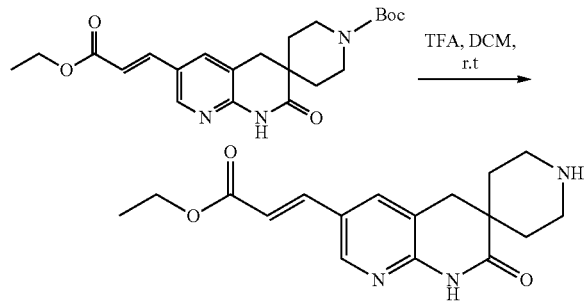

Trifluoroacetic acid (5 mL) was added to a suspension of (E)-tert-butyl 6-(3-ethoxy-3-oxoprop-1-enyl)-2-oxo-2,4-dihydro-1H-spiro[[1,8]naphthyridine-3,4'-piperidine]-1'-carboxylate (1.52 g, 3.66 mmol) in dichloromethane (20 mL). The reaction mixture was stirred at room temperature for 1 hour and concentrated to dryness. The resulting residue was partitioned between an aqueous solution of sodium hydroxide (1N, 60 mL) and dichloromethane (40 mL). The aqueous layer was separated and extracted with dichloromethane (2×70 mL). The combined organic phases were dried over sodium sulfate, filtered and concentrated to dryness. The title product was obtained as a pale yellow solid (904 mg, 79%).

$^1$H NMR (CDCl$_3$, 400 MHz): δ (ppm): 8.29 (s, 1H), 8.27 (br s, 1H), 7.68 (s, 1H), 7.61 (d, J=16 Hz, 1H), 6.40 (d, J=16 Hz, 1H), 4.27 (q, J=7.2 Hz, 2H), 3.06-3.04 (m, 2H), 2.94 (s, 2H), 2.90-2.87 (m, 2H), 1.99-1.96 (m, 2H), 1.44-1.40 (m, 2H), 1.34 (t, J=7.6 Hz, 3H).

Step 6: (E)-Ethyl 3-(1'-methyl-2-oxo-2,4-dihydro-1H-spiro[[1,8]naphthyridine-3,4'-piperidine]-6-yl)acrylate

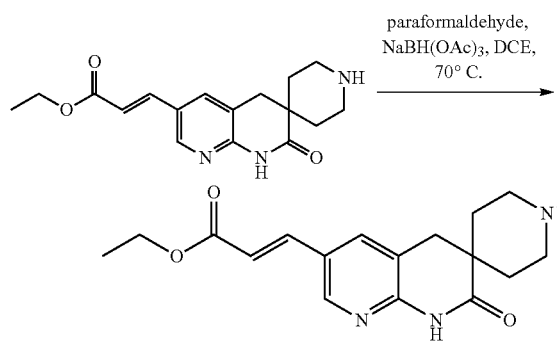

Sodium triacetoxyborohydride (1.2 g, 5.73 mmol) and paraformaldehyde (172 mg, 5.73 mmol) were successively added to a suspension of (E)-ethyl 3-(2-oxo-2,4-dihydro-1H-spiro[[1,8]naphthyridine-3,4'-piperidine]-6-yl)acrylate (904 mg, 2.87 mmol) in 1,2-dichloroethane (40 mL) at room temperature. The reaction mixture was then heated up to 70° C. and stirred for 2 hours. After cooling down to room temperature, the reaction mixture was diluted by addition of ethyl acetate (50 mL) and water (50 mL). The aqueous layer was separated and extracted with ethyl acetate (2×50 mL). The combined organic phases were washed with a saturated solution of sodium hydrogenocarbonate (3×60 mL), dried over sodium sulfate, filtered and concentrated to dryness. The title product was obtained as a white solid (862 mg, 91%).

$^1$H NMR (CDCl$_3$, 400 MHz): δ (ppm): 8.29 (s, 1H), 8.24 (br s, 1H), 7.67 (s, 1H), 7.61 (d, J=16 Hz, 1H), 6.40 (d, J=16 Hz, 1H), 4.27 (q, J=7.2 Hz, 2H), 2.88 (s, 2H), 2.64-2.60 (m, 2H), 2.42-2.40 (m, 2H), 2.32 (s, 2H), 2.08-2.04 (m, 2H), 1.54-1.51 (m, 2H), 1.34 (t, J=7.2 Hz, 3H).

Step 7: (E)-3-(7-Oxo-5,6,7,8-tetrahydro-1,8-naphthyridin-3-yl)-acrylic acid hydrochloride

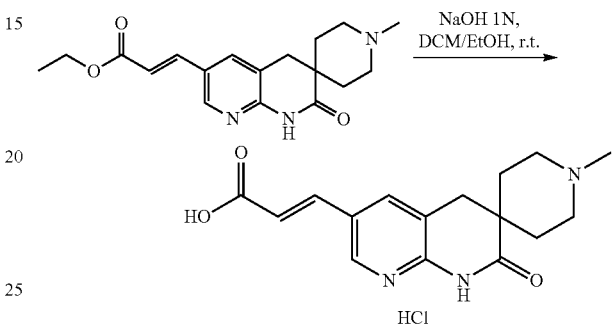

An aqueous solution of sodium hydroxide (1N, 7.83 mL) was added to a solution of (E)-ethyl 3-(1'-methyl-2-oxo-2,4-dihydro-1H-spiro[[1,8]naphthyridine-3,4'-piperidine]-6-yl)acrylate (860 mg, 2.61 mmol) in a mixture of dichloromethane (10 mL) and ethanol (10 mL) at room temperature. The reaction mixture was stirred at 45° C. overnight then concentrated to dryness. The residue was acidified by addition of an aqueous solution of hydrochloric acid (1N, 30 mL) until pH 1. The resulting solid was filtered and washed with water and diethyl ether. The title product was obtained as a white solid (586 mg, 66%).

LCMS (ESI-APCI) m/z 302.2 (M+H)$^+$

Step 8: (E)-1'-Methyl-6-(3-oxo-3-(3-(thiophen-2-ylmethoxy)azetidin-1-yl)prop-1-enyl)-1H-spiro[[1,8]naphthyridine-3,4'-piperidin]-2(4H)-one

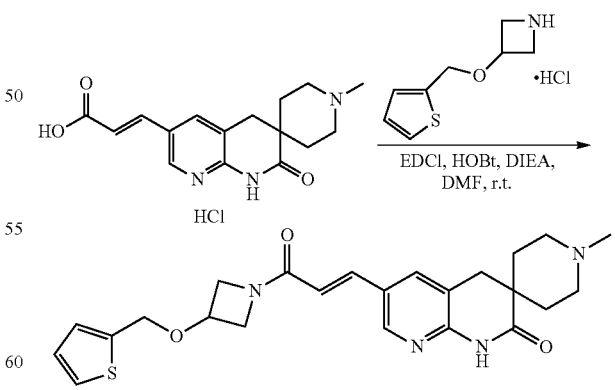

3-(Thiophen-2-ylmethoxy)-azetidine hydrochloride (45.8 mg, 0.22 mmol), EDCI (40.26 mg, 0.21 mmol), HOBt (28.5 mg, 0.21 mmol) and diisopropylethylamine (62 μL, 0.35 mmol) were successively added to a solution of (E)-3-(7-oxo-5,6,7,8-tetrahydro-1,8-naphthyridin-3-yl)-acrylic acid hydrochloride (47.0 mg, 0.14 mmol) in dimethylformamide (5 mL) at room temperature. The reaction mixture was stirred overnight and then diluted by addition of ethyl acetate (20 ml) and water (20 mL). The aqueous layer was separated and extracted with ethyl acetate (2×20 mL). The combined organic phases were washed with a saturated solution of sodium chloride (3×20 mL), dried over sodium sulfate, filtered and concentrated to dryness. The residue was purified by chromatography on silica gel using dichloromethane/methanol (95:5 to 0:1) as eluent. After precipitation in a mixture dichloromethane/diethylether/pentane, the title product was obtained as a white solid (12 mg, 24%).

LCMS (ESI-APCI) m/z 453.1 (M+H)+

$^1$H NMR (CDCl$_3$, 400 MHz): δ (ppm): 8.33 (s, 1H), 8.22 (s, 1H), 7.68 (s, 1H), 7.62 (d, J=15.6 Hz, 1H), 7.41-7.38 (m, 1H), 7.10-7.04 (m, 2H), 6.44 (d, J=15.6 Hz, 1H), 4.76-4.74 (m, 2H), 4.53-4.45 (m, 2H), 4.32-4.20 (m, 2H), 4.09-4.04 (m, 1H), 2.93 (s, 2H), 2.72-2.67 (m, 2H), 4.50-2.38 (m, 2H), 2.38 (s, 3H), 2.16-2.09 (m, 2H), 1.68-1.65 (m, 2H).

Example 42

(E)-7-(3-Oxo-3-(3-(thiophen-2-ylmethoxy)azetidin-1-yl)prop-1-enyl)-4,5-dihydro-1H-pyrido[2,3-e][1,4]diazepin-2(3H)-one (E42)

Step 1: (E)-Methyl 2-(4-methoxybenzylideneamino)acetate

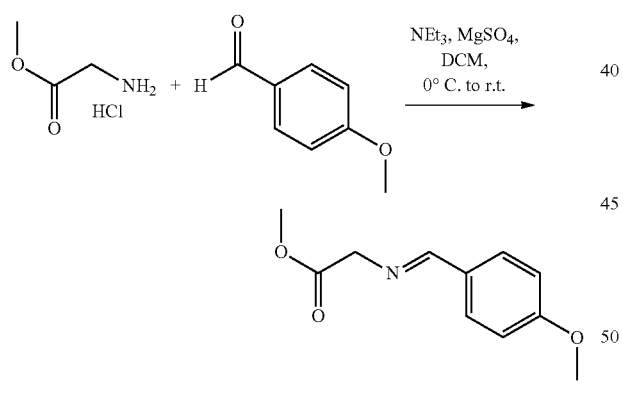

Triethylamine (4.6 mL, 33 mmol) and glycine methyl ester hydrochloride (3.8 g, 30.26 mmol) were successively added to a solution of p-anisaldehyde (2.0 g, 14.7 mmol) in dichloromethane (150 mL) at 0° C. Sodium sulfate (10 g) was added and the reaction mixture was stirred overnight at room temperature. The reaction mixture was then filtered and concentrated to dryness. The resulting residue was portioned in ethyl acetate and filtered in order to remove the triethylamine salts. The title compound was obtained as a pale yellow solid (4.43 g, 100%).

$^1$H NMR (CDCl$_3$, 400 MHz): δ (ppm): 8.22 (s, 1H), 7.23 (d, J=8.4 Hz, 2H), 6.93 (d, J=8.4 Hz, 2H), 4.39 (s, 2H), 3.85 (s, 3H), 3.78 (s, 3H).

Step 2: Methyl 2-(4-methoxybenzylamino)acetate

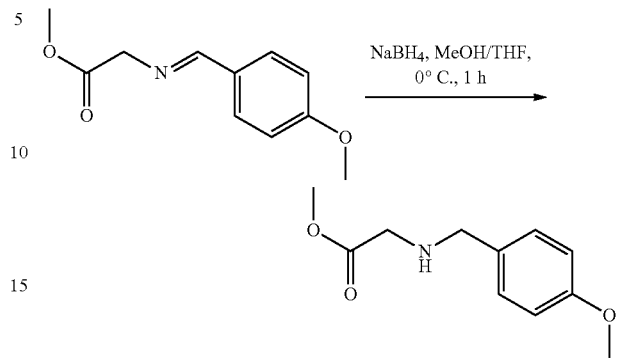

Sodium borohydride (438 mg, 1.2 mmol) was added to a solution of (E)-methyl 2-(4-methoxybenzylideneamino)acetate (2.0 g, 9.6 mmol) in a mixture of methanol (22 mL) and THF (11 mL) at 0° C. The reaction mixture was stirred 1 hour at room temperature then partioned between a solution of saturated ammonium chloride (20 mL) and ethyl acetate (30 mL). The aqueous phase was separated and extracted with ethyl acetate (3×50 mL). The combined organic phases were dried over sodium sulfate, filtered and concentrated to dryness. The title compound was obtained as a white oil (1.7 g, 85%).

$^1$H NMR (CDCl$_3$, 400 MHz): δ (ppm): 7.31 (m, 2H), 6.92 (m, 2H), 3.85 (s, 2H), 3.83 (s, 3H), 3.78 (s, 3H), 3.48 (s, 2H), 2.49 (br s, 1H).

Step 3: Methyl 2-(((2-amino-5-bromopyridin-3-yl)methyl)(4-methoxybenzyl)amino)acetate

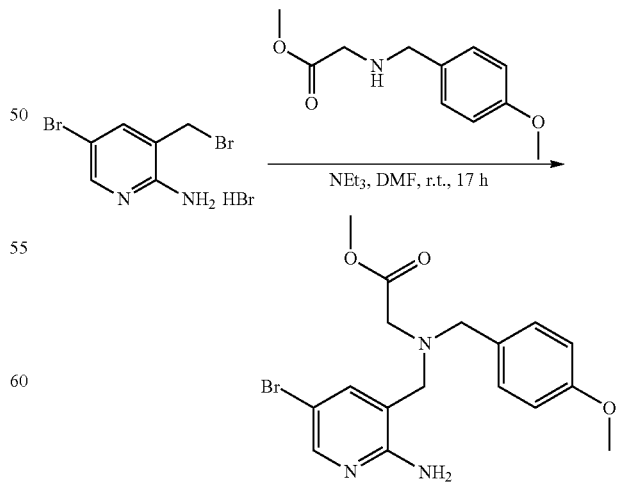

Methyl 2-(4-methoxybenzylamino)acetate (760 mg, 3.63 mmol) and triethylamine (840 μL, 6.60 mmol) were successively added to a solution of 5-bromo-3-(bromomethyl)pyridine-2-amine hydrobromide (1.0 g, 3.30 mmol) in DMF (17 mL) at room temperature. The reaction mixture was stirred for 8 hours then diluted by addition of water (50 mL) and ethyl acetate (50 mL). The aqueous phase was separated and extracted with ethyl actetate (3×50 mL). The combined organic phases were washed with a saturated solution of sodium chloride (3×50 mL), dried over sodium sulphate, filtered and concentrated to dryness. The title compound was obtained as an orange oil (1.05 g, 93%) which was used in the next step without further purification.

LCMS (ESI-APCI) m/z 394.1 (M+H)$^+$

Step 4: 7-Bromo-4-(4-methoxybenzyl)-4,5-dihydro-1H-pyrido[2,3-e][1,4]diazepin-2(3H)-one

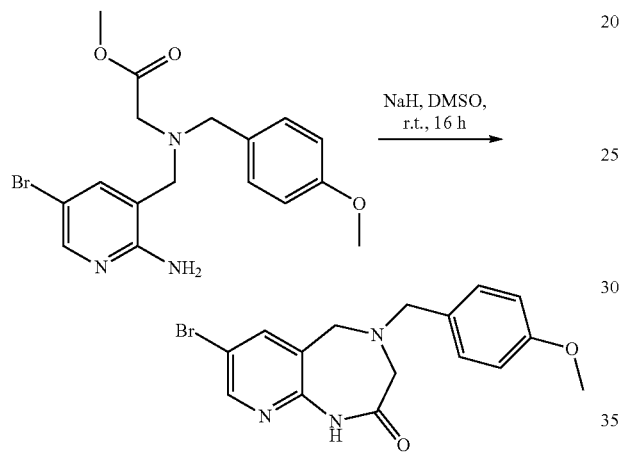

Sodium hydride (60% in oil, 140 mg, 3.40 mmol) was added to a solution of methyl 2-(((2-amino-5-bromopyridin-3-yl)methyl)(4-methoxybenzyl)amino)acetate (1.05 g, 2.66 mmol) in DMSO (17 mL) at room temperature. The reaction mixture was stirred overnight then diluted by addition of water (45 mL). After 2 hours stirring at room temperature, the reaction mixture was filtered. The resulting solid was dried under high vacuum to give the title compound as a yellow solid (600 mg, 63%)

$^1$H NMR (DMSO-d$_6$, 400 MHz): δ (ppm): 10.37 (s, 1H), 8.37 (s, 1H), 7.88 (s, 1H), 7.19 (d, J=8.4 Hz, 2H), 6.89 (d, J=8.4 Hz, 2H), 3.81 (s, 2H), 3.75 (s, 3H), 3.62 (s, 2H), 3.39 (s, 2H).

Step 5: (E)-tert-Butyl 3-(4(4-methoxybenzyl)-2-oxo-2,3,4,5-tetrahydro-1H-pyrido[2,3-e][1,4]diazepin-7-yl)acrylate

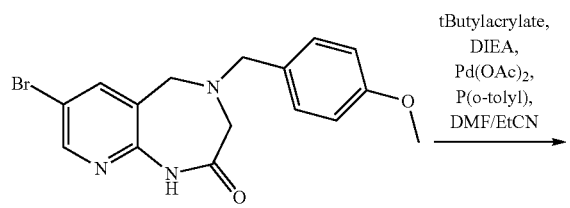

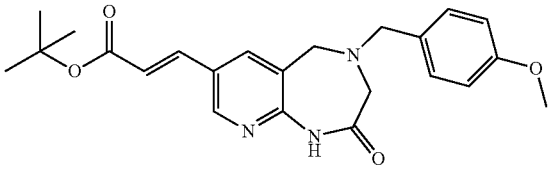

tert-Butyl acrylate (972 μL, 6.64 mmol), diisopropylethylamine (612 μL, 3.47 mmol) and P(o-tolyl)$_3$ (100 mg, 0.33 mmol) were successively added to a suspension of 7-bromo-4-(4-methoxybenzyl)-4,5-dihydro-1H-pyrido[2,3-e][1,4]diazepin-2(3H)-one (600 mg, 1.66 mmol) in propionitrile (10 mL) and dimethylformamide (2 mL). The resulting mixture was then purged with argon prior to the addition of palladium acetate (40 mg, 0.16 mmol). The mixture was purged with argon a second time and refluxed overnight. The reaction mixture was then filtered on Celite®. The filtrate was concentrated to dryness and the residue was solubilized in ethyl acetate (30 mL). The aqueous phase was separated and extracted with ethyl acetate (2×40 mL). The combined organic phases were washed with a saturated solution of sodium chloride (2×20 mL), dried over sodium sulfate, filtered and concentrated to dryness. The residue was purified by chromatography on silica gel, using dichloromethane/ethyl acetate (7:3) as eluent. The title product was obtained as a yellow solid (112 mg, 16%).

LCMS (ESI-APCI) m/z 410.2 (M+H)$^+$

Step 6: (E)-3-(4-(4-Methoxybenzyl)-2-oxo-2,3,4,5-tetrahydro-1H-pyrido[2,3-e][1,4]diazepin-7-yl) acrylic acid hydrochloride

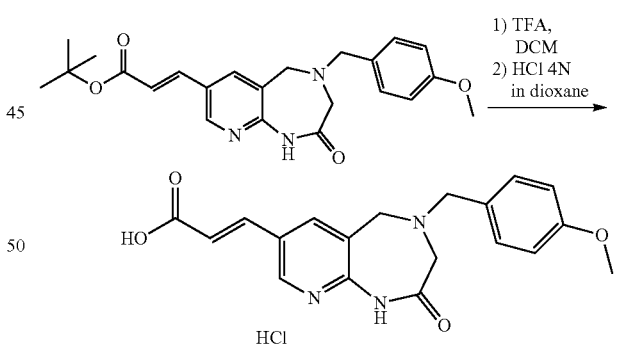

Trifluoroacetic acid (1 mL) was added to a suspension of (E)-tert-butyl 3-(4(4-methoxybenzyl)-2-oxo-2,3,4,5-tetrahydro-1H-pyrido[2,3-e][1,4]diazepin-7-yl)acrylate (112 mg, 0.27 mmol) in dichloromethane (1 mL) at room temperature. The reaction mixture was then stirred for 1 hour and concentrated to dryness. The resulting residue was suspended in a solution of hydrochloric acid in dioxane 4N (2 mL). After 10 minutes stirring at room temperature, the precipitate was filtered and washed with diethyl ether to afford the title product as a pale yellow solid (110 mg, quantitative).

LCMS (ESI-APCI) m/z 354.2 (M+H)$^+$

Step 7: (E)-4-(4-Methoxybenzyl)-7-(3-oxo-3-(3-(thiophen-2-ylmethoxy)azetidin-1-yl)prop-1-enyl)-4,5-dihydro-1H-pyrido[2,3-e][1,4]diazepin-2(3H)-one

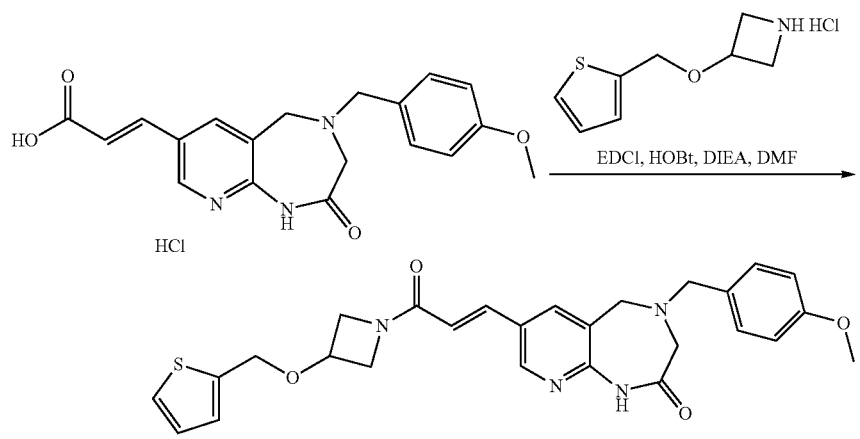

3-(Thiophen-2-ylmethoxy)-azetidine hydrochloride (231 mg, 1.12 mmol), EDCI (215 mg, 1.12 mmol), HOBt (152 mg, 1.12 mmol) and diisopropylethylamine (321 μL, 1.87 mmol) were successively added to a solution of (E)-3-(4-(4-methoxybenzyl)-2-oxo-2,3,4,5-tetrahydro-1H-pyrido[2,3-e][1,4]diazepin-7-yl)acrylic acid hydrochloride (292 mg, 0.75 mmol) in dimethylformamide (20 mL) at room temperature. The reaction mixture was stirred overnight and then diluted by addition of ethyl acetate (30 ml) and water (30 mL). The aqueous layer was separated and extracted with ethyl acetate (2×30 mL) and dichloromethane (2×20 mL). The combined organic phases were washed with a saturated solution of sodium chloride (3×20 mL), dried over sodium sulfate, filtered and concentrated to dryness. The residue was precipitated from a mixture ethyl acetate/diethyl ether to afford the title product as an off-white solid (151 mg, 40%).

LCMS (ESI-APCI) m/z 505.2 (M+H)$^+$

Step 8: (E)-2-Chloropropyl 2-oxo-7-(3-oxo-3-(3-(thiophen-2-ylmethoxy)azetidin-1-yl)prop-1-enyl)-2,3-dihydro-1H-pyrido[2,3-e][1,4]diazepine-4(5H)-carboxylate

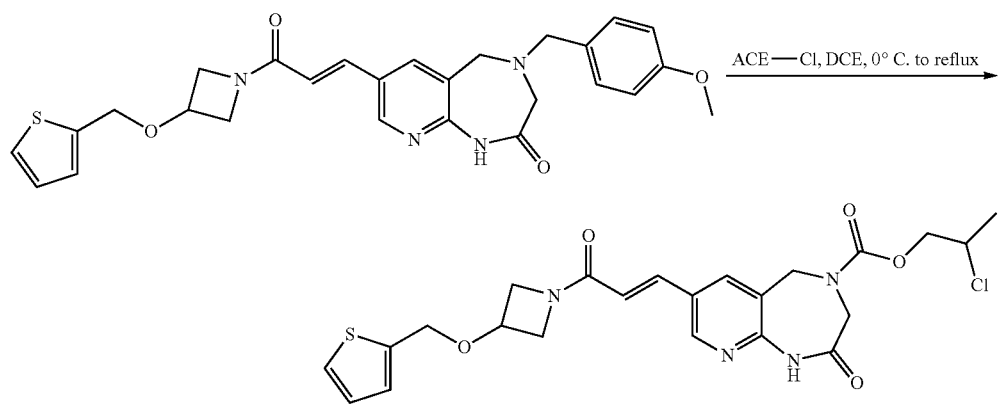

1-Chloroethyl chloroformate (49 μL, 0.45 mmol) was added to a solution of (E)-4-(4-methoxybenzyl)-7-(3-oxo-3-(3-(thiophen-2-ylmethoxy)azetidin-1-yl)prop-1-enyl)-4,5-dihydro-1H-pyrido[2,3-e][1,4]diazepin-2(3H)-one (151 mg, 0.3 mmol) in dichloroethane (4.5 mL) at 0° C. The reaction mixture was stirred for 1 hour at room temperature and for 2 hours at reflux. After concentration to dryness, the residue was purified by chromatography on silica gel, using dichloromethane/methanol (98:2) as eluent. A final trituration in diethyl ether afforded the title product as a white solid (75 mg, 51%).

LCMS (ESI-APCI) m/z 491.1 (M+H)+

Step 9: (E)-7-(3-Oxo-3-(3-(thiophen-2-ylmethoxy)azetidin-1-yl)prop-1-enyl)-4,5-dihydro-1H-pyrido[2,3-e][1,4]diazepin-2(3H)-one

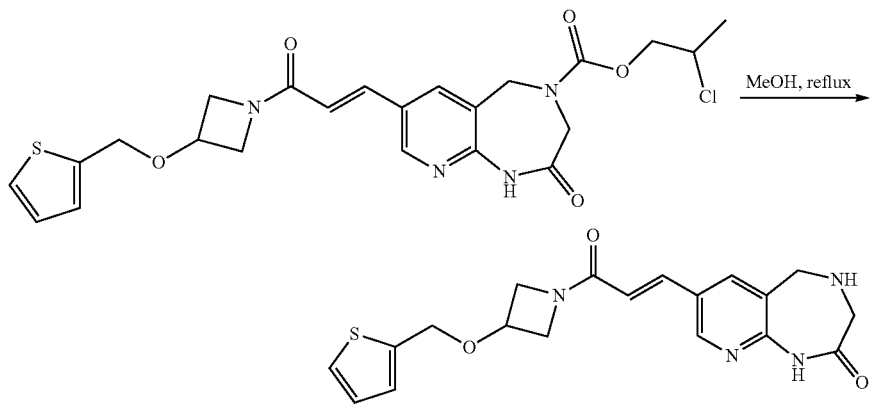

A solution of (E)-2-chloropropyl 2-oxo-7-(3-oxo-3-(3-(thiophen-2-ylmethoxy)azetidin-1-yl)prop-1-enyl)-2,3-dihydro-1H-pyrido[2,3-e][1,4]diazepine-4(5H)-carboxylate (75 mg, 0.15 mmol) in methanol (3 mL) was refluxed for 2 hours. After concentration to dryness, the residue was triturated in methanol. The title product was obtained as a white solid (75 mg, 19%).

LCMS (ESI-APCI) m/z 385.1 (M+H)+

$^1$H NMR (DMSO-$d_6$, 400 MHz): δ (ppm): 11.10 (s, 1H), 9.77 (s, 1H), 8.72 (s, 1H), 8.23 (s, 1H), 7.57-7.55 (m, 1H), 7.48 (d, J=15.6 Hz, 1H), 7.12 (s, 1H), 7.05-7.02 (m, 1H), 6.80 (d, J=15.6 Hz, 1H), 4.68 (s, 2H), 4.49-4.46 (m, 2H), 4.26 (s, 2H), 4.15-4.09 (m, 2H), 3.84 (s, 2H), 3.77-3.74 (m, 1H).

Example 43

(E)-Ethyl 2-(2-oxo-6-(3-oxo-3-(3-(thiophen-2-ylmethoxy)azetidin-1-yl)prop-1-enyl)-1,2-dihydropyrido[2,3-d]pyrimidin-3(4H)-yl)acetate (E43)

Step 1: Ethyl 2-((2-amino-5-bromopyridin-3-yl)methylamino)acetate

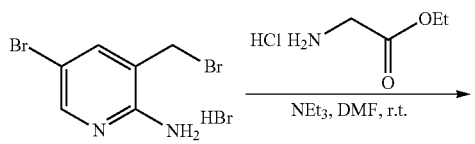

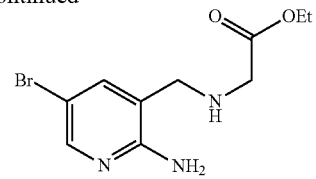

Glycine ethyl ester hydrochloride (805 mg, 5.7 mmol) and triethylamine (2.6 mL, 18.46 mmol) were successively added to a solution of 5-bromo-3-(bromomethyl)pyridin-2-amine hydrobromide (2, 5.7 mmol) in dimethylformamide (65 mL) at room temperature. The reaction mixture was stirred overnight then partitioned between ethyl acetate (70 ml) and water (100 mL). The aqueous phase was separated and extracted with ethyl acetate (2×50 mL). The combined organic phases were washed with a saturated solution of sodium chloride (3×40 mL), dried over sodium sulfate, filtered and concentrated to dryness. The residue was purified by chromatography on silica gel, using dichloromethane/methanol (10:0 to 95:5) as eluent. The title product was obtained as a yellow solid (1.1 g, 68%).

$^1$H NMR (CDCl$_3$, 400 MHz): δ (ppm): 7.96 (s, 1H), 7.29 (s, 1H), 5.66 (br s, NH$_2$), 4.15 (q, J=7.6 Hz, 2H), 3.64 (s, 2H), 3.31 (s, 2H), 1.21 (t, J=7.6 Hz, 3H).

Step 2: Ethyl 2-(6-bromo-2-oxo-1,2-dihydropyrido[2,3-d]pyrimidin-3(4H)-yl)acetate

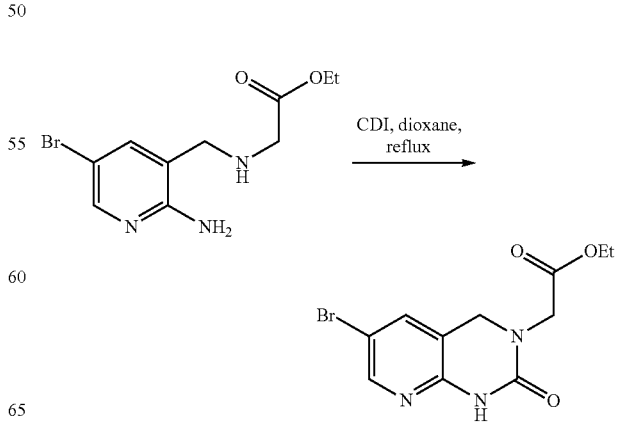

CDI (1.8 g, 114 mmol) was added to a solution of ethyl 2-((2-amino-5-bromopyridin-3-yl)methylamino)acetate (1.1 g, 38.17 mmol) in dioxane (36 mL). The reaction mixture was stirred at reflux for 5 hours and then concentrated to dryness. The residue was partitioned between dichloromethane (40 mL) and water (30 mL). The aqueous phase was separated and extracted with dichloromethane (2×30 mL). The combined organic phases were washed with brine (50 mL), dried over sodium sulfate, filtered and concentrated to dryness. The isolated compound was finally precipitated from a mixture dichloromethane/pentane to give the title product as a yellow solid (670 mg, 56%).

$^1$H NMR (CDCl$_3$, 400 MHz): δ (ppm): 8.16 (s, 1H), 7.87 (s, 1H), 7.41 (s, 1H), 4.48 (s, 2H), 4.14 (q, J=7.6 Hz, 2H), 4.11 (s, 2H), 1.23 (t, J=7.6 Hz, 3H).

Step 3: (E)-tert-Butyl 3-(3-(2-ethoxy-2-oxoethyl)-2-oxo-1,2,3,4-tetrahydropyrido[2,3-d]pyrimidin-6-yl)acrylate

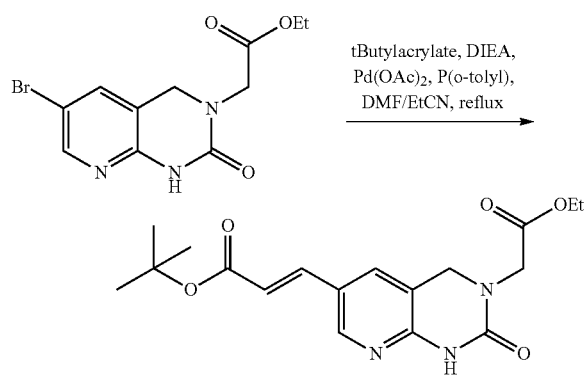

tert-Butyl acrylate (1.25 mL, 8.53 mmol), diisopropylethylamine (730 μL, 4.26 mmol) and P(o-tolyl)$_3$ (130 mg, 0.43 mmol) were successively added to a suspension of ethyl 2-(6-bromo-2-oxo-1,2-dihydropyrido[2,3-d]pyrimidin-3(4H)yl)acetate (670 mg, 2.13 mmol) in propionitrile (11 mL) and dimethylformamide (2.5 mL). The resulting mixture was purged with argon prior to the addition of palladium acetate (48 mg, 0.213 mmol). The mixture was purged with argon a second time and refluxed overnight. The reaction mixture was then filtered on Celite® and washed with ethyl acetate (75 mL) and dichloromethane (75 mL). The filtrate was concentrated to dryness and the residue was partitioned between dichloromethane (50 mL) and water (50 mL). The aqueous phase was separated and extracted with dichloromethane (2×100 mL). The combined organic phases were washed with a saturated solution of sodium chloride (3×100 mL), dried over sodium sulfate, filtered and concentrated to dryness. The residue was precipitated from a mixture dichloromethane/diethylether to afford the title product as a white solid (460 mg, 60%).

$^1$H NMR (CDCl$_3$, 400 MHz): δ (ppm): 8.27 (s, 1H), 7.58 (s, 1H), 7.52 (s, 1H), 7.48 (d, J=16 Hz, 1H), 6.28 (d, J=16 Hz, 1H), 4.58 (s, 2H), 4.25 (q, J=6.8 Hz, 2H), 4.19 (s, 2H), 1.52 (s, 9H), 1.30 (t, J=6.8 Hz, 3H).

Step 4: (E)-3-(3-(2-Ethoxy-2-oxoethyl)-2-oxo-1,2,3,4-tetrahydropyrido[2,3-d]pyrimidin-6-yl)acrylic acid hydrochloride

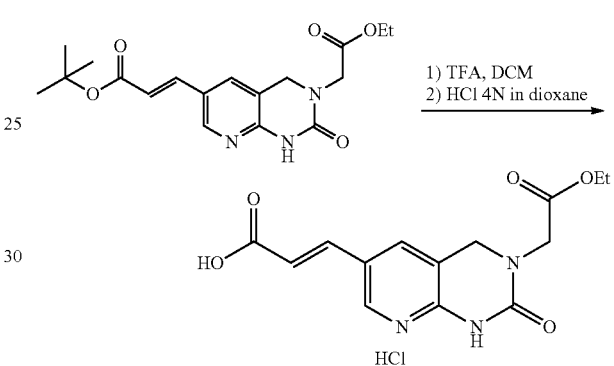

Trifluoroacetic acid (5 mL) was added to a solution of (E)-tert-butyl 3-(3-(2-ethoxy-2-oxoethyl)-2-oxo-1,2,3,4-tetrahydropyrido[2,3-d]pyrimidin-6-yl)acrylate (460 mg, 1.27 mmol) in dichloromethane (5 mL) at room temperature. The reaction mixture was stirred at room temperature for 30 minutes. After concentration to dryness, the residue was suspended in a solution of hydrochloric acid in dioxane 4N (10 mL). The resulting white precipitate was filtered and washed with diethyl ether to give the title compound (470 mg; quantitative).

$^1$H NMR (DMSO-d$_6$, 400 MHz): δ (ppm): 8.37 (s, 1H), 7.95 (s, 1H), 7.54 (d, J=15.6 Hz, 1H), 6.48 (d, J=15.6 Hz, 1H), 4.52 (s, 2H), 4.14 (m, 4H), 1.22 (t, J=6.8 Hz, 3H)

Step 5: (E)-Ethyl 2-(2-oxo-6-(3-oxo-3-(3-(thiophen-2-ylmethoxy)azetidin-1-yl)prop-1-enyl)-1,2-dihydropyrido[2,3-d]pyrimidin-3(4H)-yl)acetate

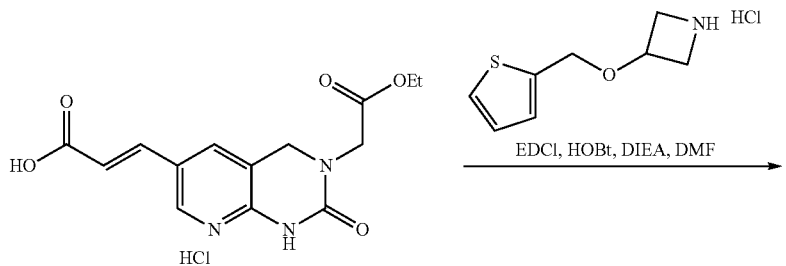

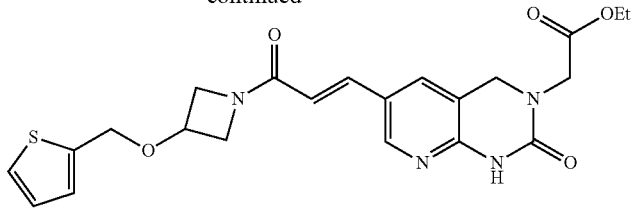

3-(Thiophen-2-ylmethoxy)-azetidine hydrochloride (243 mg, 1.18 mmol), EDCI (227 mg, 1.18 mmol), HOBt (160 mg, 0.6 mmol) and diisopropylethylamine (340 µL, 1.97 mmol) were successively added to a solution of (E)-3-(3-(2-ethoxy-2-oxoethyl)-2-oxo-1,2,3,4-tetrahydropyrido[2,3-d]pyrimidin-6-yl)acrylic acid hydrochloride (270 mg, 0.79 mmol) in dimethylformamide (15 mL) at room temperature. The reaction mixture was stirred for 2 days then partitioned between ethyl acetate (30 mL) and water (40 mL). The aqueous layer was separated and successively extracted with ethyl acetate (2×30 mL) and dichloromethane (2×30 mL). The combined organic phases were washed with a saturated solution of sodium chloride (3×40 mL), dried over sodium sulfate, filtered and concentrated to dryness. The residue was purified by chromatography on silica gel using dichloromethane/methanol (10:0 to 98:2) as eluent. The title product was obtained as an off-white solid (215 mg, 60%).

$^1$H NMR (CDCl$_3$, 400 MHz): δ (ppm): 8.36 (s, 1H), 7.76 (s, 1H), 7.59 (d, J=15.6 Hz, 1H), 7.54 (s, 1H), 7.39 (m, 1H), 7.09-7.04 (m, 2H), 6.69 (d, J=15.6 Hz, 1H), 4.77-4.72 (m, 2H), 4.64 (s, 2H), 4.53-4.43 (m, 2H), 4.31-4.17 (m, 6H), 4.08-4.03 (m, 1H), 1.35 (t, J=6.8 Hz, 3H).

Step 6: Sodium (E)-2-(2-oxo-6-(3-oxo-3-(3-(thiophen-2-ylmethoxy)azetidin-1-yl)prop-1-enyl)-1,2-dihydropyrido[2,3-d]pyrimidin-3(4H)-yl)acetate

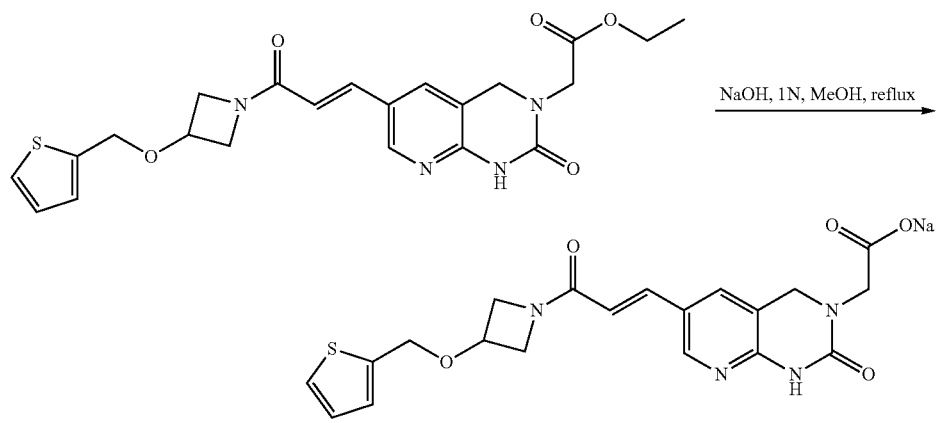

A solution of sodium hydroxide (1N, 438 µL, 0.44 mmol) was added to a suspension of (E)-ethyl 2-(2-oxo-6-(3-oxo-3-(3-(thiophen-2-ylmethoxy)azetidin-1-yl)prop-1-enyl)-1,2-dihydropyrido[2,3-d]pyrimidin-3(4H)-yl)acetate (100 mg, 0.22 mmol) in methanol (5 mL) at room temperature. The reaction mixture was refluxed for 15 minutes then poured into cold water. The resulting precipitate was filtered and washed with diethyl ether. The title product was obtained as a white solid (53.5 mg, 54%).

LCMS (ESI-APCI) m/z 429.1 (M+H)$^+$ (acid form)
$^1$H NMR (DMSO-d$_6$, 400 MHz): δ (ppm): 9.66 (br s, NH), 8.27 (s, 1H), 7.89 (s, 1H), 7.57-7.54 (m, 1H), 7.36 (d, J=15.6 Hz, 1H), 7.13-7.11 (m, 1H), 7.05-7.02 (m, 1H), 6.63 (d, J=15.6 Hz, 1H), 4.67 (s, 2H), 4.48 (s, 2H), 4.48-4.43 (m, 2H), 4.18-4.05 (m, 2H), 3.74-3.70 (m, 1H), 3.53 (s, 2H).

Example 44

(E)-3-(2-(4-Methylpiperazin-1-yl)ethyl)-6-(3-oxo-3-(3-(thiophen-2-ylmethoxy)azetidin-1-yl)prop-1-enyl)-3,4-dihydropyrido[2,3-d]pyrimidin-2(1H)-one (E44)

Step 1: 2-Amino-5-bromonicotinaldehyde hydrobromide

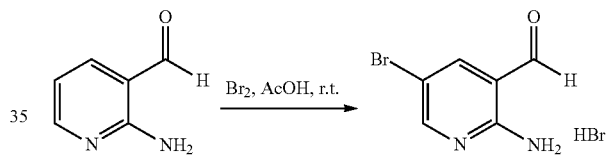

A solution of bromine (1.05 mL, 20.0 mmol) in acetic acid (20 mL) was added to a solution of 2-amino-3-pyridinecarboxaldehyde (2.5 g, 20 mmol) in acetic acid (50 mL) at room temperature. The reaction mixture was then stirred overnight. The resulting precipitate was filtered and washed with diethyl ether to give the title compound as a white solid (4.66 g, 80%).

$^1$H NMR (DMSO-d$_6$, 400 MHz): δ (ppm): 9.82 (s, 1H), 8.32 (s, 1H), 8.26 (s, 1H), 7.74 (br s, NH$_2$).

Step 2: 5-Bromo-3-((2-(4-methylpiperazin-1-yl)ethylamino)methyl)pyridin-2-amine

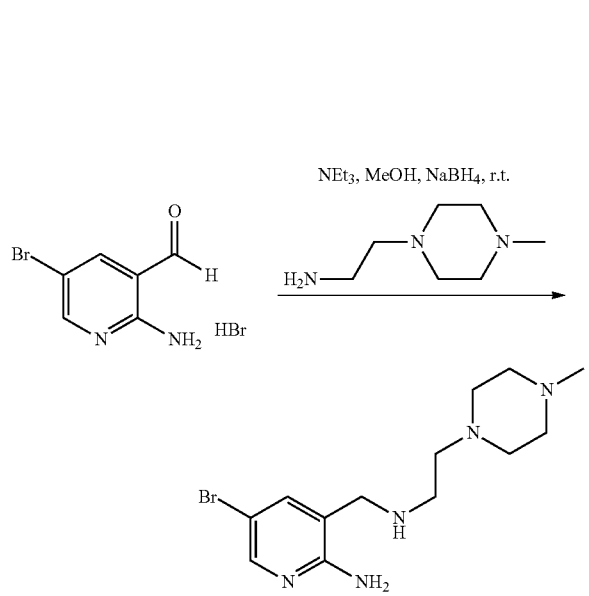

Triethylamine (1.0 mL, 7.09 mmol) was added to a solution of 2-amino-5-bromonicotinaldehyde hydrobromide (1.0 g, 3.54 mmol) in methanol (24 mL) at room temperature. The reaction mixture was stirred for 10 minutes prior to the addition of 2-(4-methylpiperazin-1-yl)ethanamine (558 mg, 3.90 mmol). The reaction mixture was then stirred overnight and cooled to 0° C. Sodium borohydride (201 mg, 5.32 mmol) was added portionwise at 0° C. and the reaction mixture was allowed to reach room temperature and stirred for 4 hours. After concentration to dryness, the residue was purified by chromatography on silica gel using dichloromethane/methanol/ammoniac (10:0:0.1 to 9:1:0.1) as eluent. The title product was obtained as a yellow solid (560 mg, 48%).

LCMS (ESI-APCI) m/z 328.1-330.1 (M+H)$^+$

Step 3: 6-Bromo-3-(2-(4-methylpiperazin-1-yl)ethyl)-3,4-dihydropyrido[2,3-d]pyrimidin-2(1H)-one

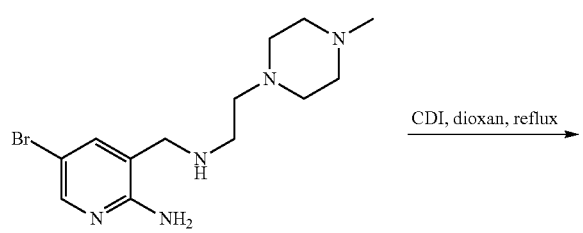

CDI (815 mg, 5.0 mmol) was added to a solution of 5-bromo-3-((2-(4-methylpiperazin-1-yl)ethylamino)methyl)pyridin-2-amine (550 mg, 1.67 mmol) in dioxane (13 mL). The reaction mixture was stirred overnight at reflux. After concentration to dryness, the residue was purified by chromatography on silica gel using dichloromethane/methanol/ammoniac (10:0:0.1 to 9:1:0.1) as eluent. The title product was obtained as a yellow solid (430 mg, 72%).

LCMS (ESI-APCI) m/z 354.1-356.1 (M+H)$^+$

Step 4: (E)-tert-Butyl 3-(3-(2-(4-methylpiperazin-1-yl)ethyl)-2-oxo-1,2,3,4-tetrahydropyrido[2,3-d]pyrimidin-6-yl)acrylate

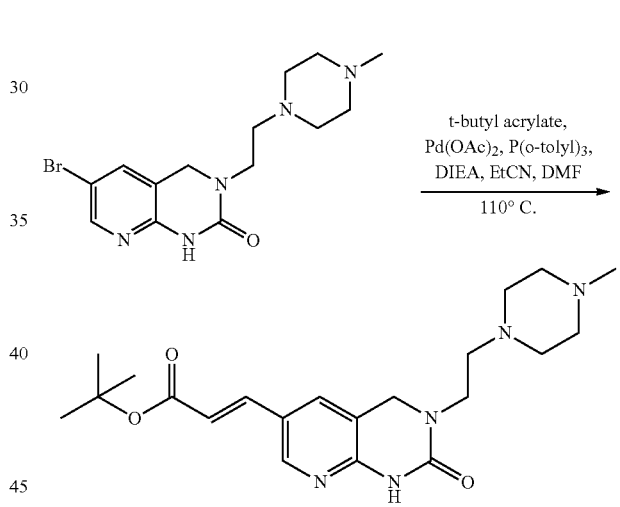

tert-Butyl acrylate (830 μL, 5.64 mmol), diisopropylethylamine (500 μL, 2.82 mmol) and P(o-tolyl)$_3$ (86 mg, 0.28 mmol) were successively added to a suspension of 6-bromo-3-(2-(4-methylpiperazin-1-yl)ethyl)-3,4-dihydropyrido[2,3-d]pyrimidin-2(1H)-one (500 mg, 1.41 mmol) in propionitrile (6 mL) and dimethylformamide (2 mL). The resulting mixture was purged with argon prior to the addition of palladium acetate (32 mg, 0.14 mmol). The mixture was then purged a second time with argon and refluxed overnight. The reaction mixture was filtered on Celite® and washed with ethyl acetate (100 mL) and dichloromethane (100 mL). The filtrate was concentrated to dryness and the residue was solubilized in dichloromethane (100 mL). The resulting solution was washed with a saturated solution of sodium chloride (3×100 mL), dried over sodium sulfate, filtered and concentrated to dryness. The residue was purified by chromatography on silica gel using dichloromethane/methanol/ammoniac (1:0:0.1 to 98:2:0.1) as eluent. The title product was obtained as a brown solid (83 mg, 15%).

LCMS (ESI-APCI) m/z 402.3 (M+H)$^+$

Step 5: (E)-3-(3-(2-(4-Methylpiperazin-1-yl)ethyl)-2-oxo-1,2,3,4-tetrahydropyrido[2,3-d]pyrimidin-6-yl)acrylic acid hydrochloride

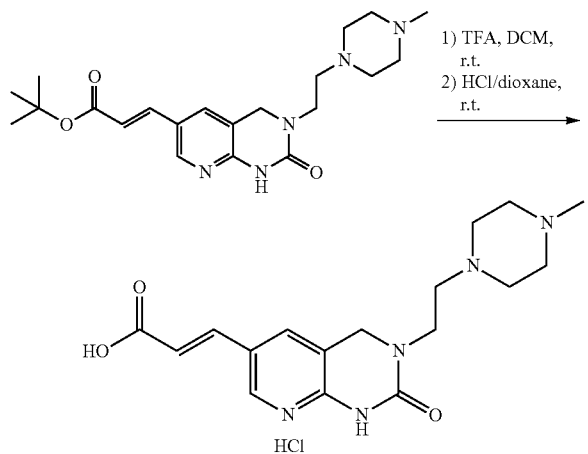

Trifluoroacetic acid (2 mL) was added to a suspension (E)-tert-butyl 3-(3-(2-(4-methylpiperazin-1-yl)ethyl)-2-oxo-1,2,3,4-tetrahydropyrido[2,3-d]pyrimidin-6-yl)acrylate (1.1 g, 3.76 mmol) in dichloromethane (2 mL). The reaction mixture was stirred at room temperature for 1 hour and concentrated to dryness. The resulting residue was solubilized in a solution of hydrochloric acid in dioxane (4N, mL). After 10 minutes stirring at room temperature, the precipitate was filtered and washed with diethyl ether to afford the title product as a pale yellow solid (90 mg, quantitative).

LCMS (ESI-APCI) m/z 346.2 (M+H)$^+$

Step 6: (E)-3-(2-(4-Methylpiperazin-1-yl)ethyl)-6-(3-oxo-3-(3-(thiophen-2-ylmethoxy)azetidin-1-yl)prop-1-enyl)-3,4-dihydropyrido[2,3-d]pyrimidin-2(1H)-one 3-(Thiophen-2-ylmethoxy)-azetidine hydrochloride (38 mg, 0.18 mmol), EDCI (35 mg, 0.18 mmol), HOBt (26 mg, 0.18 mmol) and diisopropylethylamine (54 µL, 0.31 mmol) were successively added to a solution of (E)-3-(3-(2-(4-methylpiperazin-1-yl)ethyl)-2-oxo-1,2,3,4-tetrahydropyrido[2,3-d]pyrimidin-6-yl)acrylic acid hydrochloride (54 mg, 0.12 mmol) in dimethylformamide (6 mL) at room temperature. The reaction mixture was stirred for 2 days and then diluted by addition of ethyl acetate (50 mL) and water (50 mL). The aqueous layer was separated and extracted with ethyl acetate (2×50 mL). The combined organic phases were washed with a saturated solution of sodium chloride (3×50 mL), dried over sodium sulfate, filtered and concentrated to dryness. The residue was purified by chromatography on silica gel using dichloromethane/methano/ammoniac (1:0:0.1 to 9:1:0.1) as eluent. After several triturations of the compound in diethylether and pentane and a recristallisation from acetone, the title product was obtained as an off-white solid (2 mg, 3%).

LCMS (ESI-APCI) m/z 497.3 (M+H)$^+$ $^1$H NMR (CDCl$_3$, 400 MHz): δ (ppm): 8.28 (s, 1H), 7.54 (d, J=15.6 Hz, 1H), 7.49-4.47 (m, 2H), 7.35-7.33 (m, 1H), 7.04-6.98 (m, 2H), 6.34 (d, J=15.6 Hz, 1H), 4.69 (d, J=6 Hz, 2H), 4.56 (s, 2H), 4.48-4.38 (m, 2H), 4.28-4.23 (m, 1H), 4.16-4.13 (m, 1H), 4.03-3.99 (m, 1H), 3.58 (t, J=7.6 Hz, 2H), 2.63 (t, J=7.6 Hz, 2H), 2.68-2.46 (m, 8H), 1.65 (s, 3H).

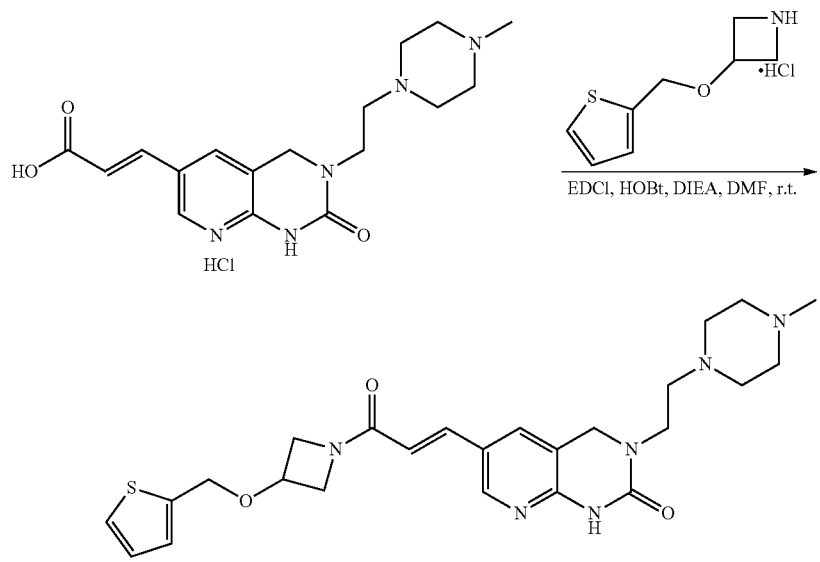

Example 45

(E)-3-(3-((Dimethylamino)methyl)-1H-pyrrolo[2,3-b]pyridin-5-yl)-1-(3-(thiophen-2-ylmethoxy)azetidin-1-yl)prop-2-en-1-one (E45)

Step 1: (E)-tert-Butyl 3-(1H-pyrrolo[2,3-b]pyridin-5-yl)acrylate t-butyl acrylate

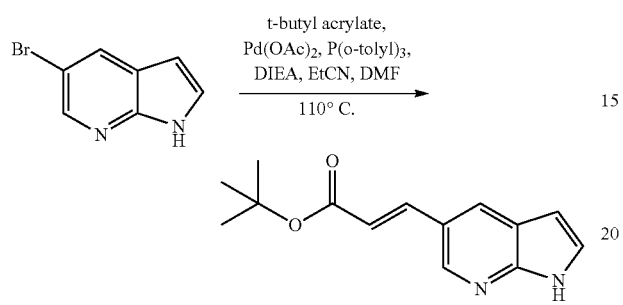

tert-Butyl acrylate (5.9 mL, 40.6 mmol), diisopropylethylamine (3.5 mL, 20.3 mmol) and P(o-tolyl)₃ (618 mg, 2.0 mmol) were successively added to a suspension of 5-bromo-1H-pyrrolo[2,3-b]pyridine (2.0 g, 10.15 mmol) in propionitrile (40 mL) and dimethylformamide (10 mL). The resulting mixture was purged with argon prior to the addition of palladium acetate (227 mg, 1.0 mmol). The mixture was then purged with argon a second time and refluxed overnight. The reaction mixture was filtered on Celite®. The filtrate was concentrated to dryness and the residue was solubilized in ethyl acetate (3×100 mL). The organic layers were washed with a saturated solution of sodium chloride (3×50 mL), dried over sodium sulfate, filtered and concentrated to dryness. The crude was purified by flash chromatography on silica gel using dichloromethane/ethyl acetate (1:0 to 7:3) as eluent. The title compound was obtained as a yellow solid (465 mg, 28%)

¹H NMR (CDCl₃, 400 MHz): δ (ppm): 10.39 (s, 1H, NH), 8.49 (s, 1H), 8.12 (s, 1H), 7.75 (d, J=16 Hz, 1H), 7.38 (d, J=1.6 Hz, 1H), 6.54 (d, J=2.8 Hz, 1H), 6.45 (d, J=16 Hz, 1H), 1.55 (s, 9H).

Step 2: (E)-tert-Butyl 3-(3-((dimethylamino)methyl)-1H-pyrrolo[2,3-b]pyridin-5-yl)acrylate

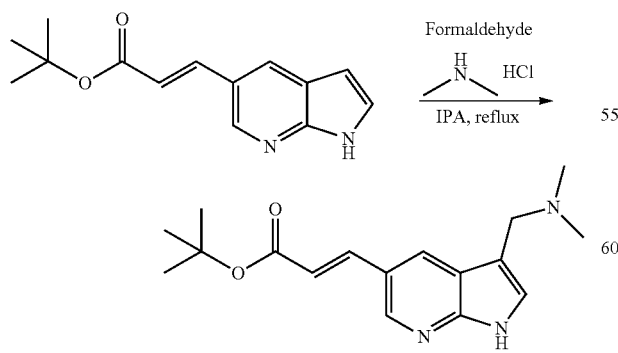

Formaldehyde (37% in water, 219 μL, 2.92 mmol) and dimethylamine hydrochloride (237 mg, 2.92 mmol) were added to a solution of (E)-tert-butyl 3-(1H-pyrrolo[2,3-b]pyridin-5-yl)acrylate (420 mg, 1.72 mmol) in isopropanol (42 mL) at room temperature. The reaction mixture was stirred at reflux overnight. Since the LCMS monitoring still indicated the presence of remaining starting material, formaldehyde (25 μL) and dimethyl amine hydrochloride (28 mg) were added. The reaction mixture was stirred at reflux for an additional 4 hours and concentrated to dryness. The residue was solubilized in an aqueous solution of potassium carbonate (3N, 100 mL) and the solution was extracted with ethyl acetate (3×100 mL). The combined organic layers were washed with a saturated solution of sodium chloride (50 mL), dried over sodium sulfate, filtered and concentrated to dryness. The crude was tritured in pentane to give the title compound as a white solid (242 mg, 46%).

¹H NMR (CDCl₃, 400 MHz): δ (ppm): 8.75 (s, 1H), 8.38 (s, 1H), 8.14 (s, 1H), 7.65 (d, J=16 Hz, 1H), 6.37 (d, J=16 Hz, 1H), 3.54 (s, 2H), 2.21 (s, 6H), 1.06 (s, 9H).

Step 3: (E)-3-(3-((Dimethylamino)methyl)-1H-pyrrolo[2,3-b]pyridin-5-yl)acrylic acid hydrochloride

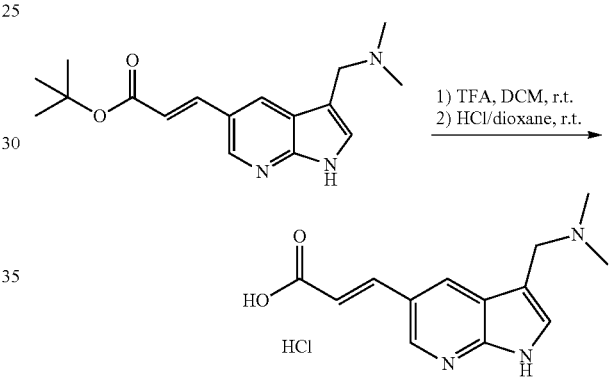

Trifluoroacetic acid (2 mL) was added to a suspension of (E)-tert-butyl 3-(3-((dimethylamino)methyl)-1H-pyrrolo[2,3-b]pyridin-5-yl)acrylate (120 mg, 0.39 mmol) in dichloromethane (2 mL). The reaction mixture was stirred at room temperature for 30 minutes and concentrated to dryness. The resulting residue was solubilized in a solution of hydrochloric acid in dioxane (4N, 2 mL). After 10 minutes stirring at room temperature, the precipitate was filtered and washed with diethyl ether to afford the title product as a pale yellow solid (112 mg, quantitative).

Step 4: (E)-3-(3-((Dimethylamino)methyl)-1H-pyrrolo[2,3-b]pyridin-5-yl)-1-(3-(thiophen-2-ylmethoxy)azetidin-1-yl)prop-2-en-1-one

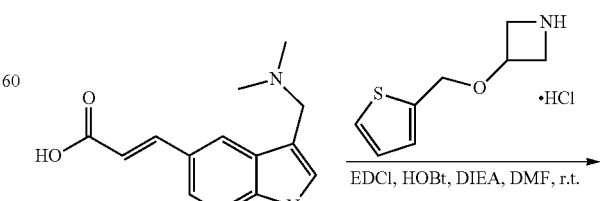

-continued

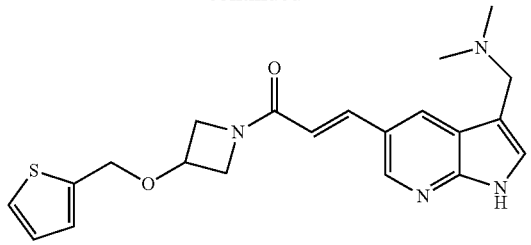

3-(Thiophen-2-ylmethoxy)-azetidine hydrochloride (61 mg, 0.30 mmol), EDCI (71.5 mg, 0.37 mmol), HOBt (52 mg, 0.37 mmol) and diisopropylethylamine (110 µL, 0.62 mmol) were successively added to a solution of (E)-3-(3-((dimethylamino)methyl)-1H-pyrrolo[2,3-b]pyridin-5-yl)acrylic acid hydrochloride (70 mg, 0.25 mmol) in dimethylformamide (10 mL) at room temperature. The reaction mixture was stirred overnight then partitioned between ethyl acetate (30 mL) and water (30 mL). The aqueous layer was separated, basified with an aqueous solution of sodium hydroxyde (2N) until pH 12 and finally extracted with ethyl acetate (2×50 mL). The combined organic phases were washed with a saturated solution of sodium chloride (3×50 mL), dried over sodium sulfate and concentrated to dryness. The residue was purified by chromatography on silica gel using dichloromethane/methanol/ammoniac (1:0:0.1 to 9:1:0.1) as eluent. The title product was obtained as a yellow solid (10 mg, 10%).

LCMS (ESI-APCI) m/z 397.2 (M+H)$^+$ $^1$H NMR (DMSO-d$_6$, 400 MHz): δ (ppm): 11.69 (s, NH), 8.51 (s, 1H), 8.29 (s, 1H), 7.56 (d, J=15.6 Hz, 1H), 7.54 (s, 1H), 7.39 (s, 1H), 7.13-7.11 (m, 1H), 7.03-7.01 (m, 1H), 6.74 (d, J=15.6 Hz, 1H), 4.67 (s, 2H), 4.53-4.43 (m, 2H), 4.17-4.10 (m, 2H), 3.75-3.56 (m, 1H), 3.56 (s, 2H), 2.16 (s, 6H).

Example 46

(E)-6-(3-Oxo-3-(3-(thiophen-2-ylmethoxy)azetidin-1-yl)prop-1-enyl)-1H-imidazo[4,5-b]pyridin-2(3H)-one (E46)

Step 1:
6-Bromo-1H-imidazo[4,5-b]pyridin-2(3H)-one

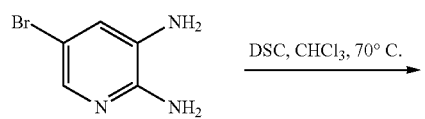

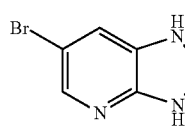

DSC (4.4 g, 17.54 mmol) was added to a suspension of 5-bromopyridine-2,3-diamine (3.0 g, 15.95 mmol) in chloroform (150 mL) at room temperature. The reaction mixture was then heated up to 70° C. and stirred overnight. After concentration to dryness, the resulting brown solid was triturated in a mixture petroleum ether/ethyl acetate (6:4, 300 mL) and washed successively with water (100 mL) and diethyl ether (100 mL). The title product was isolated as a brown solid (2.7 g, 81%).

$^1$H NMR (DMSO-d$_6$, 400 MHz): δ (ppm): 11.53 (s, 1H, NH), 11.04 (s, 1H, NH), 7.95 (d, J=2 Hz, 1H), 7.41 (d, J=2 Hz, 1H).

Step 2: (E)-tert-Butyl 3-(3-(2-(4-methylpiperazin-1-yl)ethyl)-2-oxo-1,2,3,4-tetrahydropyrido[2,3-d]pyrimidin-6-yl)acrylate

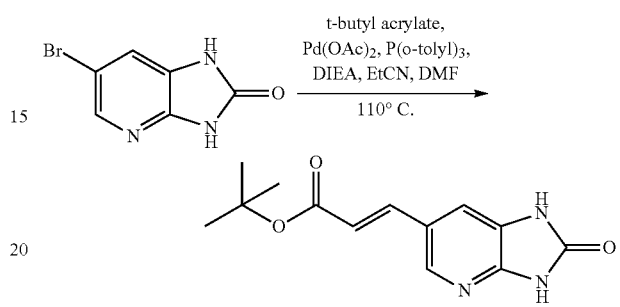

tert-Butyl acrylate (2.74 mL, 18.6 mmol), diisopropylethylamine (1.6 mL, 9.8 mmol) and P(o-tolyl)$_3$ (272 mg, 0.89 mmol) were successively added to a suspension of 6-bromo-1H-imidazo[4,5-b]pyridin-2(3H)-one (1.0 g, 4.67 mmol) in propionitrile (27 mL) and dimethylformamide (7 mL) at room temperature. The resulting mixture was purged with argon prior to the addition of palladium acetate (100 mg, 0.44 mmol). The mixture was then purged with argon a second time and refluxed overnight. The reaction mixture was filtered on Celite® and the filtrate was concentrated to dryness. The residue was partitioned between ethyl acetate (20 mL) and water (30 mL). The organic phase was washed with a saturated solution of sodium chloride (2×30 mL), dried over sodium sulfate, filtered and concentrated to dryness. The residue was triturated in diethyl ether to give the title product as a brown solid (667 mg, 56%).

$^1$H NMR (DMSO-d$_6$, 400 MHz): δ (ppm): 11.55 (s, 1H, NH), 11.05 (s, 1H, NH), 8.14 (s, 1H), 7.59 (s, 1H), 7.56 (d, J=16 Hz, 1H), 6.51 (d, J=14 Hz, 1H), 1.49 (s, 9H).

Step 3: (E)-3-(2-Oxo-2,3-dihydro-1H-imidazo[4,5-b]pyridin-6-yl)acrylic acid hydrochloride

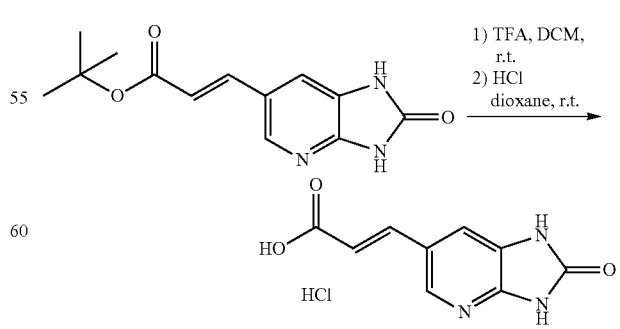

Trifluoroacetic acid (2 mL) was added to a suspension of (E)-tert-butyl 3-(2-oxo-2,3-dihydro-1H-imidazo[4,5-b]pyridin-6-yl)acrylate (400 mg, 1.54 mmol) in dichloromethane (2 mL) at room temperature. The reaction mixture was stirred for 1 hour then concentrated to dryness. The resulting residue was suspended in a solution of hydrochloric acid in dioxane 4N (2 mL). After 10 minutes stirring at room temperature, the precipitate was filtered and washed with diethyl ether to afford the title product as a pale yellow solid (381 mg, quantitative).

$^1$H NMR (DMSO-d$_6$, 400 MHz): δ (ppm): 11.58 (br s, NH), 11.06 (s, NH), 8.14 (s, 1H), 7.60 (d, J=16 Hz, 1H), 7.58 (s, 1H), 6.51 (d, J=16 Hz, 1H).

Step 4: (E)-6-(3-Oxo-3-(3-(thiophen-2-ylmethoxy)azetidin-1-yl)prop-1-enyl)-1H-imidazo[4,5-b]pyridin-2(3H)-one

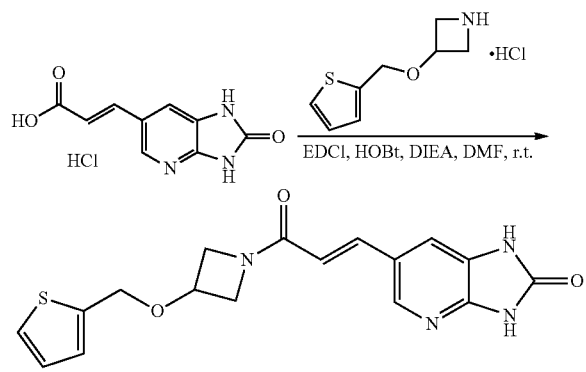

3-(Thiophen-2-ylmethoxy)-azetidine hydrochloride (127 mg, 0.62 mmol), EDCI (120 mg, 0.62 mmol), HOBt (86 mg, 0.62 mmol) and diisopropylethylamine (180 µL, 1.03 mmol) were successively added to a solution of (E)-3-(2-oxo-2,3-dihydro-1H-imidazo[4,5-b]pyridin-6-yl)acrylic acid hydrochloride (100 mg, 0.41 mmol) in dimethylformamide (10 mL) at room temperature. The reaction mixture was stirred overnight then partitioned between ethyl acetate (20 mL) and water (30 mL). The aqueous layer was separated and successively extracted with ethyl acetate (2×20 mL) and dichloromethane (2×20 mL). The combined organic phases were washed with a saturated solution of sodium chloride (3×30 mL), dried over sodium sulfate, filtered and concentrated to dryness. The residue was purified by chromatography on silica gel using dichloromethane/methanol (98:2 to 93:7) as eluent. The residue was triturated in pentane to afford the title product as a pale orange solid (21 mg, 14%).

LCMS (ESI-APCI) m/z 357.1 (M+H)$^+$ $^1$H NMR (DMSO-d$_6$, 400 MHz): δ (ppm): 11.54 (s, NH), 11.06 (s, NH), 8.13 (s, 1H), 7.6 (s, 1H), 7.57-7.54 (m, 1H), 7.44 (d, J=15.6 Hz, 1H), 7.13-7.10 (m, 1H), 7.05-7.02 (m, 1H), 6.69 (d, J=15.6 Hz, 1H), 4.67 (s, 2H), 4.48-4.45 (m, 2H), 4.13-4.08 (m, 2H), 3.75-3.70 (m, 1H).

Example 47

(E)-6-(3-Oxo-3-(3-(3,3,3-trifluoropropoxy)azetidin-1-yl)prop-1-enyl)-3,4-dihydro-1,8-naphthyridin-2(1H)-one (E47)

Step 1: 1-Benzhydryl-3-(3,3,3-trifluoropropoxy)azetidine

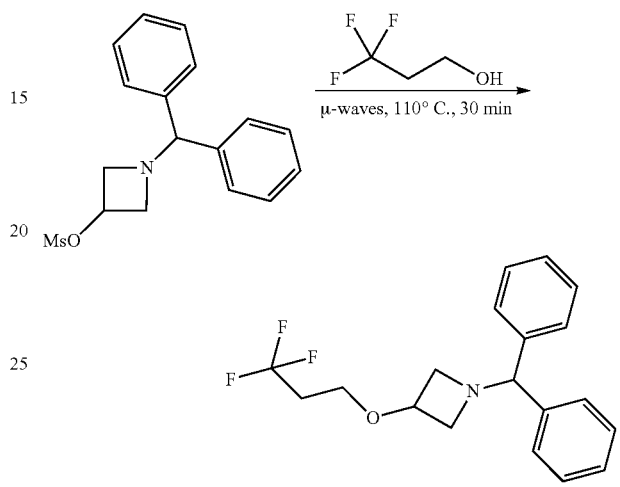

A solution of 1-benzhydrylazetidin-3-yl methanesulfonate (500 mg, 1.57 mmol) in trifluoroethanol (3.5 mL, 30.7 mmol) was stirred under microwaves at 110° C. for 30 minutes. The reaction mixture was diluted by addition of dichloromethane (100 mL) and a saturated solution of sodium hydrogencarbonate (25 mL). The aqueous layer was separated and extracted with dichloromethane (2×10 mL). The combined organic phase was dried over sodium sulfate, filtered and concentrated to dryness. The residue was purified by chromatography on silica gel using dichloromethane/ethyl acetate (90:10) as eluent. The title product was obtained as a light yellow gum (170 mg, 32%).

LCMS (ESI-APCI) m/z 336.1 (M+H)$^+$

Step 2: 3-(3,3,3-Trifluoropropoxy)azetidine hydrochloride

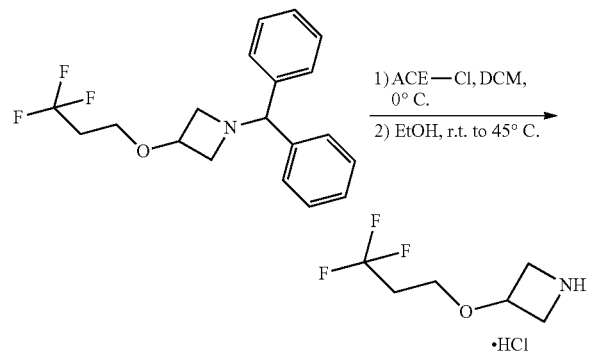

1-Chloroethyl chloroformate (136 µL, 1.25 mmol) was added to a solution of 1-benzhydryl-3-(3,3,3-trifluoropropoxy)-azetidine (400 mg, 1.19 mmol) in dichloromethane (10 mL) at 0° C. The reaction mixture was stirred for 1 hour. Ethanol (10 mL) was added and the reaction mixture was stirred for 1 hour at room temperature and for 2 hours at 45° C. After concentration to dryness, the crude mixture was triturated in petroleum ether (2×20 mL) to give a yellow oil (245 mg, quantitative) which was used in the next step without further purification.

$^1$H NMR (DMSO-$d_6$, 400 MHz): δ (ppm): 9.25 (s, NH$_2$), 4.43-4.40 (m, 1H), 4.13-4.09 (m, 2H), 3.80-3.77 (m, 2H), 3.61 (t, J=6.4 Hz, 2H), 2.65-2.55 (m, 2H).

Step 3: (E)-6-(3-Oxo-3-(3-(3,3,3-trifluoropropoxy)azetidin-1-yl)prop-1-enyl)-3,4-dihydro-1,8-naphthyridin-2(1H)-one

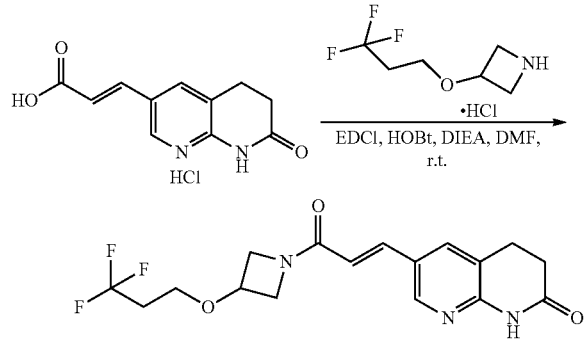

3-(3,3,3-Trifluoropropoxy)azetidine hydrochloride (194 mg, 0.94 mmol), EDCI (181 mg, 0.94 mmol), HOBt (128 mg, 0.94 mmol) and diisopropylethylamine (274 µL, 1.57 mmol) were successively added to a solution of (E)-3-(7-oxo-5,6,7,8-tetrahydro-1,8-naphthyridin-3-yl)-acrylic acid hydrochloride (160 mg, 0.63 mmol) in dimethylformamide (15 mL) at room temperature. The reaction mixture was stirred overnight then diluted by addition of ethyl acetate (30 mL) and water (40 mL). The aqueous layer was separated and extracted with ethyl acetate (2×30 mL). The combined organic phases were washed with a saturated solution of sodium chloride (3×30 mL), dried over sodium sulfate, filtered and concentrated to dryness. The residue was purified by chromatography on silica gel using dichloromethane/methanol (98:2) as eluent. The residue was finally precipitated from methanol to afford the title product as a white solid (90 mg, 39%).

LCMS (ESI-APCI) m/z 370.1 (M+H)$^+$ $^1$H NMR (DMSO-$d_6$, 400 MHz): δ (ppm): 10.68 (s, NH), 8.34 (s, 1H), 8.02 (s, 1H), 7.40 (d, J=15.6 Hz, 1H), 6.72 (d, J=15.6 Hz, 1H), 4.50-4.38 (m, 2H), 4.18-4.07 (m, 2H), 3.76-3.72 (m, 1H), 3.63-3.59 (m, 2H), 2.91 (t, J=7.6 Hz, 2H), 2.5 (t, J=7.6 Hz, 2H), 2.63-2.51 (m, 2H). The CH$_2$ at 2.5 ppm is partially hidden by DMSO.

Example 48

(E)-6-(3-Oxo-3-(3-(4,4,4-trifluorobutoxy)azetidin-1-yl)prop-1-enyl)-3,4-dihydro-1,8-naphthyridin-2(1H)-one (E48)

Step 1: 1-Benzhydryl-3-(4,4,4-trifluorobutoxy)-azetidine

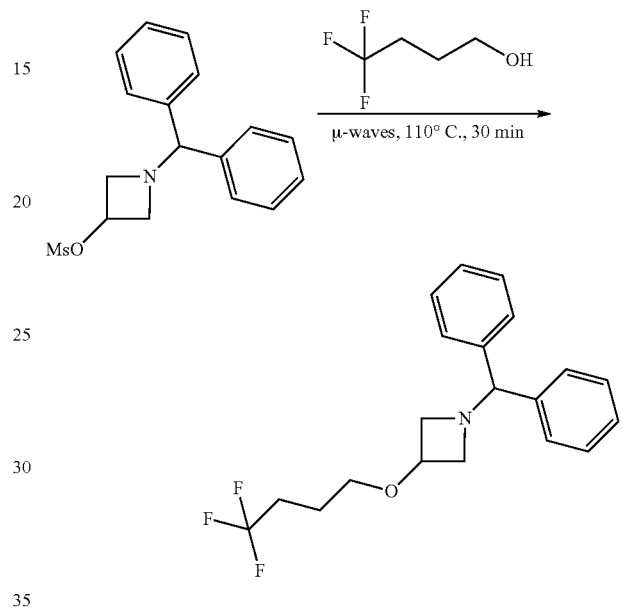

A suspension of 1-benzhydrylazetidin-3-yl methanesulfonate (247 mg, 0.78 mmol) in trifluoropropanol (1 g, 7.8 mmol) was placed under micro-wave irradiations (100 W) and heated at 100° C. during 30 minutes. The reaction mixture was diluted by addition of dichloromethane (50 mL) and water (30 mL). The two phases were separated and the aqueous phase was extracted with dichloromethane (2×20 mL). The combined organic phases were dried over sodium sulphate and concentrated to dryness. The residue was purified by chromatography on silica gel using petroleum ether/ethyl acetate (8:2) as eluent. The title product was isolated as a yellow oil (191 mg, 33%).

LCMS (ESI-APCI) m/z 350.2 (M+H)$^+$

Step 2: 3-(4,4,4-Trifluorobutoxy)-azetidine hydrochloride

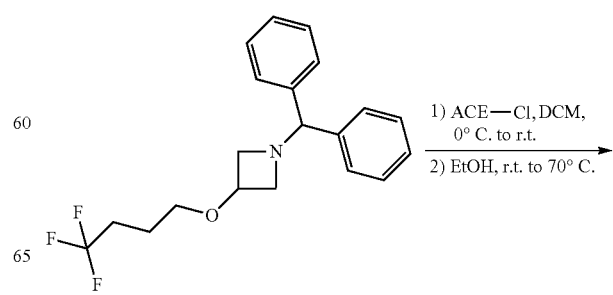

-continued

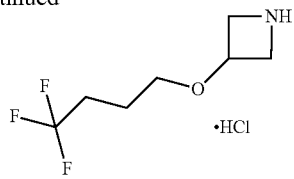

1-Chloroethyl chloroformate (65 µL, 0.60 mmol) was added to a solution of 1-benzhydryl-3-(4,4,4-trifluorobutoxy)-azetidine (200 mg, 0.57 mmol) in dichloromethane (5 mL) at 0° C. The reaction mixture was stirred for 3 hours and minutes at room temperature. Ethanol (5 mL) was then added and the mixture was stirred for an additional 2 hours at 0° C. and 2 hours at 70° C. The reaction mixture was concentrated under vacuum and the residue was triturated in petroleum ether (2×20 mL) to give a colorless oil (130 mg, quantitative) which was used without further purification.

$^1$H NMR (CDCl$_3$, 400 MHz): δ (ppm): 9.14 (br s, NH$_2$), 4.36-4.32 (m, 1H), 4.15-4.05 (m, 2H), 3.82-3.75 (m, 2H), 3.45-3.40 (m, 2H), 2.34-2.31 (m, 2H), 1.74-1.70 (m, 2H).

Step 3: (E)-6-(3-Oxo-3-(3-(4,4,4-trifluorobutoxy)azetidin-1-yl)prop-1-enyl)-3,4-dihydro-1,8-naphthyridin-2(1H)-one

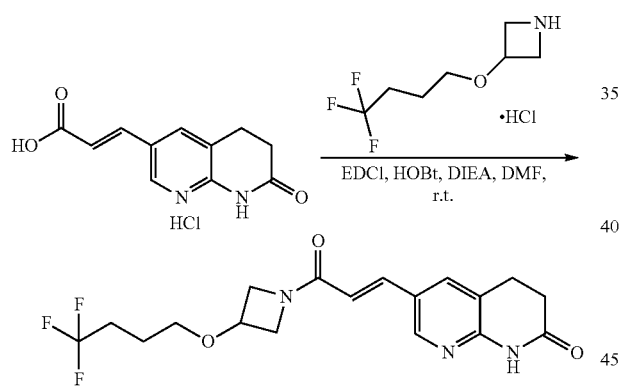

3-(4,4,4-Trifluorobutoxy)-azetidine (129 mg, 0.59 mmol), EDCI (113 mg, 0.59 mmol), HOBt (80 mg, 0.59 mmol) and diisopropylethylamine (170 µL, 0.97 mmol) were successively added to a solution of (E)-3-(7-oxo-5,6,7,8-tetrahydro-1,8-naphthyridin-3-yl)-acrylic acid hydrochloride (100 mg, 0.039 mmol) in dimethylformamide (10 mL) at room temperature. The reaction mixture was stirred overnight then diluted with ethyl acetate (50 mL) and water (50 mL). The aqueous layer was separated and extracted with ethyl acetate (2×50 mL). The combined organic phases were washed with a saturated solution of sodium chloride (3×100 mL), dried over sodium sulfate and concentrated to dryness. The residue was purified by chromatography on silica gel using dichloromethane/methanol (95:5 to 9:1) as eluent. The residue was finally triturated in diethylether to give the title product as a pale yellow solid (52.5 mg, 35%).

LCMS (ESI-APCI) m/z 384.2 (M+H)$^+$ $^1$H NMR (DMSO-d$_6$, 400 MHz): δ (ppm): 10.68 (s, NH), 8.34 (s, 1H), 8.01 (s, 1H), 7.4 (d, J=15.6 Hz, 1H), 6.72 (d, J=15.6 Hz, 1H), 4.51-4.33 (m, 2H), 4.17-4.07 (m, 2H), 3.77-3.73 (m, 1H), 3.46-3.42 (m, 2H), 2.92 (t, J=7.6 Hz, 2H), 2.5 (t, J=7.6 Hz, 2H), 2.36-2.29 (m, 2H), 1.79-1.24 (m, 2H). The CH$_2$ at 2.5 ppm is partially hidden by DMSO.

Examples 49 and 50

6-((E)-3-(3-((E)-But-2-enyloxy)azetidin-1-yl)-3-oxoprop-1-enyl)-3,4-dihydro-1,8-naphthyridin-2(1H)-one (E49) & 6-((E)-3-(3-((Z)-But-2-enyloxy)azetidin-1-yl)-3-oxoprop-1-enyl)-3,4-dihydro-1,8-naphthyridin-2(1H)-one (E50)

Step 1: 1-Benzhydryl-3-(but-2-enyloxy)-azetidine

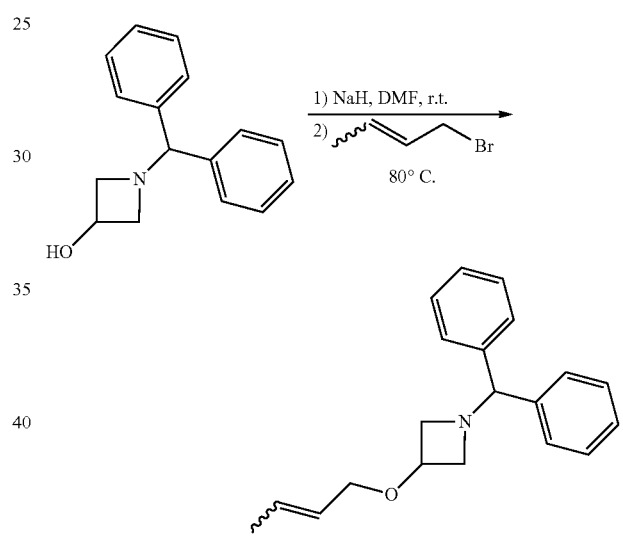

Sodium hydride (60% in oil, 160 mg, 4.17 mmol) was added to a solution of 1-benzhydryl-3-azetidin-3-ol (500 mg, 2.09 mmol) in dimethylformamide (2 mL) at room temperature. The reaction mixture was stirred for 30 minutes prior to the addition of crotyl bromide (430 µL, 4.17 mmol) in solution in dimethylformamide (3 mL). The reaction mixture was stirred at 80° C. overnight and cooled to room temperature. The mixture was then partitioned between ethyl acetate (30 mL) and water (50 mL). The aqueous layer was separated and extracted with ethyl acetate (2×100 mL). The combined organic phases were washed with a saturated solution of sodium chloride (3×100 mL), dried over sodium sulfate and concentrated to dryness. The residue was purified by chromatography on silica gel using dichloromethane/methanol (1:0 to 98:2) as eluent. The title product was obtained as a yellow oil (292 mg, 74%, mixture of the 2 isomers).

LCMS (ESI-APCI) m/z 294.2 (M+H)$^+$

Step 2: 3-(But-2-enyloxy)-azetidine hydrochloride

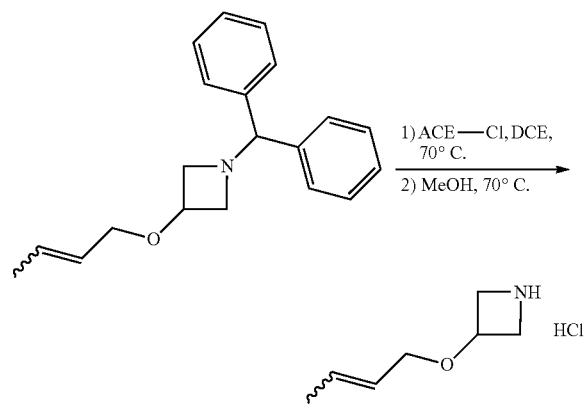

1-Chloroethylchloroformate (140 μL, 1.28 mmol) was added to a solution of 1-benzhydryl-3-(but-2-enyloxy)-azetidine (290 mg, 0.98 mmol) in dichloroethane (5 mL) at room temperature. The reaction mixture was then heated up to 70° C. and stirred for 1 hour. After cooling down to room temperature, methanol (5 mL) was added and the reaction mixture was stirred for an additional 1 hour at 70° C. After concentration to dryness, the crude mixture was triturated in pentane (2×15 mL) to give a yellow solid (161 mg, quantitative) which was used in the next step without further purification.

$^1$H NMR (CDCl$_3$, 400 MHz): δ (ppm): 9.77 and 9.57 (br s, NH$_2$), 5.77-5.69 (m, 1H), 5.51-5.46 (m, 1H), 4.46-4.42 (m, 1H), 4.17-4.12 (m, 2H), 4.04-3.97 (m, 2H), 3.98 (d, J=6.2 Hz, 2H), 1.66 (d, J=6.2 Hz, 3H).

Step 3: 6-((E)-3-(3-((E)-But-2-enyloxy)azetidin-1-yl)-3-oxoprop-1-enyl)-3,4-dihydro-1,8-naphthyridin-2(1H)-one & 6-((E)-3-(3-((Z)-But-2-enyloxy)azetidin-1-yl)-3-oxoprop-1-enyl)-3,4-dihydro-1,8-naphthyridin-2(1H)-one

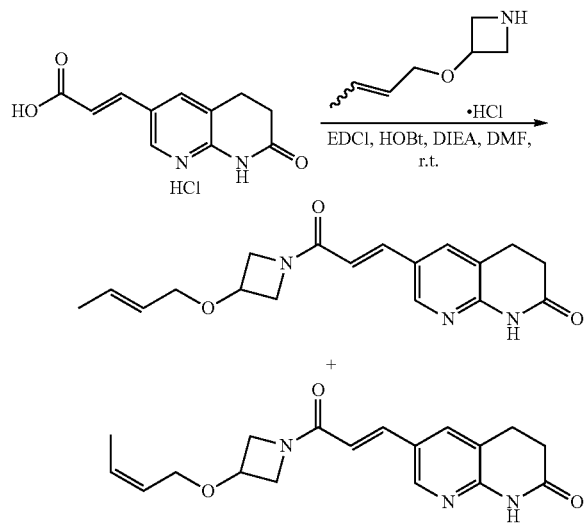

3-(But-2-enyloxy)-azetidine hydrochloride (129 mg, 0.79 mmol), EDCI (151 mg, 0.79 mmol), HOBt (106 mg, 0.79 mmol) and diisopropylethylamine (230 μL, 1.31 mmol) were successively added to a solution of (E)-3-(7-oxo-5,6,7,8-tetrahydro-1,8-naphthyridin-3-yl)-acrylic acid hydrochloride (134 mg, 0.52 mmol) in dimethylformamide (13 mL) at room temperature. The reaction mixture was stirred overnight then diluted by addition of ethyl acetate (50 mL) and a saturated solution of water (50 mL). The aqueous layer was successively extracted with ethyl acetate (3×50 mL) and dichloromethane (3×50 mL). The combined organic phases were washed with a saturated solution of sodium chloride (3×50 mL), dried over sodium sulfate and concentrated to dryness. The residue was purified by chromatography on silica gel using dichloromethane/methanol (1:0 to 95:5) as eluent. The 2 isomers were finally separated by preparative HPLC to afford the trans-isomer (45 mg, 26%) and the cis-isomer (14 mg, 8%).

Trans-Isomer:

LCMS (ESI-APCI) m/z 328.2 (M+H)$^+$ $^1$H NMR (CDCl$_3$, 400 MHz): δ (ppm): 8.35 (s, 1H), 8.30 (s, 1H), 7.63 (s, 1H), 7.58 (d, J=15.6 Hz, 1H), 6.41 (d, J=15.6 Hz, 1H), 5.81-5.72 (m, 1H), 5.62-5.56 (m, 1H), 4.46-4.36 (m, 2H), 4.30-4.25 (m, 1H), 4.18-4.15 (m, 1H), 4.03-3.99 (m, 1H), 3.91 (d, J=6.2 Hz, 2H), 3.02 (t, J=7.6 Hz, 2H), 2.70 (t, J=7.6 Hz, 2H), 1.74 (d, J=6.2 Hz, 3H).

Cis-Isomer:

LCMS (ESI-APCI) m/z 328.2 (M+H)$^+$ $^1$H NMR (CDCl$_3$, 400 MHz): δ (ppm): 8.33 (s, 2H), 7.63 (s, 1H), 7.58 (d, J=15.6 Hz, 1H), 6.42 (d, J=15.6 Hz, 1H), 5.76-5.71 (m, 1H), 5.58-5.54 (m, 1H), 4.45-4.38 (m, 2H), 4.32-4.27 (m, 1H), 4.21-4.17 (m, 1H), 4.06-4.03 (m, 3H), 3.00 (t, J=7.6 Hz, 2H), 2.70 (t, J=7.6 Hz, 2H), 1.69 (d, J=6.8 Hz, 3H).

Example 51

6-((E)-3-(3-((E)-2-methylbut-2-enyloxy)azetidin-1-yl)-3-oxoprop-1-enyl)-3,4-dihydro-1,8-naphthyridin-2(1H)-one (E51)

Step 1: (E)-2-Methylbut-2-en-1-ol

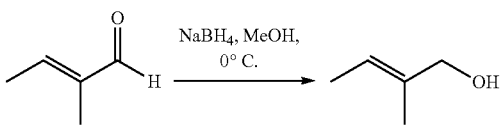

Sodium borohydride (1.08 g, 28.5 mmol) was added to a solution of trans-2-methyl-2-butenal (2.0 g, 23.8 mmol) in methanol (10 mL) at 0° C. The reaction mixture was stirred for 1 hour then diluted by addition of water (10 mL) and ethyl acetate (15 mL). The aqueous layer was separated and extracted with ethyl acetate (2×20 mL). The combined organic phases were washed with a saturated solution of sodium chloride (2×25 mL), dried over sodium sulfate, filtered and concentrated carefully to dryness (volatile compound). The title product was obtained as a colorless oil (1.2 g, 60%).

$^1$H NMR (CDCl$_3$, 400 MHz): δ (ppm): 5.46-5.42 (m, 1H), 3.42 (s, 2H), 1.87 (s, OH), 1.62 (s, 3H), 1.57 (d, J=2 Hz, 3H).

Step 2: (E)-1-Benzhydryl-3-(2-methylbut-2-enyloxy) azetidine

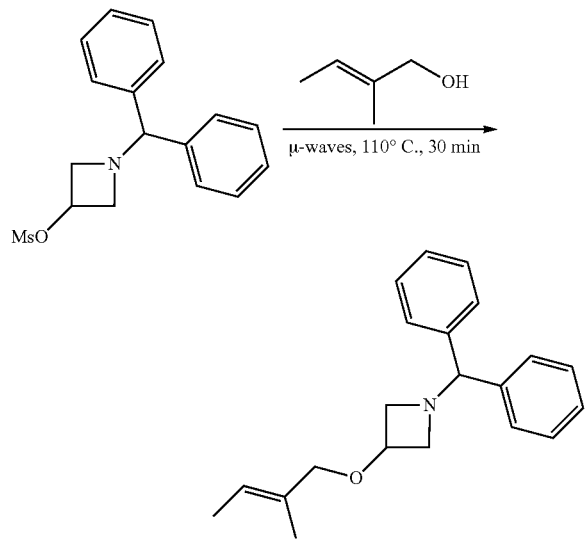

A solution of 1-benzhydrylazetidin-3-yl methanesulfonate (447 mg, 1.41 mmol) in (E)-2-methylbut-2-en-1-ol (1.2 g, 14.1 mmol) was stirred under microwaves at 110° C. for 30 minutes. After concentration to dryness, the residue was purified by chromatography on silica gel using petroleum ether/ethyl acetate (9:1) as eluent. The title product was obtained as a colorless oil (290 mg, 67%).

LCMS (ESI-APCI) m/z 308.2 (M+H)+

Step 3: (E)-3-(2-Methylbut-2-enyloxy)azetidine hydrochloride

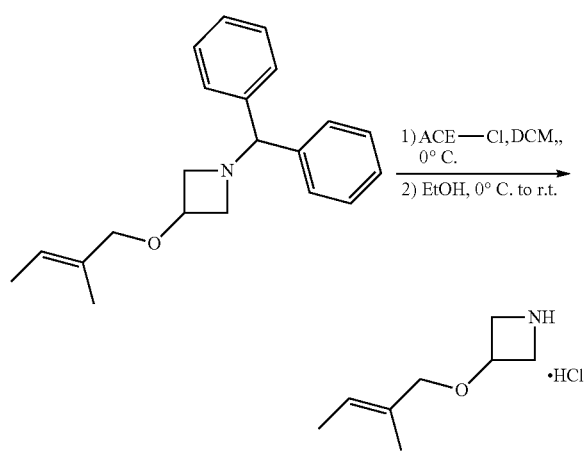

1-Chloroethyl chloroformate (107 µL, 1.0 mmol) was added to a solution of (E)-1-benzhydryl-3-(2-methylbut-2-enyloxy)azetidine (290 mg, 0.941 mmol) in dichloromethane (10 mL) at 0° C. The reaction mixture was stirred for 2 hours. Ethanol (10 mL) was then added and the reaction mixture was stirred for an additional 2 hours at 0° C. and 16 hours at room temperature. After concentration to dryness, the crude mixture was triturated in pentane (5 mL) and petroleum ether (5 mL) to afford a colorless oil (211 mg, quantitative).

$^1$H NMR (CDCl$_3$, 400 MHz): δ (ppm): 9.87 (br s, NH$_2$), 9.55 (br s, NH$_2$), 5.52-5.45 (m, 1H), 4.43-4.37 (m, 1H), 4.16-4.12 (m, 2H), 4.02-4.0 (m, 2H), 3.8 (s, 2H), 1.63-1.60 (m, 6H).

Step 4: 6-((E)-3-(3-((E)-2-Methylbut-2-enyloxy) azetidin-1-yl)-3-oxoprop-1-enyl)-3,4-dihydro-1,8-naphthyridin-2(1H)-one

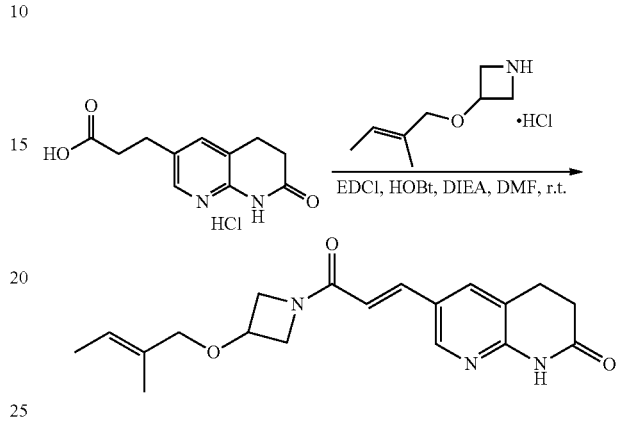

(E)-3-(2-Methylbut-2-enyloxy)azetidine hydrochloride (168 mg, 0.94 mmol), EDCI (182 mg, 0.94 mmol), HOBt (132 mg, 0.94 mmol) and diisopropylethylamine (276 µL, 1.58 mmol) were successively added to a solution of (E)-3-(7-oxo-5,6,7,8-tetrahydro-1,8-naphthyridin-3-yl)-acrylic acid hydrochloride (161 mg, 0.63 mmol) in dimethylformamide (12 mL) at room temperature. The reaction mixture was stirred overnight then diluted by addition of ethyl acetate (40 mL) and water (40 mL). The aqueous layer was separated and extracted with ethyl acetate (2×40 mL). The combined organic phases were washed with a saturated solution of sodium chloride (3×50 mL), dried over sodium sulfate, filtered and concentrated to dryness. The residue was purified by chromatography on silica gel using dichloromethane/methanol (98:2) as eluent. After trituration in diethyl ether, petroleum ether and methanol, the title product was obtained as a white solid (46 mg, 21%).

LCMS (ESI-APCI) 342.2 m/z (M+H)+

$^1$H NMR (DMSO-d$_6$, 400 MHz): δ (ppm): 10.68 (s, 1H), 8.37 (s, 1H), 8.04 (s, 1H), 7.43 (d, J=16 Hz, 1H), 6.74 (d, J=16 Hz, 1H), 5.56-5.50 (m, 1H), 4.51-4.46 (m, 1H), 4.36-4.33 (m, 1H), 4.17-4.08 (m, 2H), 3.84 (s, 2H), 3.78-3.74 (m, 1H), 2.94 (t, J=7.6 Hz, 2H), 2.5 (t, J=7.6 Hz, 2H), 1.64 (s, 3H), 1.63 (d, J=8 Hz, 3H). The CH$_2$ at 2.5 ppm is partially hidden by DMSO.

Example 52

(E)-6-(3-(3-(Benzo[b]thiophen-2-ylmethoxy)azetidin-1-yl)-3-oxoprop-1-enyl)-3,4-dihydro-1,8-naphthyridin-2(1H)-one (E52)

Step 1: 2-(Bromomethyl)benzo[b]thiophene

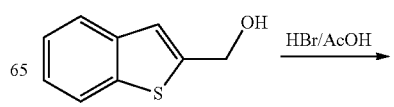

-continued

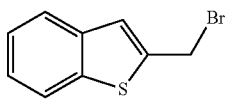

HBr in acetic acid (6 mL) was added to a suspension of benzo[b]thiophen-2-ylmethanol (1 g, 6.1 mmol) in dichloromethane (6 mL) at room temperature. The reaction mixture was stirred for 3 hours then diluted by addition of chloroform (20 mL). The organic phase was washed with a saturated solution of hydrogenocarbonate (20 mL), dried over sodium sulfate and concentrated to dryness. The title product was obtained as a yellow oil (1.3 g, quantitative).

$^1$H NMR (CDCl$_3$, 400 MHz): δ (ppm): 7.91 (m, 1H), 7.83 (m, 1H), 7.53-7.45 (m, 2H), 7.33 (s, 1H), 4.86 (s, 2H).

Step 2: 1-Benzhydryl-3-(benzo[b]thiophen-2-yl-methoxy)-azetidine

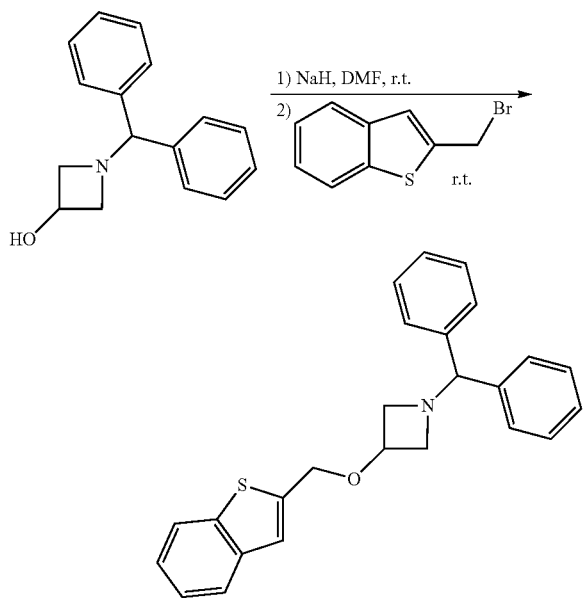

Sodium hydride (60% in oil, 243 mg, 6.0 mmol) was added to a solution of 1-benzhydryl-3-azetidin-3-ol (727 mg, 3.0 mmol) in dimethylformamide (5 mL) at room temperature. The reaction mixture was stirred for 30 minutes prior to the addition of a solution of 2-(bromomethyl)benzo[b]thiophene (1.38 g, 6 mmol) in dimethylformamide (5 mL). The reaction mixture was stirred for 3 hours at room temperature. The reaction mixture was then diluted by addition of ethyl acetate (30 mL) and water (30 mL). The aqueous layer was separated and extracted with ethyl acetate (2×30 mL). The combined organic phases were washed with a saturated solution of sodium chloride (3×50 mL), dried over sodium sulfate, filtered and concentrated to dryness. The residue was purified by chromatography on silica gel using petroleum ether/ethyl acetate (9:1 to 8:2) as eluent. The title product was obtained as a white solid (1.04 g, 85%).

LCMS (ESI-APCI) m/z 386.2 (M+H)$^+$

Step 3: 3-(Benzo[b]thiophen-2-ylmethoxy)-azetidine hydrochloride

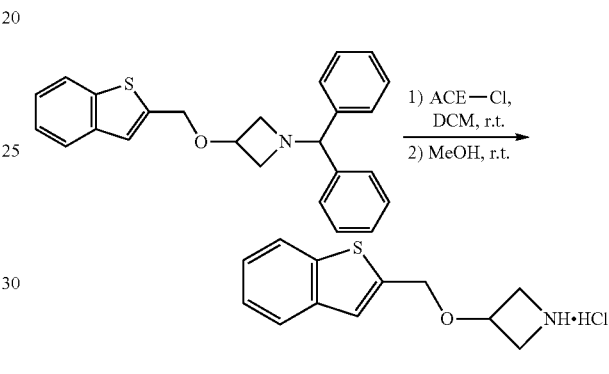

1-Chloroethyl chloroformate (322 μL, 1.1 mmol) was added to a solution of 1-benzhydryl-3-(benzo[b]thiophen-2-ylmethoxy)-azetidine (1.04 g, 2.7 mmol) in dichloromethane (17 mL) at room temperature. The reaction mixture was stirred for 2 hours. Methanol (17 mL) was added and the reaction mixture was stirred for an additional 16 hours at room temperature. The reaction mixture was then concentrated to dryness and the residue was triturated in petroleum ether (20 mL) to afford the title compound as a yellow solid (600 mg, 90%).

$^1$H NMR (DMSO-d$_6$, 400 MHz): δ (ppm): 8.92 (br s, NH), 8.77 (br s, NH), 7.97-7.95 (m, 1H), 7.85-7.83 (m, 1H), 7.39-7.35 (m, 3H), 4.81 (s, 2H), 4.53-4.56 (m, 1H), 4.14-4.09 (m, 2H), 3.88-8.84 (m, 2H).

Step 4: (E)-6-(3-(3-(Benzo[b]thiophen-2-ylmethoxy)azetidin-1-yl)-3-oxoprop-1-enyl)-3,4-dihydro-1,8-naphthyridin-2(1H)-one

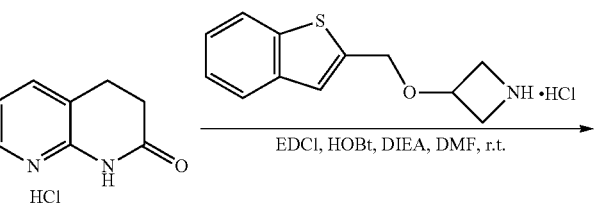

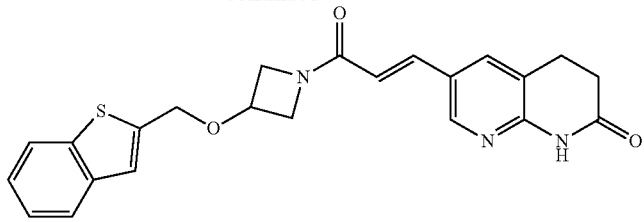

3-(Benzo[b]thiophen-2-ylmethoxy)-azetidine hydrochloride (136 mg, 0.76 mmol), EDCI (146 mg, 0.76 mmol), HOBt (103 mg, 0.76 mmol) and diisopropylethylamine (222 μL, 1.27 mmol) were successively added to a solution of (E)-3-(7-oxo-5,6,7,8-tetrahydro-1,8-naphthyridin-3-yl)-acrylic acid hydrochloride (130 mg, 0.51 mmol) in dimethylformamide (10 mL) at room temperature. The reaction mixture was stirred for 3 days. The reaction mixture was then diluted by addition of ethyl acetate (50 mL) and water (50 mL). The aqueous phase was extracted with ethyl acetate (3×100 mL) and dichloromethane (3×100 mL). The combined organic phases were washed with a saturated solution of sodium chloride (3×50 mL), dried over sodium sulfate and concentrated to dryness. The residue was purified by chromatography on silica gel using dichloromethane/methanol (1:0 to 95:5) as eluent. After trituration in acetone and methanol, the title product was obtained as a white solid (112 mg, 45%).

LCMS (ESI-APCI) m/z 420.2 (M+H)+

$^1$H NMR (CDCl$_3$, 400 MHz): δ (ppm): 8.33 (s, 1H), 8.29 (s, 1H), 7.96-7.94 (m, 1H), 7.84-7.81 (m, 1H), 7.43-7.34 (m, 4H), 7.71 (d, J=15.6 Hz, 1H), 4.8 (s, 2H), 4.52-4.48 (m, 2H), 4.17-4.11 (m, 2H), 3.79-3.76 (m, 1H), 2.99 (t, J=7.6 Hz, 2H), 2.69 (t, J=7.6 Hz, 2H).

Example 53

(E)-6-(3-(3-((4-Bromothiophen-2-yl)methoxy)azetidin-1-yl)-3-oxoprop-1-enyl)-3,4-dihydro-1,8-naphthyridin-2(1H)-one (E53)

Step 1: 4-Bromothiophen-2-yl)methanol

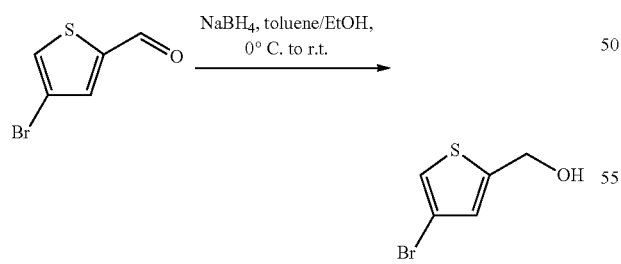

Sodium borohydride (594 mg, 15.7 mmol) was added to a solution of 2-bromothiophene carboxaldehyde (2.5 g, 13 mmol) in a mixture toluene/ethanol (16 mL, 1:1) at 0° C. The reaction mixture was stirred for 2 hours at room temperature then partitioned between water (20 mL) and ethyl acetate (20 mL). The aqueous phase was separated and extracted with ethyl acetate (2×30 mL). The combined organic phases were washed with a saturated solution of sodium chloride (2×20 mL), dried over sodium sulphate, filtered and concentrated to dryness. The residue was purified by chromatography on silica gel using petroleum ether/ethyl acetate (7:3) as eluent. The title product was obtained as a white solid (2.47 g, 98%).

$^1$H NMR (CDCl$_3$, 400 MHz): δ (ppm): 7.21 (d, J=1.2 Hz, 1H), 6.88 (d, J=1.2 Hz, 1H), 4.75 (d, J=6 Hz, 2H).

Step 2: 4-Bromo-2-(chloromethyl)thiophene

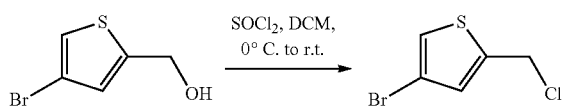 [SMILES: OCc1cc(Br)cs1 ; ClCc1cc(Br)cs1]

Thionyl chloride (1.12 mL, 15.3 mmol) was added to a solution of 4-bromothiophen-2-yl)methanol (2.47 g, 12.8 mmol) in dichloromethane (25 mL) at 0° C. The reaction mixture was stirred for 2 h 30 at room temperature. The reaction mixture was then diluted by addition of water (20 mL) and dichloromethane (20 mL). The aqueous phase was separated and the organic phase was washed with a saturated solution of sodium chloride (20 mL), dried over sodium sulphate, filtered and concentrated to dryness. The title product was obtained as a yellow oil (2.57 g, 95%) and used without further purification.

$^1$H NMR (CDCl$_3$, 400 MHz): δ (ppm): 7.20 (s, 1H), 7.00 (s, 1H), 4.72 (s, 2H).

Step 3: 1-Benzhydryl-3-((4-bromothiophen-2-yl)methoxy)-azetidine

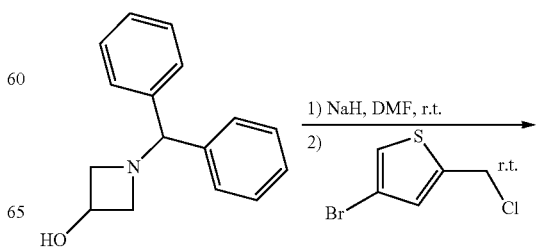

-continued

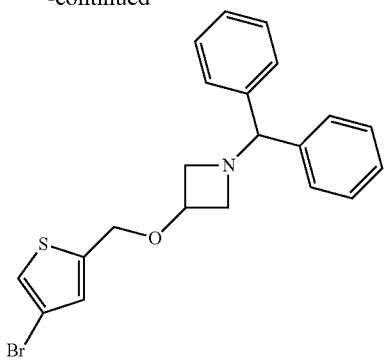

Sodium hydride (60% in oil, 167 mg, 4.18 mmol) was added to a solution of 1-benzhydryl-3-azetidin-3-ol (500 mg, 2.09 mmol) in dimethylformamide (10 mL) at room temperature. The reaction mixture was stirred for 30 minutes prior to the addition of a solution of 4-bromo-2-(chloromethyl) thiophene (884 mg, 4.18 mmol) in dimethylformamide (3 mL). The reaction mixture was stirred overnight and then diluted by addition of ethyl acetate (30 mL) and water (30 mL). The aqueous layer was separated and extracted with ethyl acetate (3×30 mL). The combined organic phases were washed with a saturated solution of sodium chloride (3×30 mL), dried over sodium sulfate, filtered and concentrated to dryness. The residue was purified by chromatography on silica gel using petroleum ether/ethyl acetate (95:5) as eluent. The title product was obtained as a yellow solid (793 mg, 92%).

LCMS (ESI-APCI) m/z 414.1; 416.1 (M+H)$^+$

Step 4:
3-((4-Bromothiophen-2-yl)methoxy)-azetidine hydrochloride

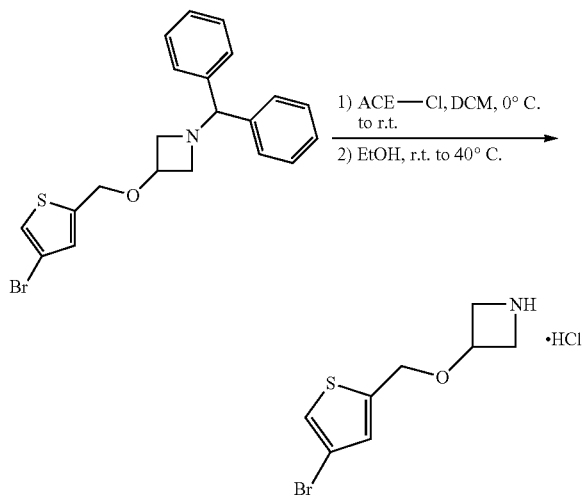

1-Chloroethyl chloroformate (218 µL, 2.0 mmol) was added to a solution of 1-benzhydryl-3-((4-bromothiophen-2-yl)methoxy)-azetidine (793 mg, 1.91 mmol) in dichloromethane (10 mL). The reaction mixture was stirred for 1 hour at 0° C. and for an additional 1 hour at room temperature. Ethanol (10 mL) was then added and the reaction mixture was stirred overnight. After concentration to dryness, the crude mixture was precipitated from a mixture dichloromethane/diethyl ether to afford a white solid (417 mg, 77%) which was used in the next step whitout further purification.

$^1$H NMR (DMSO-d$_6$, 400 MHz): δ (ppm): 8.81 (br s, NH$_2$), 7.72 (s, 1H), 7.18 (s, 1H), 4.68 (s, 2H), 4.49-4.44 (m, 1H), 4.14-4.10 (m, 2H), 3.87-3.82 (m, 2H)

Step 5: (E)-6-(3-(3-((4-Bromothiophen-2-yl)methoxy)azetidin-1-yl)-3-oxoprop-1-enyl)-3,4-dihydro-1,8-naphthyridin-2(1H)-one

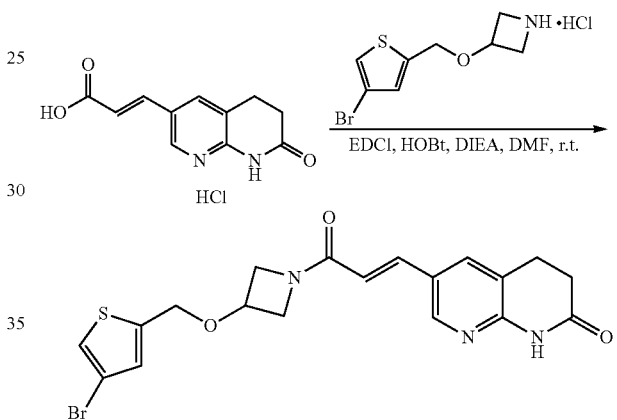

3-((4-Bromothiophen-2-yl)methoxy)-azetidine hydrochloride (168 mg, 0.59 mmol), EDCI (113 mg, 0.59 mmol), HOBt (82 mg, 0.59 mmol) and diisopropylethylamine (171 µL, 1.00 mmol) were successively added to a solution of (E)-3-(7-oxo-5,6,7,8-tetrahydro-1,8-naphthyridin-3-yl)-acrylic acid hydrochloride (100 mg, 0.39 mmol) in dimethylformamide (10 mL) at room temperature. The reaction mixture was stirred overnight then diluted by addition of ethyl acetate (40 mL) and water (40 mL). The aqueous phase was separated and extracted with ethyl acetate (2×40 mL). The combined organic phases were washed with a saturated solution of sodium chloride (3×40 mL), dried over sodium sulfate, filtered and concentrated to dryness. The residue was triturated in diethyl ether to afford a pale yellow solid (109 mg, 62%).

LCMS (ESI-APCI) m/z 448.1; 450.0 (M+H)$^+$ $^1$H NMR (CDCl$_3$, 400 MHz): δ (ppm): 8.39 (s, 1H), 8.30 (s, 1H), 7.64 (s, 1H), 7.58 (d, J=15.6 Hz, 1H), 7.23 (d, J=1.2 Hz, 1H), 6.95 (d, J=1.2 Hz, 1H), 6.39 (d, J=15.6 Hz, 1H), 4.63 (m, 2H), 4.47-4.43 (m, 2H), 4.29-4.26 (m, 1H), 4.19-4.16 (m, 1H), 4.04-4.00 (m, 1H), 3.00 (t, J=7.6 Hz, 2H), 2.70 (t, J=7.6 Hz, 2H).

Example 54

(E)-6-(3-(3-((4-Chlorothiophen-2-yl)methoxy)azetidin-1-yl)-3-oxoprop-1-enyl)-3,4-dihydro-1,8-naphthyridin-2(1H)-one (E54)

Step 1: (4-Chlorothiophen-2-yl)methanol

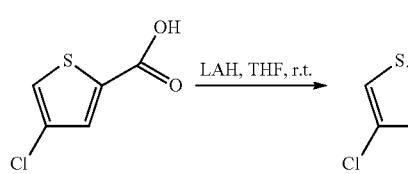

Lithium aluminium hydride (117 mg, 3.08 mmol) was added to a solution of 2-chlorothiophene carboxylique acid (500 mg, 3.08 mmol) in tetrahydrofuran (5 mL) at 0° C. The reaction mixture was stirred for 1 hour at room temperature and then diluted by addition of water (10 mL) and an aqueous solution of sodium hydroxide (1N, 10 mL). The aqueous solution was extracted with ethyl acetate (2×30 mL). The combined organic phases were dried over sodium sulphate, filtered and concentrated to dryness. The residue was purified by chromatography on silica gel using petroleum ether/ethyl acetate (9:1) as eluent. The title product was obtained as a white solid (330 mg, 72%).

$^1$H NMR (CDCl$_3$, 400 MHz): δ (ppm): 7.05 (d, J=1.6 Hz, 1H), 6.88 (d, J=1.6 Hz, 1H), 4.78 (s, 2H).

Step 2: 4-Chloro-2-(chloromethyl)thiophene

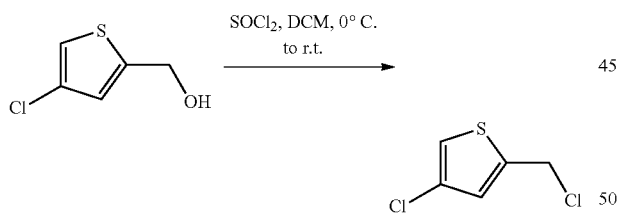

Thionyl chloride (117 □L, 1.60 mmol) in solution in dichloromethane (1 mL) was added to a solution of (4-chlorothiophen-2-yl)methanol (140 mg, 0.94 mmol) in dichloromethane (3 mL) at 0° C. The reaction mixture was stirred for 2 h 30 at room temperature then 30 minutes at 40° C. The reaction mixture was diluted by addition of water (20 mL) and dichloromethane (20 mL). The organic phase was washed with a saturated solution of sodium chloride (20 mL), dried over sodium sulphate, filtered and concentrated to dryness. The title product was obtained as an orange oil (165 mg, 77%) and used in the next step without further purification.

$^1$H NMR (CDCl$_3$, 400 MHz): δ (ppm): 7.08 (d, J=1.6 Hz, 1H), 6.96 (d, J=1.6 Hz, 1H), 4.69 (s, 2H).

Step 3: 1-Benzhydryl-3-((4-chlorothiophen-2-yl)methoxy)-azetidine

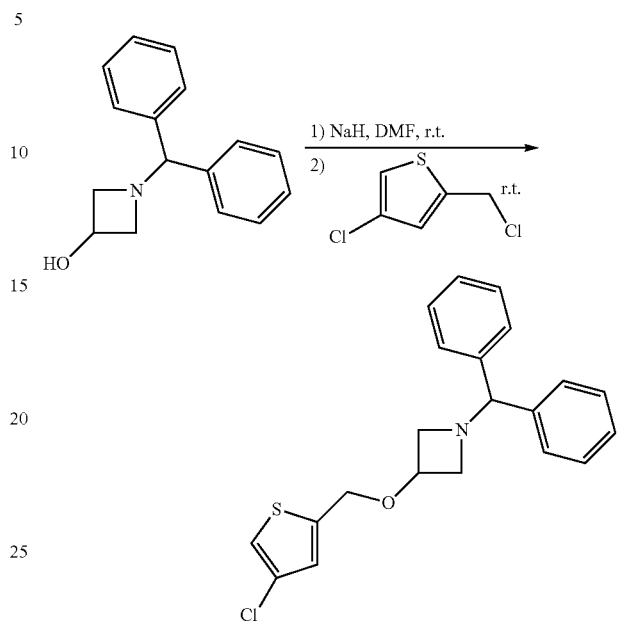

Sodium hydride (60% in oil, 167 mg, 4.18 mmol) was added to a solution of 1-benzhydryl-3-azetidin-3-ol (500 mg, 2.09 mmol) in dimethylformamide (10 mL) at room temperature. The reaction mixture was stirred for 30 minutes prior to the addition of a solution of 4-chloro-2-(chloromethyl) thiophene (884 mg, 4.18 mmol) in dimethylformamide (3 mL). The reaction mixture was then stirred overnight. The reaction mixture was diluted by addition of ethyl acetate (30 mL) and water (30 mL). The aqueous layer was separated and extracted with ethyl acetate (3×30 mL). The combined organic phases were washed with a saturated solution of sodium chloride (3×30 mL), dried over sodium sulfate, filtered and concentrated to dryness. The residue was purified by chromatography on silica gel using petroleum ether/ethyl acetate (95:5) as eluent. The title product was obtained as a yellow solid (793 mg, 92%).

LCMS (ESI-APCI) m/z 414.1; 416.1 (M+H)$^+$

Step 4: 3-((4-Chlorothiophen-2-yl)methoxy)-azetidine hydrochloride

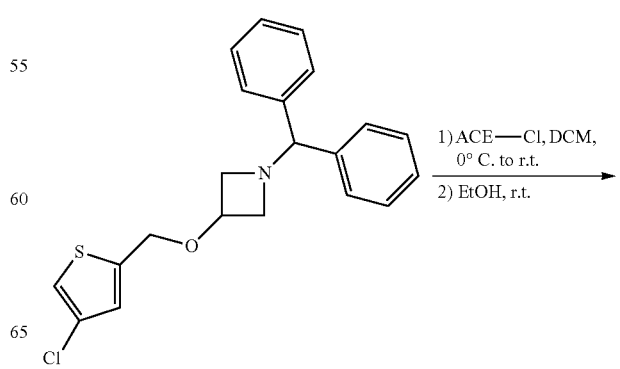

-continued

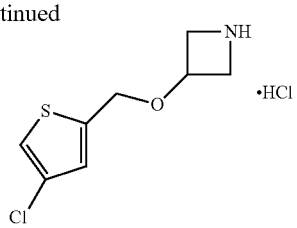

1-Chloroethyl chloroformate (218 μL, 2.0 mmol) was added to a solution of 1-benzhydryl-3-((4-chlorothiophen-2-yl)methoxy)-azetidine (793 mg, 1.91 mmol) in dichloromethane (10 mL) at 0° C. The reaction mixture was stirred for 1 hour at 0° C. and for an additional 1 hour at room temperature. Ethanol (10 mL) was added and the reaction mixture was stirred overnight. After concentration to dryness, the crude mixture was precipitated from a mixture dichloromethane/diethyl ether to afford the title compound as a white solid (417 mg, 77%) which was used whitout further purification.

$^1$H NMR (DMSO-d$_6$, 400 MHz): δ (ppm): 8.81 (br s, NH$_2$), 7.72 (s, 1H), 7.18 (s, 1H), 4.68 (s, 2H), 4.49-4.44 (m, 1H), 4.14-4.10 (m, 2H), 3.87-3.82 (m, 2H).

Step 5: (E)-6-(3-(3-((4-Chlorothiophen-2-yl)methoxy)azetidin-1-yl)-3-oxoprop-1-enyl)-3,4-dihydro-1,8-naphthyridin-2(1H)-one

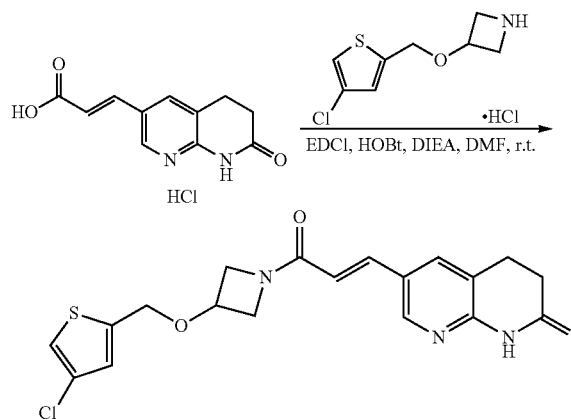

3-((4-Chlorothiophen-2-yl)methoxy)-azetidine hydrochloride (141 mg, 0.59 mmol), EDCI (113 mg, 0.59 mmol), HOBt (82 mg, 0.59 mmol) and diisopropylethylamine (171 μL, 1.00 mmol) were successively added to a solution of (E)-3-(7-oxo-5,6,7,8-tetrahydro-1,8-naphthyridin-3-yl)-acrylic acid hydrochloride (100 mg, 0.39 mmol) in dimethylformamide (6 mL) at room temperature. The reaction mixture was stirred overnight and then diluted by addition of ethyl acetate (40 mL) and water (40 mL). The aqueous phase was extracted with ethyl acetate (2×40 mL). The combined organic phases were washed with a saturated solution of sodium chloride (3×40 mL), dried over sodium sulfate, filtered and concentrated to dryness. The residue was triturated in diethyl ether to afford the title compound as a pale yellow solid (37 mg, 23%).

LCMS (ESI-APCI) m/z 404.1 (M+H)$^+$ $^1$H NMR (CDCl$_3$, 400 MHz): δ (ppm): 8.30 (s, 1H), 8.19 (s, 1H), 7.62 (s, 1H), 7.58 (d, J=15.6 Hz, 1H), 7.11 (d, J=1.4 Hz, 1H), 6.90 (d, J=1.4 Hz, 1H), 6.39 (d, J=15.6 Hz, 1H), 4.64-4.60 (m, 2H), 4.46-4.42 (m, 2H), 4.29-4.26 (m, 1H), 4.19-4.15 (m, 1H), 4.06-4.02 (m, 1H), 2.99 (t, J=7.2 Hz, 2H), 2.7 (m, J=7.2 Hz, 2H).

Example 55

6-((E)-3-Oxo-3-(3-((Z)-1-(propoxyimino)ethyl)azetidin-1-yl)prop-1-enyl)-3,4-dihydro-1,8-naphthyridin-2(1H)-one (E55)

Step 1: Azetidine-1,3-dicarboxylic acid mono-tert-butyl ester

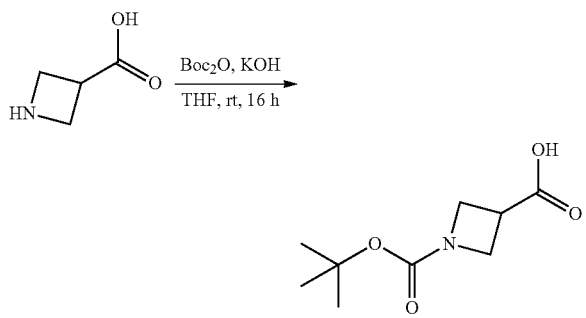

Di-tert-buyldicarbonate (2.5 g, 11.88 mmol) was added to a stirred solution of 3-azetidinecarboxylic acid (1.0 g, 9.9 mmol) in a mixture of THF/water (12 mL:2 mL) and 1M KOH (1 mL) at room temperature. The reaction mixture was stirred for 16 hours and then concentrated to dryness. The crude was partitioned between an aqueous solution of 1N NaOH (10 mL) and diethyl ether (50 mL). The ether layer was discarded and the aqueous layer was acidified with a 3M aqueous solution of KHSO$_4$ until pH=2 and extracted with diethyl ether (3×100 ml). The combined organic phases were washed with brine, dried over magnesium sulfate and concentrated in vacuo to give the title compound as a white solid (1.4 g, 70%).

$^1$H NMR (400 MHz, DMSO-d$_6$) δ (ppm): 12.64 (s, 1H), 4.02-3.93 (m, 2H), 3.87-3.80 (m, 2H), 3.36-3.27 (m, 1H), 1.36 (s, 9H).

Step 2: 3-(2,2-Dimethyl-4,6-dioxo-[1,3]dioxane-5-carbonyl)-azetidine-1-carboxylic acid tert-butyl ester

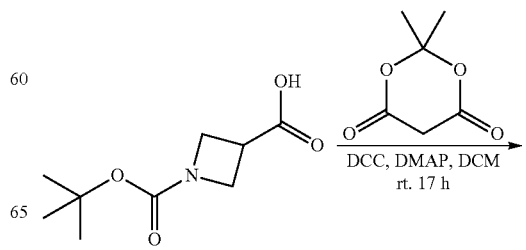

-continued

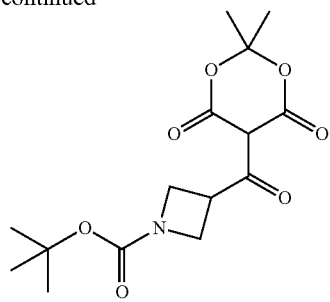

Meldrum's acid (0.85 g, 5.97 mmol), DCC (1.22 g, 5.97 mmol), and DMAP (1.45 g, 11.94 mmol) were successively added to a solution of azetidine-1,3-dicarboxylic acid mono-tert-butyl ester (1.2 g, 5.97 mmol) in dichloromethane (25 mL) at room temperature. The reaction mixture was stirred overnight and then diluted by addition of cyclohexane (25 mL). The precipitate of dicyclohexyl urea was then filtered and rinsed with diethyl ether (100 mL). The mother liquors were diluted with DCM (100 mL) and washed with a 1M solution of aqueous HCl (2×30 mL), dried over sodium sulfate, filtered and concentrated to dryness. After trituration in diethyl ether the title compound was obtained as a white solid (1.9 g, 100%).

$^1$H NMR (400 MHz, CDCl$_3$) δ (ppm): 4.52-4.48 (m, 1H), 4.25-4.20 (t, 2H), 4.12-4.07 (m, 2H), 3.36-3.27 (m, 1H), 1.71 (s, 6H), 1.41 (s, 9H).

Step 3: 3-Acetyl-azetidine-1-carboxylic acid tert-butyl ester

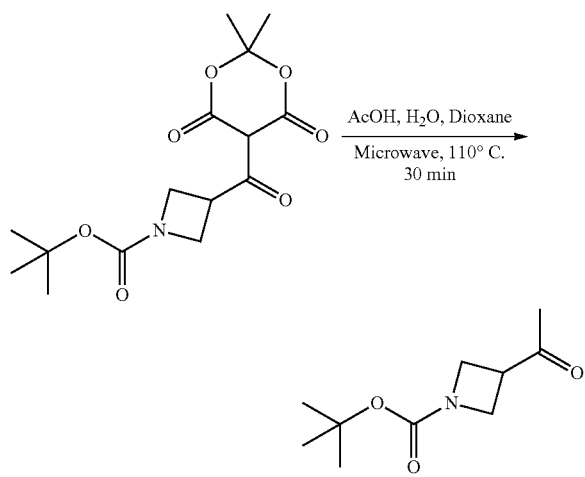

A solution of 3-(2,2-dimethyl-4,6-dioxo-[1,3]dioxane-5-carbonyl)-azetidine-1-carboxylic acid tert-butyl ester (1.0 g, 3.05 mmol) in a mixture of acetic acid (0.5 mL), water 0.25 mL and dioxane (3 mL) was stirred under microwaves at 100° C. for minutes. After concentration to dryness, the residue was coeveoparted with dichloromethane (2×100 mL). The title product was obtained as a colorless gum (600 mg, 100%).

LCMS (ESI-APCI) m/z 308.2 (M+H)$^+$

Step 4: 1-Azetidin-3-yl-ethanone TFA

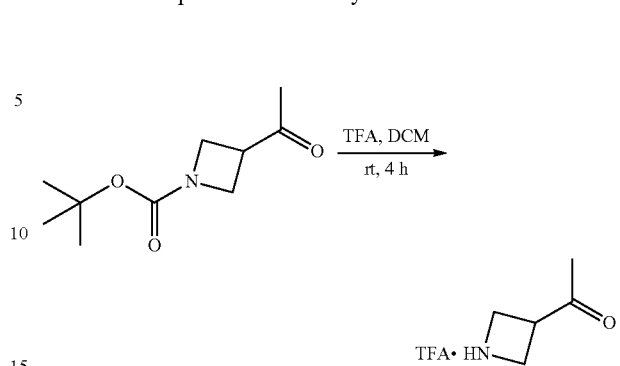

Trifluoroacetic acid (8 mL) was added to a suspension of 3-acetyl-azetidine-1-carboxylic acid tert-butyl ester (800 mg, 4.0 mmol) in dichloromethane (20 mL). The reaction mixture was stirred at room temperature for 4 hours and concentrated to dryness to afford the title product as a colorless gum (800 mg, 100%).

$^1$H NMR (400 MHz, DMSO-d$_6$) δ (ppm): 4.02-4.06 (m, 4H), 3.75-3.80 (m, 1H), 2.13 (s, 3H).

Step 5: 6-[3-(3-Acetyl-azetidin-1-yl)-3-oxo-propenyl]-3,4-dihydro-1H-[1,8]naphthyridin-2-one

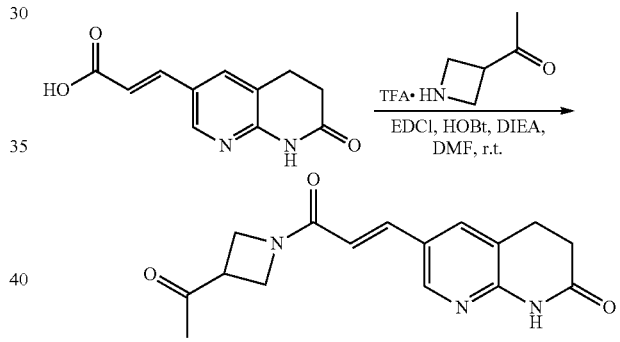

1-Azetidin-3-yl-ethanone TFA (700 mg, 3.54 mmol), EDCI (676 mg, 3.54 mmol), HOBt (477 mg, 3.54 mmol) and diisopropylethylamine (2.1 mL, 11.8 mmol) were successively added to a solution of (E)-3-(7-oxo-5,6,7,8-tetrahydro-1,8-naphthyridin-3-yl)-acrylic acid hydrochloride (600 mg, 2.36 mmol) in dimethylformamide (15 mL) at room temperature. The reaction mixture was stirred overnight. The reaction mixture was then diluted by addition of ethyl acetate (40 mL) and water (40 mL). The organic layer was discarded and the aqueous layer was basified with an aqueous solution of saturated sodium carbonate until pH=12 and finally extracted with ethyl acetate (2×50 mL). The combined organic phases were washed with a saturated solution of sodium chloride (3×50 mL), dried over sodium sulfate and concentrated to dryness. The residue was purified by chromatography on silica gel using dichloromethane/methanol (1:0 to 95:5) as eluent to obtain the title compound as a white solid (354 mg, 50%).

LCMS (ESI-APCI) m/z 390.1 (M+H)$^+$ $^1$H NMR (DMSO-d$_6$, 400 MHz): δ (ppm): 10.64 (s, 1H), 8.34 (d, 1H), 8.01 (s, 1H), 7.41-7.37 (d, 1H), 6.72-6.68 (d, 2H), 4.33-4.44 (m, 2H), 4.05-4.09 (m, 1H), 3.96-3.99 (m, 1H), 3.62-3.66 (m, 1H), 3.31-3.51 (m, 1H), 2.89-2.92 (t, 3H), 2.50 (t, 2H), 2.16 (s, 3H)

Step 6: 6-((E)-3-Oxo-3-(3-((Z)-1-(propoxyimino)ethyl)azetidin-1-yl)prop-1-enyl)-3,4-dihydro-1,8-naphthyridin-2(1H)-one

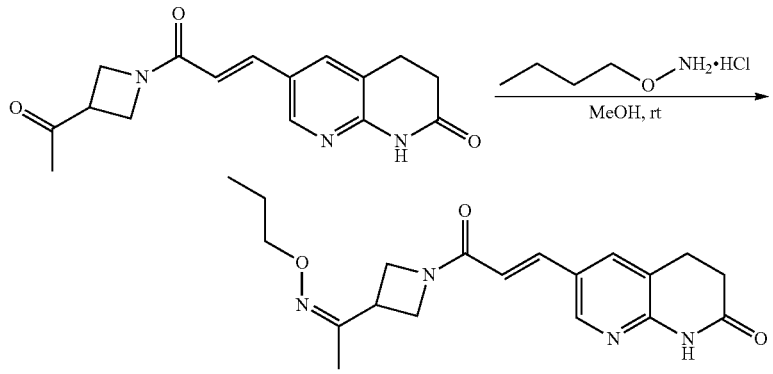

1-(Amino-oxy)-propane hydrochloride (32 mg, 0.29 mmol) was added to a solution of (E)-6-(3-(3-acetylazetidin-1-yl)-3-oxoprop-1-enyl)-3,4-dihydro-1,8-naphthyridin-2(1H)-one (61.3 mg, 0.20 mmol) in a mixture methanol/dichloromethane (8:2, 3.5 mL) at room temperature. The reaction mixture was stirred overnight. After concentration to dryness, the residue was purified by chromatography on silica gel using dichloromethane/methanol (95:5) as eluent. The title product was obtained as a white solid (56.0 mg, 76%).

HPLC isomer ratio 86:14, geometry not assigned (the minor isomer has the shortest retention time).

LCMS (ESI-APCI) m/z 357.2 (M+H) $^+$ $^1$H NMR (DMSO-$d_6$, 400 MHz) (mixture of 2 isomers): δ (ppm): 10.64 (s, 1H), 8.35 (s, 1H), 8.03 (s, 1H), 7.40 (d, J=15.6 Hz, 1H), 6.72 (d, J=15.6 Hz, 1H), 4.45-4.33 (m, 2H), 4.13-4.10 (m, 1H), 3.99-3.94 (m, 3H), 3.48-3.44 (m, 1H), 2.92 (t, J=7.2 Hz, 2H), 2.54 (t, J=7.2 Hz, 2H), 1.96-1.84 (s, 3H), 1.65-1.57 (m, 2H), 0.92-0.86 (m, 3H). The CH$_2$ at 2.5 ppm is partially hidden by DMSO.

Example 56

6-((E)-3-Oxo-3-(3-((Z)-1-(2,2,2-trifluoroethoxyimino)ethyl)azetidin-1-yl)prop-1-enyl)-3,4-dihydro-1,8-naphthyridin-2(1H)-one (E56)

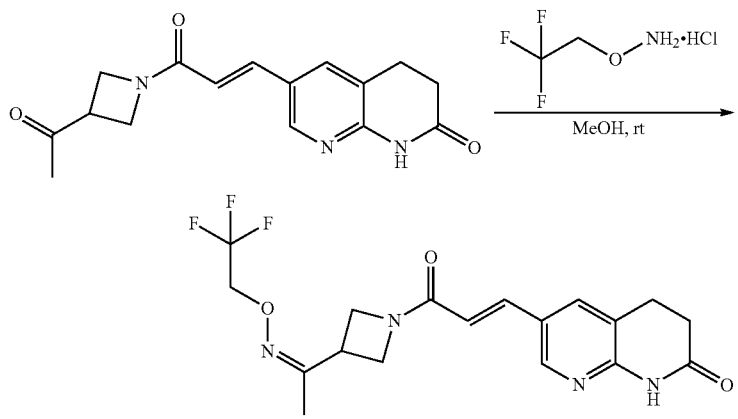

2,2,2-Trifluoroethoxyamine hydrochloride (37 mg, 0.24 mmol) was added to a solution of (E)-6-(3-(3-acetylazetidin-1-yl)-3-oxoprop-1-enyl)-3,4-dihydro-1,8-naphthyridin-2(1H)-one (50 mg, 0.16 mmol) in methanol (4 mL). The reaction mixture was stirred at room temperature for 3 hours. After concentration to dryness the residue was diluted by addition of dichloromethane (50 mL) and saturated sodium bicarbonate solution (10 mL). The aqueous phase was extracted with dichloromethane (2×40 mL). The combined organic phases were washed with a saturated solution of sodium chloride (1×20 mL), dried over sodium sulfate, filtered and concentrated to dryness. The residue was purified by chromatography on silica gel using ethyl acetate/methanol (95:5) as eluent to obtain the title product as a white solid (47 mg, 50%).

HPLC isomer ratio 90:10, geometry not assigned (the minor isomer has the shortest retention time).

LCMS (ESI-APCI) m/z 397.1 (M+H) $^+$ $^1$H NMR (CDCl$_3$, 400 MHz) (mixture of 2 isomers): δ (ppm): 8.31 (s, 1H), 8.26 (s, 1H), 7.63 (s, 1H), 7.59 (d, J=15.6 Hz, 1H), 6.42 (d, J=15.6 Hz, 1H), 4.46-4.39 (m, 2H), 4.33-4.28 (m, 2H), 4.16-4.11 (m, 2H), 3.50-3.41 (m, 1H), 2.99 (t, J=7.6 Hz, 2H), 2.70 (t, J=7.6 Hz, 2H), 2.04-1.95 (s, 3H).

Example 57

6-((E)-3-(3-((Z)-1-(Ethoxyimino)ethyl)azetidin-1-yl)-3-oxoprop-1-enyl)-3,4-dihydro-1,8-naphthyridin-2(1H)-one (E57)

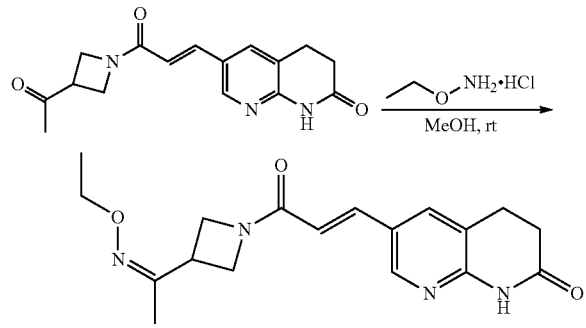

1-(Aminooxy)ethane hydrochloride (23 mg, 0.23 mmol) was added to a solution of (E)-6-(3-(3-acetylazetidin-1-yl)-3-oxoprop-1-enyl)-3,4-dihydro-1,8-naphthyridin-2(1H)-one (50.0 mg, 0.16 mmol) in a mixture methanol/dichloromethane (8:2, 3.5 mL) at room temperature. The reaction mixture was stirred overnight. After concentration to dryness, the residue was purified by chromatography on silica gel using ethyl acetate/methanol (95:5) as eluent. The title product was obtained as a white solid (20 mg, 35%).

HPLC isomer ratio 87:13, geometry not assigned (the minor isomer has the shortest retention time).

LCMS (ESI-APCI) m/z 343.1 (M+H)+

$^1$H NMR (CDCl$_3$, 400 MHz) (mixture of 2 isomers): δ (ppm): 8.45 (s, 1H), 8.26 (s, 1H), 7.57 (s, 1H), 7.52 (d, J=15.6 Hz, 1H), 6.37 (d, J=15.6 Hz, 1H), 4.39-3.99 (m, 6H), 3.39-3.37 (m, 1H), 2.93 (t, J=7.2 Hz, 2H), 2.63 (t, J=7.2 Hz, 2H), 1.94-1.83 (s, 3H), 1.22-1.15 (m, 3H).

Example 58

(E)-6-(3-(3-(Benzofuran-3-yl)azetidin-1-yl)-3-oxoprop-1-enyl)-3,4-dihydro-1,8-naphthyridin-2(1H)-one (E58)

Step 1: 1-Benzhydrylazetidin-3-one

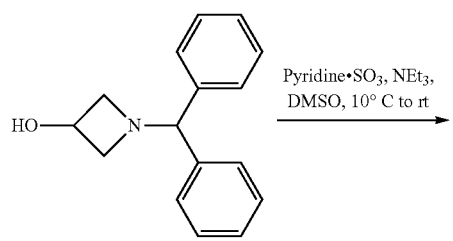

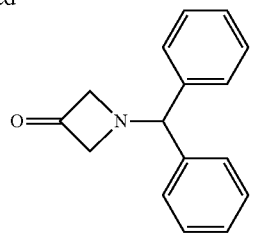

Triethylamine (29.1 mL, 209 mmol) and a solution of sulphur trioxide pyridine complex (21.3 g, 134 mmol) in DMSO (100 mL) were added at 10° C. to a solution of 1-benzhydrylazetidin-3-ol (5.0 g, 20.9 mmol) in DMSO (60 mL). The resulting mixture was stirred at 10° C. for 45 minutes, then at room temperature for 4 hours, subsequently quenched by pouring onto crushed ice (~200 g) and extracted with ethyl acetate (3×200 mL). The combined organic layers were washed with water (400 mL) and brine (400 mL), dried over sodium sulfate, filtered and concentrated under reduced pressure. The residue was purified by column chromatography on silica gel using petroleum ether/ethyl acetate (80:20 to 70:30) as eluent. The title product was obtained as a yellowish solid (4.35 g, 88%).

$^1$H NMR (CDCl$_3$, 400 MHz): δ (ppm): 7.50-7.20 (m, 10H), 4.60 (s, 1H), 4.01 (s, 4H).

Step 2: 1-Benzhydryl-3-(benzofuran-3-yl)azetidin-3-ol

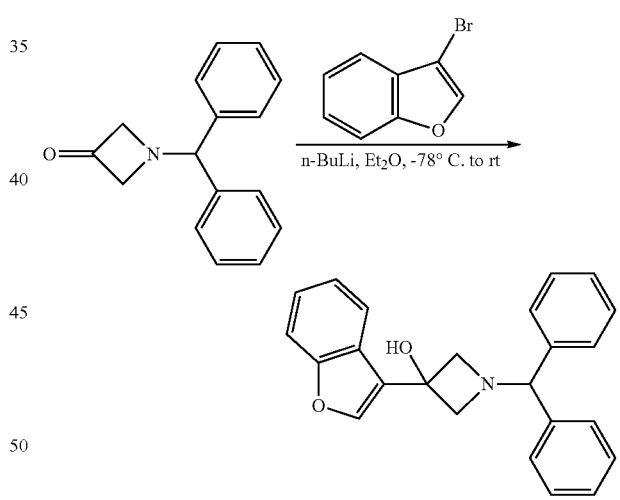

A 2.5 M solution of n-butyllithium in hexanes (3.25 mL, 8.13 mmol) was added dropwise to a solution of 3-bromobenzofuran (1.0 g, 5.08 mmol) in diethyl ether (22 mL) at −78° C. The reaction mixture was stirred for 20 minutes at −78° C. and then a solution of 1-benzhydrylazetidin-3-one (1.2 g, 5.08 mmol) in diethyl ether (10 mL) was added dropwise at the same temperature. The mixture was stirred for minutes at −78° C., then allowed to warm back to room temperature and stirred for 2 hours. Water (30 mL) was added and the mixture was extracted with ethyl acetate (3×30 mL). The combined organic layers were dried over sodium sulfate, filtered and concentrated. The crude residue was combined with another crude mixture which was obtained in the same manner from 3-bromobenzofuran (500 mg, 0.25 mmol). The combined crude materials were purified by chromatography on silica gel using petroleum ether/dichloromethane (50:50 to 0:100) as eluent. The title compound was obtained as a yellow sticky solid (761 mg, 40%).

LCMS (ESI-APCI) m/z 356.2 (M+H)⁺.

¹H NMR (CDCl₃, 400 MHz): δ (ppm): 7.91 (d, J=7.2 Hz, 1H), 7.66 (s, 1H), 7.52-7.13 (m, 13H), 4.53 (s, 1H), 3.73 (d, J=8.8 Hz, 2H), 3.43 (d, J=8.8 Hz, 2H), 2.42 (br s, 1H).

Step 3:
1-Benzhydryl-3-(benzofuran-3-yl)-3-chloroazetidine

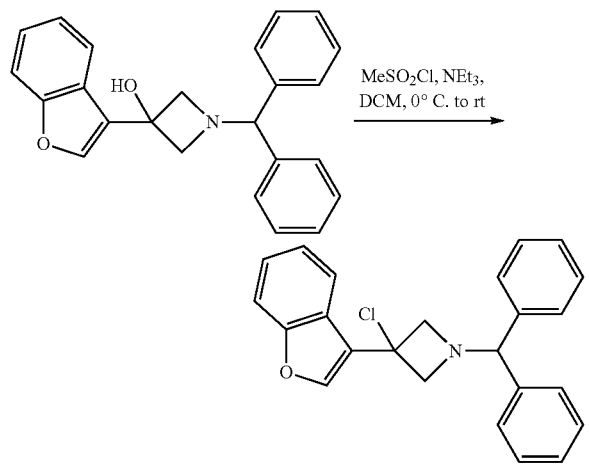

To a solution of 1-benzhydryl-3-(benzofuran-3-yl)azetidin-3-ol (760 mg, 2.14 mmol) in dichloromethane (10 mL) was added at 0° C. triethylamine (387 μL, 2.78 mmol) and then dropwise a solution of methanesulfonyl chloride (216 μL, 2.78 mmol) in dichloromethane (3 mL). The reaction mixture was stirred for 1 hour at room temperature, then diluted with water (50 mL) and extracted with dichloromethane (3×50 mL). The combined organic layers were dried over sodium sulfate, filtered and concentrated to dryness. The crude title compound was obtained as a yellow gum (873 mg, 109%) and used for the next step without further purification.

LCMS (ESI-APCI) m/z 374.1 (M+H)⁺.

¹H NMR (CDCl₃, 400 MHz): δ (ppm): 7.77 (d, J=8.0 Hz, 1H), 7.65 (s, 1H), 7.57-7.17 (m, 13H), 4.58 (s, 1H), 3.92-3.86 (m, 4H).

Step 4: 1-Benzhydryl-3-(benzofuran-3-yl)azetidine

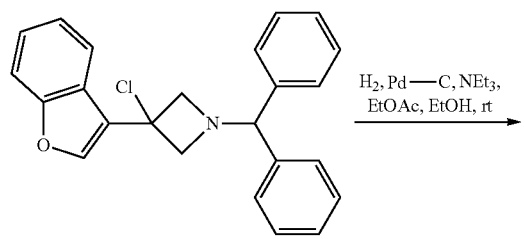

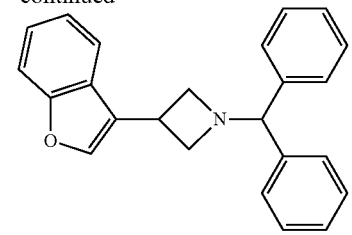

A mixture of 1-benzhydryl-3-(benzofuran-3-yl)-3-chloroazetidine as obtained in the previous step (873 mg, ≤2.14 mmol), triethylamine (299 μL, 2.14 mmol) and 10% palladium on carbon (227 mg) in ethyl acetate (15 mL) and ethanol (15 mL) was stirred at room temperature under hydrogen atmosphere (~1 atm) for 3 days. After removal of hydrogen, the mixture was diluted with dichloromethane (100 mL), filtered through Clarcel® and concentrated. The residue was taken up in dichloromethane (50 mL) and washed with aqueous saturated sodium hydrogencarbonate (50 mL). The aqueous layer was back-washed with dichloromethane (2×50 mL) and all the combined organic layers were dried over sodium sulfate, filtered and concentrated. The residue was purified by chromatography on silica gel using petroleum ether/ethyl acetate (100:0 to 95:5) as eluent followed by preparative TLC on reversed phase C18 using acetonitrile/water (90:10) as eluent. The title compound was obtained as a yellow gum (52 mg, 7%).

LCMS (ESI-APCI) m/z 340.2 (M+H)⁺.

¹H NMR (CDCl₃, 400 MHz): δ (ppm): 7.68 (d, J=7.6 Hz, 1H), 7.47-7.17 (m, 14H), 4.45 (s, 1H), 3.84-3.76 (m, 1H), 3.72-3.68 (m, 2H), 3.27-3.23 (m, 2H).

Step 5: 3-(Benzofuran-3-yl)azetidine hydrochloride

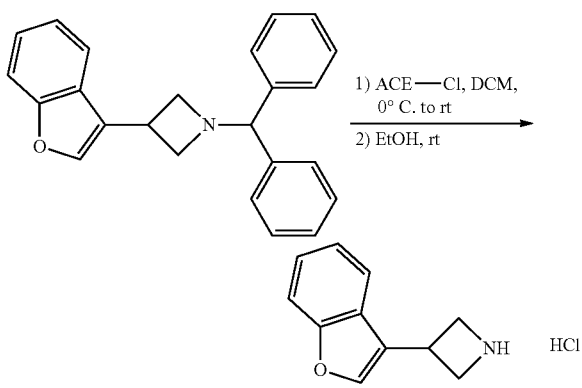

1-Chloroethyl chloroformate (18 μL, 0.16 mmol) was added to a solution of 1-benzhydryl-3-(benzofuran-3-yl)azetidine (52 mg, 0.15 mmol) in dichloromethane (1.5 mL) at 0° C. The reaction mixture was stirred for 15 minutes at 0° C. and for 4 hours at room temperature. An additional amount of 1-chloroethyl chloroformate (8 μL, 0.07 mmol) was added and stirring continued for 1 hour at room temperature. Ethanol (1.5 mL) was added and the reaction mixture was stirred for 3 days at room temperature. After concentration to dryness, the crude mixture was triturated in n-pentane (2×2 mL) to afford the title compound as a pink solid (42 mg, 130%) which was used without further purification.

LCMS (ESI-APCI) m/z 174.1 (M+H)⁺.

Step 6: (E)-6-(3-(3-(Benzofuran-3-yl)azetidin-1-yl)-3-oxoprop-1-enyl)-3,4-dihydro-1,8-naphthyridin-2(1H)-one

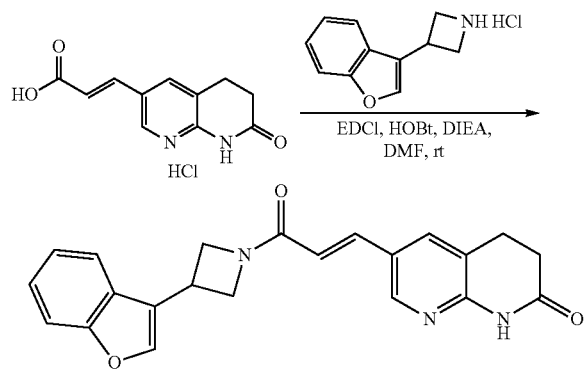

A mixture of (E)-3-(7-oxo-5,6,7,8-tetrahydro-1,8-naphthyridin-3-yl)acrylic acid hydrochloride (26 mg, 0.10 mmol), 3-(benzofuran-3-yl)azetidine hydrochloride as obtained in the previous step (42 mg, ≤0.15 mmol), EDCI (29.3 mg, 0.15 mmol), HOBt (20.7 mg, 0.15 mmol) and diisopropylethylamine (105 µL, 0.61 mmol) in DMF (3 mL) was stirred at room temperature for 19 hours, then diluted with water (15 mL) and extracted with ethyl acetate (3×15 mL). The combined organic phases were washed with brine (3×50 mL), dried over sodium sulfate, filtered and concentrated to dryness. The residue was purified by chromatography on silica gel using dichloromethane/methanol (100:0 to 97:3) as eluent. After trituration in acetone (3×2 mL), co-evaporation with dichloromethane (3×2 mL) and vacuum-drying, the title compound was obtained as an off-white solid (8 mg, 21%).

MS (ESI-APCI) m/z 374.1 (M+H)+.

$^1$H NMR (CDCl$_3$, 400 MHz): δ (ppm): 8.32-8.31 (m, 1H), 8.05 (s, 1H), 7.68-7.51 (m, 5H), 7.37-7.26 (m, 2H, overlapping with CDCl$_3$), 6.49 (d, J=15.6 Hz, 1H), 4.78-4.74 (m, 1H), 4.62-4.57 (m, 1H), 4.49-4.46 (s, 1H), 4.40-4.36 (m, 1H), 4.10-4.02 (m, 1H), 3.00 (t, J=7.6 Hz, 2H), 2.70 (t, J=7.6 Hz, 2H).

Example 59

(E)-6-(3-(3-(Benzofuran-2-yl)azetidin-1-yl)-3-oxoprop-1-enyl)-3,4-dihydro-1,8-naphthyridin-2(1H)-one (E59)

Step 1:
1-Benzhydryl-3-(benzofuran-2-yl)azetidin-3-ol

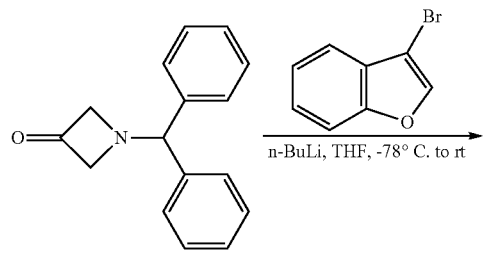

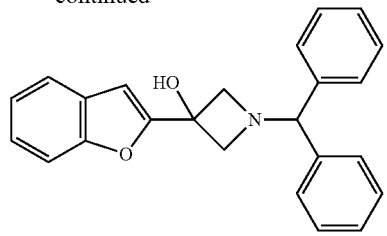

A 2.5 M solution of n-butyllithium in hexanes (2.23 mL, 5.58 mmol) was added dropwise to a solution of 3-bromobenzofuran (1.0 g, 5.08 mmol) in THF (35 mL) at −78° C. The reaction mixture was stirred for 30 minutes at −78° C. and then a solution of 1-benzhydrylazetidin-3-one (1.2 g, 5.08 mmol, as prepared in step 1 of example FAB270) in THF (10 mL) was added dropwise at the same temperature. The mixture was allowed to warm back to room temperature overnight. Water (50 mL) was added and the mixture was extracted with ethyl acetate (3×50 mL). The combined organic layers were dried over sodium sulfate, filtered and concentrated. The residue was purified by chromatography on silica gel using petroleum ether/dichloromethane (50:50 to 0:100) as eluent. The title compound was obtained as a yellow solid (230 mg, 13%).

LCMS (ESI-APCI) m/z 356.2 (M+H)+.

$^1$H NMR (CDCl$_3$, 400 MHz): δ (ppm): 7.60-7.17 (m, 14H), 6.79 (s, 1H), 4.58 (s, 1H), 3.82-3.72 (m, 2H), 3.55-3.45 (m, 2H), 2.95 (br s, 1H).

Step 2:
1-Benzhydryl-3-(benzofuran-2-yl)-3-chloroazetidine

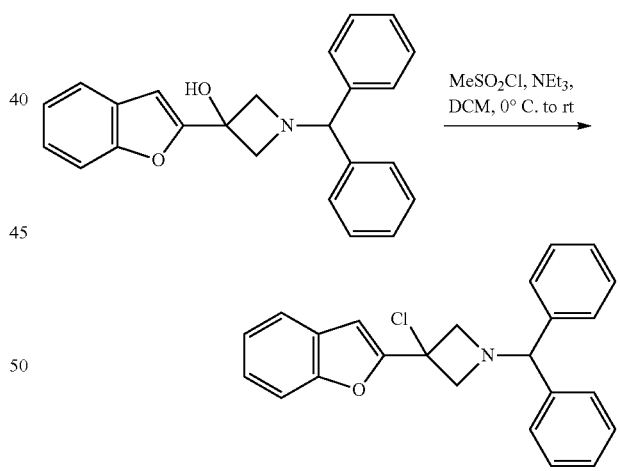

To a solution of 1-benzhydryl-3-(benzofuran-2-yl)-3-chloroazetidine (400 mg, 1.13 mmol) and triethylamine (204 µL, 1.46 mmol) in dichloromethane (5 mL) was added at 0° C. dropwise a solution of methanesulfonyl chloride (114 µL, 1.46 mmol) in dichloromethane (1.6 mL). The reaction mixture was stirred for 1 hour at room temperature, then diluted with water (30 mL) and extracted with dichloromethane (3×30 mL). The combined organic layers were dried over sodium sulfate, filtered and concentrated to dryness. The crude title compound was obtained as a yellow solid (430 mg, 102%) and used without further purification.

LCMS (ESI-APCI) m/z 374.1 (M+H)+.

¹H NMR (CDCl₃, 400 MHz): δ (ppm): 7.58-7.10 (m, 14H), 6.77 (s, 1H), 4.57 (s, 1H), 3.98-3.92 (m, 2H), 3.79-3.73 (m, 2H).

Step 3: 1-Benzhydryl-3-(benzofuran-2-yl)azetidine

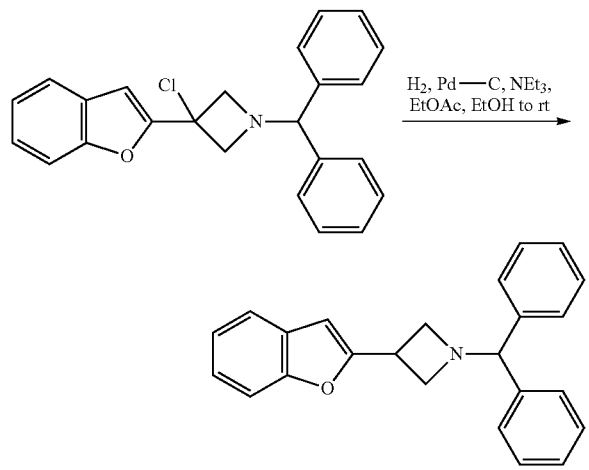

A mixture of 1-benzhydryl-3-(benzofuran-2-yl)-3-chloro-azetidine (458 mg, 1.23 mmol) and 10% palladium on carbon (130 mg) in ethyl acetate (6 mL) and ethanol (6 mL) was stirred at room temperature under hydrogen atmosphere (~1 atm) for 1 day. An additional amount of 10% palladium on carbon (130 mg) was added as well as triethylamine (171 µL, 1.23 mmol) and hydrogenation was continued under same conditions for 3 days. After removal of hydrogen, the mixture was diluted with dichloromethane (50 mL), filtered through Clarcel® and concentrated. The residue was taken up in dichloromethane (30 mL) and washed with aqueous saturated sodium hydrogencarbonate (30 mL). The aqueous layer was back-washed with dichloromethane (2×30 mL) and all the combined organic layers were dried over sodium sulfate, filtered and concentrated. The residue was purified by chromatography on silica gel using petroleum ether/ethyl acetate (100:0 to 95:5) as eluent. The title compound was obtained as a yellow gum (111 mg, 27%).

LCMS (ESI-APCI) m/z 340.2 (M+H)⁺.

¹H NMR (CDCl₃, 400 MHz): δ (ppm): 7.52-7.17 (m, 14H), 6.50 (s, 1H), 4.48 (s, 1H), 3.91-3.59 (m, 3H), 3.40-3.28 (m, 2H).

Step 4: 3-(Benzofuran-2-yl)azetidine hydrochloride

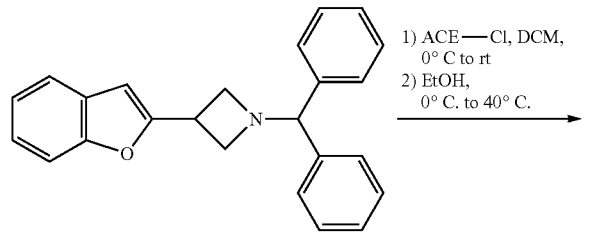

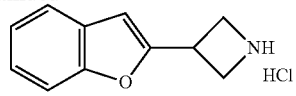

1-Chloroethyl chloroformate (36 µL, 0.33 mmol) was added to a solution of 1-benzhydryl-3-(benzofuran-2-yl)azetidine (108 mg, 0.32 mmol) in dichloromethane (3 mL) at 0° C. The reaction mixture was stirred for 2 hours at 0° C. and for 1 hour at room temperature. Ethanol (3 mL) was added at 0° C. and the reaction mixture was stirred for 2 hours at 0° C., for 19 hours at room temperature and for 4 hours at 40° C. After concentration to dryness, the crude mixture was triturated in n-pentane (2×4 mL) to afford the title compound as a pink solid (82 mg, 123%) which was used without further purification.

LCMS (ESI-APCI) m/z 174.2 (M+H)⁺.

Step 5: (E)-6-(3-(3-(Benzofuran-2-yl)azetidin-1-yl)-3-oxoprop-1-enyl)-3,4-dihydro-1,8-naphthyridin-2(1H)-one

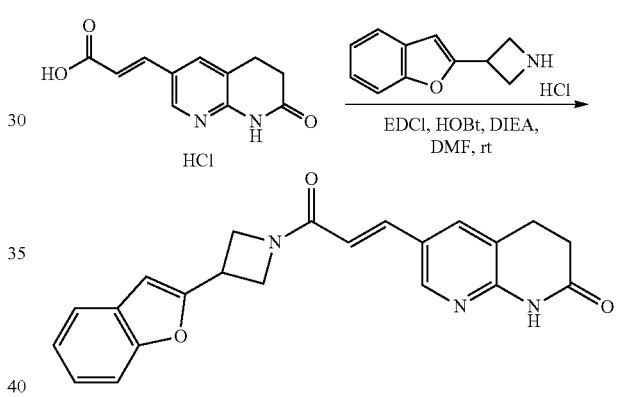

A mixture of (E)-3-(7-oxo-5,6,7,8-tetrahydro-1,8-naphthyridin-3-yl)acrylic acid hydrochloride (54 mg, 0.21 mmol), 3-(benzofuran-2-yl)azetidine hydrochloride as obtained in the previous step (82 mg, ≤0.32 mmol), EDCI (61 mg, 0.32 mmol), HOBt (43 mg, 0.32 mmol) and diisopropylethylamine (181 µL, 1.06 mmol) in DMF (6 mL) was stirred at room temperature for 19 hours, then diluted with water (15 mL) and extracted with ethyl acetate (3×15 mL). The combined organic phases were washed with brine (45 mL), dried over sodium sulfate, filtered and concentrated to dryness. The residue was purified by chromatography on silica gel using dichloromethane/methanol (100:0 to 97:3) as eluent, preparative TLC on silica gel using ethyl acetate/methanol (90:10) as eluent and finally preparative TLC on reversed phase C18 using acetonitrile/water (70:30) as eluent. After trituration in acetone (3×3 mL) and co-evaporation with dichloromethane (4×3 mL), the title compound was obtained as a beige solid (15 mg, 19%).

MS (ESI-APCI) m/z 374.1 (M+H)⁺.

¹H NMR (CDCl₃, 400 MHz): δ (ppm): 8.36-8.33 (m, 2H), 7.66-7.62 (m, 2H), 7.54-7.45 (m, 2H), 7.30-7.20 (m, 2H, overlapping with CDCl₃), 6.60 (s, 1H), 6.48 (d, J=15.6 Hz, 1H), 4.69-4.65 (m, 1H), 4.55-4.49 (m, 2H), 4.41-4.37 (s, 1H), 4.11-4.03 (m, 1H), 3.00 (t, J=7.6 Hz, 2H), 2.70 (t, J=7.6 Hz, 2H).

Example 60

(E)-6-(3-(3-(Benzofuran-7-yloxy)azetidin-1-yl)-3-oxoprop-1-enyl)-3,4-dihydro-1,8-naphthyridin-2(1H)-one (E60)

Step 1: 1-Benzhydryl-3-(benzofuran-7-yloxy)-azetidine

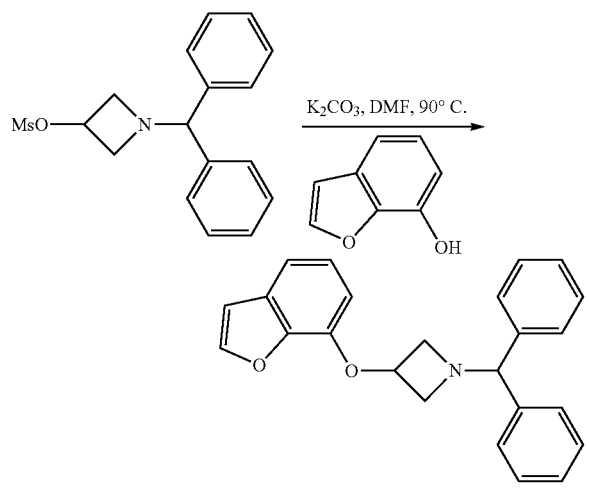

Potassium carbonate (348 mg, 2.52 mmol) and benzofuran-7-ol (169 mg, 1.26 mmol) were successively added to a solution of 1-benzhydrylazetidin-3-yl methanesulfonate (400 mg, 1.26 mmol) in DMF (8 mL). The reaction mixture was stirred overnight at 90° C. and then diluted by addition of ethyl acetate (20 mL) and water (20 mL). The aqueous phase was separated and extracted with ethyl acetate (4×50 mL). The combined organic phases were washed with a saturated solution of sodium chloride (5×50 mL), dried over sodium sulfate, filtered and concentrated to dryness. The residue was purified by chromatography on silica gel using petroleum ether/dichloromethane (1:0 to 2:8 to 0:1) as eluent. The title product was obtained as a yellow oil (350 mg, 69%).

LCMS (ESI-APCI) m/z 356.2 (M+H)$^+$

Step 2: 3-(Benzofuran-7-yloxy)-azetidine hydrochloride

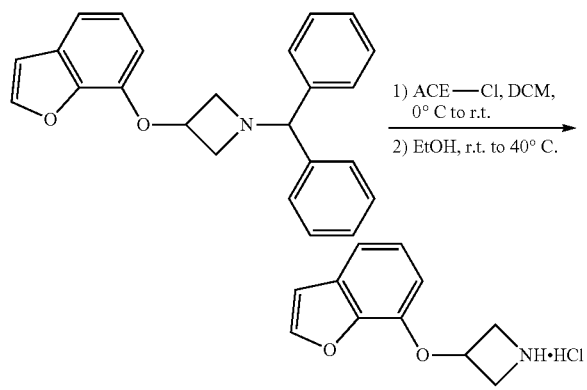

1-Chloroethyl chloroformate (107 µL, 0.99 mmol) was added to a solution of 1-benzhydryl-3-(benzofuran-7-yloxy)-azetidine (349 mg, 0.98 mmol) in dichloromethane (10 mL) at 0° C. The reaction mixture was stirred for 4 hours at room temperature. Ethanol (10 mL) was added and the reaction mixture was stirred for an additional 2 hours at room temperature and 3 hours at 40° C. After concentration to dryness, the residue was taken in a mixture dichloromethane/diethyl ether to afford the title compound as a white solid (193 mg, 87%).

$^1$H NMR (CDCl$_3$, 400 MHz): 10.11 (s, NH$_2$), 9.98 (s, 1H), 7.60 (d, J=2 Hz, 1H), 7.11 (t, J=2 Hz, 1H), 6.77 (d, J=2 Hz, 1H), 6.65 (d, J=7.6 Hz, 1H), 5.41-5.34 (m, 1H), 4.55-4.49 (m, 2H), 4.42-4.35 (m, 2H).

Step 3: (E)-6-(3-(3-(Benzofuran-7-yloxy)azetidin-1-yl)-3-oxoprop-1-enyl)-3,4-dihydro-1,8-naphthyridin-2(1H)-one

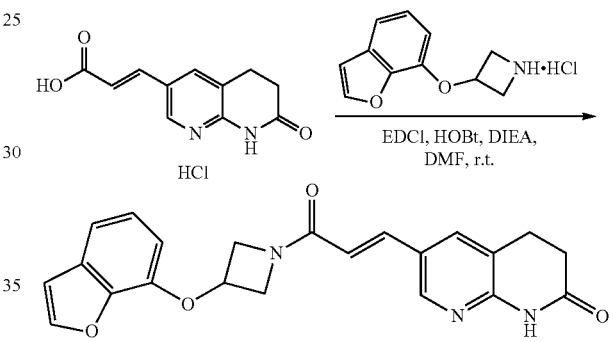

3-(Benzofuran-7-yloxy)-azetidine hydrochloride (190 mg, 0.84 mmol), EDCI (161 mg, 0.84 mmol), HOBt (113 mg, 0.84 mmol) and diisopropylethylamine (240 µL, 1.40 mmol) were successively added to a solution of (E)-3-(7-oxo-5,6,7,8-tetrahydro-1,8-naphthyridin-3-yl)-acrylic acid hydrochloride (143 mg, 0.56 mmol) in dimethylformamide (14 mL) at room temperature. The reaction mixture was stirred overnight. The reaction mixture was then diluted by addition of ethyl acetate (40 mL) and water (40 mL). The aqueous phase was separated and extracted with ethyl acetate (2×40 mL). The combined organic phases were washed with a saturated solution of sodium chloride (3×40 mL), dried over sodium sulfate, filtered and concentrated to dryness. The residue was purified by chromatography on silica gel using dichloromethane/methanol (1:0 to 95:5) as eluent. After trituration in diethyl ether and acetone, the title compound was obtained as a white solid (80 mg, 37%).

LCMS (ESI-APCI) m/z 390.1 (M+H)$^+$ $^1$H NMR (CDCl$_3$, 400 MHz): δ (ppm): 8.31 (s, 1H), 8.22 (s, 1H), 7.64 (s, 1H), 7.63 (s, 1H), 7.62 (d, J=15.6 Hz, 1H), 7.28 (d, J=8 Hz, 1H), 7.15 (t, J=7.6 Hz, 1H), 6.79 (s, 1H), 6.61 (d, 8 Hz, 1H), 6.45 (d, J=15.6 Hz, 1H), 5.31-5.26 (m, 1H), 4.75-4.70 (m, 1H), 4.60-4.55 (m, 1H), 4.51-4.48 (m, 1H), 4.35-4.31 (m, 1H), 3.00 (t, J=8 Hz, 2H), 2.70 (t, J=8 Hz, 2H).

Example 61

(E)-6-(3-(3-(Benzo[b]thiophen-3-yloxy)azetidin-1-yl)-3-oxoprop-1-enyl)-3,4-dihydro-1,8-naphthyridin-2(1H)-one (E61)

Step 1': Benzo[b]thiophen-3-ol

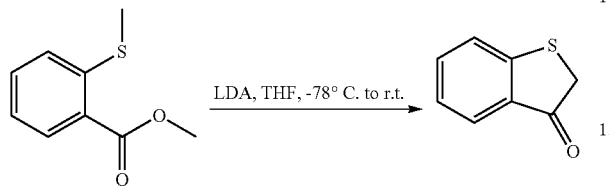

A solution of methyl 2-(methylthio)benzoate (4.0 g, 22.00 mmol) in THF (60 mL) was added to a solution of freshly prepared LDA (2M in THF, 17.5 mL, 35 mmol) placed at −78° C. The reaction mixture was stirred for 1 hour at −78° C., then overnight at room temperature. The reaction mixture was diluted by addition of a saturated solution of ammonium chloride (50 mL). The aqueous phase was separated and extracted with ethyl acetate (3×70 mL). The combined organic phases were washed with a saturated solution of sodium chloride (40 mL), dried over sodium sulfate, filtered and concentrated to dryness. The residue was purified by chromatography on silica gel using petroleum ether/ethyl acetate (95:5 to 9:1) as eluent. The title product was obtained as a pink solid (1.74 g, 53%).

$^1$H NMR (CDCl$_3$, 400 MHz): δ (ppm): 7.71 (d, J=8 Hz, 1H), 7.49 (t, J=8 Hz, 1H), 7.38 (d, J=8 Hz, 1H), 7.17 (t, J=8 Hz, 1H), 3.73 (s, 2H).

Step 1: 1-Benzhydryl-3-iodoazetidine

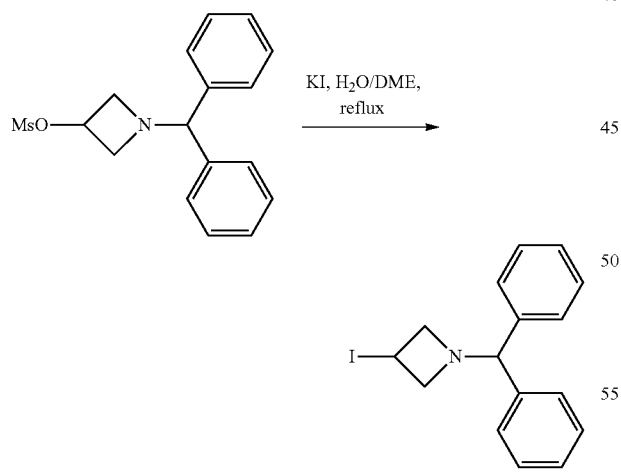

Potassium iodide (530 mg, 3.14 mmol) was added to a solution of 1-benzhydrylazetidin-3-yl methanesulfonate (500 mg, 1.57 mmol) in a mixture of water (2.5 mL) and 1,2-dimethoxyethane (2.5 mL) at room temperature. The reaction mixture was then heated up to reflux and stirred for 3 hours. After cooling down to room temperature, the reaction mixture was diluted by addition of water (50 mL) and ethyl acetate (50 mL). The aqueous phase was separated and extracted with ethyl acetate (2×70 mL). The combined organic phases were washed with a saturated solution of sodium chloride (40 mL), dried over sodium sulfate, filtered and concentrated to dryness. The title compound was obtained as a yellow solid (550 mg, 100%).

LCMS (ESI-APCI) m/z 350.0 (M+H)$^+$

Step 2: 1-Benzhydryl-3-(benzo[b]thiophen-3-yloxy)azetidine

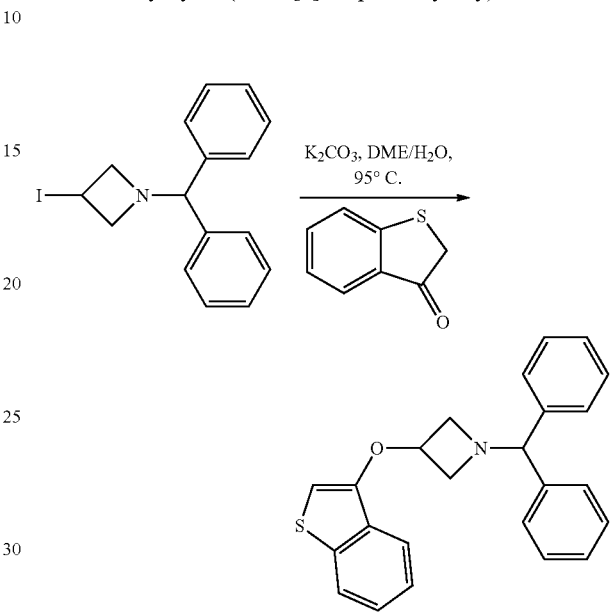

Benzo[b]thiophen-3-ol (215 mg, 1.43 mmol) and potassium carbonate (237 mg, 1.72 mmol) were successively added to a solution of 1-benzhydryl-3-iodoazetidine (500 mg, 1.43 mmol) in a mixture of 1,2-dimethoxyethane (12 mL) and water (6 mL) at room temperature. The reaction mixture was then heated up to 95° C. and stirred for 3 hours. After cooling down to room temperature, the reaction mixture was diluted by addition of water (50 mL) and ethyl acetate (50 mL). The aqueous phase was separated and extracted with ethyl acetate (5×50 mL). The combined organic phases were washed with a saturated solution of sodium chloride (2×50 mL), dried over sodium sulfate, filtered and concentrated to dryness. The residue was purified by chromatography on silica gel using petroleum ether/ethyl acetate (1:0 to 9:1) as eluent. The title compound was obtained as a yellow oil (220 mg, 21%).

LCMS (ESI-APCI) m/z 372.1 (M+H)$^+$

Step 3: 3-(Benzo[b]thiophen-3-yloxy)azetidine hydrochloride

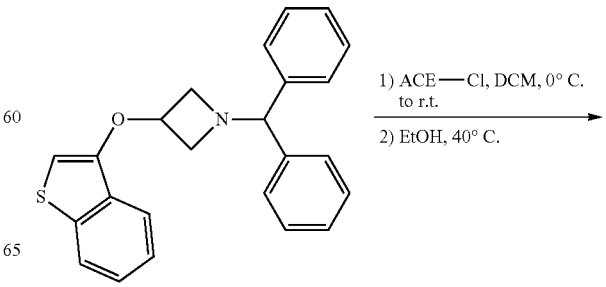

-continued

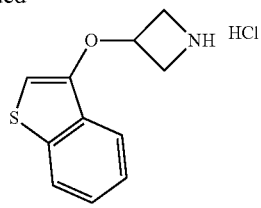

1-Chloroethyl chloroformate (67.3 µL, 0.621 mmol) was added to a solution of 1-benzhydryl-3-(benzo[b]thiophen-3-yloxy)azetidine (220 mg, 0.592 mmol) in dichloromethane (5 mL) at 0° C. The reaction mixture was stirred for 2 hours at 0° C. and for 5 hours at room temperature. Ethanol (5 mL) was added and the reaction mixture was stirred for 1 hour at 40° C. After concentration to dryness, the crude mixture was precipitated from a mixture dichloromethane/pentane to afford a pale orange solid (140 mg, quantitative) which was used without further purification.

$^1$H NMR (DMSO-$d_6$, 400 MHz): δ (ppm): 9.23 (s, 1H), 9.08 (s, 1H), 7.96-7.63 (m, 1H), 7.79-7.77 (m, 1H), 7.47-7.42 (m, 2H), 6.80 (s, 1H), 5.15-5.18 (m, 1H), 4.45-4.52 (m, 2H), 4.09-4.02 (m, 2H).

Step 4: (E)-6-(3-(3-(Benzo[b]thiophen-3-yloxy)azetidin-1-yl)-3-oxoprop-1-enyl)-3,4-dihydro-1,8-naphthyridin-2(1H)-one

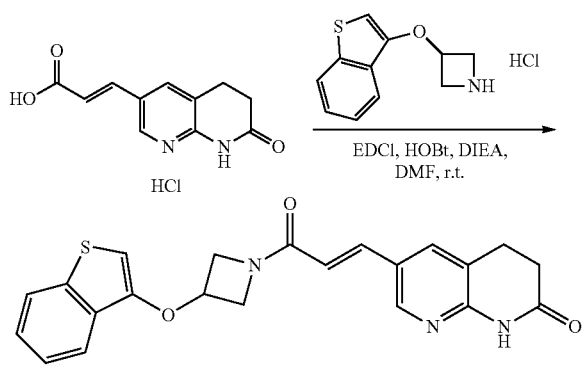

3-(benzo[b]thiophen-3-yloxy)azetidine hydrochloride (140 mg, 0.58 mmol), EDCI (111 mg, 0.48 mmol), HOBt (78 mg, 0.58 mmol) and diisopropylethylamine (420 µL, 2.41 mmol) were successively added to a solution of (E)-3-(7-oxo-5,6,7,8-tetrahydro-1,8-naphthyridin-3-yl)-acrylic acid hydrochloride (123 mg, 0.48 mmol) in dimethylformamide (10 mL) at room temperature. The reaction mixture was stirred overnight and then diluted by addition of ethyl acetate (40 mL) and water (40 mL). The aqueous phase was extracted with ethyl acetate (2×40 mL). The combined organic phases were washed with a saturated solution of sodium chloride (3×40 mL), dried over sodium sulfate, filtered and concentrated to dryness. The residue was purified by chromatography on silica gel using dichloromethane/methanol (98:2 to 95:5) as eluent. The title product was obtained as a white solid (52 mg, 26%).

LCMS (ESI-APCI) m/z 406.1 (M+H)$^+$ $^1$H NMR (CDCl$_3$, 400 MHz): δ (ppm): 8.32 (s, 1H), 8.23 (s, 1H), 7.83-7.76 (m, 2H), 7.65-7.61 (m, 1H), 7.41-7.38 (m, 2H), 6.46 (d, J=15.6 Hz, 1H), 6.13 (s, 1H), 5.17-5.13 (m, 1H), 4.75-4.71 (m, 1H), 4.61-4.56 (m, 1H), 4.46-4.43 (m, 1H), 4.34-4.30 (m, 1H), 2.99 (t, J=7.6 Hz, 2H), 2.70 (t, J=7.6 Hz, 2H).

Example 62

(E)-6-(3-Oxo-3-(3-(thiophen-2-ylthio)azetidin-1-yl)prop-1-enyl)-3,4-dihydro-1,8-naphthyridin-2(1H)-one (E62)

Step 1: 1-Benzhydryl-3-(thiophen-2-ylthio)-azetidine

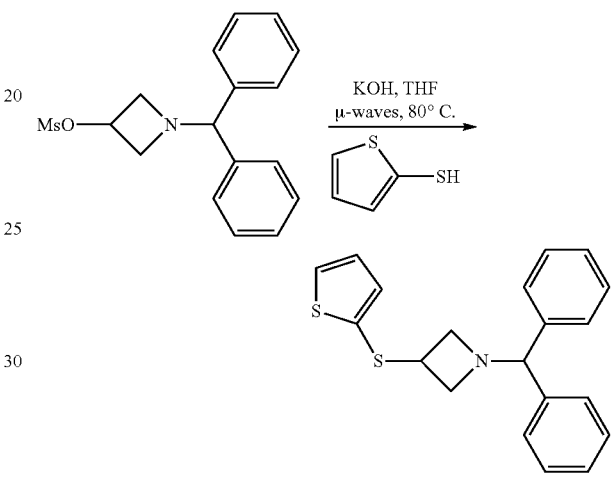

Potassium hydroxide (141 mg, 2.52 mmol) and thiophene-2-thiol (292 mg, 238 µL) were added to a solution of 1-benzhydrylazetidin-3-yl methanesulfonate (400 mg, 1.26 mmol) solubilized in THF (7 mL). The reaction mixture was stirred a first time under microwave irradiations (100 W) at 80° C. for 30 minutes. Potassium hydroxide (141 mg, 2.52 mmol) and thiophene-2-thiol (292 mg, 238 µL) were added and the reaction mixture was stirred for a second time under microwave irradiations (100 W) at 80° C. for 30 minutes. After concentration to dryness, the residue was purified by chromatography on silica gel using petroleum ether/ethyl acetate (1:0 to 9:1) as eluent. The title product was obtained as a yellow solid (160 mg, 37%).

LCMS (ESI-APCI) m/z 338.1 (M+H)$^+$

Step 2: 3-(Thiophen-2-ylthio)-azetidine hydrochloride

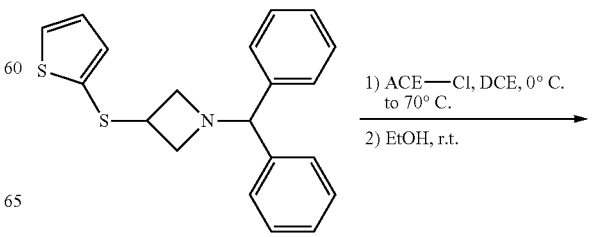

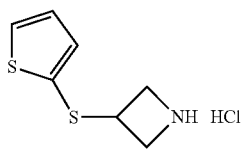

1-Chloroethyl chloroformate (140 μL, 1.3 mmol) was added to a solution of 1-benzhydryl-3-(thiophen-2-ylthio)-azetidine (340 mg, 1.00 mmol) in dichloroethane (11 mL) at 0° C. The reaction mixture was stirred for 3 hours at room temperature and for 2 hours at 70° C. Ethanol (11 mL) was added and the reaction mixture was stirred for an additional 2 days at room temperature. After concentration to dryness, the residue was triturated in pentane (2×20 mL) to afford a brown oil (171 mg, 81%) which was used in the next step without further purification.

$^1$H NMR (CDCl$_3$, 400 MHz): δ (ppm): 9.87 and 8.44 (s, NH$_2$), 7.43-7.41 (m, 2H), 7.02-7.00 (m, 1H), 4.16-4.13 (m, 2H), 4.04-4.02 (m, 1H), 3.94-3.90 (m, 2H).

Step 3: (E)-6-(3-Oxo-3-(3-(thiophen-2-ylthio)azetidin-1-yl)prop-1-enyl)-3,4-dihydro-1,8-naphthyridin-2(1H)-one

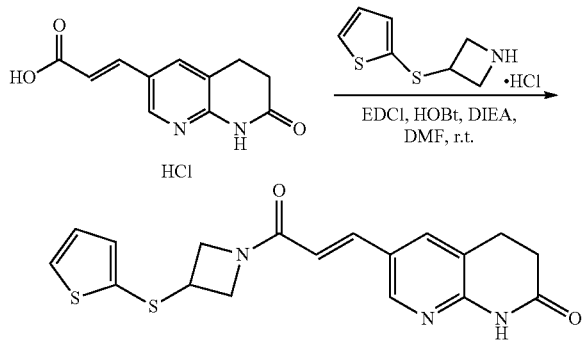

3-(Thiophen-2-ylthio)-azetidine hydrochloride (170 mg, 0.82 mmol), EDCI (157 mg, 0.82 mmol), HOBt (110 mg, 0.82 mmol) and diisopropylethylamine (240 μL, 1.36 mmol) were successively added to a solution of (E)-3-(7-oxo-5,6,7,8-tetrahydro-1,8-naphthyridin-3-yl)-acrylic acid hydrochloride (139 mg, 0.55 mmol) in dimethylformamide (14 mL) at room temperature. The reaction mixture was stirred overnight and then diluted by addition of ethyl acetate (40 mL) and water (40 mL). The aqueous phase was extracted with ethyl acetate (2×40 mL). The combined organic phases were washed with a saturated solution of sodium chloride (3×40 mL), dried over sodium sulfate, filtered and concentrated to dryness. The residue was purified by chromatography on silica gel using petroleum ether/ethyl acetate (1:0 to 95:5) as eluent. After trituration in acetone, the title product was obtained as a white solid (114 mg, 37%).

LCMS (ESI-APCI) m/z 372.1 (M+H)$^+$ $^1$H NMR (CDCl$_3$, 400 MHz): δ (ppm): 8.29 (s, 1H), 8.27 (s, 1H), 7.61 (s, 1H), 7.55 (d, J=15.6 Hz, 1H), 7.44-4.72 (m, 1H), 7.23-7.21 (m, 1H), 7.06-7.03 (m, 1H), 6.34 (d, J=15.6 Hz, 1H), 4.60-4.55 (m, 1H), 4.43-4.38 (m, 1H), 4.27-4.22 (m, 1H), 4.12-4.06 (m, 1H), 3.96-3.87 (m, 1H), 2.99 (t, J=7.2 Hz, 2H), 2.69 (t, J=7.2 Hz, 2H).

Example 63

(E)-6-(3-(3-Butoxyazetidin-1-yl)-3-oxoprop-1-enyl)-1'-methyl-1H-spiro[[1,8]naphthyridine-3,4'-piperidin]-2(4H)-one (E63)

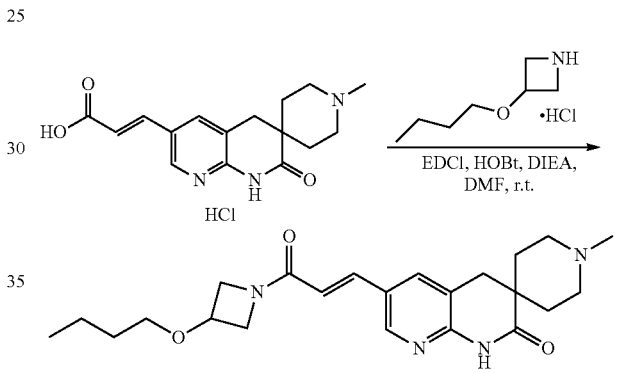

3-Butoxyazetidine hydrochloride (33 mg, 0.20 mmol), EDCI (72 mg, 0.4 mmol), HOBt (54 mg, 0.4 mmol) and diisopropylethylamine (116 μL, 0.66 mmol) were successively added to a solution of (E)-3-(7-oxo-5,6,7,8-tetrahydro-1,8-naphthyridin-3-yl)-acrylic acid hydrochloride (45 mg, 0.13 mmol) in dimethylformamide (5 mL) at room temperature. The reaction mixture was stirred overnight and then diluted by addition of ethyl acetate (40 mL) and water (40 mL). The aqueous phase was extracted with ethyl acetate (2×40 mL). The combined organic phases were washed with a saturated solution of sodium chloride (3×40 mL), dried over sodium sulfate, filtered and concentrated to dryness. The residue was purified by chromatography on silica gel using dichloromethane/methanol (7:3 to 5:5) as eluent. After precipitation in DCM/Et$_2$O and triturations in acetone, the title product was obtained as a white solid (10 mg, 17%).

LCMS (ESI-APCI) m/z 413.3 (M+H)$^+$ $^1$H NMR (CDCl$_3$, 400 MHz): δ (ppm): 8.55 (s, 1H), 8.31 (s, 1H), 7.66 (s, 1H), 7.58 (d, J=15.6 Hz, 1H), 6.43 (d, J=15.6 Hz, 1H), 4.46-3.98 (m, 5H), 3.42-3.40 (m, 2H), 2.89 (s, 2H), 2.88-2.81 (m, 2H), 2.46-2.42 (m, 2H), 2.44 (s, 3H), 2.06-2.02 (m, 2H), 1.78-1.74 (m, 2H), 1.61-1.56 (m, 2H), 1.42-1.37 (m, 2H), 0.93 (t, J=5.2 Hz, 3H).

Example 64

1'-Methyl-6-((E)-3-oxo-3-(3-((E)-1-(benzyloxy-imino)ethyl)azetidin-1-yl)prop-1-enyl)-1H-spiro[[1,8]naphthyridine-3,4'-piperidin]-2(4H)-one (E64)

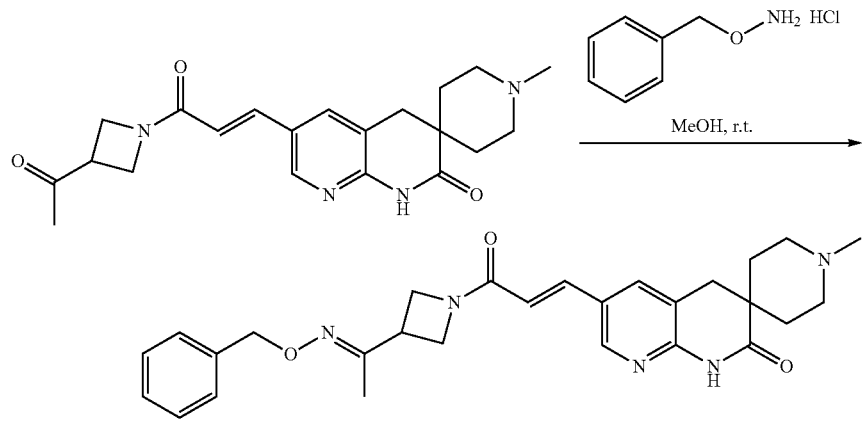

O-benzylhydroxylamine hydrochloride (13.5 mg, 0.08 mmol) was added to a solution of (E)-6-(3-(3-acetylazetidin-1-yl)-3-oxoprop-1-enyl)-1'-methyl-1H-spiro[[1,8]naphthyridine-3,4'-piperidin]-2(4H)-one (23.0 mg, 0.06 mmol) in methanol (1.5 mL) at room temperature. The reaction mixture was stirred overnight. After concentration to dryness, the residue was purified by chromatography on silica gel using dichloromethane/methanol (9:1) as eluent. The title product was obtained as a pink solid (9 mg, 31%).

HPLC isomer ratio 88:12, the major isomer adopts an (E) configuration (determined by $^1$HMR and selective NOE experiments).

LCMS (ESI-APCI) m/z 488.3 (M+H)$^+$ $^1$H NMR (CDCl$_3$, 400 MHz): δ (ppm): 8.34 (s, 1H), 8.30 (s, 1H), 7.67 (s, 1H), 7.59 (d, J=15.6 Hz, 1H), 7.36-7.37 (m, 5H), 6.43 (d, J=15.6 Hz, 1H), 5.10 (s, 2H), 4.44-4.12 (m, 4H), 3.47-3.43 (m, 1H), 2.89 (s, 2H), 2.90-2.83 (m, 2H), 2.73-2.68 (m, 2H), 2.46 (s, 3H), 2.02-1.98 (m, 2H), 1.93 (s, 3H), 1.76-1.72 (m, 2H).

Example 65

1'-Methyl-6-((E)-3-oxo-3-(3-((E)-1-(propoxyimino)ethyl)azetidin-1-yl)prop-1-enyl)-1H-spiro[[1,8]naphthyridine-3,4'-piperidin]-2(4H)-one (E65)

Step 1: (E)-6-(3-(3-Acetylazetidin-1-yl)-3-oxoprop-1-enyl)-1'-methyl-1H-spiro[[1,8]naphthyridine-3,4'-piperidin]-2(4H)-one

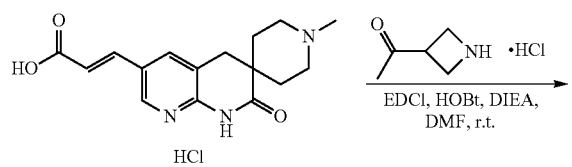

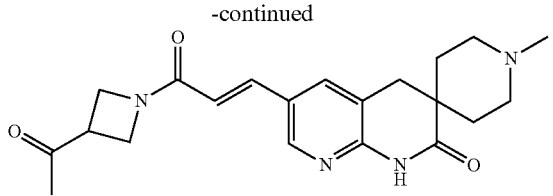

1-(Azetidin-3-yl)ethanone hydrochloride (110 mg, 0.8 mmol), EDCI (153 mg, 0.8 mmol), HOBt (108 mg, 0.8 mmol) and diisopropylethylamine (700 µL, 4.0 mmol) were successively added to a solution of (E)-3-(1'-methyl-2-oxo-2,4-dihydro-1H-spiro[[1,8]naphthyridine-3,4'-piperidine]-6-yl) acrylic acid hydrochloride (136 mg, 0.4 mmol) in dimethylformamide (15 mL) at room temperature. The reaction mixture was stirred overnight. After concentration to dryness, the residue was purified by chromatography on silica gel using dichloromethane/methanol/ammoniac (9:1:0.1) as eluent. Precipitation in a mixture DCM/pentane allowed isolation of the title product as a yellow solid (44.6 mg, 29%).

LCMS (ESI-APCI) m/z 383.3 (M+H)+

Step 2: 1'-Methyl-6-((E)-3-oxo-3-(3-((E)-1-(propoxyimino)ethyl)azetidin-1-yl)prop-1-enyl)-1H-spiro[[1,8]naphthyridine-3,4'-piperidin]-2(4H)-one

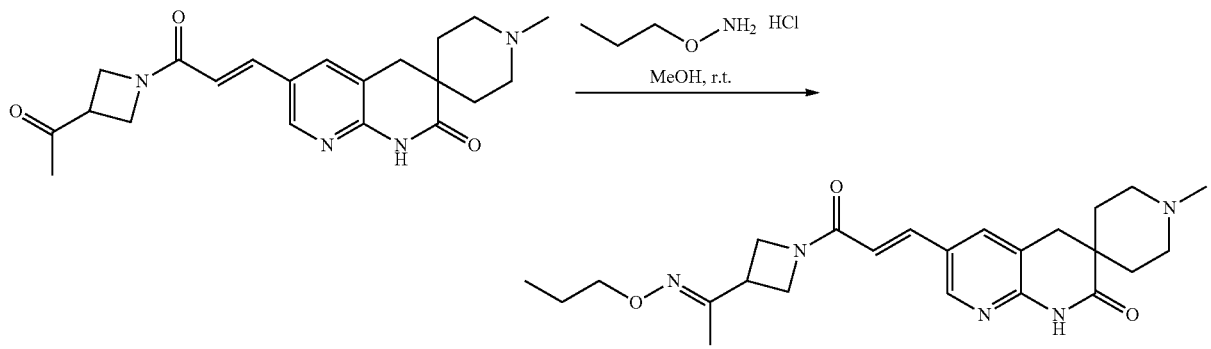

1-(Aminooxy)propane hydrochloride (10.5 mg, 0.093 mmol) was added to a solution of (E)-6-(3-(3-acetylazetidin-1-yl)-3-oxoprop-1-enyl)-1'-methyl-1H-spiro[[1,8]naphthyridine-3,4'-piperidin]-2(4H)-one (20.0 mg, 0.052 mmol) in methanol/dichloromethane (1.5 mL, 9:1) at room temperature. The reaction mixture was stirred overnight. After concentration to dryness, the residue was purified by chromatography on silica gel using chloroforme/methanol (9:1) as eluent. Triturations in acetone allowed isolation of the title product as a white solid (9 mg, 39%).

HPLC isomer ratio 89:11, geometry not assigned (the minor isomer has the shortest retention time).

LCMS (ESI-APCI) m/z 440.3 (M+H)+

1H NMR (CDCl3, 400 MHz) (mixture of 2 isomers): δ (ppm): 8.20 (s, 1H), 7.95 (s, 1H), 7.65 (s, 1H), 7.52 (d, J=15.6 Hz, 1H), 6.39 (d, J=15.6 Hz, 1H), 4.39-4.36 (m, 2H), 4.24-4.19 (m, 1H), 4.11-4.07 (m, 1H), 3.96-3.93 (m, 2H), 3.41-3.28 (m, 5H), 2.88 (s, 2H), 2.72 (s, 3H), 2.44-2.40 (m, 2H), 1.96-1.92 (m, 2H), 1.84 (s, 3H), 1.62-1.58 (m, 2H), 0.87 (t, J=7.2 Hz, 3H).

Example 66

(E)-1'-Methyl-6-(3-oxo-3-(3-(2-(thiophen-2-yl)ethoxy)azetidin-1-yl)prop-1-en-1-yl)-1H-spiro[[1,8]naphthyridine-3,4'-piperidin]-2(4H)-one (E66)

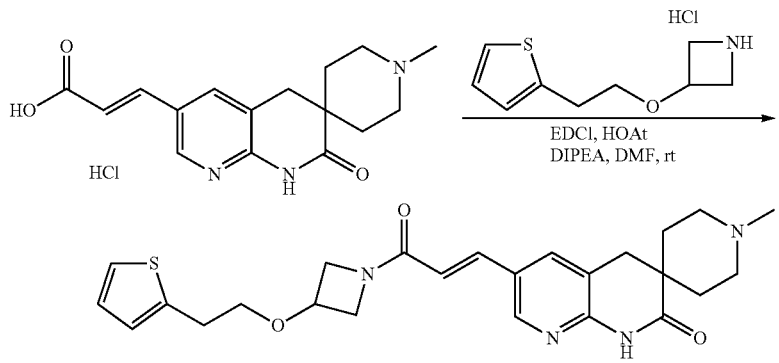

3-(2-(Thiophen-2-yl)ethoxy)azetidine hydrochloride (0.377 g, 1.718 mmol), EDCI.HCl (0.658 g, 3.44 mmol), 1-hydroxy-7-azabenzotriazole (0.468 g, 3.44 mmol) and N,N-diisopropylethylamine (0.980 mL, 5.73 mmol) were successively added to a solution of (E)-3-(1'-methyl-2-oxo-2,4-dihydro-1H-spiro[[1,8]naphthyridine-3,4'-piperidine]-6-yl)acrylic acid hydrochloride (0.387 g, 1.145 mmol) in dry DMF (25 mL) at room temperature. The reaction mixture was stirred during for 4 days and then diluted by addition of EtOAc (40 mL) and water (40 mL). The aqueous phase was separated and extracted with EtOAc (2×40 mL). The combined organic phases were washed with brine (60 mL), dried over Na$_2$SO$_4$, filtered and concentrated to dryness to yield a dark orange oil from which some solids precipitated (0.7 g). The crude product was purified using preparative LCMS (Waters X-Bridge 50×19 mm 5 μm ODB in combination with Waters X-Bridge guard 10×9 mm 5 μm, at 25 ml/min flow rate; detection of product by mass and UV signal; eluent 10 mM ammonia in milliQ water to 10 mM ammonia in MeCN 5% to 95% gradient). After lyophilization, FAB306 was obtained as a tan powder (53 mg, 10%) which was still contaminated by a minor impurity. This material was stirred in ml Et$_2$O for 2 h, then filtered off and dried in an air stream to yield target FAB306 (22 mg, 4%), which was pure according to LCMS and NMR analysis.

LCMS (ESI$^+$): 467.2 (M+H)$^+$;

$^1$H-NMR (CDCl$_3$, 400 MHz): δ (ppm): 8.29 (d, J=2 Hz, 1H), 8.15 (br s, 1H), 7.65 (d, J=2 Hz, 1H), 7.59 (d, J=15 Hz, 1H), 7.17 (dd, J=1 Hz, 5 Hz, 1H), 6.95 (m, 1H), 6.87 (m, 1H), 6.42 (d, J=15 Hz), 4.45 (m, 1H), 4.38 (m, 1H), 4.29 (m, 1H), 4.17 (m, 1H, 4.03 (m, 1H), 6.67 (m, 2H), 3.13 (t, J=4 Hz, 2H), 2.88 (s, 1H), 2.62 (m, 2H), 2.42 (m, 2H), 2.32 (s, 3H), 2.08 (m, 2H), 1.5-1.7 (m, 2H+H$_2$O)

Example 67

(E)-6-(3-(3-(3-Methylbenzofuran-2-yl)azetidin-1-yl)-3-oxoprop-1-enyl)-3,4-dihydro-1,8-naphthyridin-2(1H)-one (E67)

Step 1: 1-Benzhydrylazetidin-3-one

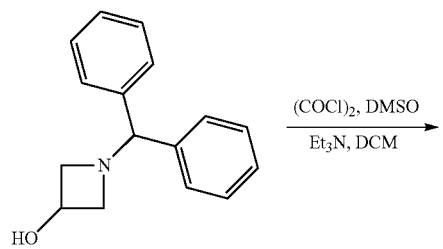

To a stirring solution of DMSO (12.45 ml, 176 mmol) in DCM (150 mL) at −78° C. under an argon atmosphere was added dropwise oxalyl chloride (8.61 mL, 100 mmol). After stirring for 30 minutes at −78° C., a solution of 1-benzhydrylazetidin-3-ol (20 g, 84 mmol) in DCM (75 mL) was added dropwise. The reaction mixture was stirred for 1 h at −78° C. before triethylamine (58.2 ml, 418 mmol) was added. The reaction mixture was allowed to reach 0° C. and was quenched with saturated NH$_4$Cl (150 mL), and then extracted with DCM (3×). The combined organic layers were washed with water, brine, dried on Na$_2$SO$_4$ and concentrated to give crude 1-benzhydrylazetidin-3-one (20.8 g, 105%) as a yellow solid.

LCMS (ESI$^+$): m/z 238.2 (M+H)$^+$

Step 2: 1-Benzhydryl-3-(3-methylbenzofuran-2-yl)azetidin-3-ol

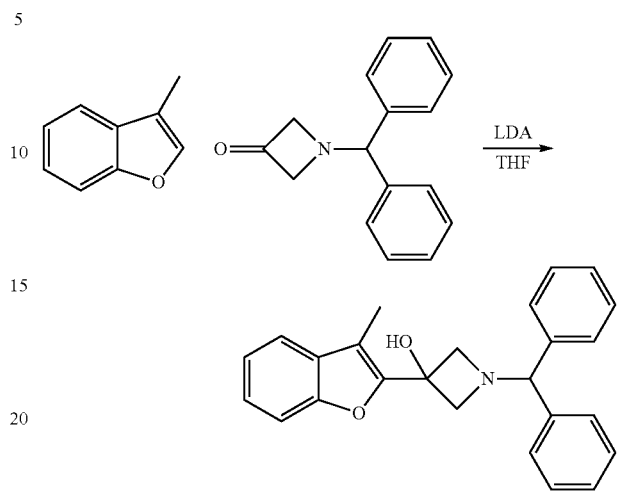

A solution of 3-methylbenzofuran (550 mg, 4.16 mmol) in dry THF (17 mL) was cooled to −78° C. and LDA (1.8 M in THF/heptane/ethylbenzene) (2.8 mL, 5.04 mmol) was added dropwise under N$_2$ over 5 min. After stirring for 30 min, 1-benzhydrylazetidin-3-one (1.61 g, 6.78 mmol) was added portionwise over 10 min. The reaction was stirred under N$_2$ at −78° C. for 15 min, and was then allowed to warm to rt and stirred for 1.5 h. The reaction was quenched with 0.5N HCl and extracted with EtOAc. The organic layer was washed with water and brine, dried on Na$_2$SO$_4$ and concentrated. The residue was purified by flash chromatography (heptane/EtOAc, 5%→35%), yielding the product (472 mg, 31%) as a yellow oil.

LCMS (ESI$^+$): m/z 370.2 (M+H)$^+$

Step 3: 1-Benzhydryl-3-(3-methylbenzofuran-2-yl)azetidine

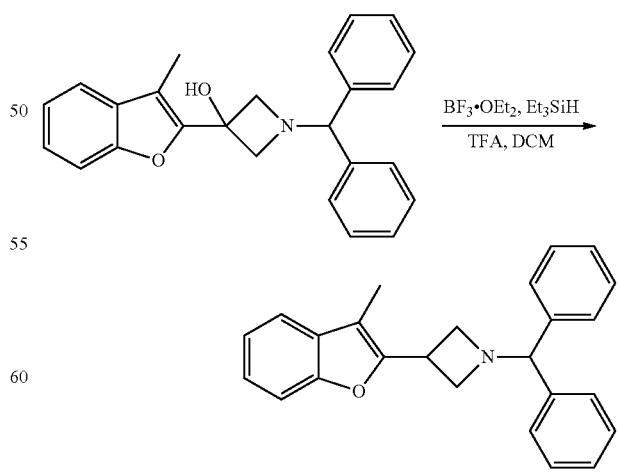

To a cooled (0° C.) solution of 1-benzhydryl-3-(3-methylbenzofuran-2-yl)azetidin-3-ol (406 mg, 1.099 mmol) in dichloromethane (50 mL) were added triethylsilane (1.775 mL, 10.99 mmol) and trifluoroacetic acid (1.630 mL, 22.01 mmol). The reaction mixture was warmed to rt and stirred for 23 h. After 18 h, boron trifluoride etherate (0.6 mL, 4.73 mmol) was added and the reaction was allowed to stir for an additional 5 h. The reaction mixture was partitioned between sat. NaHCO₃ and DCM. The layers were separated, the organic layer was washed with sat. NaHCO₃ and brine, dried on Na₂SO₄ and concentrated. The residue was purified by flash chromatography (heptane/EtOAc, 0%→30%), yielding the title product (244 mg, 63%) as an off-white solid.

LCMS (ESI⁺): m/z 354.2 (M+H)⁺

Step 4: 3-(3-Methylbenzofuran-2-yl)azetidine hydrochloride

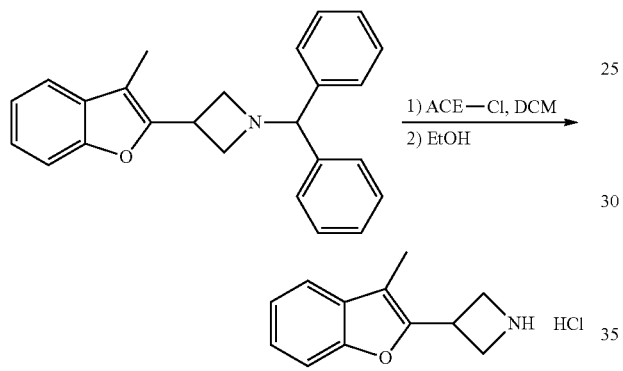

To a cooled (0° C.) solution of 1-benzhydryl-3-(3-methyl-benzofuran-2-yl)azetidine (52.0 mg, 0.147 mmol) in DCM (4 mL) under N₂ was added 1-chloroethyl chloroformate (18.0 µL, 0.167 mmol) and the reaction was stirred at rt under N₂ for 4 h. Next, EtOH was added and the mixture was stirred under nitrogen at 50° C. for 21 h. The mixture was concentrated in vacuo and the residue triturated with Et₂O (3×5 mL), yielding the title product (20.4 mg, 62%) as an off-white solid.

LCMS (ESI⁺): m/z 188.2 (M+H)⁺

Step 5: (E)-6-(3-(3-(3-Methylbenzofuran-2-yl)azetidin-1-yl)-3-oxoprop-1-enyl)-3,4-dihydro-1,8-naphthyridin-2(1H)-one

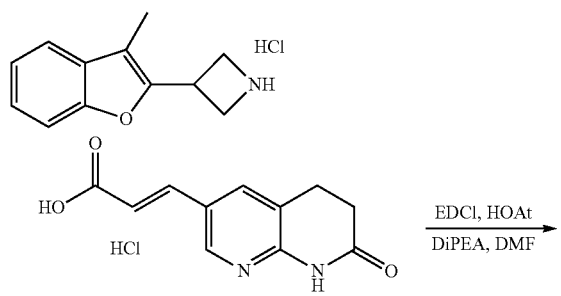

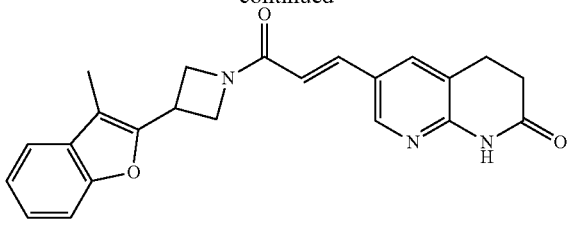

To a solution of 3-(3-methylbenzofuran-2-yl)azetidine hydrochloride (19.9 mg, 0.089 mmol) in DMF (2 mL) were added (E)-3-(7-oxo-5,6,7,8-tetrahydro-1,8-naphthyridin-3-yl)acrylic acid hydrochloride (15.8 mg, 0.062 mmol), EDCI·HCl (19.9 mg, 0.104 mmol), HOAt (14.0 mg, 0.103 mmol) and N,N-diisopropylethylamine (58 µL, 0.339 mmol). The reaction was stirred at rt for 21 h, after which the mixture was partitioned between EtOAc and H₂O. The layers were separated and the aqueous layer extracted with EtOAc. The combined organic layers were washed with brine (3×), dried with Na₂SO₄ and concentrated. The residue was triturated twice with Et₂O and the dried to yield (the title compound (14.0 mg, 58%) as a pale orange solid.

LCMS (APCI⁺): m/z 388 (M+H)⁺

¹H-NMR (CDCl₃, 400 MHz): δ (ppm): 8.82 (br s, 1H), 8.38 (s, 1H), 7.66 (m, 2H), 7.45 (m, 2H), 7.26 (m, 2H, partially overlapping with solvent signal), 6.51 (d, J=15.6 Hz, 1H), 4.62 (m, 2H), 4.45 (m, 2H), 4.12 (m, 1H), 3.01 (t, J=7.6 Hz, 2H), 2.71 (t, J=7.6 Hz, 2H), 2.21 (s, 3H).

Example 68

(E)-1'-Methyl-6-(3-(3-(3-methylbenzofuran-2-yl)azetidin-1-yl)-3-oxoprop-1-enyl)-1H-spiro[[1,8]naphthyridine-3,4'-piperidin]-2(4H)-one (E68)

Step 1: (E)-Ethyl 3-(1'-methyl-2-oxo-2,4-dihydro-1H-spiro[[1,8]naphthyridine-3,4'-piperidine]-6-yl)acrylate

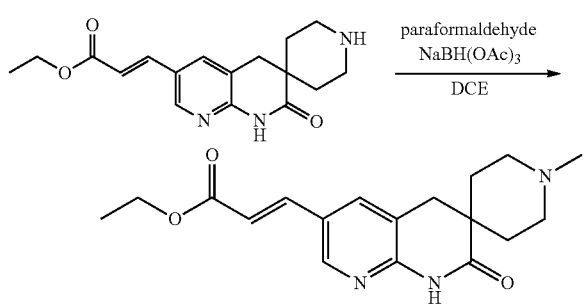

To a suspension of (E)-ethyl 3-(2-oxo-2,4-dihydro-1H-spiro[[1,8]naphthyridine-3,4'-piperidine]-6-yl)acrylate (99.8 mg, 0.316 mmol) in 1,2-dichloroethane (5 mL) were added sodium triacetoxyborohydride (139 mg, 0.656 mmol) and paraformaldehyde (21 mg, 0.699 mmol). The reaction mixture was heated to 70° C. for 5 h. After cooling to room temperature, the reaction mixture was partitioned between DCM (25 mL) and water (25 mL). The aqueous layer was separated and extracted with DCM (2×20 mL). The combined organic phases were washed with saturated NaHCO₃ (3×25 mL) and brine (25 mL), dried over sodium sulfate and concentrated. The crude product was used directly in the next step.

LCMS (ESI⁺): 330.2 (M+H)⁺

Step 2: (E)-3-(1'-Methyl-2-oxo-2,4-dihydro-1H-spiro[[1,8]naphthyridine-3,4'-piperidine]-6-yl)acrylic acid hydrochloride

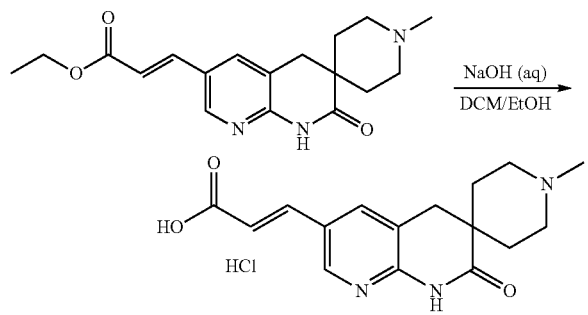

To a solution of (E)-ethyl 3-(1'-methyl-2-oxo-2,4-dihydro-1H-spiro[[1,8]naphthyridine-3,4'-piperidine]-6-yl)acrylate (95 mg, 0.288 mmol) in DCM (2 mL) and EtOH (2 mL) was added 1N aqueous sodium hydroxide (1 mL, 1.000 mmol) and the reaction was stirred at rt overnight, after which TLC (DCM/MeOH, 9:1) showed full conversion. Next, the mixture was concentrated and the residue acidified with 1N HCl (5 mL) and stirred for 1 h. The resulting white solids were isolated by filtration, washed with H$_2$O and Et$_2$O and dried on the filter. The product (47 mg, 48%) was obtained as an off-white solid.

LCMS (ESI$^+$): m/z 302.2 (M+H)$^+$

Step 3: (E)-1'-Methyl-6-(3-(3-(3-methylbenzofuran-2-yl)azetidin-1-yl)-3-oxoprop-1-enyl)-1H-spiro[[1,8]naphthyridine-3,4'-piperidin]-2(4H)-one

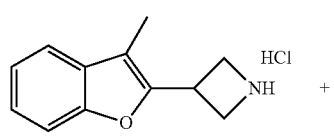 +

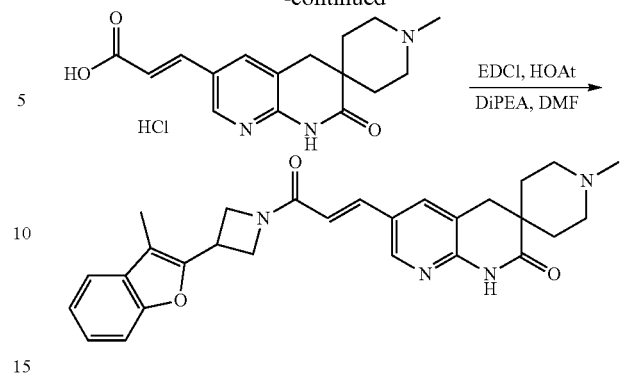

To a solution of 3-(3-methylbenzofuran-2-yl)azetidine hydrochloride (21.7 mg, 0.097 mmol) and (E)-3-(1'-methyl-2-oxo-2,4-dihydro-1H-spiro[[1,8]naphthyridine-3,4'-piperidine]-6-yl)acrylic acid hydrochloride (22.0 mg, 0.065 mmol) in DMF (3 mL) were added EDCI.HCl (18.9 mg, 0.099 mmol), HOAt (13.9 mg, 0.102 mmol) and N,N-diisopropylethylamine (57 µL, 0.333 mmol). The reaction was stirred at rt for 20 h., after which the mixture was partitioned between DCM and H$_2$O. The layers were separated and the aqueous layer extracted with DCM (3×). The combined organic layers were washed with brine (3×), dried over Na$_2$SO$_4$ and concentrated and the residue was purified by flash chromatography (DCM/MeOH, 5%→20%). The product (10.6 mg, 35%) was obtained as a white powder.

LCMS (ESI$^+$): m/z 471.3 (M+H)$^+$ $^1$H-NMR (CDCl$_3$/CD$_3$OD, 400 MHz): δ (ppm): 8.79 (br s, 1H), 8.30 (s, 1H), 7.80 (s, 1H), 7.64 (d, 15.6 Hz, 1H), 7.45 (dd, J=7.7, 12.4 Hz, 2H), 7.24 (m, 2H, overlapping with solvent signal), 6.54 (d, J=15.4 Hz, 1H), 4.67 (m, 2H), 4.47 (m, 2H), 4.12 (m, 1H), 2.97 (s, 2H), 2.80 (s, 3H), 2.31 (m, 2H), 2.21 (s, 3H), 2.05 (m, 2H), 1.95-1.50 (m, 4H, overlapping with H$_2$O-signal).

Example 69

(E)-6-(3-(3-(Benzofuran-2-yl)azetidin-1-yl)-3-oxoprop-1-en-1-yl)-1'-methyl-1H-spiro[[1,8]naphthyridine-3,4'-piperidin]-2(4H)-one (E69)

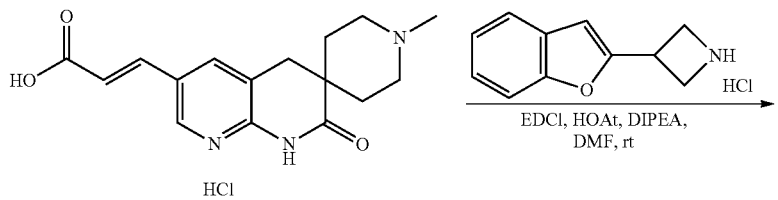

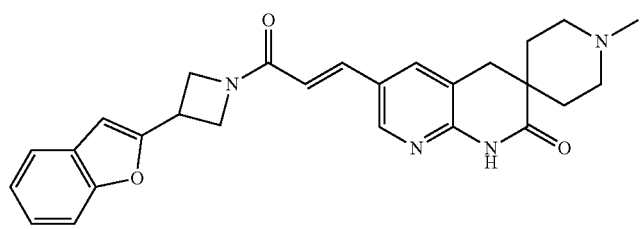

To a solution of 3-(benzofuran-2-yl)azetidine hydrochloride (30 mg, 0.086 mmol) and (E)-3-(1'-methyl-2-oxo-2,4-dihydro-1H-spiro[[1,8]naphthyridine-3,4'-piperidine]-6-yl) acrylic acid hydrochloride (20 mg, 0.059 mmol) in dry DMF (4 mL) were added EDCI.HCl (17.02 mg, 0.089 mmol), HOAt (12.09 mg, 0.089 mmol) and DIPEA (51 µL, 0.296 mmol). The reaction was stirred at room temperature overnight. The mixture was partitioned between dichloromethane and H$_2$O, the layers were separated and the aqueous layer was extracted with dichloromethane (2×5 mL). The combined organic layers were washed with brine (3×3 mL), dried over Na$_2$SO$_4$ and concentrated. The residue was chromatographic purified (silica gel, eluent dichloromethane/7M NH$_3$ in MeOH 98:2 to 95:5). The residue was further purified by preparative LCMS (Waters X-Bridge 50×19 mm 5 µm ODB in combination with Waters X-Bridge guard 10×19 mm 5 µm, at 25 ml/min flow rate; detection of product by mass and UV signal; eluent 10 mM ammonia in milliQ water to 10 mM ammonia in MeCN 5% to 95% gradient), to yield the title compound (2.6 mg, 9.6%).

LCMS (ESI$^+$): no target mass observed.

$^1$H NMR (CDCl$_3$, 400 MHz): δ (ppm): 8.30 (d, J=2.0 Hz, 1H), 7.83 (s, 1H), 7.67-7.62 (m, 2H), 7.53 (d, J=7.6 Hz, 1H), 7.46 (d, J=7.6 Hz, 1H), 7.31-7.21 (m, 2H, overlapping with CDCl$_3$), 6.60 (s, 1H), 6.48 (d, J=15.4 Hz, 1H), 4.68 (t, J=8.3 Hz, 1H), 4.53 (q, J=8.6 Hz, 2H), 4.40 (dd, J=6.0 Hz and 10.3 Hz, 1H), 4.08 (m, 1H), 2.88 (s, 2H), 2.65-2.61 (m, 2H), 2.43-2.39 (m, 2H), 2.32 (s, 3H), 2.07-2.01 (m, 2H), 1.55-1.48 (m, 2H, overlapping with H$_2$O).

Example 70 and 71

6-((E)-3-Oxo-3-(3-((E)-1-(propoxyimino)ethyl)azetidin-1-yl)prop-1-enyl)-3,4-dihydro-1,8-naphthyridin-2(1H)-one (E70) and 6-((E)-3-Oxo-3-(3-((Z)-1-(propoxyimino)ethyl)azetidin-1-yl)prop-1-enyl)-3,4-dihydro-1,8-naphthyridin-2(1H)-one (E71)

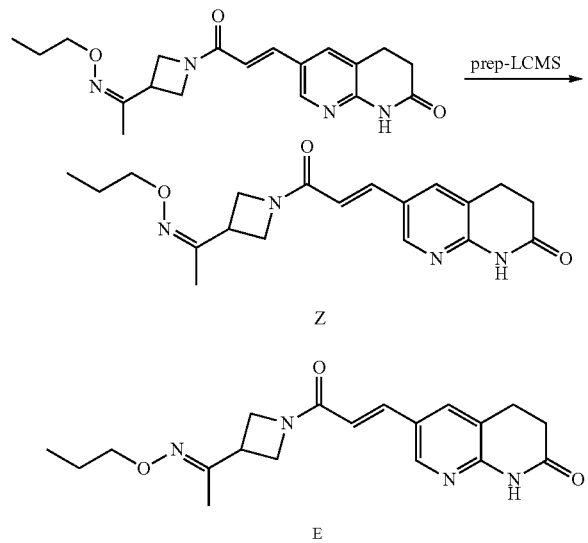

An isomeric mixture (ratio 87:13) of 6-((1E)-3-oxo-3-(3-(1-(propoxyimino)ethyl)azetidin-1-yl)prop-1-enyl)-3,4-dihydro-1,8-naphthyridin-2(1H)-one (162 mg, 0.455 mmol) was separated by preparative LCMS (Waters X-Bridge 50×19 mm 5 µm ODB in combination with Waters Xbridge guard 10×19 mm 5 µm, at 25 ml/min flow rate; detection of product by mass and UV signal; eluent mM ammonia in milliQ water to 10 mM ammonia in MeCN 5% to 95% gradient). The first eluting isomer (6.4 mg, 0.018 mmol) was identified as the Z-isomer (FAB311) and the second eluting isomer (89.0 mg, 0.25 mmol) was identified as the E-isomer (FAB310). This identification was based on a weak NOE-interaction which was observed between the methyl-group (1.91 ppm) and the propyl-tail (4.01 ppm) for the E-isomer, which was absent in the NOESY-spectrum of the Z-isomer.

E-isomer (FAB310): LCMS (ESI$^+$): 357.2 (M+H)$^+$;

$^1$H-NMR (CDCl$_3$, 400 MHz): δ (ppm): 10.38 (s, 1H), 8.42 (s, 1H), 7.62 (m, 2H), 6.45 (d, J=15.7 Hz, 1H), 4.44 (m, 2H), 4.30 (m, 1H), 4.15 (m, 1H), 4.01 (t, J=6.7 Hz, 2H), 3.45 (m, 1H), 3.01 (t, J=7.6 Hz, 2H), 2.71 (t, J=7.6 Hz, 2H), 1.91 (s, 3H), 1.67 (m, 2H), 0.94 (t, J=7.4 Hz, 3H).

Z-isomer (FAB311): LCMS (ESI$^+$): 357.2 (M+H)$^+$;

$^1$H-NMR (CDCl$_3$, 400 MHz): δ (ppm): 9.53 (s, 1H), 8.39 (s, 1H), 7.63 (m, 2H), 6.43 (d, J=15.6 Hz, 1H), 4.54 (m, 1H), 4.36-4.23 (m, 2H), 4.14 (m, 1H), 3.98 (m, 3H), 3.01 (t, J=7.6 Hz, 2H), 2.71 (t, J=7.6 Hz, 2H), 2.02 (s, 3H), 1.64 (m, 2H), 0.93 (t, J=7.5 Hz, 3H).

Assay Data

1. FabI Inhibition

The compounds of the invention are useful inhibitors of bacterial FabI enzyme.

Compound inhibitory activity of FabI enzyme is measured in vitro by the IC$_5$ so determination using a fluorescence based assay.

The protein FabI from *S. aureus* is prepared and purified using standard methods for recombinant protein expression after cloning of the gene in a prokaryotic expression vector.

The biochemical activity of the FabI enzyme is assessed using the following method.

The assay buffer "AB" contained 50 mM ADA (N-(2-acetamido)iminodiacetic acid monosodium salt) pH 6.5, 1 mM dithiothreitol, 0.006% Triton-X100 and 50 mM NaCl.

The following components are added in a white polystyrene Costar plate (Ref 3912) up to a final volume of 55.5 µL: 1.5 µL DMSO or inhibitor dissolved in DMSO and 54 µL of a FabI/NADPH/NADP+ mixture in AB. After 60 min of pre-incubation at room temperature, the reaction is started by addition of 5 µL of trans-2-octenoyl N-acetylcysteamine thioester (t-o-NAC) to a final volume of 60.5 µL. This reaction mixture is then composed of 2 nM FabI, 40 µM NADPH (Sigma, N7505), 10 µM NADP+ (Sigma, N5755), 100 µM t-O-NAC and compound at defined concentration. Fluorescence intensity of NADPH (λex=360 nm, λem=520 nm) is measured immediately after t-O-NAC addition (T0), and approximately 50 min later (T50) by a Fluostar Optima (BMG) so as to achieve ±30% of NADPH conversion. Enzyme activity is calculated by first subtracting T0 signal to T50 and then subtracting background signal (FabI=0). Percentages of inhibition are calculated against untreated samples (Inhibitor=0) and IC$_{50}$ are fitted to a classical Langmuir equilibrium model using XLFIT (IDBS).

TABLE 1

In vitro inhibition of recombinant *S. aureus* FabI enzyme by selected compounds of formula (I)

| Example | FabI Inhibition IC$_{50}$ (µM) |
| --- | --- |
| 1 | 11 |
| 2 | 5.5 |
| 3 | 9.9 |

TABLE 1-continued

In vitro inhibition of recombinant *S. aureus* FabI enzyme by selected compounds of formula (I)

| Example | FabI Inhibition IC$_{50}$ (µM) |
|---------|-------------------------------|
| 4 | 5.3 |
| 5 | 0.25 |
| 6 | 1.0 |
| 7 | 7.1 |
| 8 | 0.041 |
| 9 | 1.3 |
| 10 | 0.12 |
| 11 | 0.15 |
| 12 | 0.013 |
| 13 | 4.1 |
| 14 | 0.34 |
| 15 | 0.025 |
| 16 | 0.93 |
| 17 | 0.05 |
| 18 | 1.8 |
| 19 | 0.17 |
| 20 | 0.057 |
| 21 | 0.87 |
| 22 | 8.6 |
| 23 | 1.8 |
| 24 | 0.26 |
| 25 | 0.060 |
| 26 | 0.078 |
| 27 | 0.55 |
| 28 | 0.081 |

2. Antibacterial Activity

The compounds of the invention are useful antibacterial agents having a selective spectrum of activity in vitro against bacterial strains relying on FabI and related targets. Notably the compounds of the invention show activity against *Staphylococcus aureus* including multiresistant strains. The activity is presented as Minimum Inhibitory Concentration (MIC) expressed in µg/ml and was determined using broth microdilution or Agar dilution methods.

Strains

Antibacterial activity was determined on strains from Mutabilis internal collection. A description of the strains used in this study is provided in Table 2:

MIC Determination Using Broth Microdilution Method

This protocol is compliant with Clinical Laboratory Standards Institute (CLSI) methodology as described in M7-A7 document of the CLSI. The compound to be tested is diluted according to a geometric series of reason 2 in pure DMSO. Dilutions are transferred in sterile polystyrene microplates, followed by mid-log phase bacteria in cation-adjusted Muller-Hinton broth (ca-MHB, Fluka, Reference 90922) with a final inoculum of 5×10$^5$ cfu/ml. Microplates are incubated overnight at 35° C. MIC is defined as the lowest concentration of antimicrobial agent that completely prevents visible bacterial growth. All manipulations, but compound handling (in pure DMSO), are performed under sterile conditions. The final concentration of DMSO in the plates is 2%.

TABLE 3

Representative Examples of MIC (µg/ml) (Broth microdilution) by selected compounds of formula (I):

| Example | *S. aureus* CIP 54.146 |
|---------|------------------------|
| 8 | 4 |
| 10 | 4 |
| 12 | 4 |
| 15 | 4 |

MIC Determination Using Agar Dilution Method

This protocol is compliant with Clinical Laboratory Standards Institute (CLSI) methodology as described in M7-A7 document of the CLSI. The compound to be tested is incorporated into Mueller-Hinton Agar medium (Fluka, Reference 70191) at one concentration per plate according to a geometric series of reason 2. Plates are inoculated with mid-log phase bacteria (inoculum=1×10$^4$ cfu/spot) and incubated overnight at 35° C. MIC is defined as the lowest concentration of antimicrobial agent that completely inhibits bacterial growth. All manipulations, but compound handling (in pure DMSO), are performed under sterile conditions. The final DMSO concentration of DMSO in the plates is 2%. Vancomycin is used as reference.

TABLE 2

Description of Strains Used in Antibacterial Study

| Genus | Species | Strain ID | Phenotype | Genotype | Provider |
|-------|---------|-----------|-----------|----------|----------|
| *Staphylococcus* | *aureus* | CIP 54.146 | MSSA | | CRBIP |
| *Staphylococcus* | *aureus* | NRS22 | MRSA GISA, EryR, ClinR, SxtR, GmR, LevR | mecA+, USA600 | NARSA |
| *Staphylococcus* | *aureus* | NRS100 | MRSA TetR | mecA+ | NARSA |
| *Staphylococcus* | *aureus* | NRS119 | MRSA LinR, GmR, SxtR, CipR | mecA+, G2576T | NARSA |
| *Staphylococcus* | *aureus* | NRS120 | MRSA LinR, GmR, SxtR, CipR | mecA+, G2576T | NARSA |
| *Staphylococcus* | *aureus* | NRS121 | MRSA LinR, CipR | mecA+, G2576T | NARSA |
| *Staphylococcus* | *aureus* | NRS123 | MRSA TetR | mecA+, USA400 | NARSA |
| *Staphylococcus* | *aureus* | NRS127 | MRSA LinR, CipR, EryR | mecA+ | NARSA |
| *Staphylococcus* | *aureus* | NRS128 | MSSA PenR, EryR, ClinR | mecA− | NARSA |
| *Staphylococcus* | *aureus* | NRS130 | MSSA EryR | mecA− | NARSA |
| *Staphylococcus* | *aureus* | NRS192 | MRSA | mecA+ | NARSA |
| *Staphylococcus* | *aureus* | NRS262 | MSSA PenR | mecA− | NARSA |
| *Staphylococcus* | *aureus* | NRS269 | MRSA TigR, EryR, ClinR, CipR, GenR | mecA+ | NARSA |
| *Staphylococcus* | *aureus* | NRS382 | MRSA EryR, ClinR, CipR | mecA+, USA100 | NARSA |
| *Staphylococcus* | *aureus* | NRS383 | MRSA EryR, ClinR, TetR, SxtR, LevR, GmR | mecA+, USA200 | NARSA |
| *Staphylococcus* | *aureus* | NRS384 | MRSA EryR, TetR | mecA+, USA300 | NARSA |
| *Staphylococcus* | *aureus* | NRS385 | MRSA EryR, ClinR, TetR, SxtR, LevR, GmR | mecA+, USA500 | NARSA |
| *Staphylococcus* | *aureus* | NRS386 | MRSA EryR | mecA+, USA700 | NARSA |
| *Staphylococcus* | *aureus* | NRS482 | MRSA CipR, EryR, OxaR | USA300 | NARSA |
| *Staphylococcus* | *aureus* | NRS483 | MRSA | mecA+, USA1000 | NARSA |
| *Staphylococcus* | *aureus* | NRS484 | MRSA | mecA+, USA1100 | NARSA |

(NARSA = Network on Antimicrobial Resistance in *Staphylococcus aureus*, CRBIP = Centre de Ressources Biologiques de l'Institut Pasteur)

TABLE 4

Representative examples of MIC (μg/ml) (Agar dilution)
by selected compounds (Examples 12 and 15) of formula (I):

| Strains | Vancomycin | Example 12 | Example 15 |
|---|---|---|---|
| NRS22 | 4 | 4 | 4 |
| NRS100 | 1 | 2 | 1 |
| NRS119 | 1 | 2 | 2 |
| NRS120 | 1 | 2 | 2 |
| NRS121 | 1 | 2 | 2 |
| NRS123 | 1 | 2 | 2 |
| NRS127 | 1 | 2 | 2 |
| NRS128 | 1 | 1 | 1 |
| NRS130 | 1 | 2 | 2 |
| NRS192 | 1 | 4 | 4 |
| NRS262 | 1 | 4 | 4 |
| NRS269 | 2 | 4 | 4 |
| NRS382 | 1 | 4 | 4 |
| NRS383 | 0.5 | 4 | 4 |
| NRS384 | 1 | 4 | 4 |
| NRS385 | 1 | 2 | 4 |
| NRS386 | 1 | 4 | 4 |
| NRS482 | 1 | 4 | 4 |
| NRS483 | 1 | 4 | 4 |
| In NRS484 | 1 | 4 | 4 |

MIC Determination Using Susceptibility Method

Minimum inhibitory concentrations (MICs) were determined by broth microdilution according to CLSI guidelines (CLSI, M100-20[1], M7-A8[2], M27-A3[3]). The compounds were tested in the range from 012-128 μg/ml. Colonies were taken directly from a second-pass culture plate and prepared to a suspension equivalent to the 0.5 McFarland standard using normal saline. Inoculation of the MIC plates took place within 15 minutes after adjustment of the inoculum suspension turbidity. The panels were incubated at 35° C. for 16 to 20 hours before reading the MIC endpoints. The compounds of Examples 12, 29, 59, 63 and 66-71 were dissolved in DMSO to make the initial solutions of 5120 μg/ml. These solutions were diluted 1:10 in sterile water to a stock solution of 512 μg/ml. The stock solutions were further diluted into the appropriate broth medium for the sequential dilutions used in the broth microdilution panels. S. pneumoniae was tested in Mueller Hinton (MH) broth with 3% lysed horse blood and C. albicans was tested in RPMI-1640 medium. All other organisms were tested in MH broth.

The most active compounds were found to be Examples 59 and 67 which exhibited MICs of 0.06 μg/ml against both MRSA and MSSA strains.

3. In vivo Antibacterial Activity of Examples 12 and 15

An experimental model of infection by S. aureus was used to assess the antibacterial activity of FabI inhibitors.

Briefly in vivo studies were performed using groups of 5 week-old neutropenic female Swiss mice (five mice per group for each condition).

The virulent methicillin susceptible Staphylococcus aureus strain ATCC 29213 was grown to exponential phase in Tryptic soy (TS) broth culture. The bacterial culture is diluted to obtain a bacterial suspension of 1-3 $10^5$ cfu/ml, washed in physiological serum and then inoculated to mice (100 μl per mouse) by intra-muscle injection. The inoculums count was verified by plating 10-fold dilutions of the suspension on TS agar plates immediately after inoculation.

The compound of Example 12 was dissolved and diluted in a formulation containing 80% Poly-Ethylen Glycol (PEG) 400 and an appropriate volume of the solution (corresponding to a dose level of 100 mg/kg of body weight) was administered orally to each mouse, 1.5 h after the bacterial infection. The negative control group received the 80% PEG400 solution alone and Linezolid at 100 mg/kg was used as the positive control.

The compound of Example 15 was dissolved and diluted in a formulation containing 10% dimethyl sulfoxide (DMSO) and 20% hydroxy-propyl beta cyclodextrine (HPCD) and an appropriate volume of the solution (corresponding to a dose level of 50 mg/kg of body weight) was administered subcutaneously to each mouse, 1.5 h after the bacterial infection. The negative control group received the 10% DMSO and 20% HPCD solution alone and Linezolid at 50 mg/kg was used as the positive control.

Mice health and clinical signs were recorded during 20 h. At the end of this period mice were euthanized, thigh muscle recovered and homogenized and bacterial count was determined by 10 fold dilution and plating method on TS agar plates.

All animal experiments were carried out in accordance with institutional guidelines. Compound activity is measure by its effect at a given dose to reduce the bacterial burden in the thigh of infected mice.

Figure 2:
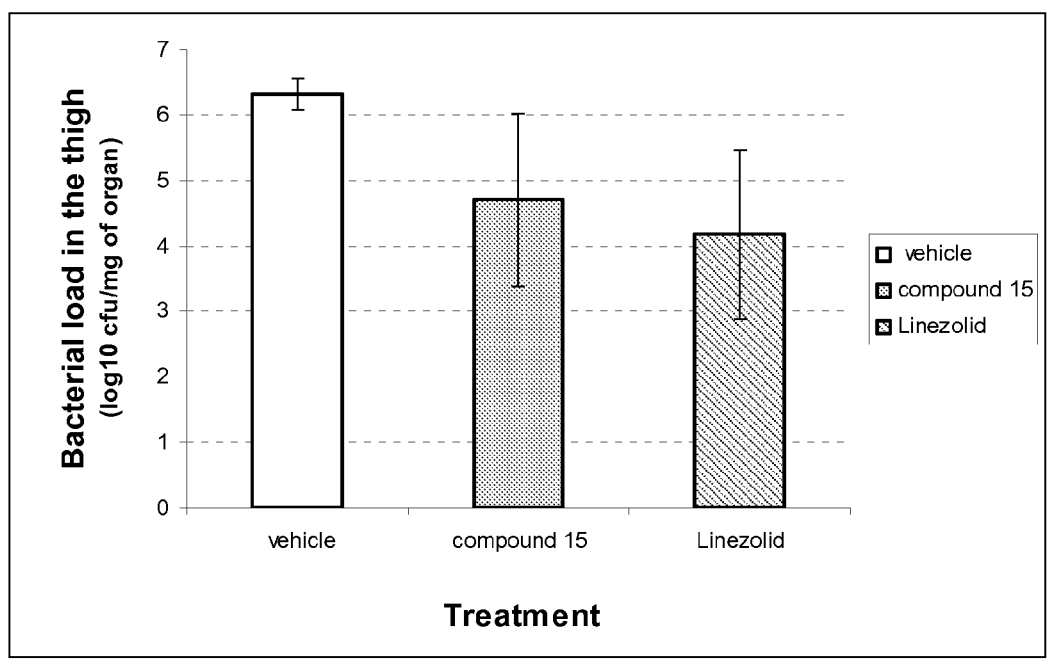
FIG. 2 relates to the in vivo antibacterial activity of Example 15 at 50 mg/kg.

As shown in FIG. 1 with the compound of Example 12 at 100 mg/kg and FIG. 2 with the compound of Example 15 at 50

TABLE 5

Representative Examples of MIC (μg/ml) (Broth microdilution)
of compounds of Examples 12, 29, 59, 63 and 66-71:

| No | MSSA (IHMA #555189) | MRSA (IHMA #510059) | S. aureus ATCC 29213 | E. coli (ATCC 25922) | E. faecalis (ATCC 29212) | S. pneumoniae (ATCC 49619) | C. albicans (ATCC 90028) |
|---|---|---|---|---|---|---|---|
| 12 | 1 | 1 | 1 | >128 | >128 | >128 | >128 |
| 29 | 0.5 | 0.5 | 0.5 | >128 | >128 | >128 | >128 |
| 59 | 0.06 | 0.06 | 0.06 | 64 | 64 | 32 | 128 |
| 63 | 1 | 1 | 1 | 64 | 64 | 64 | 128 |
| 66 | 0.25 | 0.5 | 0.25 | 64 | 64 | 64 | 64 |
| 67 | 0.06 | 0.06 | 0.06 | >128 | >128 | 128 | >128 |
| 68 | 0.5 | 0.5 | 0.5 | >128 | >128 | 128 | >128 |
| 69 | 1 | 1 | 1 | >128 | >128 | 128 | >128 |
| 70 | 0.5 | 0.5 | 0.5 | >128 | >128 | >128 | >128 |
| 71 | 8 | 4 | 4 | >128 | >128 | 128 | >128 | mg/kg, the compounds of the invention, are able to protect mice against thigh dissemination.

4. HSA Binding Analysis of Examples 12, 29, 59, 63 and 67-71 Using a Chiral HSA Column Test System The test system used in this analysis was an HSA chiral column.

Reagents and Chemicals

Potassium phosphate monobasic $KH_2PO_4$ and potassium phosphate dibasic trihydrate $K_2HPO_4, 3H_2O$ were obtained from Sigma-Aldrich. DMSO, 2-propanol and sodium azide were purchased from Sigma-Aldrich. Water was MilliQ grade obtained from Millipore system Milli-Q Plus (Waters).

Preparation of Reagents 20 mM $K_2HPO_4$: 3.484 g in 1 L of water
20 mM $KH_2PO_4$: 2.722 g in 1 L of water
20 mM Phosphate buffer pH 7.0: 58.7% of 20 mM $K_2HPO_4$+41.3% of 20 mM
$KH_2PO_4$ (the pH is adjusted if necessary).

Preparation of Stock Solutions, Calibration and Quality Control Samples

Solutions of Examples 12, 29, 59, 63 and 67-71 were prepared in potassium phosphate buffer, pH 7.0 to concentrations of 1 mM.

Equipment

HPLC system Alliance 2695 (Waters)
PDA UV detector 996 (Waters)
Column Chiral HSA 50×3.0 mm, 5 µm (Chromtec)
AT261 scale (Mettler-Toledo)
pH-meter easy seven (Mettler-Toledo)
Pipetman (Eppendorf)
Vortex (Fisher-Bioblock)
Ultrasound bath
4 mL glass vials (Dutscher)
2 mL glass vials for chromatography (Waters)

Liquid Chromatography Parameters

Liquid Chromatography was used in accordance with the parameters shown in Table 6:

TABLE 6

Chromatographic parameters

| | |
|---|---|
| HPLC system | Alliance 2695 (Waters) |
| Column | Chiral HSA 50 × 3.0 mm, 5 µm (Chromtec) |
| Flow rate | 0.5 mL/min |
| Column temperature | 37° C. |
| Auto sampler temperature | Room Temperature |
| Mobile Phase | 94% 20 mM Potassium phosphate buffer pH 7.0 |
| | 6% 2-propanol |
| Detection | For each unknown compound the optimal wavelength ($\lambda_{max}$) was determined and subsequent detections were performed at the specific $\lambda_{max}$ of the compound |
| Injected volume | 10 µL |
| Monitoring and processing data softwares | Empower2 (Waters) |

Percentage Binding Calculation

The relationship between the retention time (Tr) and percentage of albumin binding (AB %) depended on the dead time (T0) and the capacity factor (k'):

$$AB\% = [k'/(k'+1)]*100$$

where k'=(Tr−T0)/T0

HSA binding was classified as follows:

AB<75%: Low binding
75%≤AB<90%: Moderate binding
AB≥90%: High binding

Results

The results of the HSA binding analysis are shown in Table 7 wherein it can be seen that five compounds had a low affinity (E12, E29, E63, E70 and E71), three compounds had a moderate affinity (E59, E67 and E69) and one compound (E68) had a high affinity in vitro to human albumin.

TABLE 7

HSA binding data for Examples 12, 29, 59, 63 and 67-71

| Example Number | T0 (min) | Tr (min) | k' | HSA Binding (%) | Conclusion |
|---|---|---|---|---|---|
| E12 | 0.772 | 1.410 | 0.826 | 45.2 | Low binding |
| E29 | 0.771 | 1.743 | 1.259 | 55.7 | Low binding |
| E59 | 0.771 | 4.378 | 4.678 | 82.4 | Moderate binding |
| E63 | 0.769 | 1.760 | 1.288 | 56.3 | Low binding |
| E67 | 0.772 | 7.229 | 8.360 | 89.3 | Moderate binding |
| E68 | 0.771 | 9.414 | 11.216 | 91.8 | High binding |
| E69 | 0.771 | 6.734 | 7.730 | 88.5 | Moderate binding |
| E70 | 0.771 | 1.219 | 0.580 | 36.7 | Low binding |
| E71 | 0.772 | 1.084 | 0.404 | 28.8 | Low binding |

CLSI Guideline References

1. M100-S20

Clinical and Laboratory Standards Institute, 2010. *Performance Standards for Antimicrobial Susceptibility Testing; Twentieth Informational Supplement*. CLSI document M100-S20. Clinical and Laboratory Standards Institute (CLSI), Wayne, Ps. 19087-1898 USA.

2. M7-A8

Clinical and Laboratory Standards Institute (CLSI), 2009. *Methods for Dilution Antimicrobial Test for Bacteria That Grow Aerobically; Approved Standard—Eighth Edition*. CLSI document M07-A8 [ISBN 1-56238-689-1]. CLSI, 940 West Valley Road, Suite 1400, Wayne, Pa. 19087 USA.

3. M27-A3

Clinical and Laboratory Standards Institute, 2009. *Reference method for broth dilution antifungal broth susceptibility testing of yeasts—Approved Standard Third Edition*. CLSI document M27-A3. Clinical and Laboratory Standards Institute (CLSI), Wayne, Pa. 19087-1898 USA.

The invention embraces all combinations of preferred and more preferred groups and suitable and more suitable groups and embodiments of groups recited above.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

We claim:

1. A compound which is a compound of formula (I):

[Structure of formula (I): an N-containing ring with X and W, substituents R1, R2 on carbon, and an acryloyl group C(=O)-CH=CH-R3 on N]

wherein:
- W and X independently represent a bond or a —$(CH_2)_{1-4}$— group, such that W and X together contain 1-5 carbon atoms;
- R1 represents an H, F, CN, ($C_1$-$C_6$) alkyl, ($C_2$-$C_6$) alkenyl, ($C_2$-$C_6$) alkynyl, $CO_2R_d$, $COR_d$, $CONR_aR_b$, $OCOR_d$, $OR_d$, $NR_aR_b$, $ON=CR_dR_e$, $NR_cCOR_d$, $NR_cCOOR_d$, $OCONR_aR_b$, $NR_cCONR_aR_b$, $NR_cSO_2R_a$, $S(O)_nR_a$, $SO_2NR_aR_b$, —$C(R_a)=N$—O—$R_f$, Y—Ar or a Z-Het group, wherein Ar represents phenyl or naphthyl, Het represents a 4-10 membered monocyclic or bicyclic saturated or unsaturated heterocycle containing 1-5 heteroatoms selected from N, O and S and Y and Z independently represent a bond or a linker selected from O, S, CO, ($C_1$-$C_6$) alkylene, —O—($C_1$-$C_6$) alkylene, —CO—($C_1$-$C_6$) alkylene or —ON=$CR_d$—($C_1$-$C_6$) alkylene, wherein said R1 group may be optionally substituted by one or more R4 groups;
- R2 represents an H, F, CN, ($C_1$-$C_6$) alkyl, ($C_2$-$C_6$) alkenyl, ($C_2$-$C_6$) alkynyl, $CO_2R_d$, $COR_d$, $CONR_aR_b$, $OCOR_d$, $OR_d$, $NR_aR_b$, $ON=CR_dR_e$, $NR_cCOR_d$, $NR_cCOOR_d$, $OCONR_aR_b$, $NR_cCONR_aR_b$, $NR_cSO_2R_a$, $S(O)_nR_a$ or $SO_2NR_aR_b$ group;
- $R_a$, $R_b$ and $R_c$ independently represent H, ($C_1$-$C_6$) alkyl, ($C_2$-$C_6$) alkenyl, ($C_2$-$C_6$) alkynyl, or an $NR_aR_b$ group may optionally form a 3- to 7-membered nitrogen containing saturated heterocycle optionally containing 1 to 3 additional heteroatoms selected from N, O or S wherein said heterocycle may be optionally substituted by one or more ($C_1$-$C_6$) alkyl groups;
- $R_d$ and $R_e$ independently represent H, ($C_1$-$C_6$) alkyl, ($C_2$-$C_6$) alkenyl, ($C_2$-$C_6$) alkynyl, halo($C_1$-$C_6$) alkyl, halo($C_1$-$C_6$) alkyl-O—($C_1$-$C_6$) alkyl- or ($C_1$-$C_6$) alkyl-O—($C_1$-$C_6$) alkyl-;
- $R_f$ represents ($C_1$-$C_6$) alkyl, ($C_2$-$C_6$) alkenyl, ($C_2$-$C_6$) alkynyl, halo($C_1$-$C_6$) alkyl or —($C_1$-$C_6$) alkyl-Ar, wherein Ar represents phenyl or naphthyl; —R4 represents halogen, CN, ($C_1$-$C_6$) alkyl, ($C_2$-$C_6$) alkenyl, ($C_2$-$C_6$) alkynyl, $CO_2R_d$, $COR_d$, $CONR_aR_b$, $OCOR_d$, $OR_d$, $NR_aR_b$, $ON=CR_dR_e$, $NR_cCOR_d$, $NR_cCOOR_d$, $OCONR_aR_b$, $NR_cCONR_aR_b$, $NR_cSO_2R_a$, $S(O)_nR_a$, or $SO_2NR_aR_b$;
- n represents an integer selected from 0 to 2;

R3 represents a heterocycle of formula (a):

[Structure (a): a methyl-substituted 3,4-dihydro-1,8-naphthyridin-2(1H)-one]

wherein said R3 group may be optionally substituted by one or more R5 groups;
R5 is selected from the group consisting of F, $CO_2R_d$, $COR_d$, $CONR_aR_b$, $OR_d$, =O, $NR_aR_b$, $NR_aCOR_d$ or ($C_1$-$C_6$) alkyl optionally substituted by F, $CO_2R_d$, $CONR_aR_b$, $OR_d$, $NR_aR_b$, $NR_aCOR_d$ or Het optionally substituted by one or more ($C_1$-$C_6$) alkyl groups;
or a pharmaceutically acceptable salt or solvate thereof.

2. A compound as defined in claim 1, wherein W and X both represent $CH_2$, one of W and X represents $CH_2$ and the other represents $CH_2CH_2$,
one of W and X represents a bond and the other represents $CH_2CH_2CH_2$,
W and X both represent $CH_2CH_2$, one of W and X represents $CH_2$ and the other represents $CH_2CH_2$, or one of W and X represents a bond and the other represents $CH_2CH_2CH_2CH_2$.

3. A compound as defined in claim 2, wherein W and X both represent $CH_2$.

4. A compound as defined in claim 1, wherein R1 represents an H, F, ($C_1$-$C_6$) alkyl, ($C_2$-$C_6$) alkenyl, $OR_d$, $S(O)_nR_a$, —$C(R_a)=N$—O—$R_f$, Y—Ar or Z-Het group each of which may be optionally substituted by one or more R4 groups.

5. A compound as defined in claim 4, wherein R1 represents $OR_d$, Z-Het or —$C(R_a)=N$—O—$R_f$.

6. A compound as defined claim 1, wherein R2 represents an H or $OR_d$ group.

7. A compound as defined in claim 1, wherein R4 represents halogen, ($C_1$-$C_6$) alkyl, ($C_2$-$C_6$) alkenyl or ($C_2$-$C_6$) alkynyl.

8. A compound as defined in claim 1, wherein R3 represents a heterocycle of formula (a) optionally substituted by one or more R5 groups selected from the group consisting of $CO_2R_d$, $CONR_aR_b$ and ($C_1$-$C_6$) alkyl optionally substituted by $OR_d$.

9. A compound selected from the group consisting of
6-[(1E)-3-Azetidin-1-yl-3-oxoprop-1-en-1-yl]-3,4-dihydro-1,8-naphthyridin-2(1H)-one (E1);
6-[(1E)-3-oxo-3-pyrrolidin-1-ylprop-1-en-1-yl]-3,4-dihydro-1,8-naphthyridin-2(1H)-one (E2);
6-[(1E)-3-oxo-3-piperidin-1-ylprop-1-en-1-yl]-3,4-dihydro-1,8-naphthyridin-2(1H)-one (E3);
6-{(1E)-3-[4-(2-Hydroxyethyl)piperidin-1-yl]-3-oxoprop-1-en-1-yl}-3,4-dihydro-1,8-naphthyridin-2(1H)-one (E4);
6-[(1E)-3-{[4-(4-Fluorophenoxy)methyl]piperidin-1-yl}-3-oxoprop-1-en-1-yl]-3,4-dihydro-1,8-naphthyridin-2(1H)-one (E5);
6-[(1E)-3-oxo-3-(3-phenoxyazetidin-1-yl)prop-1-en-1-yl]-3,4-dihydro-1,8-naphthyridin-2(1H)-one (E6);
6-[(1E)-3-oxo-3-(2-phenylpyrrolidin-1-yl)prop-1-en-1-yl]-3,4-dihydro-1,8-naphthyridin-2(1H)-one (E7);
6-[(1E)-3-oxo-3-(4-propylpiperidin-1-yl)prop-1-en-1-yl]-3,4-dihydro-1,8-naphthyridin-2(1H)-one (E8);
6-[(1E)-3-{[3-(4-Fluorophenoxy)methyl]piperidin-1-yl}-3-oxoprop-1-en-1-yl]-3,4-dihydro-1,8-naphthyridin-2(1H)-one (E9);
6-[(1E)-3-oxo-3-(3-phenoxypyrrolidin-1-yl)prop-1-en-1-yl]-3,4-dihydro-1,8-naphthyridin-2(1H)-one (E10);

6-{(1E)-3-[3-(5-Methyl-1,2,4-oxadiazol-3-yl)azetidin-1-yl]-3-oxoprop-1-en-1-yl}-3,4-dihydro-1,8-naphthyridin-2(1H)-one (E11);
6-{(1E)-3-oxo-3-[3-(2-thienylmethoxy)azetidin-1-yl]prop-1-en-1-yl}-3,4-dihydro-1,8-naphthyridin-2(1H)-one (E12);
6-{(1E)-3-[2-(5-Methyl-1,2,4-oxadiazol-3-yl)piperidin-1-yl]-3-oxoprop-1-en-1-yl}-3,4-dihydro-1,8-naphthyridin-2(1H)-one (E13);
6-{(1E)-3-[4-Hydroxy-4-phenylpiperidin-1-yl]-3-oxoprop-1-en-1-yl}-3,4-dihydro-1,8-naphthyridin-2(1H)-one (E14);
6-{(1E)-3-oxo-3-[3-(pentyloxy)azetidin-1-yl]prop-1-en-1-yl}-3,4-dihydro-1,8-naphthyridin-2(1H)-one (E15);
6-{(1E)-3-oxo-3-[3-(pyridin-3-yloxy)pyrrolidin-1-yl]prop-1-en-1-yl}-3,4-dihydro-1,8-naphthyridin-2(1H)-one (E16);
6-{(1E)-3-[3-(Benzyloxy)azetidin-1-yl]-3-oxoprop-1-en-1-yl}-3,4-dihydro-1,8-naphthyridin-2(1H)-one (E17);
6-{(1E)-3-[2-(1,3-Benzoxazol-2-yl)piperidin-1-yl]-3-oxoprop-1-en-1-yl}-3,4-dihydro-1,8-naphthyridin-2(1H)-one (E18);
6-[(1E)-3-{3-[(2-Methylprop-2-en-1-yl)oxy]azetidin-1-yl}-3-oxoprop-1-en-1-yl]-3,4-dihydro-1,8-naphthyridin-2(1H)-one (E19);
6-{(1E)-3-oxo-3-[3-(1,3-thiazol-2-ylmethoxy)azetidin-1-yl]prop-1-en-1-yl}-3,4-dihydro-1,8-naphthyridin-2(1H)-one (E20);
6-{(1E)-3-[3-({[(1E)-1-Methyl-2-pyrimidin-2-ylethylidene]amino}oxy)azetidin-1-yl]-3-oxoprop-1-en-1-yl}-3,4-dihydro-1,8-naphthyridin-2(1H)-one (E21);
6-{(1E)-3-[3-(Pentylsulfonyl)azetidin-1-yl]-3-oxoprop-1-en-1-yl}-3,4-dihydro-1,8-naphthyridin-2(1H)-one (E22);
Methyl 6-[(1E)-3-{4-[(4-fluorophenoxy)methyl]piperidin-1-yl}-3-oxoprop-1-en-1-yl]-2-oxo-1,2,3,4-tetrahydro-1,8-naphthyridine-3-carboxylate (E25);
6-[(1E)-3-{4-[(4-Fluorophenoxy)methyl]piperidin-1-yl}-3-oxoprop-1-en-1-yl]-2-oxo-1,2,3,4-tetrahydro-1,8-naphthyridine-3-carboxamide (E26);
3-(Hydroxymethyl)-6-[(1E)-3-{4-[(4-fluorophenoxy)methyl]piperidin-1-yl}-3-oxoprop-1-en-1-yl]-3,4-dihydro-1,8-naphthyridin-2(1H)-one (E28);
(E)-6-(3-oxo-3-(3-(2-(thiophen-2-yl)ethoxy)azetidin-1-yl)prop-1-enyl)-3,4-dihydro-1,8-naphthyridin-2(1H)-one (E29);
(E)-6-(3-oxo-3-(3-(3-(thiophen-2-yl)propoxy)azetidin-1-yl)prop-1-enyl)-3,4-dihydro-1,8-naphthyridin-2(1H)-one (E30);
(E)-6-(3-(3-((3-Methylthiophen-2-yl)methoxy)azetidin-1-yl)-3-oxoprop-1-enyl)-3,4-dihydro-1,8-naphthyridin-2(1H)-one (E31);
6-[3-(3-(4-Methyl-thiophen-2-ylmethoxy)-azetidin-1-yl)-3-oxo-propenyl]-3,4-dihydro-1H-[1,8]naphthyridin-2-one (E32);
(E)-6-(3-(3-((5-Methylthiophen-2-yl)methoxy)azetidin-1-yl)-3-oxoprop-1-enyl)-3,4-dihydro-1,8-naphthyridin-2(1H)-one (E33);
(E)-6-[3-(2-Methoxyethoxy)azetidin-1-yl)-3-oxoprop-1-enyl]-3,4-dihydro-1,8-naphthyridin-2(1H)-one (E34);
(E)-6-[3-(3-Methoxypropoxy)azetidin-1-yl)-3-oxoprop-1-enyl]-3,4-dihydro-1,8-naphthyridin-2(1H)-one (E35);
(E)-6-[3-(3-Butoxyazetidin-1-yl)-3-oxoprop-1-enyl]-3,4-dihydro-1,8-naphthyridin-2(1H)-one (E36);
(E)-6-[3-(3-Isobutoxyazetidin-1-yl)-3-oxoprop-1-enyl]-3,4-dihydro-1,8-naphthyridin-2(1H)-one (E37);
(E)-6-(3-(3-((1-Methyl-1H-pyrazol-3-yl)methoxy)azetidin-1-yl)-3-oxoprop-1-enyl)-3,4-dihydro-1,8-naphthyridin-2(1H)-one (E38);
(E)-6-(3-oxo-3-(3-(thiazol-5-ylmethoxy)azetidin-1-yl)prop-1-enyl)-3,4-dihydro-1,8-naphthyridin-2(1H)-one (E39);
(E)-6-(3-(3-(Furan-2-ylmethoxy)azetidin-1-yl)-3-oxoprop-1-enyl)-3,4-dihydro-1,8-naphthyridin-2(1H)-one (E40);
(E)-6-(3-oxo-3-(3-(3,3,3-trifluoropropoxy)azetidin-1-yl)prop-1-enyl)-3,4-dihydro-1,8-naphthyridin-2(1H)-one (E47);
(E)-6-(3-oxo-3-(3-(4,4,4-trifluorobutoxy)azetidin-1-yl)prop-1-enyl)-3,4-dihydro-1,8-naphthyridin-2(1H)-one (E48);
6-((E)-3-(3-((E)-But-2-enyloxy)azetidin-1-yl)-3-oxoprop-1-enyl)-3,4-dihydro-1,8-naphthyridin-2(1H)-one (E49);
6-((E)-3-(3-((Z)-But-2-enyloxy)azetidin-1-yl)-3-oxoprop-1-enyl)-3,4-dihydro-1,8-naphthyridin-2(1H)-one (E50);
6-((E)-3-(3-((E)-2-Methylbut-2-enyloxy)azetidin-1-yl)-3-oxoprop-1-enyl)-3,4-dihydro-1,8-naphthyridin-2(1H)-one (E51);
(E)-6-(3-(3-(Benzo[b]thiophen-2-ylmethoxy)azetidin-1-yl)-3-oxoprop-1-enyl)-3,4-dihydro-1,8-naphthyridin-2(1H)-one (E52);
(E)-6-(3-(3-((4-Bromothiophen-2-yl)methoxy)azetidin-1-yl)-3-oxoprop-1-enyl)-3,4-dihydro-1,8-naphthyridin-2(1H)-one (E53);
(E)-6-(3-(3-((4-Chlorothiophen-2-yl)methoxy)azetidin-1-yl)-3-oxoprop-1-enyl)-3,4-dihydro-1,8-naphthyridin-2(1H)-one (E54);
6-((E)-3-oxo-3-(3-((Z)-1-(propoxyimino)ethyl)azetidin-1-yl)prop-1-enyl)-3,4-dihydro-1,8-naphthyridin-2(1H)-one (E55);
6-((E)-3-Oxo-3-(3-((Z)-1-(2,2,2-trifluoroethoxyimino)ethyl)azetidin-1-yl)prop-1-enyl)-3,4-dihydro-1,8-naphthyridin-2(1H)-one (E56);
6-((E)-3-(3-((Z)-1-(Ethoxyimino)ethyl)azetidin-1-yl)-3-oxoprop-1-enyl)-3,4-dihydro-1,8-naphthyridin-2(1H)-one (E57);
(E)-6-(3-(3-(Benzofuran-3-yl)azetidin-1-yl)-3-oxoprop-1-enyl)-3,4-dihydro-1,8-naphthyridin-2(1H)-one (E58);
(E)-6-(3-(3-(Benzofuran-2-yl)azetidin-1-yl)-3-oxoprop-1-enyl)-3,4-dihydro-1,8-naphthyridin-2(1H)-one (E59);
(E)-6-(3-(3-(Benzofuran-7-yloxy)azetidin-1-yl)-3-oxoprop-1-enyl)-3,4-dihydro-1,8-naphthyridin-2(1H)-one (E60);
(E)-6-(3-(3-(Benzo[b]thiophen-3-yloxy)azetidin-1-yl)-3-oxoprop-1-enyl)-3,4-dihydro-1,8-naphthyridin-2(1H)-one (E61);
(E)-6-(3-oxo-3-(3-(thiophen-2-ylthio)azetidin-1-yl)prop-1-enyl)-3,4-dihydro-1,8-naphthyridin-2(1H)-one (E62);
(E)-6-(3-(3-Methylbenzofuran-2-yl)azetidin-1-yl)-3-oxoprop-1-enyl)-3,4-dihydro-1,8-naphthyridin-2(1H)-one (E67);
6-((E)-3-oxo-3-(3-((E)-1-(propoxyimino)ethyl)azetidin-1-yl)prop-1-enyl)-3,4-dihydro-1,8-naphthyridin-2(1H)-one (E70); or
6-((E)-3-oxo-3-(3-((Z)-1-(propoxyimino)ethyl)azetidin-1-yl)prop-1-enyl)-3,4-dihydro-1,8-naphthyridin-2(1H)-one (E71);
or a pharmaceutically acceptable salt or solvate thereof.

10. A compound of formula (I) as defined in claim 9 which is:
- (E)-6-(3-(3-(Benzofuran-2-yl)azetidin-1-yl)-3-oxoprop-1-enyl)-3,4-dihydro-1,8-naphthyridin-2(1H)-one (E59); or
- (E)-6-(3-(3-(3-Methylbenzofuran-2-yl)azetidin-1-yl)-3-oxoprop-1-enyl)-3,4-dihydro-1,8-naphthyridin-2(1H)-one (E67);

or a pharmaceutically acceptable salt or solvate thereof.

11. A pharmaceutical composition comprising a compound of formula (I) as defined in claim 1, in association with a pharmaceutically acceptable excipient or carrier.

12. A pharmaceutical composition comprising a compound of formula (I) as defined in claim 1 for use in the treatment of microbial infections.

13. A process for preparing the compound of formula (I) as defined in claim 1, which comprises:
(a) reacting a compound of formula (II):

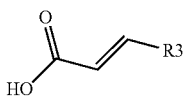

(II)

wherein R3 is as defined above for compounds of formula (I), with a compound of formula (III):

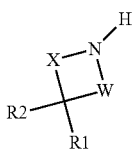

(III)

wherein W, X, R1 and R2 are as defined above for compounds of formula (I); or (b) reacting a compound of formula (IV):

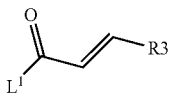

(IV)

wherein R3 is as defined above for compounds of formula (I) and $L^1$ represents a suitable leaving group, with a compound of formula (III):

(III)

wherein W, X, R1 and R2 are as defined above for compounds of formula (I); or (c) reacting a compound of formula (V):

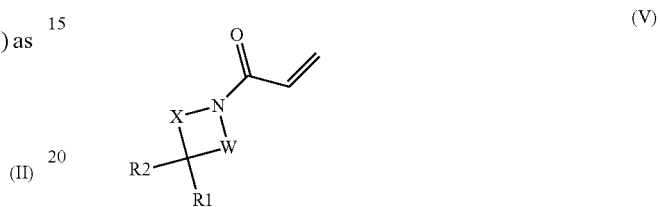

(V)

wherein W, X, R1 and R2 are as defined above for compounds of formula (I), with a compound of formula $L^2$-R3, wherein $L^2$ represents a suitable leaving group; optionally thereafter followed by:

(d) deprotecting a protected derivative of compound (I); and optionally thereafter followed by:

(e) interconversion of a compound of formula (I) to a further compound of formula (I).

14. A compound of formula (I) as defined in claim 9, which is 6-((E)-3-oxo-3-(3-((E)-1-(propoxyimino)ethyl)azetidin-1-yl)prop-1-enyl)-3,4-dihydro-1,8-naphthyridin-2(1H)-one (E70).

15. A compound as defined in claim 5, wherein R1 represents benzofuranyl optionally substituted by a methyl group.

16. A compound as defined claim 6, wherein R2 represents an H or OH group.

17. A compound as defined claim 16, wherein R2 represents an H group.

18. A compound as defined claim 7, wherein R4 represents bromine, chlorine, fluorine or methyl.

19. A compound as defined in claim 8, wherein R5 is 3-$CO_2$Me, 3-$CONH_2$ or 3-$CH_2$OH.

20. A process of claim 13 wherein the leaving group is a halogen or alkoxy group.

21. A process of claim 20 wherein the halogen is fluorine, chlorine or bromine.

* * * * *